US008852103B2

(12) United States Patent
Rothberg et al.

(10) Patent No.: US 8,852,103 B2
(45) Date of Patent: Oct. 7, 2014

(54) TRANSMISSIVE IMAGING AND RELATED APPARATUS AND METHODS

(71) Applicant: Butterfly Network, Inc., Guilford, CT (US)

(72) Inventors: Jonathan M. Rothberg, Guilford, CT (US); Nevada J. Sanchez, Guilford, CT (US); Gregory L. Charvat, Westbrook, CT (US); Tyler S. Ralston, Clinton, CT (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 13/654,337

(22) Filed: Oct. 17, 2012

(65) Prior Publication Data

US 2013/0116561 A1    May 9, 2013
US 2014/0066763 A2    Mar. 6, 2014

Related U.S. Application Data

(60) Provisional application No. 61/548,047, filed on Oct. 17, 2011.

(51) Int. Cl.
*A61B 8/00*  (2006.01)
*A61B 8/14*  (2006.01)
*A61N 7/00*  (2006.01)
*A61B 8/08*  (2006.01)
*A61B 17/32* (2006.01)
*A61N 7/02*  (2006.01)
*A61B 19/00* (2006.01)

(52) U.S. Cl.
CPC ............... *A61B 8/4254* (2013.01); *A61N 7/00* (2013.01); *A61B 8/4245* (2013.01); *A61B 2019/5276* (2013.01); *A61B 8/483* (2013.01); *A61B 17/320068* (2013.01); *A61B 8/08* (2013.01); *A61B 8/4477* (2013.01); *A61B 8/4494* (2013.01); *A61N 7/02* (2013.01); *A61B 8/5207* (2013.01); *A61B 8/4209* (2013.01); *A61B 8/4488* (2013.01)
USPC ................ 600/438; 600/439; 600/459; 601/2

(58) Field of Classification Search
CPC .... A61B 8/4254; A61B 8/4245; A61B 8/483; A61B 8/08; A61B 8/4477; A61B 8/4494; A61B 8/5207; A61B 8/4209; A61B 8/4488; A61B 2019/5276; A61B 17/320068; A61N 7/00; A61N 7/02
USPC ............... 600/407, 438, 439, 443, 459; 601/2
See application file for complete search history.

(56) References Cited

U.S. PATENT DOCUMENTS 4,074,564 A    2/1978   Anderson
4,075,883 A    2/1978   Glover (Continued)

FOREIGN PATENT DOCUMENTS

AU    2003261073 A1    12/2003
AU    2003297650 A1    7/2004

(Continued)

OTHER PUBLICATIONS

Declaration of Non-Establishment of International Search Report, and Written Opinion for International Application PCT/US2012/060665 mailed Jan. 7, 2013.

(Continued)

*Primary Examiner* — Michael Rozanski
(74) *Attorney, Agent, or Firm* — Wolf, Greenfield & Sacks, P.C.

(57) ABSTRACT

Apparatus and methods are described that include ultrasound imaging devices, which may operate in a transmissive ultrasound imaging modality, and which may be used to detect properties of interest of a subject such as index of refraction, density and/or speed of sound. Devices suitable for performing high intensity focused ultrasound (HIFU), as well as HIFU and ultrasound imaging, are also described.

186 Claims, 59 Drawing Sheets

(56) References Cited

U.S. PATENT DOCUMENTS

| | | |
|---|---|---|
| 4,100,916 A | 7/1978 | King |
| 4,149,247 A | 4/1979 | Pavkovich et al. |
| 4,281,550 A | 8/1981 | Erikson |
| 4,317,369 A | 3/1982 | Johnson |
| 4,541,434 A | 9/1985 | Okado |
| 4,594,662 A | 6/1986 | Devaney |
| 4,662,222 A | 5/1987 | Johnson |
| 4,798,209 A | 1/1989 | Klingenbeck et al. |
| 5,206,165 A | 4/1993 | Pauley et al. |
| 5,206,637 A | 4/1993 | Warren |
| 5,226,422 A | 7/1993 | McKeighen et al. |
| 5,291,893 A | 3/1994 | Slayton |
| 5,335,663 A | 8/1994 | Oakley et al. |
| 5,370,121 A | 12/1994 | Reichenberger et al. |
| 5,382,521 A | 1/1995 | Raz et al. |
| 5,409,002 A | 4/1995 | Pell |
| 5,409,010 A | 4/1995 | Beach et al. |
| 5,471,515 A | 11/1995 | Fossum et al. |
| 5,471,988 A | 12/1995 | Fujio et al. |
| 5,520,188 A | 5/1996 | Hennige et al. |
| 5,619,476 A | 4/1997 | Haller et al. |
| 5,650,500 A | 7/1997 | Raz et al. |
| 5,677,491 A | 10/1997 | Ishrak et al. |
| 5,769,790 A | 6/1998 | Watkins et al. |
| 5,820,564 A | 10/1998 | Slayton et al. |
| 5,823,962 A | 10/1998 | Schaetzle et al. |
| 5,834,442 A | 11/1998 | Raz et al. |
| 5,873,902 A | 2/1999 | Sanghvi et al. |
| 5,894,452 A | 4/1999 | Ladabaum et al. |
| 5,922,962 A | 7/1999 | Ishrak et al. |
| 5,982,709 A | 11/1999 | Ladabaum et al. |
| 5,990,506 A | 11/1999 | Fossum et al. |
| 6,004,832 A | 12/1999 | Haller et al. |
| 6,005,916 A | 12/1999 | Johnson et al. |
| 6,007,499 A | 12/1999 | Martin et al. |
| 6,014,897 A | 1/2000 | Mo |
| 6,036,646 A | 3/2000 | Barthe et al. |
| 6,042,556 A | 3/2000 | Beach et al. |
| 6,049,159 A | 4/2000 | Barthe et al. |
| 6,093,883 A | 7/2000 | Sanghvi et al. |
| 6,128,523 A | 10/2000 | Bechtold et al. |
| 6,153,123 A | 11/2000 | Hampden-Smith et al. |
| 6,180,029 B1 | 1/2001 | Hampden-Smith et al. |
| 6,197,218 B1 | 3/2001 | Hampden-Smith et al. |
| 6,217,530 B1 | 4/2001 | Martin et al. |
| 6,224,556 B1 | 5/2001 | Schwartz et al. |
| 6,238,346 B1 | 5/2001 | Mason |
| 6,262,946 B1 | 7/2001 | Khuri-Yakub et al. |
| 6,385,474 B1 | 5/2002 | Rather et al. |
| 6,419,633 B1 | 7/2002 | Robinson et al. |
| 6,419,648 B1 | 7/2002 | Vitek et al. |
| 6,425,867 B1 | 7/2002 | Vaezy et al. |
| 6,430,109 B1 | 8/2002 | Khuri-Yakub et al. |
| 6,432,067 B1 | 8/2002 | Martin et al. |
| 6,440,071 B1 | 8/2002 | Slayton et al. |
| 6,443,896 B1 | 9/2002 | Detmer |
| 6,450,960 B1 | 9/2002 | Rather et al. |
| 6,456,326 B2 | 9/2002 | Fossum et al. |
| 6,500,133 B2 | 12/2002 | Martin et al. |
| 6,506,154 B1 | 1/2003 | Ezion et al. |
| 6,506,171 B1 | 1/2003 | Vitek et al. |
| 6,517,487 B1 | 2/2003 | Mazess et al. |
| 6,522,142 B1 | 2/2003 | Freundlich |
| 6,540,678 B2 | 4/2003 | Rather et al. |
| 6,540,679 B2 | 4/2003 | Slayton et al. |
| 6,543,272 B1 | 4/2003 | Vitek |
| 6,549,235 B1 | 4/2003 | Fossum et al. |
| 6,552,841 B1 | 4/2003 | Lasser et al. |
| 6,555,842 B1 | 4/2003 | Fossum et al. |
| 6,559,644 B2 | 5/2003 | Froundlich et al. |
| 6,570,617 B2 | 5/2003 | Fossum et al. |
| 6,585,731 B1 | 7/2003 | Rattner et al. |
| 6,587,540 B1 | 7/2003 | Johnson et al. |
| 6,600,325 B2 | 7/2003 | Coates et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,636,584 B2 | 10/2003 | Johnson et al. |
| 6,645,162 B2 | 11/2003 | Friedman et al. |
| 6,645,398 B1 | 11/2003 | Hampden-Smith et al. |
| 6,666,833 B1 | 12/2003 | Friedman et al. |
| 6,666,835 B2 | 12/2003 | Martin et al. |
| 6,669,641 B2 | 12/2003 | Poland et al. |
| 6,672,165 B2 | 1/2004 | Rather et al. |
| 6,685,639 B1 | 2/2004 | Wang et al. |
| 6,685,640 B1 | 2/2004 | Fry et al. |
| 6,705,994 B2 | 3/2004 | Vortman et al. |
| 6,709,394 B2 | 3/2004 | Frisa et al. |
| 6,716,168 B2 | 4/2004 | Nock et al. |
| 6,716,184 B2 | 4/2004 | Vaezy et al. |
| 6,728,567 B2 | 4/2004 | Rather et al. |
| 6,734,847 B1 | 5/2004 | Baldeweg et al. |
| 6,735,461 B2 | 5/2004 | Vitek et al. |
| 6,744,068 B2 | 6/2004 | Fossum et al. |
| 6,755,786 B2 | 6/2004 | Frisa et al. |
| 6,755,788 B2 | 6/2004 | Demers et al. |
| 6,761,689 B2 | 7/2004 | Salgo et al. |
| 6,778,848 B1 | 8/2004 | Bechtold et al. |
| 6,783,497 B2 | 8/2004 | Grenon et al. |
| 6,790,180 B2 | 9/2004 | Vitek et al. |
| 6,835,393 B2 | 12/2004 | Hoffman et al. |
| 6,836,020 B2 | 12/2004 | Cheng et al. |
| 6,837,854 B2 | 1/2005 | Moore et al. |
| 6,875,176 B2 | 4/2005 | Mourad et al. |
| 6,926,672 B2 | 8/2005 | Moore et al. |
| 6,958,255 B2 | 10/2005 | Khuri-Yakub et al. |
| 6,974,417 B2 | 12/2005 | Lockwood et al. |
| 6,984,210 B2 | 1/2006 | Chambers et al. |
| 7,022,077 B2 | 4/2006 | Mourad et al. |
| 7,037,264 B2 | 5/2006 | Poland |
| 7,052,464 B2 | 5/2006 | Wodnicki |
| 7,070,565 B2 | 7/2006 | Vaezy et al. |
| 7,128,711 B2 | 10/2006 | Medan et al. |
| 7,175,596 B2 | 2/2007 | Vitek et al. |
| 7,229,411 B2 | 6/2007 | Slayton et al. |
| 7,274,623 B2 | 9/2007 | Bayram et al. |
| 7,285,092 B2 | 10/2007 | Duric et al. |
| 7,296,318 B2 | 11/2007 | Mourad et al. |
| 7,321,181 B2 | 1/2008 | Khuri-Yakub et al. |
| 7,374,778 B2 | 5/2008 | Hoffman et al. |
| 7,377,900 B2 | 5/2008 | Vitek et al. |
| 7,393,325 B2 | 7/2008 | Barthe et al. |
| 7,463,030 B2 | 12/2008 | He et al. |
| 7,476,411 B1 | 1/2009 | Hampden-Smith et al. |
| 7,491,171 B2 | 2/2009 | Barthe et al. |
| 7,499,745 B2 | 3/2009 | Littrup et al. |
| 7,510,536 B2 | 3/2009 | Foley et al. |
| 7,520,856 B2 | 4/2009 | Vaezy et al. |
| 7,521,930 B2 | 4/2009 | Li et al. |
| 7,530,356 B2 | 5/2009 | Slayton et al. |
| 7,530,952 B2 | 5/2009 | Huang et al. |
| 7,530,958 B2 | 5/2009 | Slayton et al. |
| 7,535,794 B2 | 5/2009 | Prus et al. |
| 7,545,075 B2 | 6/2009 | Huang et al. |
| 7,559,905 B2 | 7/2009 | Kagosaki et al. |
| 7,570,742 B2 | 8/2009 | Johnson et al. |
| 7,571,336 B2 | 8/2009 | Barthe et al. |
| 7,591,996 B2 | 9/2009 | Hwang et al. |
| 7,611,462 B2 | 11/2009 | Vortman et al. |
| 7,612,483 B2 | 11/2009 | Degertekin |
| 7,621,873 B2 | 11/2009 | Owen et al. |
| 7,646,133 B2 | 1/2010 | Degertekin |
| 7,652,410 B2 | 1/2010 | Prus |
| 7,662,114 B2 | 2/2010 | Seip et al. |
| 7,670,291 B2 | 3/2010 | Vaezy et al. |
| 7,684,846 B2 | 3/2010 | Johnson et al. |
| 7,686,763 B2 | 3/2010 | Vaezy et al. |
| 7,699,780 B2 | 4/2010 | Vitek et al. |
| 7,699,783 B2 | 4/2010 | Hanover et al. |
| 7,699,793 B2 | 4/2010 | Gotte et al. |
| 7,722,539 B2 | 5/2010 | Carter et al. |
| 7,741,686 B2 | 6/2010 | Khuri-Yakub et al. |
| 7,745,248 B2 | 6/2010 | Park et al. |

(56) References Cited

U.S. PATENT DOCUMENTS

| | | |
|---|---|---|
| 7,745,973 B2 | 6/2010 | Bayram et al. |
| 7,758,524 B2 | 7/2010 | Barthe et al. |
| 7,759,937 B2 | 7/2010 | He et al. |
| 7,763,456 B2 | 7/2010 | Li et al. |
| 7,767,484 B2 | 8/2010 | Ayazi |
| 7,771,360 B2 | 8/2010 | Johnson et al. |
| 7,779,696 B2 | 8/2010 | Huang |
| 7,792,566 B2 | 9/2010 | Roland et al. |
| 7,803,116 B2 | 9/2010 | Sikdar et al. |
| 7,815,574 B2 | 10/2010 | Mourad et al. |
| 7,824,348 B2 | 11/2010 | Barthe et al. |
| 7,825,383 B2 | 11/2010 | Vija et al. |
| 7,841,982 B2 | 11/2010 | Johnson et al. |
| 7,846,102 B2 | 12/2010 | Kupnik et al. |
| 7,850,626 B2 | 12/2010 | Vaezy et al. |
| 7,880,565 B2 | 2/2011 | Huang |
| 7,888,709 B2 | 2/2011 | Lemmerhirt et al. |
| 7,903,830 B2 | 3/2011 | Hansen et al. |
| 7,914,458 B2 | 3/2011 | Hossack et al. |
| 7,920,731 B2 | 4/2011 | Moreau-Gobard |
| 7,956,510 B2 | 6/2011 | Huang |
| 7,972,271 B2 | 7/2011 | Johnson et al. |
| 8,002,706 B2 | 8/2011 | Vortman et al. |
| 8,003,129 B2 | 8/2011 | Hoffman et al. |
| 8,004,373 B2 | 8/2011 | Huang |
| 8,008,105 B2 | 8/2011 | Huang |
| 8,008,835 B2 | 8/2011 | Degertekin |
| 8,014,231 B2 | 9/2011 | Oliver et al. |
| 8,016,757 B2 | 9/2011 | Kaczkowski et al. |
| 8,018,301 B2 | 9/2011 | Huang |
| 8,040,756 B2 | 10/2011 | Wang et al. |
| 8,052,604 B2 | 11/2011 | Lau et al. |
| 8,057,391 B2 | 11/2011 | Lau et al. |
| 8,057,409 B2 | 11/2011 | Fu et al. |
| 8,060,182 B2 | 11/2011 | He et al. |
| 8,076,821 B2 | 12/2011 | Degertekin |
| 8,088,067 B2 | 1/2012 | Vortman et al. |
| 8,105,941 B2 | 1/2012 | Huang |
| 8,116,509 B2 | 2/2012 | Wang et al. |
| 8,116,843 B2 | 2/2012 | Dai et al. |
| 8,120,229 B2 | 2/2012 | Huang |
| 8,131,341 B2 | 3/2012 | Heumann et al. |
| 8,133,182 B2 | 3/2012 | Wagner |
| 8,157,740 B2 | 4/2012 | Adachi et al. |
| 8,222,065 B1 | 7/2012 | Smeys et al. |
| 8,226,563 B2 | 7/2012 | Peteresen et al. |
| 8,231,535 B2 | 7/2012 | Hossack et al. |
| 8,247,945 B2 | 8/2012 | Huang |
| 8,276,433 B2 | 10/2012 | Kupnik et al. |
| 8,277,380 B2 | 10/2012 | Daft et al. |
| 8,309,428 B2 | 11/2012 | Lemmerhirt et al. |
| 8,315,125 B2 | 11/2012 | Lemmerhirt |
| 8,324,006 B1 | 12/2012 | Adler et al. |
| 8,327,521 B2 | 12/2012 | Dirksen et al. |
| 8,345,512 B2 | 1/2013 | Adachi et al. |
| 8,345,513 B2 | 1/2013 | Huang |
| 8,363,514 B2 | 1/2013 | Huang |
| 8,372,011 B2 | 2/2013 | Degertekin |
| 8,398,554 B2 | 3/2013 | Degertekin |
| 8,399,278 B2 | 3/2013 | Lemmerhirt et al. |
| 8,402,831 B2 | 3/2013 | Kupnik et al. |
| 2001/0042853 A1 | 11/2001 | Hampden-Smith et al. |
| 2001/0051774 A1 | 12/2001 | Littrup et al. |
| 2002/0065466 A1 | 5/2002 | Rather et al. |
| 2002/0082589 A1 | 6/2002 | Friedman et al. |
| 2002/0087080 A1 | 7/2002 | Slayton et al. |
| 2002/0138000 A1 | 9/2002 | Rather et al. |
| 2002/0143245 A1 | 10/2002 | Rather et al. |
| 2002/0180438 A1 | 12/2002 | Froundlich et al. |
| 2002/0193681 A1 | 12/2002 | Vitek et al. |
| 2003/0011362 A1 | 1/2003 | Gohlsch et al. |
| 2003/0023166 A1 | 1/2003 | Frisa et al. |
| 2003/0028111 A1 | 2/2003 | Vaezy et al. |
| 2003/0036706 A1 | 2/2003 | Slayton et al. |
| 2003/0060710 A1 | 3/2003 | Salgo et al. |
| 2003/0083597 A1 | 5/2003 | Vitek et al. |
| 2003/0097067 A1 | 5/2003 | Poland et al. |
| 2003/0105398 A1 | 6/2003 | Vitek |
| 2003/0168635 A1 | 9/2003 | Hampden-Smith et al. |
| 2003/0181806 A1 | 9/2003 | Medan et al. |
| 2003/0187371 A1 | 10/2003 | Vortman et al. |
| 2003/0195421 A1 | 10/2003 | Demers et al. |
| 2003/0195422 A1 | 10/2003 | Frisa et al. |
| 2003/0204141 A1 | 10/2003 | Nock et al. |
| 2003/0208124 A1 | 11/2003 | Poland |
| 2003/0230488 A1 | 12/2003 | Lee et al. |
| 2003/0233045 A1 | 12/2003 | Vaezy et al. |
| 2004/0006272 A1 | 1/2004 | Vortman et al. |
| 2004/0030227 A1 | 2/2004 | Littrup et al. |
| 2004/0080256 A1 | 4/2004 | Hampden-Smith et al. |
| 2004/0122304 A1 | 6/2004 | Duric et al. |
| 2004/0122313 A1 | 6/2004 | Moore et al. |
| 2004/0122322 A1 | 6/2004 | Moore et al. |
| 2004/0122323 A1 | 6/2004 | Vortman et al. |
| 2004/0122325 A1 | 6/2004 | Chambers et al. |
| 2004/0169474 A1 | 9/2004 | Hampden-Smith et al. |
| 2004/0195548 A1 | 10/2004 | Hampden-Smith et al. |
| 2004/0236253 A1 | 11/2004 | Vortman et al. |
| 2005/0038340 A1 | 2/2005 | Vaezy et al. |
| 2005/0136102 A1 | 6/2005 | Hoffman et al. |
| 2005/0177045 A1 | 8/2005 | Degertekin et al. |
| 2005/0200241 A1 | 9/2005 | Degertekin |
| 2005/0200242 A1 | 9/2005 | Degertekin |
| 2005/0203397 A1 | 9/2005 | Degertekin |
| 2005/0203399 A1 | 9/2005 | Vaezy et al. |
| 2005/0219694 A1 | 10/2005 | Vesely et al. |
| 2005/0240126 A1 | 10/2005 | Foley et al. |
| 2005/0256406 A1 | 11/2005 | Barthe et al. |
| 2005/0264558 A1 | 12/2005 | Vesely et al. |
| 2006/0009693 A1 | 1/2006 | Hanover et al. |
| 2006/0009696 A1 | 1/2006 | Hanover et al. |
| 2006/0052701 A1 | 3/2006 | Carter et al. |
| 2006/0058664 A1 | 3/2006 | Barthe et al. |
| 2006/0058667 A1 | 3/2006 | Lemmerhirt et al. |
| 2006/0058671 A1 | 3/2006 | Vitek et al. |
| 2006/0058678 A1 | 3/2006 | Vitek et al. |
| 2006/0058707 A1 | 3/2006 | Barthe et al. |
| 2006/0074313 A1 | 4/2006 | Slayton et al. |
| 2006/0074355 A1 | 4/2006 | Slayton et al. |
| 2006/0079868 A1 | 4/2006 | Makin et al. |
| 2006/0084859 A1 | 4/2006 | Johnson et al. |
| 2006/0084891 A1 | 4/2006 | Barthe et al. |
| 2006/0089632 A1 | 4/2006 | Barthe et al. |
| 2006/0111744 A1 | 5/2006 | Makin et al. |
| 2006/0184074 A1 | 8/2006 | Vaezy et al. |
| 2006/0231795 A1 | 10/2006 | Hampden-Smith et al. |
| 2006/0250391 A1 | 11/2006 | Vesely et al. |
| 2006/0257659 A1 | 11/2006 | Hampden-Smith et al. |
| 2006/0264748 A1 | 11/2006 | Vaezy et al. |
| 2006/0282691 A1 | 12/2006 | Barthe et al. |
| 2006/0287596 A1 | 12/2006 | Johnson et al. |
| 2006/0293597 A1 | 12/2006 | Johnson et al. |
| 2007/0004984 A1 | 1/2007 | Crum et al. |
| 2007/0016039 A1 | 1/2007 | Vortman et al. |
| 2007/0041961 A1 | 2/2007 | Hwang et al. |
| 2007/0066895 A1 | 3/2007 | Sikdar et al. |
| 2007/0098232 A1 | 5/2007 | Matula et al. |
| 2007/0106157 A1 | 5/2007 | Kaczkowski et al. |
| 2007/0161896 A1 | 7/2007 | Adachi et al. |
| 2007/0167781 A1 | 7/2007 | Vortman et al. |
| 2007/0167811 A1 | 7/2007 | Lemmerhirt et al. |
| 2007/0167812 A1 | 7/2007 | Lemmerhirt et al. |
| 2007/0180916 A1 | 8/2007 | Tian et al. |
| 2007/0197918 A1 | 8/2007 | Vitek et al. |
| 2007/0215964 A1 | 9/2007 | Khuri-Yakub et al. |
| 2007/0219448 A1 | 9/2007 | Seip et al. |
| 2007/0228877 A1 | 10/2007 | Huang |
| 2007/0228878 A1 | 10/2007 | Huang |
| 2007/0232913 A1 | 10/2007 | Lau et al. |
| 2007/0239011 A1 | 10/2007 | Lau et al. |
| 2007/0239020 A1 | 10/2007 | Iinuma et al. |
| 2007/0242567 A1 | 10/2007 | Daft et al. |
| 2007/0287918 A1 | 12/2007 | Huang |
| 2008/0030104 A1 | 2/2008 | Prus |

(56) References Cited

U.S. PATENT DOCUMENTS

| | | |
|---|---|---|
| 2008/0031090 A1 | 2/2008 | Prus et al. |
| 2008/0033278 A1 | 2/2008 | Assif |
| 2008/0033292 A1 | 2/2008 | Shafran |
| 2008/0051656 A1 | 2/2008 | Vaezy et al. |
| 2008/0071255 A1 | 3/2008 | Barthe et al. |
| 2008/0091123 A1 | 4/2008 | Fedewa et al. |
| 2008/0091124 A1 | 4/2008 | Fedewa et al. |
| 2008/0097207 A1 | 4/2008 | Cai |
| 2008/0138290 A1 | 6/2008 | Wang et al. |
| 2008/0139973 A1 | 6/2008 | Wang et al. |
| 2008/0183077 A1 | 7/2008 | Moreau-Gobard et al. |
| 2008/0188745 A1 | 8/2008 | Chen et al. |
| 2008/0194053 A1 | 8/2008 | Huang |
| 2008/0197751 A1 | 8/2008 | Huang |
| 2008/0203556 A1 | 8/2008 | Huang |
| 2008/0255452 A1 | 10/2008 | Entrekin |
| 2008/0260790 A1 | 10/2008 | Wang et al. |
| 2008/0269614 A1 | 10/2008 | Adachi et al. |
| 2008/0275330 A1 | 11/2008 | Mu et al. |
| 2008/0275344 A1 | 11/2008 | Glide-Hurst et al. |
| 2008/0281237 A1 | 11/2008 | Slayton et al. |
| 2008/0281252 A1 | 11/2008 | Wang et al. |
| 2008/0281255 A1 | 11/2008 | Slayton et al. |
| 2008/0287835 A1 | 11/2008 | Zhao et al. |
| 2008/0290756 A1 | 11/2008 | Huang |
| 2008/0294055 A1 | 11/2008 | Adachi et al. |
| 2008/0294073 A1 | 11/2008 | Barthe et al. |
| 2009/0003675 A1 | 1/2009 | Moreau-Gobard |
| 2009/0018446 A1 | 1/2009 | Medan et al. |
| 2009/0036773 A1 | 2/2009 | Lau et al. |
| 2009/0048522 A1 | 2/2009 | Huang |
| 2009/0054772 A1 | 2/2009 | Lin et al. |
| 2009/0069677 A1 | 3/2009 | Chen et al. |
| 2009/0069686 A1 | 3/2009 | Daft et al. |
| 2009/0088623 A1 | 4/2009 | Vortman et al. |
| 2009/0088636 A1 | 4/2009 | Lau et al. |
| 2009/0118725 A1 | 5/2009 | Auth et al. |
| 2009/0118729 A1 | 5/2009 | Auth et al. |
| 2009/0140606 A1 | 6/2009 | Huang |
| 2009/0140609 A1 | 6/2009 | Huang |
| 2009/0141592 A1 | 6/2009 | Huang |
| 2009/0152980 A1 | 6/2009 | Huang |
| 2009/0251917 A1 | 10/2009 | Wollner et al. |
| 2009/0259129 A1 | 10/2009 | Wang et al. |
| 2009/0280441 A1 | 11/2009 | Nara |
| 2009/0316151 A1 | 12/2009 | Matula et al. |
| 2010/0013574 A1 | 1/2010 | Huang |
| 2010/0018315 A1 | 1/2010 | Wang et al. |
| 2010/0036291 A1 | 2/2010 | Darlington et al. |
| 2010/0036292 A1 | 2/2010 | Darlington et al. |
| 2010/0056925 A1 | 3/2010 | Zhang et al. |
| 2010/0076351 A1 | 3/2010 | Jiang et al. |
| 2010/0081893 A1 | 4/2010 | Jarvik et al. |
| 2010/0087728 A1 | 4/2010 | Jarvik et al. |
| 2010/0106019 A1 | 4/2010 | Friemel et al. |
| 2010/0160781 A1 | 6/2010 | Carter et al. |
| 2010/0173437 A1 | 7/2010 | Wygant et al. |
| 2010/0174188 A1 | 7/2010 | Wang et al. |
| 2010/0207489 A1 | 8/2010 | Huang |
| 2010/0210976 A1 | 8/2010 | Darlington et al. |
| 2010/0225200 A1 | 9/2010 | Kupnik et al. |
| 2010/0228126 A1 | 9/2010 | Emery et al. |
| 2010/0234728 A1 | 9/2010 | Foley et al. |
| 2010/0234773 A1 | 9/2010 | Fu et al. |
| 2010/0236330 A1 | 9/2010 | Nyholt et al. |
| 2010/0237807 A1 | 9/2010 | Lemmerhirt |
| 2010/0241005 A1 | 9/2010 | Darlington et al. |
| 2010/0241036 A1 | 9/2010 | Vortman et al. |
| 2010/0244623 A1 | 9/2010 | Huang |
| 2010/0246332 A1 | 9/2010 | Huang |
| 2010/0249605 A1 | 9/2010 | Degertekin |
| 2010/0251537 A1 | 10/2010 | Huang |
| 2010/0254222 A1 | 10/2010 | Huang |
| 2010/0255623 A1 | 10/2010 | Huang |
| 2010/0256501 A1 | 10/2010 | Degertekin |
| 2010/0262070 A1 | 10/2010 | Wang |
| 2010/0268089 A1 | 10/2010 | Degertekin |
| 2010/0278015 A1 | 11/2010 | Huang |
| 2010/0280388 A1 | 11/2010 | Huang |
| 2010/0307486 A1 | 12/2010 | Chen et al. |
| 2010/0317971 A1 | 12/2010 | Fan et al. |
| 2010/0330545 A1 | 12/2010 | Tian et al. |
| 2011/0009734 A1 | 1/2011 | Foley et al. |
| 2011/0040171 A1 | 2/2011 | Foley et al. |
| 2011/0040189 A1 | 2/2011 | Petruzzello et al. |
| 2011/0040214 A1 | 2/2011 | Foley et al. |
| 2011/0050033 A1 | 3/2011 | Nikoozadeh et al. |
| 2011/0060221 A1 | 3/2011 | Fan et al. |
| 2011/0109309 A1 | 5/2011 | Levy et al. |
| 2011/0136284 A1 | 6/2011 | Huang |
| 2011/0150758 A1 | 6/2011 | Geppert et al. |
| 2011/0151608 A1 | 6/2011 | Lemmerhirt et al. |
| 2011/0178407 A1 | 7/2011 | Lu et al. |
| 2011/0178444 A1 | 7/2011 | Slayton et al. |
| 2011/0187706 A1 | 8/2011 | Vesely et al. |
| 2011/0201928 A1 | 8/2011 | Duric et al. |
| 2011/0201929 A1 | 8/2011 | Vaezy et al. |
| 2011/0201932 A1 | 8/2011 | Duric et al. |
| 2011/0201976 A1 | 8/2011 | Sanghvi et al. |
| 2011/0242932 A1 | 10/2011 | Lebental et al. |
| 2011/0251528 A1 | 10/2011 | Canney et al. |
| 2011/0288238 A1 | 11/2011 | Hoffman et al. |
| 2011/0313278 A1 | 12/2011 | Kiraly |
| 2012/0005624 A1 | 1/2012 | Vesely |
| 2012/0010538 A1 | 1/2012 | Dirksen |
| 2012/0013218 A1 | 1/2012 | Huang |
| 2012/0029353 A1 | 2/2012 | Slayton et al. |
| 2012/0035473 A1 | 2/2012 | Sanghvi et al. |
| 2012/0046592 A1 | 2/2012 | Albright et al. |
| 2012/0071759 A1 | 3/2012 | Hagy et al. |
| 2012/0074509 A1 | 3/2012 | Berg et al. |
| 2012/0086087 A1 | 4/2012 | Fitzpatrick |
| 2012/0112324 A1 | 5/2012 | Huang |
| 2012/0162204 A1 | 6/2012 | Vesely et al. |
| 2012/0187508 A1 | 7/2012 | Adler et al. |
| 2012/0250454 A1 | 10/2012 | Rohling et al. |
| 2012/0299439 A1 | 11/2012 | Huang |
| 2012/0300036 A1 | 11/2012 | Flynn |
| 2013/0050422 A1 | 2/2013 | Flynn |
| 2013/0064043 A1 | 3/2013 | Degertekin et al. |
| 2014/0180088 A1 | 6/2014 | Rothberg et al. |
| 2014/0180092 A1 | 6/2014 | Rothberg et al. |
| 2014/0180093 A1 | 6/2014 | Rothberg et al. |
| 2014/0180094 A1 | 6/2014 | Rothberg et al. |
| 2014/0180095 A1 | 6/2014 | Rothberg et al. |
| 2014/0180096 A1 | 6/2014 | Rothberg et al. |
| 2014/0180097 A1 | 6/2014 | Rothberg et al. |
| 2014/0180099 A1 | 6/2014 | Rothberg et al. |
| 2014/0180100 A1 | 6/2014 | Rothberg et al. |
| 2014/0180112 A1 | 6/2014 | Rothberg et al. |
| 2014/0180113 A1 | 6/2014 | Rothberg et al. |
| 2014/0180176 A1 | 6/2014 | Rothberg et al. |
| 2014/0180177 A1 | 6/2014 | Rothberg et al. |

FOREIGN PATENT DOCUMENTS

| | | |
|---|---|---|
| EP | 0 031 614 A1 | 7/1981 |
| EP | 0 985 007 B1 | 5/2006 |
| WO | WO 98/37165 A1 | 8/1998 |
| WO | WO 99/47046 A1 | 9/1999 |
| WO | WO 00/12649 A1 | 3/2000 |
| WO | WO 03/096883 A2 | 11/2003 |
| WO | WO 2004/061575 A2 | 7/2004 |
| WO | WO 2011/094585 A1 | 8/2011 |
| WO | WO 2011/100691 A1 | 8/2011 |
| WO | WO 2011/100697 A1 | 8/2011 |
| WO | WO 2011/156624 A2 | 12/2011 |

OTHER PUBLICATIONS

International Preliminary Report on Patentability mailed May 1, 2014 for Application No. PCT/US2012/060665.

Kim et al., Design and Test of a Fully Controllable 64×128 2-D CMUT Array Integrated with Reconfigurable Frontend ASICs for

(56) References Cited

OTHER PUBLICATIONS

Volumetric Ultrasound Imaging. IEEE. International Ultrasonics Symposium Proceedings. Oct. 7-10, 2012;77-80. doi: 10.1109/ULTSYM.2012.0019.

Nikoozadeh et al., Forward-Looking Intracardiac Ultrasound Imaging Using a 1-D CMUT Array Integrated With Custom Front-End Electronics. IEEE Trans Ultrason Ferroelectr Freq Contr. Dec. 2008;55(12):2651-60.

Um et al., An Analog-Digital-Hybrid Single-Chip RX Beamformer with Non-Uniform Sampling for 2D-CMUT Ultrasound Imaging to Achieve Wide Dynamic Range of Delay and Small Chip Area. IEEE International Solid-State Circuits Conference. Feb. 12, 2014;426-8.

Wygant et al. Integration of 2D CMUT Arrays with Front-End Electronics for Volumetric Ultrasound Imaging. IEEE Trans Ultrason Ferr Freq Control. Feb. 2008;55(2):327-42.

[No Author Listed] HIFU Treatment Process—Step by Step. http://www.hifu.ca/hifu-treatment-process-step-by=step.htm [last accessed Oct. 12, 2012]. 2 pages.

Ajdler et al., Sound Field Analysis Along a Circle and its Applications to HRTFs Interpolation. Audiovis Comm Lab EPFL. Jan. 30, 2008 43 pages.

Ajdler et al., Sound Field Analysis Along a Circle and its Applications to HRTFs Interpolation. J Audio Eng Soc. Mar. 2008;56(3):156-75.

Ali et al., Signal Processing Overview of Ultrasound Systems for Medical Imaging. Texas Instruments White Paper. Nov. 2008;SPRAB12:1-27.

Amini et al., Noninvasive Estimation of Tissue Temperature Via High-Resolution Spectral Analysis Techniques. IEEE Trans on Biomed Eng. Feb. 2005;52(2):221-8.

André et al., High-Speed Data Acquisition in a Diffraction Tomography System Employing Large-Scale Toroidal Arrays. Acoust Tom. 1997;8(1):137-47.

Arnal et al., Monitoring of Thermal Therapy Based on Shear Modulus Changes: I. Shear Wave Thermometry. IEEE Trans Ultrason Ferr Freq Control. Feb. 2011;58(2):369-78.

Arnold et al., Discrete Transparent Boundary Conditions for Wide Angle Parabolic Equations in Underwater Acoustics. J Comp Phys. 1998. 6 pages.

Bolz et al., Sparse Matrix Solver on the GPU: Conjugate Gradients and Multigrid. Acm Trans Graph. Jul. 2003;22(3):917-924.

Boufounos, Compressive Sensing for Over-the-Air Ultrasound. Mitsubishi Elec Res Lab. May 2011. http://www.merl.com. 6 pages.

Brenders et al., Waveform Tomography of a 2-D Full Wavefield, Elastic, Wide Angle, Synthetic Dataset. Commis Contr-Sour Seismol 12th Int Worksh. Oct. 2003 4 pages.

Candès et al., An Introduction to Compressive Sampling: A sensing/sampling paradigm that goes against the common knowledge in data acquisition. IEEE Signal Proc Mag. Mar. 2008;21-30.

Candes et al., Decoding by Linear Programming IEEE Trans Info Theory. Dec. 2005;51(12):4203-15.

Candes et al., Near-Optimal Signal Recovery From Random Projections: Universal Encoding Strategies? IEEE Trans Info Theory. Dec. 2006;52(12):5406-25.

Candès et al., Robust Uncertainty Principles: Exact Signal Reconstruction From Highly Incomplete Frequency Information. IEEE Trans Info Theory. Feb. 2006;52(2):489-509.

Candès et al., Sparsity and incoherence in compressive sampling. Inverse Problems. 2007;23:969-985. doi:10.1088/0266-5611/23/3/008.

Carson et al., Anniversary Paper: Evolution of ultrasound physics and the role of medical physicists and the AAPM and its journal in that evolution. Med Phys. Feb. 2009;36(2):411-28.

Chen et al., Atomic decomposition by basis pursuit. SIAM Rev. Mar. 2001;43(1):129-159.

Cheng et al., A 3D Parabolic Equation Method for Sound Propagation in Moving Inhomogeneous Media. Am Inst Aeronaut Astronaut Meeting Paper. 2007;3564. 20 pages.

Cocosco et al., BrainWeb: Online Interface to a 3D MRI Simulated Brain Database. NeuroImage. 1997; 5:S425.

Cox, Acoustics for Ultrasound Imaging. Jan. 2012 79 pages.

Dehnavi et al., Enhancing the Performance of Conjugate Gradient Solvers on Graphic Processing Units. IEEE. 2010. 1 page.

Dehnavi et al., Enhancing the performance of conjugate gradient solvers on graphic processing units. IEEE Trans Magn. May 2011;47(5):1162-5.

Denis et al., Ultrasonic Transmission Tomography in Refracting Media: Reduction of Refraction Artifacts by Curved-Ray Techniques. IEEE Trans Med Imag. Mar. 1995;14(1):173-88.

Donoho et al., Data Compression and Harmonic Analysis. IEEE Trans Info Theory. Oct. 1998;44(6):2435-76.

Donoho et al.,Uncertainty Principles and Ideal Atomic Decomposition. IEEE Trans Info Theory. Nov. 2001;47(7):2845-62.

Donoho, Compressed Sensing. IEEE Trans Info Theory. Apr. 2006;52(4):1289-306.

Dupenloup et al., Reduction of the Grating Lobes of Annular Arrays Used in Focused Ultrasound Surgery. IEEE Trans Ultrason Ferr Freq Control. Nov. 1996;43(6):991-8.

Duric et al., Detection of breast cancer with ultrasound tomography: First results with the Computed Ultrasound Risk Evaluation (CURE) prototype. Med Phys. Feb. 2007;34(2):773-85.

Duric et al., Development of ultrasound tomography for breast imaging: Technical assessment. Med Phys. May 2005;32(5):1375-86.

Ebbini et al., Multiple-Focus Ultrasound Phased-Array Pattern Synthesis: Optimal Driving-Signal Distributions for Hyperthermia. IEEE Trans Ultrason Ferr Freq Control. Sep. 1989;36(5):540-8.

Fellingham et al., Ultrasonic Characterization of Tissue Structure in the in Vivo Human Liver and Spleen. IEEE Trans Sonics Ultrason. Jul. 1984;SU-31(4):418-28.

Frigo et al., The Design and Implementation of FFTW3. Proc IEEE. Feb. 2005;93(2):216-31.

Geller et al., Two efficient algorithms for iterative linearized inversion of seismic waveform data. Geophys J Int. 1993;115:699-710.

Ghoshal et al., Use of quantitative ultrasound to detect temperature variations in biological phantoms due to heating. IEEE Int Ultrason Symp Proc. 2009;1780-3.

Haak et al., Comparison of spatiotemporal interpolators for 4D image reconstruction from 2D transesophageal ultrasound. Proc SPIE. Feb. 4, 2012;8320:832007.1-11.

Herman et al., High-Resolution Radar via Compressed Sensing. IEEE Trans Signal Proc. Jun. 2009;57(6):2275-84.

Hormati et al., Robust Ultrasound Travel-time Tomography Using the Bent Ray Model. Proc SPIE. 2010;7629:76290I.1-12.

Huang et al., Breast imaging with time-reversed ultrasound. Proc SPIE. 2006;6147:61470I.1-12.

Huang et al., In vivo breast sound-speed imaging with ultrasound tomography. Ultrasound Med Biol. 2009. 40 pages.

Jovanović et al., Acoustic Tomography for Scalar and Vector Fields: Theory and Application to Temperature and Wind Estimation. Am Meteorol Soc. Aug. 2009;26:1475-92.

Jovanović et al., Sound Speed Estimation Using Wave-based Ultrasound Tomography: Theory and GPU Implementation. Proc SPIE. 2010;7629:76290J.1-12.

Jovanović, Inverse Problems in Acoustic Tomography: Theory and Applications. Audiovis Comm Lab EPFL. Jul. 31, 2008 139 pages.

Kak, Computerized Tomography with X-Ray, Emission, and Ultrasound Sources. Proc IEEE Sep. 1979;67(9)1245-72.

Klimeš, Grid Travel-time Tracing: Second-order Method for the First Arrivals in Smooth Media. Pageoph. 1996;148(3):539-63.

Li et al., An improved automatic time-of-flight picker for medical ultrasound tomography. Ultrason. 2009;49:61-72.

Li et al., Breast ultrasound tomography with total-variation regularization. Proc SPIE. 2009;7265:726506.1-8.

Li et al., Clinical breast imaging using sound-speed reconstructions of ultrasound tomography data Proc SPIE. 2008;6920:692009.1-9.

Li et al., Comparison of ultrasound attenuation tomography methods for breast imaging. Proc SPIE. 2008;6920:692015.1-9.

Li et al., Refraction corrected transmission ultrasound computed tomography for application in brest imaging. Med Phys. May 2010;37(5):2233-46.

Liu et al., Real-Time 2-D Temperature Imaging Using Ultrasound. IEEE Trans Biomed Eng. Jan. 2010;57(1):12-16.

(56) References Cited

OTHER PUBLICATIONS

Lu et al., High Frame Rate Imaging System for Limited Diffraction Array Beam Imaging with Square-Wave Aperture Weightings. IEEE Trans Ultrason Ferr Freq Control. Oct. 10, 2006;53(10):1796-812.

Lustig et al., Sparse MRI: The application of compressed sensing for rapid MR imaging. Magn Reson Med. Dec. 2007;58(6):1182-95.

Malcolm, Introduction to Seismic Imaging. Presentation. Mit. Aug. 20, 2010 59 pages.

Mast, Aberration correction for time-domain ultrasound diffraction tomography. J Acoust Soc Am. Jul. 2002;112(1):55-64.

Matheney et al., Seismic attenuation values obtained from instantaneous-frequency matching and spectral ratios.Geophys J Int. 1995;123:1-15.

Misaridis, Ultrasound Imaging Using Coded Signals. Thesis submitted in partial fulfillment of the requirements for the degree of Doctor of Philosophy at the Technical University of Denmark. Aug. 2001 228 pages.

Moros et al., An investigation of penetration depth control using parallel opposed ultrasound arrays and a scanning reflector. J Acoust Soc Am. Mar. 1997;101(3):1734-41.

Moros et al., Experimental assessment of power and temperature penetration depth control with a dual frequency ultrasonic system. Med Phys. May 1999;26(5):810-7.

Novák et al., Treatment delivery software for a new clinical grade ultrasound system for thermoradiotherapy. Med Phys. Nov. 2005;32(11):3246-56.

Oralkan et al., Capacitive Micromachined Ultrasonic Transducers: Next-Generation Arrays for Acoustic Imaging? IEEE Trans Ultrason Ferr Freq Control. Nov. 2002;49(11)1596-1610.

Pratt et al., Seismic waveform inversion in frequency domain-II: Fault delineation in sediments using crosshole data. Queen's Univ. Sep. 8, 1998 Submitted to Geophysics Oct. 1997, revised version submitted Sep. 1998. 40 pages.

Pratt et al., Sound-speed and attenuation imaging of breast tissue using waveform tomography of transmission ultrasound data. Proc SPIE. Mar. 19, 2007;6510:651045.1-12.

Pratt, Seismic waveform inversion in the frequency domain, Part 1: Theory and verification in a physical scale model. Geophys. 1999;64(3):888-901.

Pratt, Velocity Models from Frequency-Domain Waveform Tomography: Past, Present, and Future. EAGE 66th Conf Exh. Jun. 2004 4 pages.

Pratt, Waveform Tomography: theory and practice. Queen's Univ. 4 pages.

Provost et al., The application of compressed sensing for photo-acoustic tomography. IEEE Trans Med Imag. Apr. 2009;28(4):585-594.

Rajagopalan et al., Variation of acoustic speed with temperature in various excised human tissues studied by ultrasound computerized tomography. Ultrason Tiss Char II. 1979; NBS Special Pub 525:227-233.

Rata et al., Endocavitary phased array applicator of therapeutic ultrasound with an integrated opposed-solenoid coil for high resolution MRI-guided thermotherapy: an in vivo study. Proc Intl Soc Mag Reson Med. 2009;17:441.

Ravaut et al., Multiscale imaging of complex structures from multifold wide-aperture seismic data by frequency-domain full-waveform tomography: application to a thrust belt. Geophys J Int. 2004;159:1032-56.

Roy et al., Robust Array Calibration using Time Delays with Application to Ultrasound Tomography. Proc SPIE. Mar. 3, 2011;7968:796806.1-11.

Saad, Iterative methods for sparse linear system, 2nd ed. Philadelphia: SIAM, 2003. http://www.loc.gov/catdir/enhancements/fy0665/2002044644-d.html Abstract only.

Sanchez, On the instrumentation of the omniscope. Thesis submitted to the Department of Electrical Engineering and Computer Science in Partial Fulfillment of the Requirements for the Degree of Master of Engineering in Electrical Engineering and Computer Science at the Massachusetts Institute of Technology. Jun. 2011 102 pages.

Seip et al., Noninvasive estimation of tissue temperature response to heating fields using diagnostic ultrasound. IEEE Trans Biomed Eng. Aug. 1995;42(8):828-39.

Simonetti et al., Frequency Diversity in Breast Ultrasound Tomography. Proc SPIE. 2008;6913:69134E.1-8.

Singh et al., Simulation, Fabrication and Characterization of a Novel Flexible, Conformal Ultrasound Transducer Array. IEEE Ultrason Symp. Oct. 2007;1824-7.

Sirgue et al., Efficient waveform inversion and imaging: A strategy for selecting temporal frequencies. Geophys. 2004;69(1):231-48.

Taner et al., Complex seismic trace analysis. Geophys. Jun. 1979;44(6):1041-63.

Tarantola, Inversion of seismic reflection data in the acoustic approximation. Geophys. Aug. 1984;49(8):1259-66.

Van Dongen et al., A forward model and conjugate gradient inversion technique for low-frequency ultrasonic imaging. J Acoust Soc Am. Oct. 2006;120(4):2086-95.

Van Dongen et al., A full vectorial contrast source inversion scheme for three-dimensional acoustic imaging of both compressibility and density profiles. J Acoust Soc Am. Mar. 2007;121(3):1538-49.

Wong et al., Capacitive Micromachined Ultrasonic Transducers for Therapeutic Ultrasound Applications. IEEE Trans Biomed Eng. Jan. 2010;57(1):114-23.

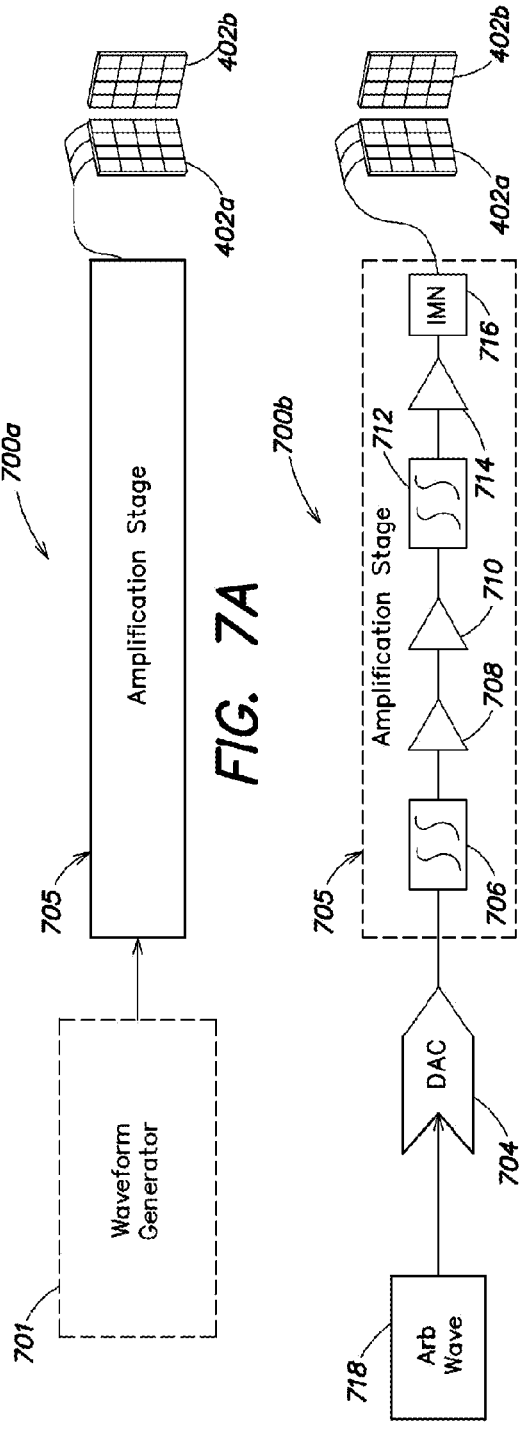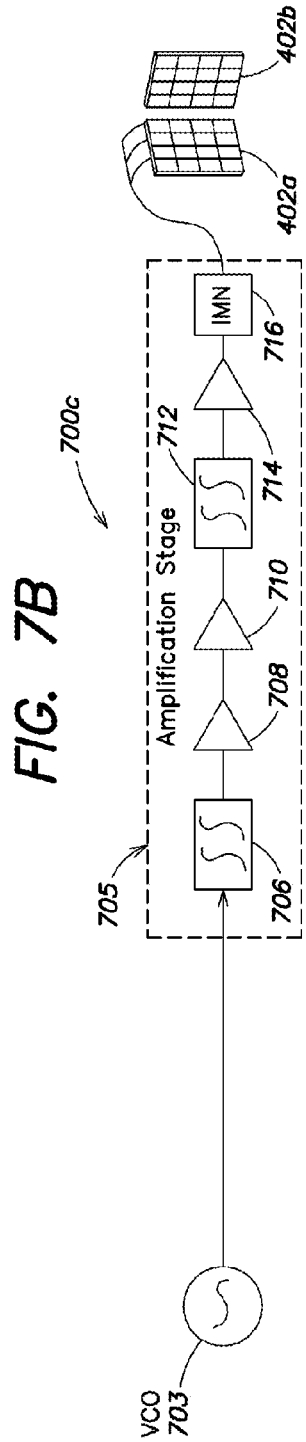
FIG. 7A
FIG. 7B
FIG. 7C

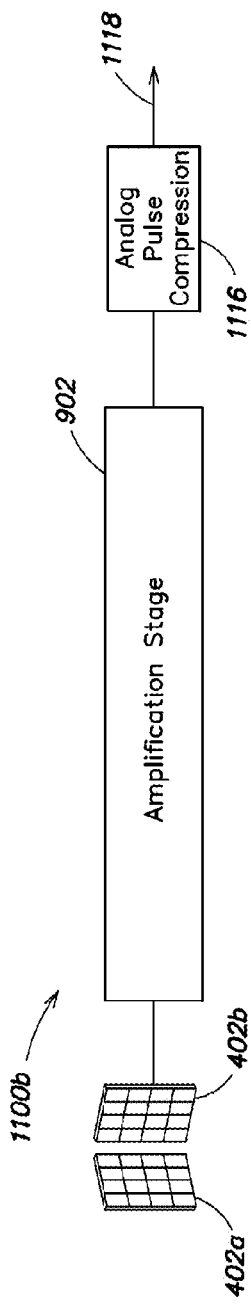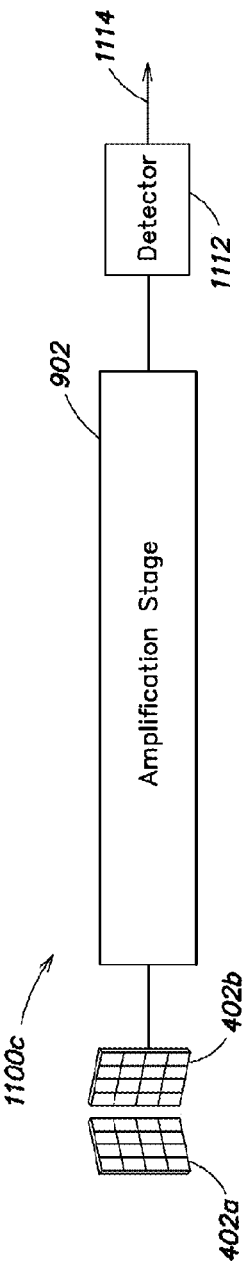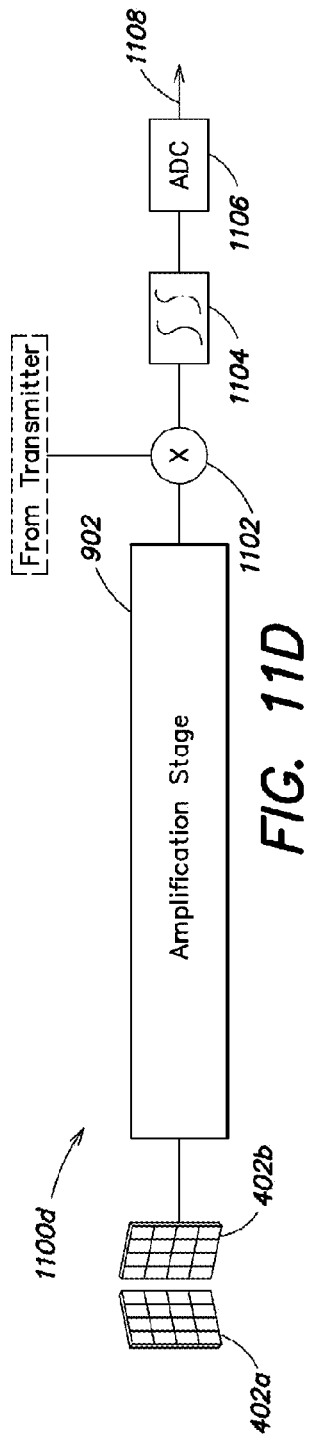

TRANSMISSIVE IMAGING AND RELATED APPARATUS AND METHODS

CROSS-REFERENCE TO RELATED APPLICATION

This Application claims the benefit under 35 U.S.C. §119 (e) of U.S. Provisional Patent Application Ser. No. 61/548, 047, entitled "OPPOSED ARRAY IMAGING AND RELATED APPARATUS AND METHODS" filed on Oct. 17, 2011, which is herein incorporated by reference in its entirety.

BACKGROUND

Imaging technologies are used for multiple purposes. One purpose is to non-invasively diagnose patients. Another purpose is to monitor the performance of medical procedures, such as surgical procedures. Yet another purpose is to monitor post-treatment progress or recovery. Thus, medical imaging technology is used at various stages of medical care.

The value of a given medical imaging technology depends on various factors. Such factors include the quality of the images produced (in terms of resolution or otherwise), the speed at which the images can be produced, the accessibility of the technology to various types of patients and providers, the potential risks and side effects of the technology to the patient, the impact on patient comfort, and the cost of the technology. The ability to produce three dimensional images is also a consideration for some applications.

Different types of medical imaging technologies have different strengths and weaknesses with respect to the above-listed factors. Typically, the speed of a particular imaging system, and therefore its usefulness in various time-constrained environments such as emergency rooms, is compromised as the resolution is increased. For instance, magnetic resonance imaging (MRI) can provide high resolution images of various types of tissue, but is generally very slow, and suffers from other drawbacks including high cost, loud noise, and the use of potentially harmful magnetic field strengths. In contrast, conventional medical ultrasound imaging is implemented with less expensive equipment which produces images more quickly than MRI. Yet, the resolution of conventional ultrasound imaging is typically less than that of MRI, and the type of data collected is different.

Conventional techniques for producing three-dimensional images involve imaging multiple two-dimensional cross-sections, or "slices" of a volume to be imaged, and then stacking the distinct images of the slices together. Such techniques provide a limited interpretation of a three-dimensional object. Moreover, at least some such techniques require the mechanical scanning of the imaging device over the area of interest, which adds substantially to the time required to collect the data for the image. Accordingly, what is needed, for example, is an imaging technology that produces high resolution, volumetric three-dimensional images in a short time.

SUMMARY OF EMBODIMENTS

Provided herein are numerous embodiments of systems, apparatus, and methods for providing imaging and/or high intensity focused ultrasound (HIFU) and/or thermometry functionality. The provision of this functionality, as described herein, may be supported by underlying technology, including in relation to imaging and/or HIFU and/or thermometry element arrays, measurement geometry, front-end processing circuitry and techniques, image reconstruction, and/or a three-dimensional (3D) interface, according to numerous non-limiting embodiments as described in detail throughout the application. Each of the systems, apparatus and methods described herein may include any one or any combination of these or other underlying technological features.

In a first aspect according to some embodiments, imaging and/or HIFU and/or thermometry element arrays may facilitate the provision of imaging and/or HIFU and/or thermometry functionality by the systems, apparatus, and methods described herein. Arrays of imaging elements and/or arrays of HIFU elements (individually or in combination) may utilize various types of imaging and/or HIFU elements in various layouts. Imaging elements may also be used for thermometry. Various materials may be used to form the elements, examples of which are described herein. The elements may assume suitable layouts to provide desired functionality, such as being arranged in arrays, being sparsely arranged, and/or irregularly arranged, as non-limiting examples. Additional features of suitable layouts according to some embodiments are described in detail throughout the application.

In a second aspect according to some embodiments, measurement geometry may facilitate the provision of imaging and/or HIFU and/or thermometry functionality by the systems, apparatus, and methods described herein. Elements configured as imaging elements may be separated in space in some embodiments, for example being arranged in an opposed relationship of sources and sensors. In some embodiments, multiple (e.g., all, or at least two, three, four, five, ten, twenty, fifty, 100, etc.) pairs correlation, described in detail below in connection with non-limiting embodiments, is utilized and is facilitated by the separation of sources from sensors. Alternatively or additionally, the relative and/or absolute positions of elements may be tracked in some embodiments, for example to facilitate processing of data collected by sensors. Various non-limiting embodiments of position tracking are described in detail below.

In a third aspect according to some embodiments, front-end processing circuitry and techniques for imaging and/or HIFU and/or thermometry systems may facilitate the provision of imaging and/or HIFU and/or thermometry functionality by the systems, apparatus, and methods described herein. Suitable circuitry (e.g., analog and/or digital) for generating suitable signals to be transmitted and received by an imaging and/or HIFU and/or thermometry system are provided. In some embodiments, beamforming is utilized in the imaging and/or HIFU and/or thermometry context, and may be facilitated by use of suitable analog and/or digital signal chain circuitry. Various waveforms may be constructed for use in imaging and/or HIFU systems described herein, and they may be processed in any suitable manner. Transmission and/or receipt of transmitted signals may be performed according to various schemes, including time-division multiple access schemes, code-divisional multiple access schemes, and/or frequency-division multiple access schemes, among others. Various parameters of interest (e.g., amplitude, phase, etc.) may be extracted from received signals using various processing. Thus, accurate imaging and/or HIFU may be achieved.

In a fourth aspect according to some embodiments, image reconstruction technology, which may apply primarily in the context of imaging, but which may also facilitate HIFU operation, as described in detail below, in connection with non-limiting embodiments, may facilitate the provision of imaging and/or HIFU and/or thermometry functionality by the systems, apparatus, and methods described herein. In some embodiments, algebraic reconstruction techniques may be utilized. Alternatively or additionally, in some embodiments, physical phenomena impacting collected imaging data, such as dispersion, refraction and/or diffraction, among others, may be accounted for in any suitable manner. Alternatively or additionally, in some embodiments, compressive sensing (sometimes termed compressed sensing) is used in image reconstruction. Images may then be used for desired analysis, such as for classification of imaged objects (e.g., tissue classification), diagnosis (e.g., in the medical context) and/or thermometry, among others.

In a fifth aspect according to some embodiments, a three-dimensional (3D) interface may facilitate the provision of imaging and/or HIFU and/or thermometry functionality by the systems, apparatus, and methods described herein. In some embodiments, 3D images may be generated and displayed to a viewer. The generation and/or display of 3D images may occur rapidly in some embodiments, for example in real time. Alternatively or additionally, in some embodiments, a user (e.g., a doctor) may provide input via a 3D interface, for example by marking points of interest on a 3D image using a suitable device or hand movement. Image analysis may also be performed, in some embodiments, using any suitable techniques. In some embodiments, a user may plan a location or path for performing a medical procedure (e.g., surgery, HIFU, etc.) by viewing and/or interacting with a 3D image in the manners described in detail below, thus allowing for 3D surgical path planning in some embodiments.

According to some embodiments of the present application, an imaging device (e.g., ultrasound imaging device) is provided that includes opposed arrays of radiation sources and sensors (e.g., arrays on completely opposite sides of a subject to be imaged). The imaging device may operate in a transmissive modality in which radiation (e.g., one or more ultrasound signals) transmitted through a subject is detected and used in generating a volumetric image of the subject. The following description focuses primarily on the non-limiting embodiments of apparatus and methods that utilize ultrasound sources and sensors for imaging, characterization, and/or treatment of the subject. In at least some embodiments, one or more of the ultrasound sensors may receive ultrasound signals from multiple ultrasound sources arranged in at least two dimensions. The ability of one or more sensors (coupled with front-end circuitry) to distinguish (or discriminate) between two or more of the signals received from multiple ultrasound sources, provides a large amount of data about the subject. In at least some embodiments, the collection and then the processing of such data is performed rapidly. Thus, in some embodiments, three-dimensional (3D) volumetric images of the subject may be rapidly generated. In at least some embodiments, the volumetric images have high resolution.

According to some embodiments of the present application, opposed arrays of ultrasound sources and sensors may be static, relative to one another, while operating, yet still provide data sufficient for reconstructing volumetric images of a subject. The sensors of the opposed arrays may be configured to receive ultrasound signals originating from multiple sources whose positions define a substantial solid angle with respect to each sensor, such as, for example, a solid angle of at least $\pi/10$ steradians, at least $\pi/5$ steradians, at least $\pi/4$ steradians, at least $\pi/2$ steradians, at least $\pi$ steradians, at least $2\pi$ steradians, between approximately $\pi/10$ and $2\pi$ steradians, between approximately $\pi/5$ and $\pi$ steradians, or any other suitable non-zero solid angle. For example, such a configuration is described with respect to non-zero solid angle 420 in FIG. 4, below. The absence of any requirement to move the arrays during operation may facilitate rapid volumetric imaging. In some embodiments, the opposed arrays may be individually and/or relatively movable.

According to some embodiments of the present application, a system and method are provided for rapid collection of data about a volume of interest (e.g., a volume containing a subject). The system and method may employ transmissive ultrasound techniques, for example, in which ultrasound sources positioned on one side of the volume are configured to transmit ultrasound signals through the volume to ultrasound sensors on an opposed side of the volume. The signals received by the ultrasound sensors may be discriminated to determine from which ultrasound source the signals were emitted. The received signals may be analyzed to determine signal characteristics such as amplitude, frequency, phase, and/or other characteristics. Such characteristics may represent or otherwise be indicative of the attenuation of the signals while passing through the volume, a phase shift of the signals while passing through the volume, and/or time-of-flight (TOF) of the signals while passing through the volume. From such information, properties of the volume being imaged (or a subject therein) may be determined, such as density, index of refraction, temperature, and/or speed of sound, as non-limiting examples.

According to some embodiments of the present application, methods and systems for performing rapid (e.g., real time) volumetric ultrasound imaging of a subject are provided. Data about a subject, such as density, index of refraction, temperature, and/or speed of sound, may be collected as described above using transmissive ultrasound techniques or any other suitable techniques. One or more volumetric images of such properties may be generated. In some embodiments, the system may be configured to produce multiple volumetric images of a subject per second, for example up to six images or more per second. In some embodiments, collection of data and/or reconstruction of volumetric images may be performed at a rate up to approximately six frames/second or more (e.g., between any of one, two, three, four, five, six, seven, eight, nine, or ten frames per second on one hand, and any of fifteen, twenty, twenty-five, thirty, forty, fifty, sixty, seventy, eighty, ninety, and 100 frames per second, on the other hand, and ranges in between), where a frame represents a grouping (or set) of data values, for example sufficient to form a single image. In some embodiments, a frame may include a data value corresponding to each radiation source of a system. In other embodiments, a frame may include a data value for each radiation source of a subset of radiation sources of a system.

According to some embodiments of the present application, measurements obtained by an ultrasound imaging device may be used to construct a volumetric image of a subject. A volumetric image may be organized in three-dimensional sub-blocks called "voxels"—analogous to pixels in a two-dimensional image—with each voxel associated with one or more values of a property (e.g., index of refraction, density, temperature, speed of sound, etc.) of the subject at a location in three-dimensional space.

Any technique or group of techniques used to construct a volumetric image of a subject from measurements of the subject, obtained by an imaging device (e.g., an ultrasound imaging device or any other suitable imaging device), is herein referred to as an image reconstruction process. In one embodiment, a compressive sensing (CS) image reconstruction process may be used to calculate a volumetric image of the subject from measurements obtained by an imaging device (e.g., an ultrasound imaging device of any of the types described herein). A CS image reconstruction process may calculate a volumetric image of the subject based, at least in part, on a sparsity basis in which the volumetric image may be sparse. It should be appreciated that sparsity of a volumetric image is not the same as, and is independent from, sparsity of elements in an array. A volumetric image may be sparse in a sparsity basis regardless of whether or not elements in an imaging array used to obtain the volumetric image are sparse. A CS image reconstruction process may take into account the geometry of any sources and sensors of the imaging device to calculate a volumetric image of the subject from measurements obtained by the imaging device. CS image reconstruction processes and other image reconstruction processes that may be used in accordance with embodiments of the present application are described in greater detail below.

According to an aspect of the present application, movable supports are described including arrangements of ultrasound elements configured as sources and sensors. The ultrasound elements may cooperatively operate to image a subject in a transmissive ultrasound modality. For example, all, substantially all, most, or at least a portion of the ultrasound radiation (e.g., at least 95%, 90%, 80%, 75%, 70%, 60%, 50%, or 40%, etc.) detected and utilized by the sensors may be transmissive radiation. In some embodiments, scattered radiation (e.g., back-scattered and/or forward-scattered radiation) may also be detected and utilized at least in part. The movable supports may be handheld, and may take the form of paddles in some non-limiting embodiments. Portable imaging devices may be realized, allowing flexibility in terms of treatment location and angle of imaging of a subject, for example by allowing for easy repositioning of arrangements of ultrasound elements during operation. The cooperative operation of the arrangements of ultrasound elements may be facilitated by detection of the orientation and/or positioning (absolute or relative) of the arrangements.

According to some embodiments of the present application, a sparse arrangement of ultrasound sources and/or sensors is provided. The ultrasound sources and/or sensors may be sparsely spaced with respect to each other compared to an operation wavelength (e.g., a center wavelength) of the sources and/or sensors. The sparse spacing of the ultrasound sources and/or sensors may reduce the number of sources and/or sensors required to achieve a particular imaging resolution of interest. The sparse spacing of ultrasound sources and/or sensors may allow for the arrangement to include multiple types of elements.

According to some embodiments of the present application, an irregular arrangement of ultrasound sources and/or sensors is provided. The arrangement may be irregular in that at least some of the sources and/or sensors may not be regularly spaced with respect to neighboring sources and/or sensors. The irregular spacing may relax design tolerances of ultrasound arrangements and allow for flexibility in operation of ultrasound devices incorporating such arrangements, such as ultrasound imaging devices. The irregular spacing of ultrasound sources and/or sensors may lead to fewer artifacts in images calculated from measurements obtained by the ultrasound sensors. The irregular spacing may lead to fewer artifacts that ordinarily result from symmetry in regular sensor arrangements. In at least some embodiments, the ultrasound elements may be randomly arranged.

According to some embodiments of the present application, an arrangement of ultrasound sources and/or sensors is provided that does not fully enclose a subject, but which is still suitable for performing volumetric imaging of the subject without any need to move the arrangement. In at least some such embodiments, the arrangement may be substantially planar, though other configurations are also possible.

According to some embodiments of the present application, apparatus, and methods for performing high intensity focused ultrasound (HIFU) are provided. The apparatus may include ultrasound elements configured to operate as HIFU elements arranged among ultrasound elements configured to operate as ultrasound imaging elements (e.g., imaging sources and/or sensors). In at least some embodiments, an apparatus is configured to operate as a multi-mode device (e.g., a dual-mode device) for performing HIFU and ultrasound imaging. In at least some embodiments, the apparatus may include HIFU elements interleaved among imaging elements, interspersed among imaging elements, between imaging elements, and/or arranged in another configuration.

According to some embodiments of the present application, apparatus and methods for performing thermometry using opposed pairs of ultrasound sources and sensors is provided. The opposed pairs may operate in combination in a transmissive ultrasound modality. Data detected from such transmissive ultrasound operation may provide an indication of temperature. For example, data detected from transmissive ultrasound operation may be indicative of changes in speed of sound through a subject, which in turn may be indicative of changes in temperature of the subject. Speed of sound and changes in speed of sound through a subject may be obtained from time-of-flight (TOF) data collected by a source-sensor pairs, attenuation data collected by source-sensor pairs, and/or any suitable combination thereof. In some embodiments, raw waveforms collected by ultrasound sensors operating in combination with ultrasound sources in a transmissive modality may be analyzed for changes (e.g., changes in amplitude, phase, TOF, attenuation, etc.). Such changes may be indicative of changes in temperature of a subject. Measurement of temperature and temperature changes may be used alone or in combination with other operations, such as imaging and/or HIFU.

Conventional techniques for producing three-dimensional images involve imaging multiple two-dimensional cross-sections, or "slices" of a volume to be imaged, and then stacking the distinct images of the slices together. Such techniques provide a limited interpretation of a three-dimensional object because the collected data represents a limited number of paths through a subject, the paths being confined to a given slice.

Thus, an aspect of the present application provides an apparatus, comprising a plurality of radiation sources comprising a first radiation source, a second radiation source, and a third radiation source. The apparatus further comprises a first radiation sensor and a second radiation sensor, and processing circuitry coupled to the first radiation sensor and the second radiation sensor and configured to receive and discriminate between, for each of the first and second radiation sensors, respective source signals emitted by the first, second, and third radiation sources. The first radiation source, the second radiation source, and the first radiation sensor may lie in a first plane, and the second radiation source, the third radiation source, and the second radiation sensor may lie in a second plane different than the first plane.

Another aspect of the present application provides an apparatus comprising a plurality of radiation sources comprising a first radiation source, a second radiation source, and a third radiation source. The apparatus further comprises a first radiation sensor and a second radiation sensor, and processing circuitry coupled to the first radiation sensor and the second radiation sensor and configured to receive and discriminate between, for each of the first and second radiation sensors, respective source signals emitted by the first, the second, and the third radiation sources. Respective center points of the first radiation source, the second radiation source, the third radiation source, and the first radiation sensor may define a first non-zero solid angle having its vertex positioned at the center point of the first radiation sensor. The respective center points of the first radiation source, the second radiation source, and the third radiation source, together with a center point of the second radiation sensor define a second non-zero solid angle having its vertex positioned at the center point of the second radiation sensor.

According to an aspect of the present application, an apparatus is provided comprising a plurality of radiation sources arranged nonlinearly in a first plane or three-dimensional space and configured to emit respective source signals through a volume to be characterized. The apparatus may comprise a plurality of radiation sensors arranged nonlinearly in a second plane or three-dimensional space and configured to oppose the first plane or three-dimensional space, and the volume, wherein each of the plurality of radiation sensors is configured to sense the source signals emitted by each of the plurality of radiation sources after the source signals pass through the volume. The apparatus may comprise processing circuitry coupled to the plurality of radiation sensors and configured to receive and discriminate between the source signals sensed by the plurality of radiation sensors. The received signals may be indicative of at least one characteristic of the volume.

According to an aspect of the present application, an apparatus comprises a plurality of radiation sources configured to emit respective source radiation signals incident upon a volume to be characterized, the volume spanning orthogonal X, Y, and Z axes. The plurality of radiation sources may occupy multiple locations in the X direction and multiple locations in the Y direction. The apparatus may further comprise a plurality of radiation sensors separated from the plurality of radiation sources along the Z direction and configured to sense the respective source radiation signals emitted by the plurality of radiation sources, the plurality of radiation sensors occupying multiple locations in the X direction and multiple locations in the Y direction. The apparatus may further comprise processing circuitry coupled to the plurality of radiation sensors and configured to receive and discriminate between, for each of the plurality of radiation sensors, the respective source signals of the plurality of radiation sources.

According to an aspect of the present application, an apparatus is provided comprising a plurality of radiation sources configured to emit respective source radiation signals directed to be incident upon a subject such that the respective source radiation signals pass through the subject along paths bounding a volume. The apparatus may comprise a radiation sensor configured to receive the respective source radiation signals after they pass through the subject. The apparatus may further comprise processing circuitry coupled to the radiation sensor and configured to discriminate between the respective source radiation signals.

According to an aspect of the present application, an apparatus is provided comprising a plurality of radiation sources configured to emit respective source radiation signals directed to be incident across a surface area of a subject. The apparatus may comprise first and second radiation sensors each configured to sense the respective source radiation signals, and may also comprise processing circuitry coupled to the first and second radiation sensors and configured to receive and discriminate between, for each of the first and second radiation sensors, the respective source radiation signals emitted by the plurality of radiation sources.

According to an aspect of the present application, an apparatus is provided comprising three radiation sources arranged in a multi-dimensional, non-linear arrangement and configured to produce respective source signals. The apparatus may further comprise a plurality of radiation sensors, and processing circuitry coupled to the plurality of radiation sensors and configured to receive and discriminate between, for at least one radiation sensor of the plurality of radiation sensors, the respective source signals produced by the three radiation sources.

According to an aspect of the present application an apparatus is provided comprising multiple arrays of ultrasound sources configured to emit respective source signals and an array of ultrasound sensors configured to sense the respective source signals. The apparatus may further comprise processing circuitry coupled to the array of ultrasound sensors and configured to receive and discriminate between, for at least one ultrasound sensor of the array of ultrasound sensors, the respective source signals of at least one ultrasound source from each of at least two arrays of the multiple arrays of ultrasound sources.

According to an aspect of the present application, an apparatus is provided comprising a plurality of N×M radiation sources forming a two-dimensional or three-dimensional radiation source arrangement and configured to produce a first plurality of N×M respective source signals, wherein N is greater than or equal to M. The apparatus may further comprise a plurality of X×Y radiation sensors forming a two-dimensional or three-dimensional radiation sensor arrangement, and processing circuitry coupled to the plurality of radiation sensors and configured to discriminate between greater than (X×Y×N) received signals from the N×M respective source signals.

Conventional ultrasound imaging technologies also suffer from the drawback that the positions of ultrasound sources and sensors have little freedom of motion relative to each other. Conventional ultrasound devices therefore typically exhibit limited flexibility in movement and limited ability to be adjusted during operation.

According to an aspect of the present application, an apparatus is provided comprising a plurality of ultrasound elements in a fixed relationship with respect to each other and configured as ultrasound imaging elements, and a detector configured to dynamically detect an orientation and/or position of the plurality of ultrasound elements.

Aspects of the present application also relate to the relative positioning of ultrasound elements of an arrangement. Conventional ultrasound devices utilize ultrasound elements that are spaced at regular intervals with respect to each other, for example along a line. Such regular spacing can create undesirable artifacts in images produced using such devices. Also, such regular spacing represents a design constraint, the deviation from which is not generally tolerated, as device performance can suffer. Furthermore, the spacing of the elements is conventionally sufficiently close to allow for sensing of at least sample point per wavelength of the ultrasound radiation, which places constraints on the spacing and number of elements required to implement an ultrasound arrangement.

According to an aspect of the present application, an apparatus is provided, comprising a plurality of ultrasound sensors forming a two-dimensional or three-dimensional ultrasound sensor arrangement, and processing circuitry coupled to the plurality of ultrasound sensors and configured to process signals from the plurality of ultrasound sensors to produce ultrasound imaging data indicative of a subject imaged at least in part by the plurality of ultrasound sensors At least some ultrasound sensors of the plurality of ultrasound sensors are not spaced at regular intervals with respect to neighboring ultrasound sensors, and may be said to create an irregular arrangement of ultrasound sensors (or elements more generally).

According to an aspect of the present application, an apparatus is provided comprising a plurality of radiation sensors forming a two-dimensional or three-dimensional sensor arrangement and configured to receive radiation of wavelength λ, emitted by one or more radiation sources. The spacing between a first radiation sensor of the plurality of radiation sensors and its nearest neighboring radiation sensor of the plurality of radiation sensors is greater than λ/2 in some embodiments, greater than λ, in some embodiments, greater than 2λ in some embodiments, and greater than 3λ, in some embodiments. Such arrangements may be termed sparse arrangements.

Aspects of the present application are also directed to three-dimensional image reconstruction techniques, for example for use in generating 3D medical images. Conventional solutions to reconstruction of 3D images either require stringent geometrical constraints of the imaging system or utilize 2D wave propagation codes which result in less faithful reconstructions (since use of 3D wave propagation codes was conventionally impractical).

Accordingly, an aspect of the present application provides a method comprising accessing a plurality of measurements of a subject, the plurality of measurements resulting at least in part from the detection of ultrasound radiation by an ultrasound imaging device operating in a transmissive modality, and generating, using at least one processor, at least one volumetric image of the subject from the plurality of measurements by using a compressive sensing image reconstruction process.

According to an aspect of the present application, a method is provided comprising accessing at least one volumetric image of a subject generated using a plurality of measurements of the subject, the plurality of measurements resulting at least in part from the detection of ultrasound radiation by an ultrasound imaging device operating in a transmissive modality. The method further comprises applying stereoscopic conversion to the at least one volumetric image to obtain a first stereoscopic image and a second stereoscopic image, and displaying three-dimensionally, via a three-dimensional display, the first stereoscopic image and the second stereoscopic image to a viewer.

According to an aspect of the present application, a method is provided comprising accessing at least one volumetric image of a subject calculated using a plurality of measurements of the subject, the plurality of measurements resulting at least in part from the detection of radiation by an imaging device. The method further comprises identifying a point of view within the subject, wherein identifying the point of view comprises identifying a location within the subject, and displaying the at least one volumetric image to a viewer from the identified point of view.

According to an aspect of the present application, a method is provided comprising accessing a plurality of measurements of a subject, the plurality of measurements resulting at least in part from the detection of ultrasound radiation by an ultrasound imaging device, the ultrasound imaging device comprising a plurality of ultrasound sources including a first ultrasound source and a plurality of ultrasound sensors including a first ultrasound sensor, and calculating, using at least one processor, a first image of the subject from the plurality of measurements by using first path length information for a path between the first ultrasound source and the first ultrasound sensor. The method may further comprise calculating, using the at least one processor, second path length information at least in part by computing refractive paths using the first image. The method may further comprise calculating, using the at least one processor, a second image of the subject from the plurality of measurements by using the second path length information.

Aspects of the present application relate to application of high intensity focused ultrasound (HIFU) to a subject. HIFU may be used for various purposes, such as cauterization or tissue ablation, among others. It may be desirable to view the location at which HIFU is applied, for example to assess the progress or effectiveness of the HIFU. HIFU probes and imaging technologies were conventionally separate.

According to an aspect of the present application, an apparatus is provided comprising a support, a first plurality of ultrasound elements configured as ultrasound imaging elements, and a second plurality of ultrasound elements configured as high intensity focused ultrasound (HIFU) elements. The first plurality and second plurality of ultrasound elements may be physically coupled to the first support, and at least some elements of the first plurality of ultrasound elements are arranged among at least some elements of the second plurality of ultrasound elements.

According to an aspect of the present application a system is provided comprising a first support, a second support, a first plurality of ultrasound elements configured as high intensity focused ultrasound (HIFU) elements and physically coupled to the first support and configured as a first source of HIFU, and a second plurality of ultrasound elements configured as ultrasound imaging elements and coupled to the first support and distinct from the first plurality of ultrasound elements. The apparatus may further comprise a third plurality of ultrasound elements configured as HIFU elements and physically coupled to the second support and configured as a second source of HIFU, and a fourth plurality of ultrasound elements configured as ultrasound imaging elements and coupled to the second support and distinct from the third plurality of ultrasound elements. The second plurality of ultrasound elements and the fourth plurality of ultrasound elements are configured to operate in combination in a transmissive ultrasound imaging modality.

According to an aspect of the present application, an apparatus is provided comprising a substrate, a first plurality of ultrasound elements configured as ultrasound imaging elements coupled to the substrate, and a second plurality of ultrasound elements configured as high intensity focused ultrasound (HIFU) elements coupled to the substrate.

An aspect of the present application provides a method comprising displaying a volumetric image of a subject to a user three dimensionally via a three-dimensional display, obtaining user input identifying at least one target point in the volumetric image corresponding to at least one location in the subject, and applying high intensity focused ultrasound (HIFU) energy to the at least one location in the subject.

Conventional HIFU also suffered from the drawback of insufficient control over the location which HIFU was applied, particularly when a patient moved. Misapplication of HIFU to a patient can be dangerous in addition to being inefficient.

According to an aspect of the present application, a method is provided comprising applying high intensity focused ultrasound (HIFU) energy to a subject, identifying, based at least in part on an image of the subject, a first target point in the subject to which the HIFU energy was applied, and automatically determining whether to continue applying the HIFU energy to the first target point at least in part by comparing the first target point to a planned target point. The method may further comprise continuing to apply the HIFU energy to the first target point based at least in part on the comparison.

According to such an aspect, accurate detection and tracking of the location at which HIFU is applied relative to a desired HIFU location may be provided. The results of such detection and tracking may be used to control to which locations HIFU is applied. Thus, the accuracy of the HIFU application may be improved, and effectiveness and safety of the HIFU process may be increased.

Aspects of the present application relate to processing of signals received by large numbers of receiving elements, for instance in the context of an ultrasound imaging system. Conventional signal processing techniques of large amounts of data can be time-consuming, so that such techniques may substantially limit the ability to rapidly create 3D images (e.g., 3D ultrasound images) based on the received signals.

According to an aspect of the present application, an apparatus is provided comprising a first ultrasound element configured as an ultrasound source, and transmit circuitry coupled to the ultrasound source and configured to provide to the ultrasound source a transmission signal to be emitted by the ultrasound source. The apparatus may further comprise a second ultrasound element configured as an ultrasound sensor and processing circuitry coupled to the ultrasound sensor and configured to process a signal emitted by the ultrasound source and received by the ultrasound sensor. The processing circuitry may be configured to combine the signal received by the ultrasound sensor with a reference signal to produce a combined signal.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIGS. 7A-7C illustrate examples of signal transmitters as may be implemented in a system in accordance with one or more embodiments of the present application.

FIGS. 11A-11D illustrate alternative implementations of the signal receiver of FIG. 9, according to various non-limiting embodiments.

DETAILED DESCRIPTION OF EMBODIMENTS

Figure 1A:
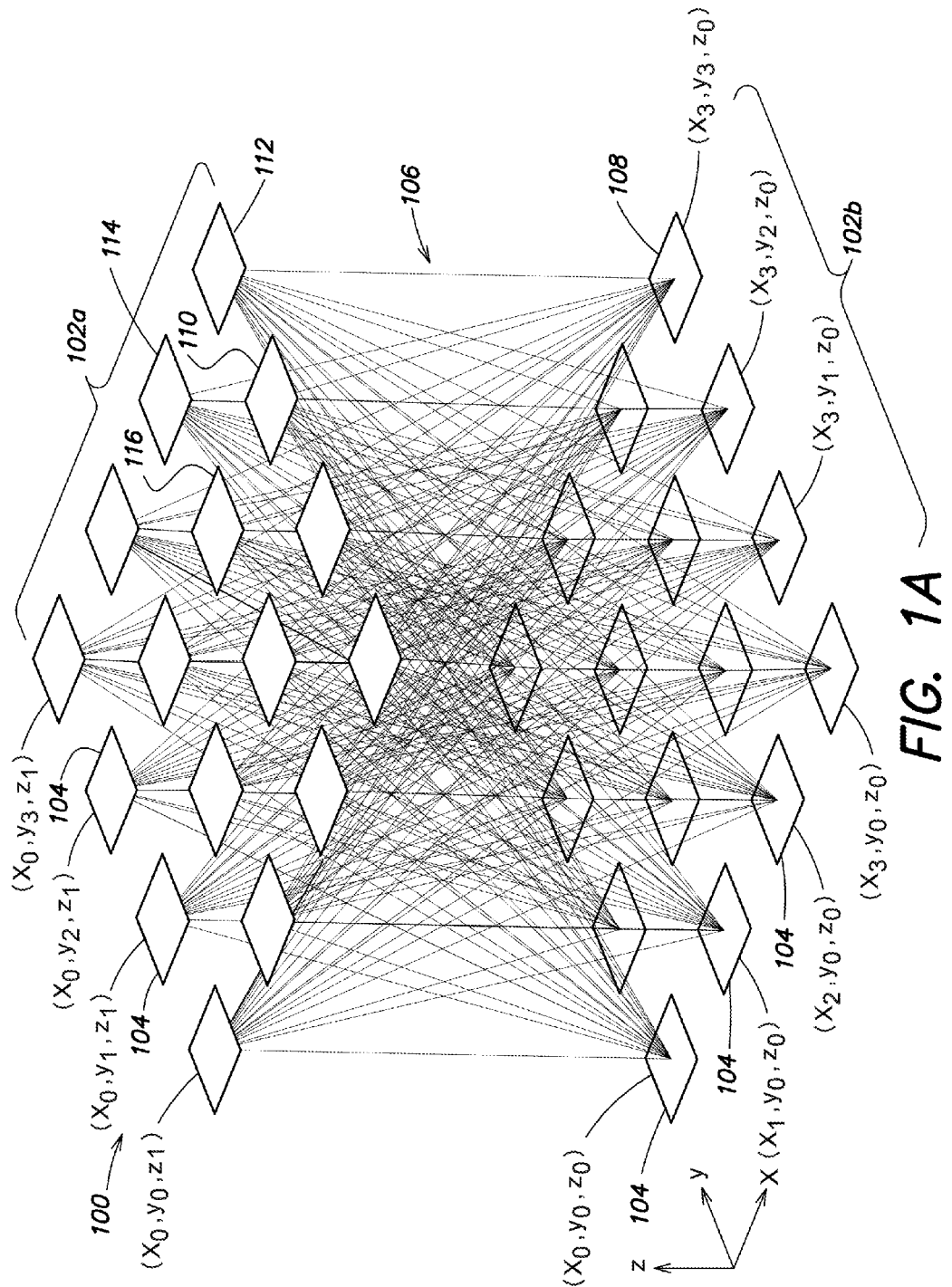
FIG. 1A illustrates opposed arrays of radiation (e.g., ultrasound) sources and sensors, according to a non-limiting embodiment.

Various embodiments described herein relate to imaging technology, both medical as well as that used for non-medical purposes. Imaging technologies generally require detection of radiation, which may take various forms. Various embodiments described herein apply irrespective of the type of radiation utilized. For purposes of illustration, the following description focuses on ultrasound radiation, and therefore many of the systems and methods disclosed are described as utilizing ultrasound radiation and ultrasound components. However, unless clearly indicated to the contrary, any reference to ultrasound is a non-limiting example and should be interpreted to also contemplate other types of radiation more generally. As an example, reference to an "ultrasound element" should be understood to be a non-limiting example, with the more general embodiment of "radiation element" also being contemplated herein.

Non-limiting examples of radiation to which embodiments of the present application may apply, in addition to ultrasound, include electromagnetic radiation as well as acoustic radiation other than ultrasound radiation (e.g., subsonic radiation). Examples include any transfer of photons, and electromagnetic radiation (gamma-rays through x-rays, ultraviolet, visible, infrared (IR), THz, and microwave, as non-limiting examples). Non-limiting examples of imaging types to which embodiments of the present application may apply (in addition to ultrasound, described in detail below) include electrical impedance tomography, proton radiography, positron emission tomography (PET), Single-Photon Emission computed tomography (SPECT), and fluorescence imaging/multi-photon imaging.

As used herein, unless indicated otherwise by the context, the term "approximately" is generally understood to mean, for example, within 15%, within 10%, or within 5%, although one of skill would appreciate there is latitude in such numbers depending on the context. As used herein, unless indicated otherwise by the context, the term "substantially" is understood to mean, for example, within 5%, within 3%, within 2%, or exactly, although one of skill would appreciate there is latitude in such numbers depending on the context.

As used herein, the phrase "three-dimensional imaging" (and words of similar import) encompasses volumetric imaging as well as slice-based imaging (i.e., the stacking of multiple two-dimensional images to form a three-dimensional image). Volumetric imaging, to be distinguished from slice-based imaging, may be described, in some embodiments, as imaging in which sensors receive signals transmitted from sources arranged in at least two dimensions, imaging in which sensors receive signals transmitted by sources defining a non-zero solid angle, non-planar imaging, non-tomographic imaging, or imaging in which a sensor receives signals transmitted by sources arranged in a same plane as the sensor in addition to signals transmitted by sources not arranged in the same plane as the sensor. Examples are described further below. In some embodiments, two or more of the received signals may be distinguished (or discriminated) from each other, such that discrete measurements may be provided corresponding to particular source from which a sensor receives a signal. As will be described further below, discrimination between signals in various embodiments may be accomplished using code division multiple access (CDMA) modes, time division multiple access (TDMA) modes, frequency division multiplexing (FDM) modes, as well as combinations of any of two or more of these modes of operation.

It should be appreciated that various types of subjects may be analyzed and imaged according to the aspects described herein. The subjects may be human (e.g., medical patients), though not all embodiments are limited in this respect. For example, one or more aspects described herein may be used to analyze and image animals, bags, packages, structures, or other subjects of interest. As another example, one or more aspects described herein may be used to analyze and image small animals. Thus, the aspects described herein are not limited to the type of subject being analyzed and imaged.

The aspects and embodiments described above, as well as additional aspects and embodiments, are described further below. These aspects and/or embodiments may be used individually, all together, or in any combination of two or more, as the application is not limited in this respect.

According to some embodiments of the present application, an imaging device (e.g., ultrasound imaging device) having opposed arrays of ultrasound sources and sensors is provided. FIG. 1A illustrates a non-limiting example. In some embodiments, the apparatus 100 includes a first array 102a of ultrasound elements 104 and a second array 102b of ultrasound elements 104. In the non-limiting example shown, each of the first and second arrays 102a-102b includes sixteen ultrasound elements 104. However, other numbers of elements may be implemented, including more or fewer elements. For example, one or both of the arrays 102a and 102b may have approximately 20 elements per side (e.g., a 20×20 array), approximately 32 elements per side (e.g., a 32×32 array), approximately 100 ultrasound elements per side (e.g., a 100×100 array), approximately 200 ultrasound elements per side (e.g., a 200×200 array), approximately 500 ultrasound elements per side, such as a 512×512 array, approximately one thousand ultrasound elements per side, such as a 1024×1024 array, any intermediate number of ultrasound elements between ten and 1024, or any other suitable number of elements.

Moreover, it should be appreciated that the arrays 102a and 102b need not have sides of equal numbers of ultrasound elements. For example, the array 102a and/or 102b may be an N×M array, where N differs from M. Also, the array 102a need not be the same size or configuration as array 102b. Further alternatives will be described further below.

The arrays may occupy any suitable size. According to a non-limiting embodiment, array 102a may be approximately 1 mm×1 mm, approximately 1 cm×1 cm, less than approximately 15 cm×15 cm, less than approximately 100 cm×100 cm, or have any other suitable size. The size may be determined, to at least some extent, by subjects of interest to be investigated using the arrays. For example, if the apparatus 100 is to be used to examine a human breast, the arrays 102a and 102b may be sized accordingly to provide suitable examination. Also, the spacing between the arrays 102a and 102b may be any suitable spacing. For example, the arrays 102a and 102b may be separated (in the z-direction in FIG. 1A) by a millimeter, by a few millimeters, up to a few inches, up to a foot, up to several feet, or more, as non-limiting examples. According to a non-limiting embodiment, each of arrays 102a and 102b may be approximately 1 mm×1 mm arrays, and may be separated in the z-direction by approximately 1 mm, such that the volume defined between the arrays is approximately 1 cubic mm.

The ultrasound elements of the array 102a and/or 102b may be configured to operate at any suitable frequencies, which in some embodiments may depend on the size(s) of the arrays. For example, the elements of one or both of the arrays may be configured to operate at a frequency in the range of 100 KHz-10 MHz (e.g., 250 KHz, 500 KHz, 1 MHz, 2.5 MHz, 5 MHz, etc.) to image a volume of approximately 10 cubic cm. As another example, the elements of one or both of the arrays may be configured to operate at approximately 40 MHz to image a volume of approximately 1 cubic mm. In some embodiments, the elements of one or both of the arrays may be configured to operate at one or more frequencies between approximately 5 MHz and approximately 50 MHz. Other frequencies of operation are also possible.

Furthermore, not all elements of an array need operate at the same frequencies. For example, one or more elements of arrays 102a may be configured to operate at a first frequency while one or more different elements of the array 102a may be configured to operate at a second frequency. The first and second frequencies may take any suitable values and may have any suitable relative values.

The arrays 102a and 102b of the apparatus 100 are opposed arrays in that the two arrays are configured in an opposing relationship with respect to each other. In the non-limiting example of FIG. 1A, the two opposed arrays have an equal number of elements as each other and may be described as having corresponding pairs of elements (i.e., each element 104 of the array 102a may be described as having a corresponding element 104 of the array 102b), but not all embodiments of opposed arrays according to the present application require the arrays to have equal numbers of ultrasound elements.

Furthermore, it should be appreciated that the relative orientations of the arrays 102a and 102b shown in FIG. 1A may be varied. FIG. 1A shows an embodiment in which the arrays 102a and 102b may be substantially parallel to each other. However, alternatives are possible. For example, the array 102a may be oriented at any suitable angle with respect to array 102b, such as between 0 degrees (parallel) and 90 degrees.

As illustrated in FIG. 1A, the ultrasound elements of each of the arrays 102a and 102b may be arranged in two dimensions. For example, the array 102a includes ultrasound elements 104 arranged in both the x and y directions. Similarly, the array 102b includes ultrasound elements 104 arranged in both the x and y directions. The arrays 102a and 102b define therebetween a volume having a third dimension, i.e., in the z-direction in the non-limiting example shown, in addition to the x and y dimensions. As will be described further below, the arrays 102a and 102b may be used to analyze a subject located within the volume. As shown in FIG. 1A, the arrangement of elements occupies multiple x positions and multiple y positions (e.g., a first element has coordinates $x_0, y_0, z_0$, a second element has coordinates $x_1, y_0, z_0$, a third element has coordinates $x_2, y_0, z_0$, a fourth element has coordinates $x_3, y_0, z_0$, a fifth element has coordinates $x_0, y_1, z_0$, a sixth element has coordinates $x_1, y_1, z_0$, and so on). In the non-limiting embodiment of FIG. 1A, the elements of each array have the same z-coordinate as each other, namely $z_0$ for the elements of array 102b and $z_1$ for the elements of array 102a. However, in some embodiments, including examples described below, the elements of an array (e.g., of array 102a) may have different z-coordinates.

As should be appreciated from FIG. 1A, an arrangement of elements in two dimensions (which may also be referred to herein as a "two-dimensional arrangement," or a "multi-dimensional arrangement" (for arrangements in two or more dimensions), or a "two-dimensional layout" or by other similar phraseology) as used herein differs from a one-dimensional arrangement of two-dimensional elements. More generally, the dimensionality of an arrangement as used herein is independent of the dimensionality of the elements included in the arrangement. The dimensionality of an arrangement as used herein relates to the dimensions spanned by the relative positioning of the elements of the arrangement, not to the dimensions of the individual elements themselves. As but a single example, three elements arranged in a straight line form a one-dimensional arrangement, irrespective of the dimensionality of the three elements themselves. By contrast, three elements forming vertices of a triangle constitute a two-dimensional arrangement. Numerous examples of multi-dimensional arrangements are described and illustrated throughout the present application.

Also, as will be described further below, the two-dimensional arrangements of the arrays 102a and 102b are non-limiting. In some embodiments, one or both of arrays 102a and 102b may employ arrangements in three dimensions. Thus, FIG. 1A represents a non-limiting example only.

According to one embodiment, the ultrasound elements 104 of the array 102a may be configured as ultrasound sources while the ultrasound elements 104 of the array 102b may be configured as ultrasound sensors, or vice versa. For ease of explanation, the following description assumes that the ultrasound elements 104 of array 102a are configured as ultrasound sources while the ultrasound elements of the array 102b are configured as ultrasound sensors. However, as described, not all embodiments are limited in this respect. For example, in some embodiments, one or both of arrays 102a and 102b may include both sources and sensors 104. Furthermore, as will be described below, one or more of the ultrasound elements 104 may be configured to operate as both sources and sensors, for example in a time-varying manner.

In some embodiments, ultrasound elements 104 configured as ultrasound sources may be of the same type as ultrasound elements 104 configured as ultrasound sensors. The difference in configuration may relate to the manner in which the ultrasound elements are electrically configured (e.g., the circuitry to which the ultrasound elements are electrically coupled). Alternatively, in some embodiments, ultrasound elements 104 configured as ultrasound sources may be of a different type than ultrasound elements 104 configured as ultrasound sensors.

The opposed arrays 102a-102b of apparatus 100 may be configured to operate in a transmissive ultrasound mode. Whereas conventional ultrasound imaging devices operate primarily by detection of ultrasound signals reflected back toward the source of the signals, the apparatus 100 may be operated such that the ultrasound elements 104 of array 102a are configured to transmit ultrasound signals toward the ultrasound elements 104 of array 102b, which receive (e.g., sense or detect) the transmitted ultrasound signals sourced (e.g., radiated or emitted) by the ultrasound elements 104 of the array 102a. In this manner, detection of ultrasound signals transmitted through a subject of interest (not illustrated in FIG. 1A) may be performed. For instance, assuming that the subject is a patient, the array 102a may be disposed on the patient's front side while the array 102b is disposed on the patient's back side. The ultrasound elements 104 of array 102a may transmit ultrasound signals which pass through the patient to the ultrasound elements 104 of the array 102b. Alternatively or additionally, in some embodiments scattered (e.g., back-scattered and/or forward-scattered) ultrasound radiation may be utilized (e.g., when one or both of arrays 102a and/or 102(b) include both ultrasound sources and sensors).

FIG. 1A illustrates the general paths of ultrasound rays between the ultrasound elements 104 of array 102a and ultrasound elements 104 of array 102b. As illustrated, a distinct ray may be drawn between each pair of ultrasound elements 104 that includes an ultrasound element from the first array 102a and an ultrasound element from the second array 102b.

Thus, it should be appreciated that one or more (e.g., all of) ultrasound elements 104 of a first of the arrays may each communicate with one or multiple ultrasound elements 104 (e.g., all of) of the opposing array. Moreover, one or more ultrasound elements of one of the arrays may each communicate with one or multiple ultrasound elements of the opposing array arranged in at least two dimensions. A non-limiting example is described with respect to ultrasound elements 108, 110, 112, 114, and 116. To facilitate understanding, these ultrasound elements (108-116) are assigned individual reference numbers even though they are all ultrasound elements 104.

As illustrated, the ultrasound element 108 may be an element of array 102b, and may, for purposes of explanation, be configured as a sensor for receiving ultrasound signals. As shown, the ultrasound element 108 may be configured to receive ultrasound signals from each of ultrasound elements 110, 112, 114, and 116 (e.g., among others) of array 102a, as illustrated by the corresponding rays. The ultrasound elements 110, 112, 114, and 116 are arranged in two dimensions (i.e., they are arranged in the x and y directions of FIG. 1A with respect to each other). Thus, the ultrasound element 108 is configured to receive ultrasound signals transmitted from a plurality of ultrasound elements 110, 112, 114, and 116 of the array 102a arranged in two dimensions. Moreover, the signals received by the ultrasound element 108 from the plurality of ultrasound elements 110, 112, 114 and 116 may be discriminated from each other, thus providing multiple distinct measurements corresponding to the ultrasound element 108. As described further below (e.g., in connection with FIGS. 4, 5, 6A, and 6B, among others), suitable processing circuitry may be coupled to the ultrasound element 108 (among others of the array 102b) to facilitate discrimination between the signals received from a plurality of ultrasound elements of array 102a.

Figure 1B:
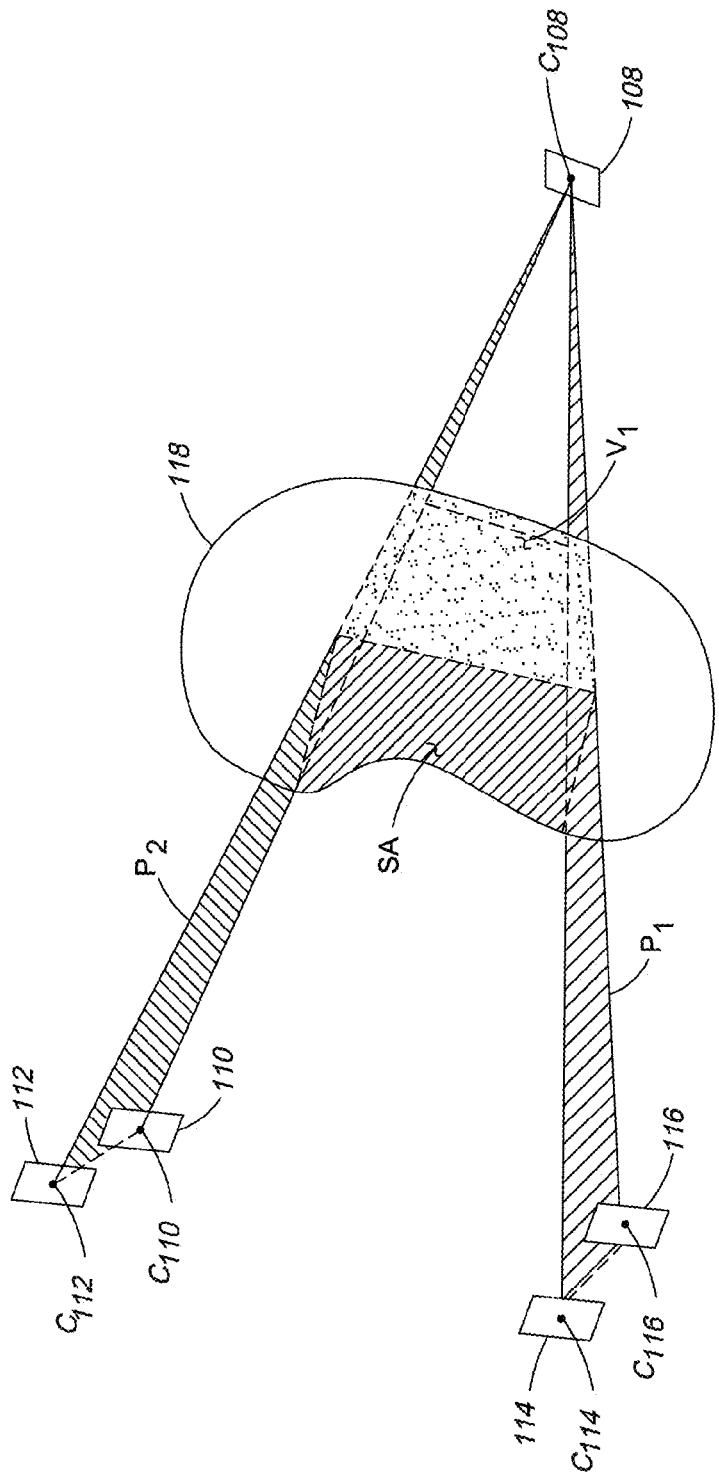
FIG. 1B illustrates a detailed view of a portion of the arrays of FIG. 1A positioned relative to a subject of interest, according to a non-limiting embodiment.

FIG. 1B provides a more detailed view of the operation just described relating to ultrasound elements 108-116. Also shown is a subject 118, positioned relative to the ultrasound elements 108-116 such that signals emitted from the ultrasound elements 110-116 pass through the subject 118 to be sensed (or received) by the ultrasound element 108. The detailed view of FIG. 1B reinforces the previous description of FIG. 1A as providing operation in which an ultrasound element (e.g., ultrasound element 108) may receive signals from ultrasound sources (e.g., ultrasound elements 110-116) arranged in two dimensions.

FIG. 1B also makes clear that in some embodiments an ultrasound element may be configured to receive signals emitted by ultrasound sources (e.g., ultrasound elements 110-116) lying in different planes (e.g., imaging planes) with respect to the ultrasound element receiving the signals. Namely, FIG. 1B illustrates that ultrasound elements 108, 114 and 116 lie in a first plane $P_1$. Ultrasound elements 108, 110, and 112 lie in a second plane $P_2$. The planes may intersect the respective center points of the ultrasound elements, as a non-limiting example. For instance, plane $P_1$ may intersect the respective center points $c_{108}$, $c_{114}$, and $c_{116}$ of ultrasound elements 108, 114 and 116. The plane $P_2$ may intersect the respective center points $c_{108}$, $c_{110}$, and $c_{112}$ of ultrasound elements 108, 110 and 112.

Thus, embodiments of the present application provide an apparatus in which one or more ultrasound sensors are configured to sense or receive signals emitted by multiple ultrasound sources defining multiple different planes with respect to the sensor. In this manner, non-slice based imaging (which may also be referred to herein as "out-of-plane" imaging) may be provided according to some embodiments. Referring again to FIG. 1A and considering the rays 106, it can be seen that one or more ultrasound elements (e.g., ultrasound element 108) may each be configured to receive signals from ultrasound sources lying in multiple, and in some cases numerous, planes with respect to the ultrasound element(s) receiving the signals. The distances (or angles) between such planes will depend on the spacing between the ultrasound elements emitting the signals. For instance, considering FIGS. 1A and 1B in combination, the angle between $P_1$ and $P_2$ will depend to some extent on the distance in the x-direction between x-coordinates $x_2$ and $x_3$ (in FIG. 1A). However, it is to be appreciated that the planes $P_1$ and $P_2$ are distinct.

FIG. 1B also makes clear that embodiments of the present application provide an apparatus in which an ultrasound element configured as a sensor receives signals emitted from multiple ultrasound elements configured as ultrasound sources which, together with the ultrasound element configured as a sensor, define a non-zero solid angle. For example, a solid angle having its vertex located at the center point $c_{108}$ of ultrasound element 108 may be defined by ultrasound elements 108, 110, 112, 114 and 116. Considering again FIG. 1A, it is to be appreciated that multiple solid angles may be defined by considering various combinations of the ultrasound elements 104 of arrays 102a and 102b. A further example is described with respect to solid angles 420 and 422 of FIG. 4, described below.

FIGS. 1A and 1B also illustrate that embodiments of the present application provide an apparatus in which a plurality of radiation sources (e.g., ultrasound elements 104 of array 102a) are configured to emit respective sources signals incident upon a volume to be characterized spanning orthogonal x, y, and z axes (e.g., the volume between arrays 102a and 102b). A plurality of radiation sensors (e.g., ultrasound elements 104 of array 102b) may be separated from the plurality of radiation sources in the z-direction. Both the radiation sources and the radiation sensors may occupy multiple locations in the x and y-directions. Such an apparatus may be operated suitably so that the radiation sensors receive respective source signals emitted by the radiation sources and that such signals are capable of being discriminated from one another (e.g., by suitable processing). In some such embodiments, receipt of and discrimination between the received signals may be performed for each of two or more (but not necessarily all) of the radiation sensors.

FIG. 1B also illustrates that embodiments of the present application provide an apparatus in which an ultrasound element (e.g., ultrasound element 108) receives respective source signals emitted from ultrasound sources positioned such that the respective emitted signals pass through a subject along paths bounding a volume. For example, FIG. 1B illustrates that respective paths between ultrasound elements 110-116 and ultrasound element 108 collectively bound a volume $V_1$ of the subject 118. In this manner, receipt of the respect source signals and discrimination between the received signals (e.g., using suitable processing circuitry) may provide information about the volume $V_1$, rather than simply a slice (of substantially zero thickness) of the subject 118, and therefore may facilitate 3D imaging of the types described herein. The extent of the volume $V_1$ may depend on the number and relative positioning of the ultrasound elements from which the ultrasound element 108 receives respective signals. Referring to FIG. 1A, it should be appreciated that a substantial volume (e.g., significantly larger than a slice of substantially zero thickness) may be bounded by the paths of respective signals received by any one or more ultrasound elements configured as sensors.

FIG. 1B also illustrates that embodiments of the present application provide an apparatus in which an ultrasound element (e.g., ultrasound element 108) receives respective source signals emitted from ultrasound sources positioned such that the respective emitted signals are incident across a surface area of a subject. As shown, signals emitted by ultrasound elements 110-116 may be incident across a surface area SA of the subject 118. The extent of the surface area may depend on the number and relative positioning of the ultrasound elements which emit respective source signals received by the ultrasound element 108. Referring to FIG. 1A and the illustrated rays 106, it should be appreciated that a substantial surface area (e.g., significantly larger than would be impacted in a slice-based imaging approach) of a subject may be impacted by the paths of respective signals received by any one or more ultrasound elements configured as sensors. In some embodiments, the surface area is between approximately 1 cm$^2$ and approximately 100 cm$^2$. In some embodiments, the surface area may be between approximately 50 cm$^2$ and approximately 100 cm$^2$, or between approximately 100 cm$^2$ and 500 cm$^2$. In some embodiments, the surface area may be up to one square meter or more. Discrimination between respective signals (e.g., using suitable processing circuitry) incident across a surface area as described may provide data useful for 3D imaging and/or 3D thermometry of the types described herein.

FIG. 1B also illustrates that embodiments of the present application provide an apparatus in which an ultrasound element receives respective source radiation signals emitted by three non-linearly arranged ultrasound elements configured as sources. The sources may be arranged in multiple dimensions. For example, ultrasound element 108 is configured to receive respective source signals emitted by ultrasound elements 110, 112, and 114, which represent three non-linearly arranged ultrasound elements. Discrimination between the respective received signals may be performed using suitable processing circuitry (examples of which are described below), according to non-limiting embodiments. It should be appreciated by reference to FIG. 1A that multiple ultrasound elements configured as sensors (e.g., in addition to ultrasound element 108) may similarly be configured to receive respective source signals emitted by multiple non-linearly arranged ultrasound elements configured as sources. However, not all ultrasound elements of the array 102b configured as ultrasound sensors need operate in this manner.

FIGS. 1A and 1B also illustrate that embodiments of the present application provide an apparatus including a plurality of radiation sources (e.g., ultrasound elements 104 of array 102a) arranged nonlinearly in a first plane or three-dimensional space and configured to emit respective source signals through a volume to be characterized (e.g., imaged). A plurality of radiation sensors (e.g., ultrasound elements 104 of array 102b) may be arranged nonlinearly in a second plane or three-dimensional space and configured to oppose the first plane or three-dimensional space, and the volume. One or more (e.g., all) of the plurality of radiation sensors may be configured to sense the source signals emitted by one or more (e.g., all) of the plurality of radiation sources after the source signals pass through the volume (e.g., after passing through a subject, such as subject 118). In some embodiments, processing circuitry (non-limiting examples of which are described below) coupled to the plurality of radiation sensors may also be provided and configured to receive and discriminate between the source signals sensed by the plurality of radiation sensors. The received signals may be indicative of at least one characteristic of the volume, such as density or refractive index, as non-limiting examples. The plurality of radiation sources and radiation sensors may be arranged in any combination of planes and three-dimensional spaces. For example, the radiation sources may be arranged in a first plane and the radiation sensors arranged in a second plane. The radiation sources may be arranged in a plane and the radiation sensors arranged in a three-dimensional space, or vice versa. The radiation sources and the radiation sensors may be arranged in respective three-dimensional spaces.

Considering FIG. 1A again, it is to be appreciated that in some embodiments, each ultrasound sensor may be configured to receive distinct ultrasound signals from each ultrasound source as illustrated by the rays 106, and discrimination between such signals may be provided (e.g., using suitable processing circuitry or otherwise, non-limiting examples of which are described in further detail below in connection with FIGS. 4, 5, 6A, and 6B, among others). Such operation may be referred to as "all pairs correlation." For example, for purposes of illustration, the ultrasound elements 104 of array 102b may be configured as ultrasound sensors while the ultrasound elements 104 of array 102a may be configured as ultrasound sources, according to a non-limiting embodiment.

It should be appreciated, however, that not all embodiments are limited to having all ultrasound elements configured as sensors receive signals from all ultrasound elements configured as sources. Rather, the number (or percentage) of ultrasound sources from which ultrasound sensors may receive and discriminate signals may depend, for example, on the size of the ultrasound source arrangement, the number of ultrasound sources in the ultrasound source arrangement, and/or the layout of the ultrasound source arrangement. Data sufficient for volumetric imaging (or other 3D data collection) may be obtained from a smaller percentage of available sources if the arrangement of available sources has a large number, whereas receipt and discrimination between signals from a greater percentage of available ultrasound sources of an arrangement may be preferred for ultrasound source arrangements having a smaller number of ultrasound sources.

For example, according to an embodiment, an ultrasound sensor of the apparatus 100 may be configured to receive, and an apparatus or system comprising apparatus 100 may be configured to discriminate between, distinct signals from at least 0.2% of the ultrasound sources of an opposed arrangement or array, from at least 0.5% of the ultrasound sources of an opposed arrangement or array, at least 1% of the ultrasound sources of an opposed arrangement or array, from at least 10% of the ultrasound sources of the opposed arrangement or array, from at least 25% of the ultrasound sources of the opposed arrangement or array, from at least 40% of the ultrasound sources of the opposed arrangement or array, from at least 50% of the ultrasound sources of an opposed arrangement or array, from at least 60% of the ultrasound sources of the opposed arrangement or array, from at least 75% of the ultrasound sources of the opposed arrangement or array, from at least 80% of the ultrasound sources of the opposed arrangement or array, from at least 85% of the ultrasound sources of the opposed arrangement or array, from at least 90% of the ultrasound sources of the opposed arrangement or array, from at least 95% of the ultrasound sources of the opposed arrangement or array, from substantially all of the ultrasound sources of the opposed arrangement or array, or any other suitable percentage of ultrasound sources of an opposed array. Depending on the number of ultrasound sources of an arrangement, such percentages may represent a large number of sources. For example, even 0.2% of ultrasound sources of an arrangement including 1,000 ultrasound sources (i.e., 2 sources out of the 1,000 sources) may represent a sufficient number of ultrasound sources from which an ultrasound sensor may receive and discriminate between distinct signals for purposes of volumetric imaging, as a non-limiting example, particularly where each sensor discriminates two different sources. In some such embodiments, the arrangement of ultrasound sources may include at least fifty ultrasound sources.

Considering absolute numbers, an ultrasound sensor of the apparatus 100 may be configured in some non-limiting embodiments to receive, and an apparatus or system comprising apparatus 100 may be configured to discriminate between, distinct signals from at least three ultrasound sources of an opposed arrangement or array, from at least five ultrasound sources of the opposed arrangement or array, from at least ten ultrasound sources of the opposed arrangement or array, from at least fifty ultrasound sources of the opposed arrangement or array, from at least 100 ultrasound sources of the opposed arrangement or array, from at least 1,000 ultrasound sources of the opposed arrangement or array, from at least 10,000 ultrasound sources of the opposed arrangement or array, from between ten and 10,000 ultrasound sources of the opposed arrangement or array, from between 100 and 20,000 ultrasound sources of the opposed arrangement or array, or from any other suitable number of ultrasound sources.

Moreover, it should be appreciated that different ultrasound sensors of the array 102b may be configured to receive ultrasound signals from different percentages of the ultrasound sources of array 102a. However, as previously described, according to an embodiment, at least some ultrasound sensors of the array 102b may be configured to receive signals from ultrasound sources of the array 102a arranged in at least two dimensions. Operation in this manner may provide a relatively large amount of data about a subject located between the arrays 102a and 102b, as will be described further below, and therefore may facilitate rapid and accurate 3D data collection and/or imaging of the subject.

As will be described in greater detail below, the apparatus 100 may be coupled to suitable circuitry to facilitate its operation. For example, the apparatus 100 may be coupled to suitable circuitry to discriminate between multiple ultrasound signals received by an ultrasound sensor from multiple ultrasound sources arranged in at least two dimensions.

While the operation of an apparatus 100 according to some embodiments of the present application may take several variations, multiple of which are described in detail below, a general overview is now provided. The arrays 102a and 102b may be suitably positioned with respect to a subject of interest. For example, if the subject is a patient, the arrays 102a and 102b may be suitably positioned in an opposing configuration to investigate the patient's abdomen, breast, head, or any other portion of interest. The ultrasound sources of array 102a may be configured to concurrently (and in some embodiments, simultaneously) transmit ultrasound signals. According to an embodiment, two of more of the ultrasound sources may concurrently transmit distinct ultrasound signals. In a non-limiting scenario, each ultrasound source may transmit a distinct ultrasound signal.

As used herein, the transmission of two signals is concurrent if the signals have any overlap in time as they are being transmitted. Depending on the context, the transmission of signals is substantially concurrent if overlapping in time by at least 80%, by at least 90%, or more. In some embodiments, signals may be transmitted generally serially such that a first one or more signals is concurrent with a second one or more signals, the second one or more signals is concurrent with a third one or more signals, etc., even though the third one or more signals may or may not be concurrent with the first one or more signals. The transmission of two signals is substantially simultaneous if overlapping in time by approximately 95% or more.

As will be described further below, not all embodiments involve concurrent or simultaneous transmission of signals from a plurality of ultrasound sources. The ultrasound sensors of array 102b may receive the ultrasound signals sourced by the ultrasound sources of array 102a. The signals may be discriminated between (e.g., based on code, time, frequency or in any other suitable manner, non-limiting examples of which are described below) and processed to determine properties of interest of the patient (or other subject), such as density of tissue, speed of sound in the tissue, and/or index of refraction of the tissue, among other possibilities. One or more images may then be reconstructed based on such data.

As described, various properties of interest of a subject may be determined, as will be described in greater detail below. Determination of such properties may be made by consideration of characteristics of the ultrasound signals received by the ultrasound sensors of array 102b. For example, one or both of attenuation and time-of-flight through a subject of the ultrasound signals may be measured. The attenuation may be determined, for example, by consideration of the amplitude (and/or power) of an ultrasound signal received by an ultrasound sensor of the array 102b relative to the amplitude (and/or power) of the ultrasound signal transmitted by an ultrasound source of the array 102a. The time-of-flight may be determined, for example, by consideration of a phase shift of the transmitted signal induced by passage of the signal through the subject.

The measured attenuation and/or time-of-flight of ultrasound signals as determined as part of operation of the apparatus 100 may be used to calculate (or otherwise determine) one or more physical properties of interest of the subject. For instance, time-of-flight may be indicative of speed of sound, and therefore may also provide information about density and/or temperature within the subject. Attenuation and/or time of flight may be indicative of the index of refraction within the subject.

One or both of the arrays may be operated according to beamforming techniques to form a beam. Beamforming is described in detail below with respect to operation of HIFU arrays, but may also be applied in the context of imaging. For example, beamforming may be applied on the transmission side (source side) of a system and/or on the receiving side of the system (termed "receive beamforming" or "receiving beamforming"). Beamforming may facilitate focused evaluation of a point of interest within the volume enclosed by the arrays. Beamforming may be used to form any suitable type of beam such as a low aperture beam, sometimes called a pencil beam, as one example. Various beamforming techniques may be used, including but not limited to broadband beamforming, dynamic beamforming, adaptive beamforming, transmit beamforming, and receiving beamforming. Apodization may also be used to augment beamforming, for example by suitable weighting of signals sent/received by the arrays. Any of the above beamforming techniques may be implemented by using digital processing circuitry, analog processing circuitry, or by using a combination of digital and analog processing circuitry.

Operation of an apparatus 100 may provide various benefits in terms of data collection and/or imaging, some of which are described in further detail below. For example, high resolution volumetric imaging may be achieved using data collected by an apparatus of the type shown in FIG. 1A. Resolution may provide a measure of the smallest volume in which the ultrasound imaging device may discern a distinct value of a property (e.g., index of refraction, attenuation, density, temperature, speed of sound, etc.) of the subject being imaged. The higher the resolution, the smaller the volume in which such a change may be detected by operating the ultrasound imaging device. Resolution on the order of millimeters (e.g., 5 cubic mm or finer, 2 cubic mm or finer, 1 cubic mm or finer, etc. in some non-limiting embodiments) may be achieved by suitable spacing of ultrasound elements in the imaging device. Such resolution may be achieved for various volumes and, for example, may be achieved for volumes on the order of 0.1-1 cubic mm, 1-10 cubic mm, 10-100 cubic mm, 100 cubic mm-1 cubic cm, 1-10 cubic cm, 10-25 cubic cm, 25-200 cubic cm, 200-500 cubic cm, 500-1000 cubic cm, 1000-2500 cubic cm, etc., in some non-limiting embodiments. As the volume being imaged gets smaller, imaging that volume at a higher resolution may be possible.

It should be appreciated that although, in some embodiments, a volumetric image may comprise voxels having a volume approximately the same as the resolution of the ultrasound imaging device (e.g., the volume of each voxel in the volumetric image is approximately 5 cubic mm when the resolution of the ultrasound imaging device is approximately cubic 5 mm), aspects of the present application are not limited in this respect. For example, in some embodiments, the volume of one or more voxels in a volumetric image may be smaller than the resolution of the ultrasound imaging device.

Rapid operation of the apparatus 100 may also be provided. For example, data collection corresponding to each source transmitting a signal and each sensor receiving the signal may be performed at a rate of approximately up to 5 frames per second, up to 10 frames per second, up to 25 frames per second, up to 50 frames per second, up to 75 frames per second, up to 100 frames per second, up to 125 frames per second, or any other suitable rate. Thus, as a non-limiting example, data collection corresponding to each source transmitting a signal and each sensor receiving the signal may be collected in less than approximately 0.5 second, less than approximately 300 milliseconds, less than approximately 200 milliseconds, or at any other suitable rate. The rate may depend, at least partially, on the number of sources and sensors of the apparatus.

Reconstruction of volumetric images using data collected with apparatus 100 may also be performed rapidly. Due to the high speeds of data collection possible with apparatus of the type described, volumetric images may be reconstructed at a rate up to approximately six volumetric images/second, as a non-limiting example. In some embodiments, real time volumetric imaging may be provided.

Another benefit that may be realized from use of an apparatus 100 is high signal fidelity. As described, the apparatus 100 of FIG. 1A may be used to collect large amounts of data in relatively short time periods. For example, in embodiments where the arrays 102a and 102b have N×N ultrasound elements, a single scan with the apparatus 100 may produce on the order of $N^4$ distinct measurements. A scan represents a single activation and collection of data from a group of elements (sometimes representing all elements of a system and other times representing a subset), and thus results in collection of a frame of data. N is four in the non-limiting example of FIG. 1A, but may be any suitable number, examples of which have been previously given, and which may include tens, hundreds, or thousands of ultrasound elements. For example, according to some embodiments arrangements of ultrasound elements configured to perform ultrasound imaging may include, as non-limiting examples, at least three ultrasound elements, at least ten ultrasound elements, at least twenty-five ultrasound elements, at least fifty ultrasound elements, at least 100 ultrasound elements, at least 1,000 ultrasound elements, or any other suitable number. In the non-limiting example of FIG. 1A, the array 102a is an N×N array, but not all embodiments are limited to arrays having sides of equal dimension. For example, one or both of the arrays may be N×M arrays, where N and M differ. However, for ease of explanation, it is currently assumed the arrays are N×N arrays.

As described previously, the apparatus 100 may be operated such that, in some embodiments, each ultrasound sensor receives a distinct signal sourced by each ultrasound source. Distinct signals may be signals that are distinguishable (i.e., that the processing circuitry can discriminate), at least in part, on the basis of content of the signals, the times at which the signals are sent, the elements transmitting the signals, the elements receiving the signals, the channel over which the signals are transmitted, etc. Therefore, in the non-limiting example of FIG. 1A, each ultrasound sensor of array 102b may receive up to $N \times N = N^2$ distinct ultrasound signals per scan, which signals may have been produced concurrently by the N×N sources in some non-limiting embodiments (though not all embodiments are limited in this respect). Considering that the array 102b itself includes $N \times N = N^2$ ultrasound sensors, a single scan with the apparatus 100 may result in $N^4$ distinct measurements. More generally, in some embodiments, an N×M arrangement of radiation sources emitting respective source signals to an X×Y arrangement of radiation sensors may provide for receipt of, and discrimination between (e.g., using suitable processing circuitry) greater than X×Y×N received signals from the N×M radiation sources. In some embodiments, up to (X×Y×N×M) respective signals may be received by the X×Y arrangement of radiation sensors from the N×M arrangement of radiation sources, and in some embodiments discrimination may be provided between approximately (X×Y×N×M) respective signals. In some non-limiting embodiments, N=M=X=Y. Such large numbers of measurements may improve signal fidelity and/or facilitate real time imaging functions (e.g., generation of 3D images), real time thermometry functions (e.g., generation of 3D temperature profiles), or other desirable functions.

The provision of $N^4$ measurements using the apparatus 100 of FIG. 1A is to be contrasted with the number of measurements which could be achieved by operating an apparatus in a slice-based ("tomographic") modality in which sensors can sense signals only from sources of a single one-dimensional row. Although operation of an apparatus in such a manner may allow for generation of 3D images by stacking "slices," the amount of data obtained from slice-based approaches is significantly less and the need to generate multiple slices can take significantly more time. Thus, operation of the apparatus 100 in the manner described above, in which ultrasound sensors may receive distinct signals from ultrasound sources arranged in at least two dimensions (and for which the signals may be discriminated, for example using suitable processing circuitry) may provide a significant increase in the number of measurements which may be made per scan and/or the timeframe within which they can be made compared to a slice-based approach.

Furthermore, it should be appreciated from that in some embodiments the apparatus 100 of FIG. 1A may be used to achieve volumetric imaging of a subject without the need to mechanically scan the arrays of ultrasound elements. Rather, the arrays may be maintained in a static relationship with respect to each other according to some aspects, while still providing data suitable to reconstruct a volumetric representation of a subject, and again without using slice-based techniques. The ability to maintain the arrays static relative to each other during operation may facilitate rapid collection of data, since mechanical scanning of ultrasound elements would, in many if not all situations, require more time than electrical excitation of different elements of the arrays. For example, the time needed to emit distinct signals from each of the ultrasound elements 104 of array 102a may be significantly less than the time which would be needed to mechanically scan a row of ultrasound elements across the distance occupied by the array 102a.

The prior description has assumed that ultrasound elements 104 of arrays 102a are configured as ultrasound sources and that ultrasound elements 104 of arrays 102b are configured as ultrasound sensors. However, as previously described, the apparatus 100 is not limited to the ultrasound elements 104 of the arrays 102a and 102b being limited to performing a single function. Rather, according to a non-limiting embodiment, the ultrasound elements 104 of arrays 102a and 102b may be configured to operate as both ultrasound sources and sensors, or may be configured to exhibit time-varying functionality. For example, in a non-limiting embodiment, the ultrasound elements 104 of array 102a may be configured to operate as ultrasound sources during a first time interval and as ultrasound sensors during a second time interval. The ultrasound elements 104 of array 102b may be configured to operate as ultrasound sensors during the first time interval and as ultrasound sources during the second time interval, as a non-limiting example. Thus, the operation of the ultrasound elements 104 may vary with time. A non-limiting example is described below with respect to FIG. 6B.

Figure 2:
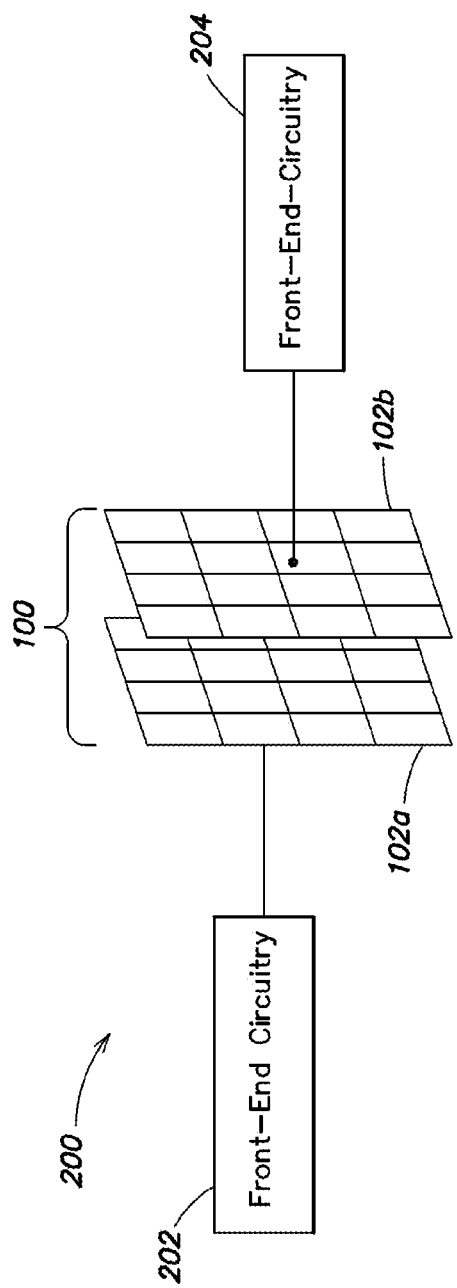
FIG. 2 illustrates a system including radiation (e.g., ultrasound) sources and sensors and front-end circuitry, according to a non-limiting embodiment.

As described, according to an aspect of the present application, an apparatus of the type illustrated in FIG. 1A may be coupled to suitable circuitry (or other components), for example as part of a system. The circuitry may facilitate operation of the apparatus 100 in any of the manners previously described. A non-limiting example is shown in FIG. 2 in the form of system 200.

As shown, the system 200, which may be considered an imaging system in some embodiments, comprises front-end circuitry 202 coupled to the apparatus 100 of FIG. 1A, and more particularly to the array 102a, as well as front-end circuitry 204 coupled to the apparatus 100, and more particularly to the array 102b. Front-end circuitry 202 and front-end circuitry 204 may be distinct circuitry in some embodiments or may be the same in other embodiments. According to one embodiment, the front-end circuitry 202 and front-end circuitry 204 may in combination form a single control circuit. The front-end circuitry 202 and front-end circuitry 204 may be any suitable circuitry for controlling operation of the apparatus 100 and processing data produced by the apparatus 100. As used herein, front-end circuitry may include circuitry which interfaces with arrangements of radiation elements. Non-limiting examples are described below.

While apparatus 100 is illustrated as being part of the system 200, it should be appreciated that systems of the type illustrated are not limited to using opposed array configurations of the type shown in FIG. 1A. Rather, the inclusion of apparatus 100 in FIG. 2 is done for the purposes of illustration, and variations are possible, as will be described in greater detail below.

The front-end circuitry 202 may control generation of signals (e.g., ultrasound signals) to be sourced by the apparatus 100, for example from the array 102a. As described previously, according to one mode of operation the signals may be transmitted from the array 102a to the array 102b, the elements of which may operate as sensors. The front-end circuitry 204 may process the signals received by the elements 104 of array 102b in any suitable manner. For example, as will be described in greater detail below, the front-end circuitry 204 may perform one or more of filtering, amplifying, digitizing, smoothing, and/or other conditioning of the received signals. The front-end circuitry 204 may analyze the received signals to determine characteristics such as one or more of time of arrival, phase, amplitude, frequency, and/or other characteristics of interest. The front-end circuitry 204 may additionally or alternatively determine one or more properties of interest of a subject based on the received signals, such as speed of sound in the subject, index of refraction in the subject, density of the subject, and/or temperature, among others. The front-end circuitry 204 may, in some embodiments, control generation of volumetric images based on data determined from the signals received by the array 102b.

Figure 3:
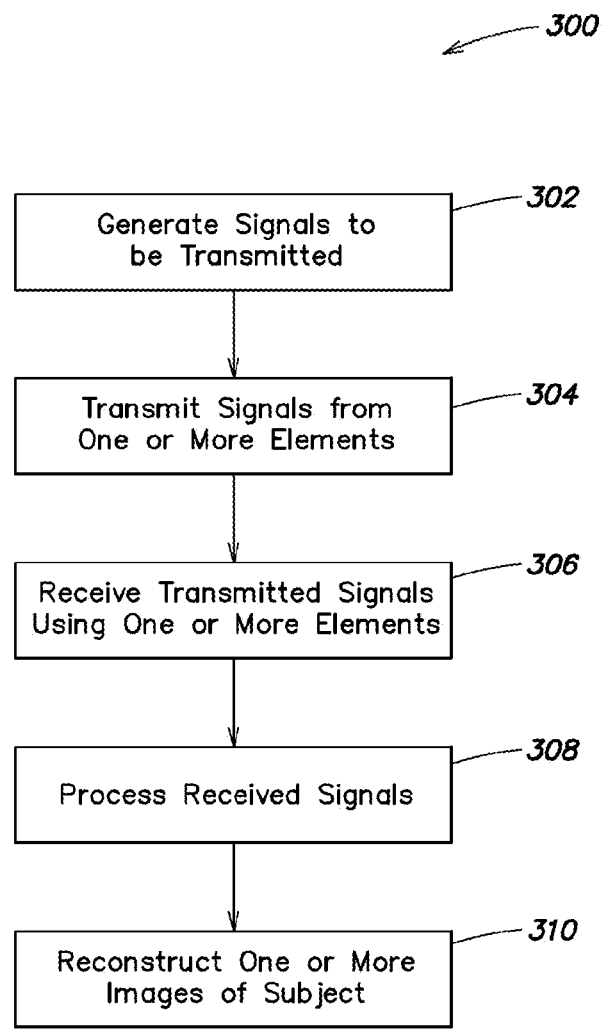
FIG. 3 illustrates a flowchart of the operation of the system of FIG. 2, according to a non-limiting embodiment.

FIG. 3 illustrates a flowchart of an example of the operation of the system 200 of FIG. 2, according to a non-limiting embodiment. The method of operation 300 may begin at 302 with generation of the signals (e.g., ultrasound signals or any other suitable signals) to be transmitted, for example by the array 102a of ultrasound elements 104. The generated signals may then be transmitted at 304 from one or more of the ultrasound elements, for example from one or more of the ultrasound elements 104 of the array 102a. As will be described in greater detail below, the transmission of signals may be performed in any suitable manner, such as using code division multiplexing, time division multiplexing, frequency division multiplexing, a combination of two or more of these multiplexing techniques, or in any other suitable manner.

At 306, the transmitted signals may be received by one or more of the ultrasound elements 104, for example by one or more of the ultrasound elements 104 of the array 102b. Depending on the manner in which the signals were transmitted at 304, the reception of signals at 306 may occur concurrently for multiple ultrasound elements configured as sensors, may occur substantially simultaneously, or may occur at different times for different ultrasound elements 104 configured as sensors.

At 308, the received signals from 306 may be processed in any suitable manner. For example, the signals may be processed in any of the manners described above (e.g., filtering, amplifying, digitizing, smoothing, etc.) or in any other suitable manner, as the aspects of the application are not limited in this respect.

At 310, one or more volumetric images may be reconstructed based at least in part on the signals received at 306 and processed at 308. It should be appreciated that any one, any two or all three acts 306, 308, and/or 310 may be performed in real time. For example, in some embodiments, signals may be received in real time at 306, processed in real time at 308, and used to reconstruct one or more volumetric images in real time at 310. In other embodiments, signals may be received in real time at 306, processed in real time at 308, but used to reconstruct one or more volumetric images at a later time at 310. In yet other embodiments, signals may be received in real time at 306, but processed at a later time at 308 and afterward used to reconstruct one or more volumetric images at 310.

Regardless of whether volumetric images are reconstructed in real-time or offline, when multiple volumetric images of a subject being imaged are obtained, in some embodiments, the obtained volumetric images may be processed to produce a sequence or movie of volumetric images. For example, if the subject being imaged is in motion (e.g., a fetus, an organ of a patient such as a heart, kidney, breast, ovary, etc.) a movie of the subject undergoing motion (e.g., a movie of a heart beating, a movie of a fetus moving, etc.) may be created.

Figure 4:
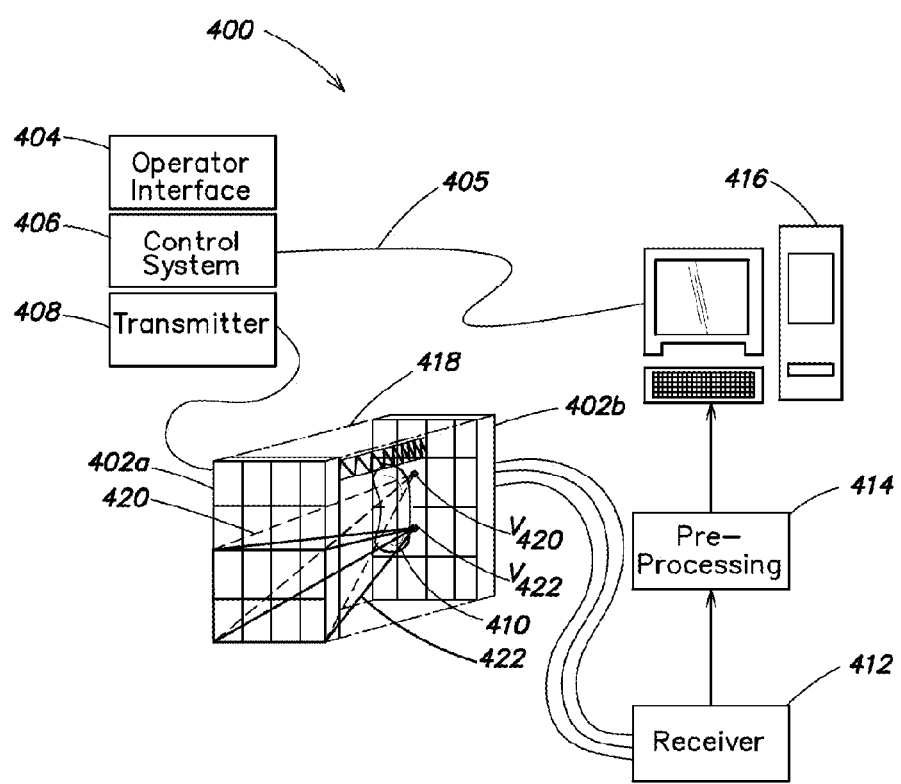
FIGS. 4, 5, 6A and 6B illustrate more detailed examples of systems of the type illustrated in FIG. 2, according to various non-limiting embodiments.

FIG. 4 illustrates a non-limiting example of an embodiment of the system 200 of FIG. 2. As shown, the system 400 may include opposed arrays 402a and 402b of ultrasound elements positioned on opposite sides of a subject 410, and defining a volume 418 therebetween. The system 400 may further comprise front-end circuitry (e.g., front-end circuitry 202 or any other suitable front-end circuitry) comprising a user interface 404, a control system 406, and a transmitter 408 configured on the front-end of opposed arrays 402a and 402b. The user interface may be any suitable user interface, including but not limited to a computer interface with which the user may interact visually (e.g., a screen, a touchscreen, etc.), verbally, via remote control, or in any other suitable manner.

According to a non-limiting embodiment, the user (e.g., a technician, doctor, investigator, or any other user) may control operation of the system 400 via the user interface. As a non-limiting example, one or more pre-programmed imaging routines may be available to the system, and may be stored in the system in suitable computer memory. Such routines may relate to aspects of the operation of the system 400 such as duration of operation, number of scans to perform, type of scan to perform, etc. For example, the user may select a pre-programmed imaging routine via the user interface. Alternatively, the user may create an imaging routine via the user interface. Others controls of the system 400 may also be provided via the user interface.

The control system 406 may control generation of signals to be sent by ultrasound elements of one or both of the opposed arrays 402a and 402b. The control system may include any suitable circuitry. For example, according to a non-limiting embodiment, the control system may be a field programmable gate array (FPGA). However, alternatives are possible, including at least one general-purpose processor, as a non-limiting example. The control system may operate in any suitable manner, for example by executing a computer program of other executable instructions governing its operation. The control system may therefore control operation of the system to perform imaging functions (e.g., collecting one or more images), HIFU functionality (described in greater detail below), or a combination of the two.

The transmitter 408 may perform any suitable functions for transmitting the signals generated by the control system 406 from the ultrasound elements of the opposed arrays 402a and 402b. For example, the transmitter 408 may include one or more amplifiers, one or more filters, and/or one or more digital-to-analog converters, as non-limiting examples. The transmitter 408 may include distinct circuitry for one or more (and in some embodiments, each) ultrasound element of the array 402a, though not all embodiments are limited in this manner. For instance, the transmitter 408 may additionally or alternatively include circuitry shared among two or more (e.g., all) ultrasound elements of the array 402a. Non-limiting examples of suitable transmitting circuitry are described in further detail below.

The system 400 also includes a receiver 412, pre-processing circuitry 414, and reconstruction computer 416. The receiver 412 may comprise circuitry suitable for, for example, conditioning the received signals detected by ultrasound elements (e.g., of the array 402b) configured as ultrasound sensors. For example, the receiver 412 may include amplifiers, filters, one or more analog to digital converters, and/or any other suitable circuitry. According to an embodiment, the receiver 412 includes distinct circuitry for one or more (and in some embodiments, each) ultrasound elements of the array 402b. Additionally or alternatively, the receiver 412 may include circuitry shared among two or more ultrasound elements of the array 402b.

The pre-processing circuitry 414 may perform one or more functions on the received signals in addition to those performed by the receiver 412, such as determining one or more characteristics of the received signals. As non-limiting examples, the pre-processing circuitry 414 may perform matched filtering, correlation (e.g., as described further below with respect to pulse compression), and/or may detect an amplitude of a received signal, a phase of the received signal, and/or a frequency of the received signal, among other signal characteristics. Other functions may additionally and/or alternatively be performed, as those listed represent non-limiting examples. Further details are provided below. In some embodiments, receiver 412 and pre-processing circuitry 414 may be combined and their functions performed by the same circuitry or computer.

Figure 40:
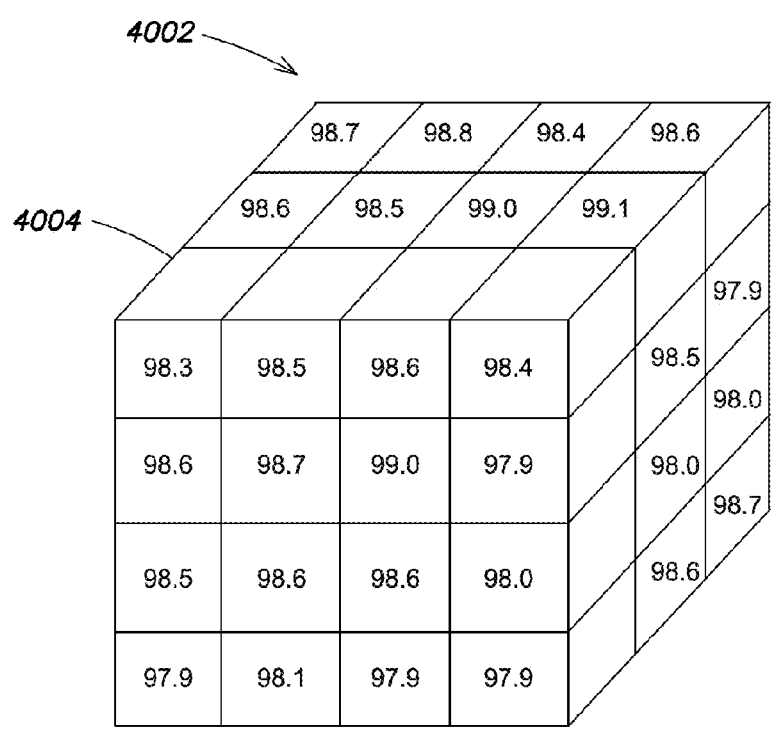
FIG. 40 illustrates a three-dimensional (3D) temperature profile according to a non-limiting embodiment.

The reconstruction computer 416 may receive data from the pre-processing circuitry and reconstruct one or more volumetric images (or three-dimensional temperature profiles, described further below with respect to FIG. 40) of the subject 410, non-limiting examples of which will be shown and described below. Additionally or alternatively, the reconstruction computer 416 may receive data from control system 406. The reconstruction computer 416 may be any suitable computer and may utilize any suitable reconstruction process(es), as aspects of the invention described herein are not limited in this respect. As one non-limiting example, in some embodiments, one or more compressive sensing techniques may be utilized to reconstruct one or more volumetric images of data collected by an ultrasound imaging system. The reconstruction computer 416 may, therefore, implement one or more compressive sensing techniques according to some embodiments. As another non-limiting example, in some embodiments, one or more algebraic reconstruction techniques may be utilized to reconstruct one or more volumetric images of data collected by an ultrasound imaging system. The reconstruction computer 416 may, therefore, implement one or more algebraic reconstruction techniques according to some embodiments.

While the reconstruction computer 416 is illustrated as a single computer, it should be appreciated that the various aspects described herein in which volumetric images are reconstructed are not limited in this manner. Rather, reconstruction of a volumetric image (or multiple volumetric images) may be performed by two or more computers, servers, graphical processing units, and/or other processors. For example, the reconstruction computer 416 may include two or more computers which perform distinct steps of a reconstruction process. Alternatively, the reconstruction computer 416 may include two or more computers which perform one or more common reconstruction functions in parallel. The reconstruction computer (or other reconstruction hardware) may be located local to the other components of the system 400, may be located remotely, or may include some hardware located locally and some located remotely. If reconstruction hardware is located remotely, communication between the reconstruction hardware and the pre-processing circuitry may be performed in any suitable manner, including wirelessly, via a wired connection, via the internet, via a cloud (as in cloud computing), or in any other suitable manner. Moreover, it should be appreciated that the functionality of the reconstruction computer 416 and the receiver 412 and/or pre-processing circuitry 414 may be performed by a single unit, e.g., a single processor. For example, a single processor may perform the functionality of 412, 414, and 416. Thus, it should be appreciated that in some embodiments a single processor may function to receive and discriminate signals sensed by radiation sensors and create a 3D image and/or 3D temperature profile based on the received and discriminated signals. Alternatively, such functionality may be divided between multiple hardware units in any suitable manner.

As described previously, in some embodiments a sensor, such as a sensor of array 402b, may be configured to receive signals originating from multiple sources whose positions define a substantial solid angle with respect to each sensor, such as, for example, a solid angle of at least $\pi/10$ steradians, at least $\pi/5$ steradians, at least $\pi/4$ steradians, at least $\pi/2$ steradians, at least $\pi$ steradians, at least $2\pi$ steradians, between approximately $\pi/10$ and $2\pi$ steradians, between approximately $\pi/5$ and $\pi$ steradians, or any other suitable non-zero solid angle. A non-limiting example is shown in FIG. 4 with respect to solid angle 420. As shown, a single sensor may be configured to receive signals originating from sources occupying the solid angle. Namely, non-zero solid angle 420 has a vertex $V_{420}$ located on a sensor of array 402b (e.g., on the center point of the sensor). The solid angle 420 encompasses eight elements of the array 402a in the illustrated non-limiting example, and thus the sensor defining the vertex of the solid angle 420 is configured to receive signals emitted by at least each of the eight elements of the array 402a encompassed by the solid angle. The solid angle 420 may have any of the values previously listed herein for solid angles, or any other suitable value.

In some embodiments, sensors of an array may be configured to define multiple different solid angles with respect to sources of an opposed array. For example, FIG. 4 illustrates a non-zero solid angle 422 in addition to the non-zero solid angle 420. The non-zero solid angle 422 has a vertex $V_{422}$ located on a different sensor of the array 402b than that on which the vertex $V_{420}$ of solid angle 420 is located. In the non-limiting example illustrated, solid angle 422 includes the same eight elements of array 402a as solid angle 420. The solid angles are distinct, however, since their vertices are aligned on different sensors of the array 402b.

Generally, then, it should be appreciated that embodiments of the present application provide apparatus in which sensors of an arrangement are configured to receive signals emitted from sources defining multiple different solid angles with respect to the sensors. Such a geometry may allow for collection of large amounts of data from the source-sensor arrangement, without the need to mechanically scan the arrangement and in a relatively short period of time. For example, much more data may be collected with such a geometry than that allowed by slice-based imaging systems.

The components in FIG. 4 may be coupled in any suitable manner, including wired and/or wireless connections. In some embodiments, high speed connections may be used to facilitate collection and processing of large amounts of data, as may be desired in various imaging applications. According to an embodiment, the arrays 402a and/or the array 402b may be coupled to the processing circuitry via a Thunderbolt™ interface, fiber-optics, Rocket IO™ from Xilinx Inc. of San Jose, Calif., or other high-speed interface.

The operation of one or more components of system 400 may be synchronized according to a non-limiting embodiment. Such synchronization may be achieved in any suitable manner. According to an embodiment, a common clock may be distributed to one or more of the various components of system 400 which utilize clock signals. For example, in some embodiments, a common clock may be distributed to the one or more digital-to-analog converters and analog-to-digital converters in system 400. Additionally, a common clock may be distributed to one or more FPGAs in system 400. Alternatively, multiple synchronized clocks may be provided to appropriate components of the system 400. Thus, the various aspects of the present application are not limited to synchronizing the operation of components in any particular manner. As another example, one or more phase-locked loops may be used to synchronize operation of components of the system 400. Moreover, it should be appreciated that such synchronization is not limited to the configuration of FIG. 4, but may be implemented in any of the systems described herein.

In some embodiments, ultrasound elements, such as those shown in FIG. 4 and the other figures herein, may be integrated with corresponding circuitry. For example, referring to FIG. 4 as a non-limiting example, the transmitter 408 may be integrated with the array 402a and/or the receiver 412 may be integrated with the array 402b. The components may be integrated on a single substrate, for example by flip-chip bonding, flex-circuit bonding, solder bump bonding, monolithic integration, or in any other suitable manner. As an example, the transmitter 408 may be monolithically integrated on a same substrate as the ultrasound elements of array 402a. Alternatively, the transmitter 408 may be formed on a first substrate and flip-chip bonded to a substrate on which the ultrasound elements of array 402a are formed. Examples of suitable transmit circuitry and receive circuitry are described in greater detail below (e.g., see FIGS. 7, 9, 10, and 11A-11D), and represent non-limiting examples of circuitry which may be integrated with ultrasound elements of one or more arrays.

In some embodiments, the substrate may be acoustically insulating, and thus formed of any suitable acoustically insulating material.

A system like that in FIG. 4, as well as the other systems described herein, may be operated in a manner to provide beamforming functionality from one or more arrays. Beamforming may be valuable in the imaging context to facilitate focused imaging of a desired part of a subject. Beamforming may be applied on the transmission side (source side) of a system and/or on the receiving side of the system.

When beamforming is used, various beamforming techniques may be applied. In some embodiments, broadband beamforming may be implemented. In such embodiments, coded signals may be transmitted on top of a single frequency, as a non-limiting example. Non-linear chirps represent one example of suitable waveforms that may be transmitted in the beamforming context. If beamforming is to be performed on a receiving side of the system (by an array like array 402b in FIG. 4), suitable techniques may include Fourier resampling and/or delay and sum techniques, and may be performed in analog or digital domains. If beamforming is to be performed on the transmitting side of the system (by an array like array 402a in FIG. 4), analog signal delay processing and/or digital signal delay processing may be implemented. In the analog domain, a single waveform may be delayed using suitable delay circuitry. In the digital domain, delay processing may involve using multiple waveforms. Other techniques may also be used.

In some embodiments, beamforming may be augmented by use of apodization, for example by weighting signals transmitted and/or received in any suitable manner to reduce sidelobes. Any suitable implementation of apodization to achieve a desired type and degree of beamforming may be implemented.

In some embodiments, time-reversal beamforming may be used in the imaging context. For example, time reversal beamforming may be valuable when imaging fatty tissue.

When beamforming is used, any suitable type of beam may be formed. Examples of beams that may be formed include, but are not limited to, Bessel beams, plane waves, unfocused beams, and Gaussian beams. Other types of beams are also possible. The type of beam formed may depend, in some embodiments, on the geometry of the imaging configuration. For example, depending on the shape of the subject and the configuration of ultrasound elements, a particular beam type may be chosen.

Figure 5:
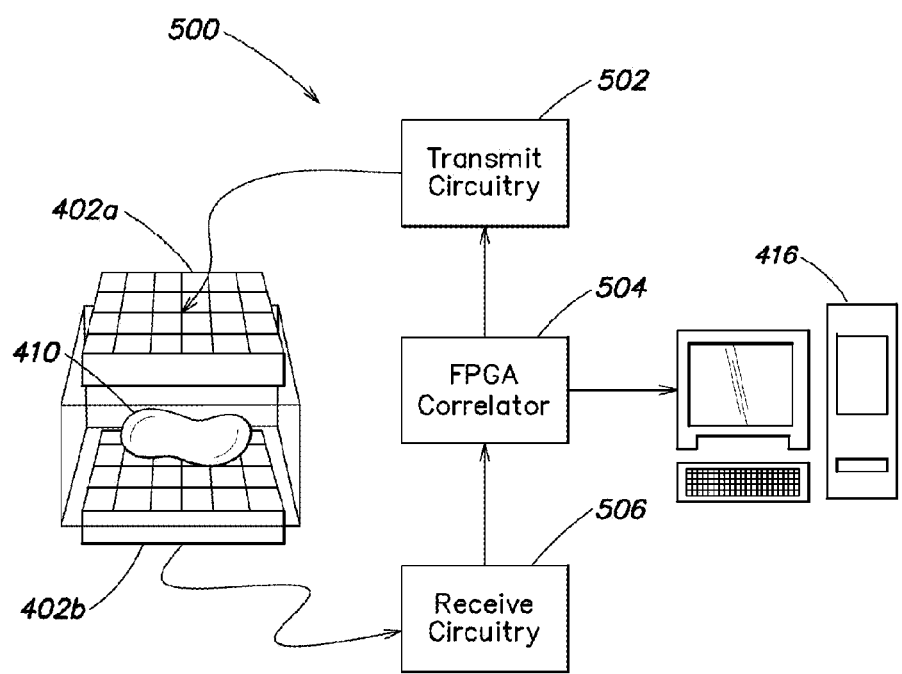

As described, the system 400 of FIG. 4 represents a non-limiting implementation of a system of the type illustrated in FIG. 2. An alternative implementation is illustrated in FIG. 5 as system 500. As shown, the system 500 includes transmit circuitry 502, an FPGA correlator 504, and receive circuitry 506. The FPGA correlator 504 is configured to generate and provide to the transmit circuitry 502 signals for transmission from one or more ultrasound elements (e.g., of the array 402a). The receive circuitry 506 is configured to receive signals detected by one or more ultrasound elements (e.g., of the array 402b) and provide received signals to the FPGA correlator 504 for further processing (e.g., correlation of the signals, etc.). The FPGA correlator 506 provides its output to the reconstruction computer 416, which may operate in the manner previously described with respect to FIG. 4.

Figure 6A:
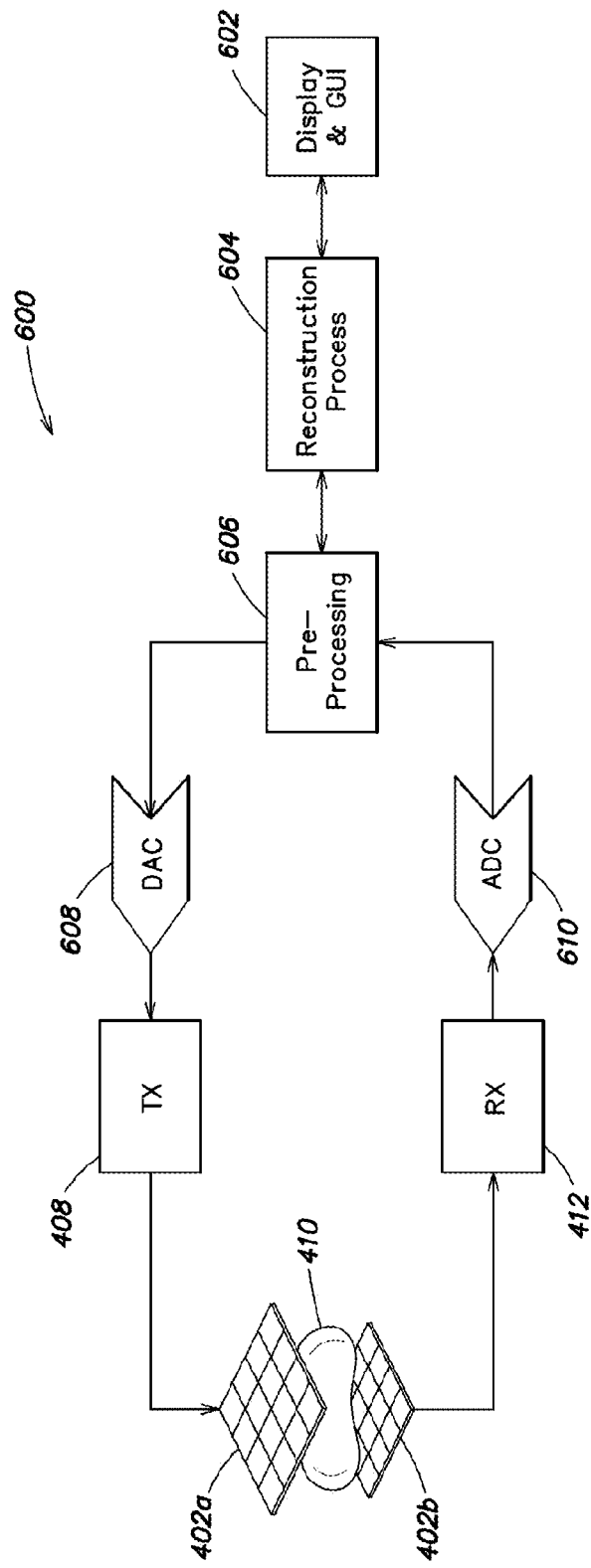

FIG. 6A illustrates another embodiment of a system of the type illustrated in FIG. 2. The system 600 of FIG. 6A includes a display and graphical user interface (GUI) 602 via which a user may input information to the system (e.g., selections of imaging parameters, operating schemes, pre-programmed imaging routines, and/or other suitable information) and/or view output data and images. The system 600 further comprises a reconstruction process 604 and pre-processing block 606. The reconstruction process, which may be stored by any suitable computer readable media and executed by any suitable hardware (e.g., a computer, such as a reconstruction computer), may receive data from the pre-processing block 606 and generate one or more reconstructions (e.g., reconstructed images). For example, the reconstruction process 604 may be used to generate one or more volumetric images of the subject 410, in a non-limiting embodiment. The pre-processing block may perform any suitable processing on signals received (e.g., by the array 402b) and initially processed by the receiver 412 and analog to digital converter (ADC) 610. For example, the pre-processing block 606 may perform the functions previously described with respect to pre-processing circuitry 414, or any other suitable functions.

In some embodiments, the pre-processing block 606 may provide initial digital waveforms to the digital to analog converter (DAC) 608. The DAC may then generate one or more analog signals to be transmitted from the array 402a using the transmitter 408. Although only a single signal chain is illustrated in system 600 for both the transmit and receive portions of the system, it should be appreciated that the system may alternatively include a respective transmit chain (one or more transmitter components) for each of two or more ultrasound elements of the arrays 402a and a respective receive chain (one or more receiver components) for each of two or more ultrasound elements of the array 402b. In some embodiments, a respective signal transmit chain may be provided for each ultrasound element of the array 402a and a respective signal receive chain may be provided for each ultrasound element of the array 402b.

Figure 6B:
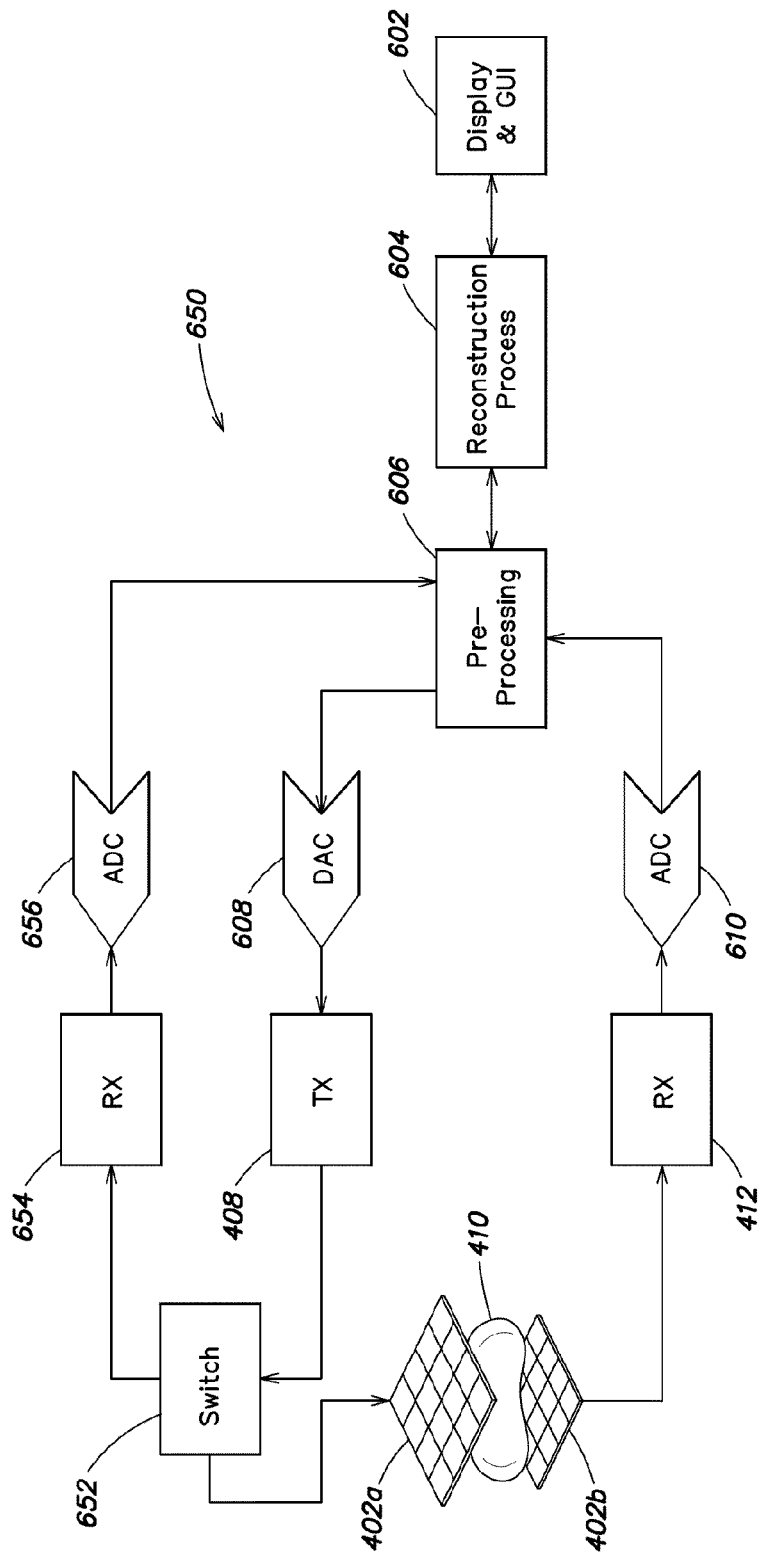

As described previously, in some embodiments one or more ultrasound elements of an arrangement may be configured to exhibit time-varying operation as a source and sensor. FIG. 6B illustrates an example of a suitable configuration for achieving such operation. The system 650 of FIG. 6B differs from the system 600 of FIG. 6A in that the array 402a is additionally coupled to a switch 652, a receiver 654, and an ADC 656. In this manner, the ultrasound elements of array 402a may be configured to operate both as ultrasound sources and ultrasound sensors. To operate the array 402a as a transmitting array, the switch 652 (which may be any suitable type of switch) may couple the array 402a to the transmitter 408, in which case the array 402a operates as previously described herein. To operate the array 402a as a receiving array, the switch 652 couples the array 402a to the receiver 654, which may operate in the manner previously described herein with respect to receiver 412. The ADC 656 may operate in the manner previously described with respect to ADC 610. Thus, suitable (time-varying) operation of the switch 652 may provide desired time-varying operation of the array 402a.

FIGS. 7A-7C illustrate non-limiting implementations of a signal transmit chain (also referred to as a transmitter) in accordance with one or more aspects of the present application, as may be used to transmit ultrasound signals from an ultrasound element. Thus, FIGS. 7A-7C illustrate non-limiting examples of signal transmit chains as may be used in systems of the types illustrated in FIGS. 2-6, or any other suitable systems. The signal chains may be linear in some embodiments. In each FIG. 7A-7C, only a single signal transmit chain is illustrated. Such a signal transmit chain may be shared among two or more ultrasound elements of an array (e.g., array 402a) or may be dedicated to a single ultrasound element of an array. According to a non-limiting embodiment, a respective signal transmit chain of the types illustrated may be dedicated to each ultrasound element configured as an ultrasound source.

The signal transmit chain 700a of FIG. 7A includes a waveform generator 701 and an amplification stage 705 coupled to the array 402a. The waveform generator 701 may be any suitable type of waveform generator for generating signals of the type to be sent from ultrasound elements of the opposed arrays. Thus, the waveform generator 701 may be an analog or digital waveform generator.

The waveforms to be generated by the waveform generator 701 may have any suitable frequency. For example, according to aspects of the present application, one or more systems of the types described herein may be configured to transmit and receive ultrasound signals having frequencies in a range from approximately 1 MHz to approximately 10 MHz, from approximately 3 MHz to approximately 8 MHz, or from approximately 4 MHz to approximately 7 MHz. The listed frequency ranges are non-limiting examples, as alternative frequency ranges are also possible. According to some embodiments, the signals may be broadband signals, which may be beneficial to spread the power of the signals across a frequency range. In some embodiments, the signals may have center frequencies of approximately 2.5 MHz, or approximately 5 MHz as non-limiting examples, with a bandwidth of approximately 50% of the center frequency.

The type of waveform generated by waveform generator 701 may depend, at least partially, on the desired use of the signals and therefore the desired characteristics of the signals to be transmitted by the ultrasound elements. For example, as described, it may be desirable to utilize a wideband waveform rather than a narrowband (or, in the extreme, a single frequency) waveform. Use of a wideband waveform may make more practical the attainment of high power signals, since the power may be spread across frequencies rather than concentrated at a single frequency. Also, as previously described with respect to FIG. 1A, in at least one embodiment it may be desirable for a system to distinguish (or discriminate) between multiple ultrasound signals received by a single ultrasound sensor from multiple ultrasound sources. Thus, it may be desirable in at least some circumstances for the signal generated by the waveform generator 701 to be of a type which may be decoded on the receiving end of the system, for example using a matched filter or any other suitable decoding technique.

As a non-limiting example, the waveform generated by waveform generator 701 may be a wideband waveform. The wideband waveform may have a center frequency chosen to substantially correspond to a center frequency of an ultrasound element from which the waveform will be sent (e.g., the ultrasound elements of array 402a) and having a bandwidth in suitable proportion to a bandwidth of the ultrasound element. For example, the bandwidth of the waveform may be selected to be approximately 100% of the bandwidth of the ultrasound elements from which it will be transmitted, may be selected to be approximately 75% of the bandwidth of the ultrasound elements from which it will be transmitted, may be selected to be approximately 50% of the bandwidth of the ultrasound element from which it will be transmitted, may be selected between approximately 40% and approximately 60% of the bandwidth of the ultrasound element from which it will be transmitted, or may have any other suitable relationship to the bandwidth of the ultrasound element, as the numbers listed are non-limiting examples.

Figure 8A:
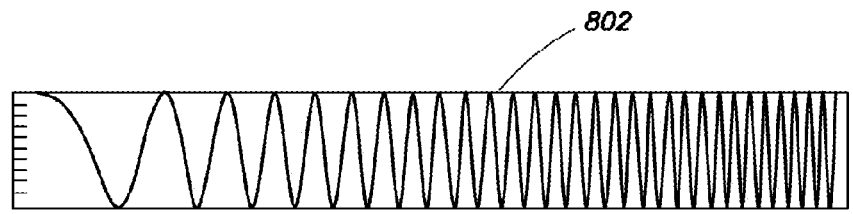
FIGS. 8A and 8B illustrate examples of waveforms which may be transmitted in an imaging mode, according to a non-limiting embodiment.

Waveform generator 701 may generate any of numerous types of wideband waveforms. One non-limiting example of a wideband waveform is a chirp. The chirp may be generated to have any suitable characteristics. For example, the chirp may be a linear chirp whose instantaneous frequency changes linearly over time. FIG. 8A illustrates a non-limiting example of a linear chirp waveform 802. As another example, the chirp may be non-linear chirp whose instantaneous frequency changes non-linearly over time (e.g., geometrically, logarithmically, or in any other suitable way). In some non-limiting embodiments, the edges of the chirp may be amplitude modulated by the application of a window (e.g., a Hamming window, a Hanning window, a Chebyshev window, a prolate-spheroidal window, a Blackmann-Tukey window, etc.) to reduce the presence of sidelobes in the corresponding received waveform.

The chirp may have any suitable duration. The duration may be selected, for example, to provide balance between competing constraints of signal-to-noise ratio (SNR) and power. The greater the chirp duration, the greater the SNR, but the greater the average power carried by the signal. In certain applications, such as imaging of human patients, limits on power deposition may be set which may factor into the desired power of a signal generated by the waveform generator. For example, in ultrasound imaging applications, guidelines or regulations (e.g., those set by the FDA, National Electrical Manufacturers Association, NEMA®, etc.) may place limits on power deposited in a patient. A balance between such considerations as power deposition and SNR may be guide selection of a chirp duration. As a non-limiting example, the chirp may have a duration of less than 200 microseconds, less than 100 microseconds (e.g., approximately 80 microseconds, approximately 70 microseconds, approximately 50 microseconds, or any other suitable value), less than approximately 50 microseconds, or any other suitable value.

In some embodiments, a chirp may be generated as part of a pulse compression technique employed by the ultrasound imaging device. Pulse compression may be used to achieve balance between the above-described competing constraints of signal-to-noise ratio (SNR) and power. Instead of transmitting a narrowband (e.g., a single-frequency sinusoid) signal at a desired power level, the power being concentrated at the frequencies of the narrowband signal (e.g., the frequency of the sinusoid), a pulse compression technique may comprise transmitting a wideband waveform (e.g., a chirp), so that the power is spread over the frequencies in the wideband waveform (e.g., over the frequencies in a range swept by the chirp). As described in more detail below, a pulse compression technique further comprises using a pulse compression filter to process the transmitted wideband waveform upon its receipt by one or more ultrasound sensors. The pulse compression filter may be a matched filter that is matched to the transmitted waveform. Though, it should be recognized that the application of a pulse compression technique is not limited to transmitting chirps as any of numerous other waveforms may be used for pulse compression, as known in the art. For example, phase modulated waveforms rather than linear or non-linear frequency modulated waveforms may be used for pulse compression.

Figure 8B:
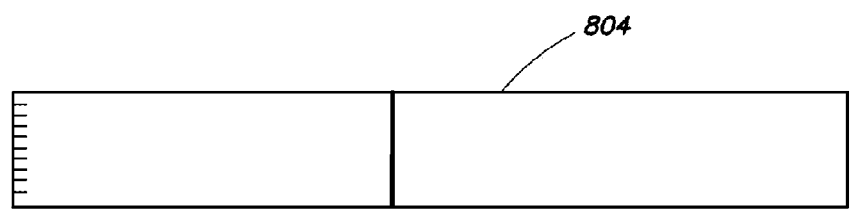

As described, a chirp is a non-limiting example of a wideband waveform, which may be used according to one or more non-limiting embodiments of the present application. An alternative includes an impulse, an example of which is shown as impulse 804 in FIG. 8B. An impulse may be beneficial in terms of simplifying detection on a receiving end (e.g., by ultrasound elements of array 402b configured as sensors), but may require significant instantaneous power output for generation.

Figure 8C:
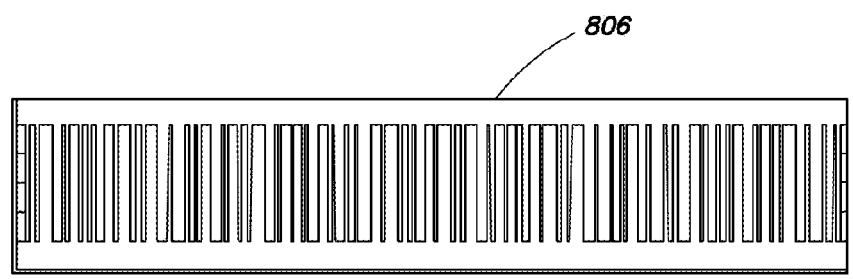
FIG. 8C demonstrates an example of a waveform derived from a binary sequence by using a box-car interpolation waveform.

Another example of a class of wideband waveforms, which may be used according to one or more non-limiting embodiments of the present application, are binary waveforms. Binary waveforms may be derived from binary sequences having suitable time localization properties (e.g., having a narrow auto-correlation function) and may be obtained in any suitable manner Examples of suitable binary waveforms include, but are not limited to, linear maximum length codes (LML codes), Barker codes, and other pseudo-random codes. A binary waveform may be obtained from a binary sequence in any suitable way. For example, in some embodiments, a binary waveform may be obtained by arranging a sequence of impulses in time with the polarity of each impulse being derived from the binary value of the corresponding element in the binary sequence. Other ways of obtaining binary waveforms from binary sequences include convolving a sequence of impulses (e.g., such as the above-described sequence of impulses) with any suitable 'interpolation' waveform. Examples of such 'interpolation' waveforms include, but are not limited to, box-car functions, triangle functions, sinusoidal pulses, sinc functions, or any function modeling the impulse response of a system, such as, for example, a measurement system including front-end circuitry, radiation sources, and signal transmission medium. FIG. 8C demonstrates an example of such a waveform derived from a binary sequence by using a box-car interpolation waveform.

Another class of binary waveforms include complementary sequences, or Golay codes. Such codes comprise pairs of sequences sometimes termed 'complementary pairs.' Each of the sequences in a complementary pair typically satisfies the time localization properties desired in a binary sequence. The complementary pairs have the additional property that their respective autocorrelation functions (i.e., the pulse compressed waveform) may be additively combined to form a signal with reduced sidelobes. Utilizing such codes may comprise transmitting two distinct pulses for each measurement and combining them after matched filtering in the processing circuitry.

In considering the use of wideband signals, it should be noted that signals of different frequency may interact differently with a subject. For example, attenuation of ultrasound signals in a subject may be frequency dependent. Similarly, index of refraction in a subject may be frequency dependent. Other properties of a subject may also be frequency dependent. Thus, according to an aspect of the present application, signals of different frequency may be used to analyze a subject (e.g., by an apparatus of the types described herein), thus providing different (and in some cases, more) information than may be obtained by using signals of only a single frequency. Such operation is not limited to the use of wideband signals.

It should be appreciated that some embodiments of the present application are not limited to using wideband waveforms. In some embodiments, additionally or alternatively, narrowband waveforms may be used. In one non-limiting illustrative example, a sinusoid having a single fixed frequency may be used. Such a fixed-frequency sinusoid is an example of a continuous waveform that may be transmitted by one or multiple ultrasound elements. Such continuous waveforms may be used to calculate values of one or more properties of the subject being imaged at one or more frequencies. Such a mode of operation may be advantageous in that the measurement of properties of a subject (e.g., index of refraction, attenuation, etc.) may depend on the frequency of the waveform. It should be appreciated that the above-described examples of waveforms are provided for purposes of illustration, and that alternative waveform types may be implemented.

The amplification stage 705, which is coupled to the output of the waveform generator 701, may be configured to amplify the signals generated by the waveform generator 701 in preparation for their transmission from the array 402a, as a non-limiting example. Also, the amplification stage 705 may perform one or more functions in addition to amplification, including, for example, filtering. In an embodiment, the amplification stage 705 may include a single amplifier and/or a single filter. In an embodiment, the amplification stage 705 may include multiple amplifiers and/or multiple filters, as the various aspects described herein implementing an amplification stage in a signal transmit chain are not limited to utilizing any particular amplification stage.

FIG. 7B illustrates a signal transmit chain 700b representing a non-limiting, more detailed example of a manner of implementing the signal transmit chain 700a of FIG. 7A, providing an example of a waveform generator and an amplification stage. The signal transmit chain 700b includes an arbitrary waveform generator 718. The arbitrary waveform generator 718 may be a digital waveform generator and may be configured to produce any suitable arbitrary waveform(s) of any suitable frequencies, such as those described above or any other suitable frequencies. The output of the arbitrary waveform generator 718 is provided to a digital-to-analog converter (DAC) 704, the output of which is provided to the amplification stage 705. The DAC 704 may be any suitable DAC having any suitable sampling frequency, as the various aspects described herein implementing a DAC are not limited to use of any particular type of DAC.

The signal transmit chain 700b illustrates an example of the amplification stage 705 in which the amplification stage includes filters 706 and 712, amplifiers 708, 710, and 714, and an optional impedance matching network (IMN) 716. The order of components illustrated in FIG. 7B illustrates a non-limiting configuration of a signal transmit chain as may be used in systems of the types described herein.

The filters 706 and 712 and amplifiers 708, 710, and 714 may be any suitable filters and amplifiers. The amplifiers 708, 710 and 714 may be linear amplifiers, and multiple amplifiers 708, 710, and 714 may be included to provide a desired amplification level recognizing that in practice each amplifier alone may not be able to provide the desired level of amplification. The filters 706 and 712 may be low pass filters having cutoff frequencies sufficient to pass the desired signals. Additionally or alternatively, filters 706 and 712 may filter out signal components such as harmonics and/or other spurious signal components.

The impedance matching network 716 may be any suitable active or passive impedance matching network for providing desired impedance matching between the array 402a and the signal transmit chain. In some embodiments, the array 402a is used to transmit wideband signals of long duration (i.e., not impulses). In such embodiments, the impedance matching network 716 may be configured to provide wideband impedance matching. In some embodiments, the impedance matching network 716 may be selected to provide a low quality factor (Q) impedance match.

FIG. 7C illustrates an alternative signal transmit chain 700c to that of FIG. 7B, and in accordance with the general architecture of FIG. 7A. As shown, the waveform generator of the signal transmit chain 700c may comprise or consist of a voltage controlled oscillator (VCO) 703 having any suitable oscillation frequency. For example, the VCO 703 may be configured to generate oscillating signals (e.g., sinusoidal signals) having any of the frequencies described above, or any other suitable frequencies. The output of the VCO 703 may be provided to the amplification stage 705, which may take the form of previously-described signal chain 700b. However, it should also be appreciated that alternatives configurations are also possible.

Figure 9:
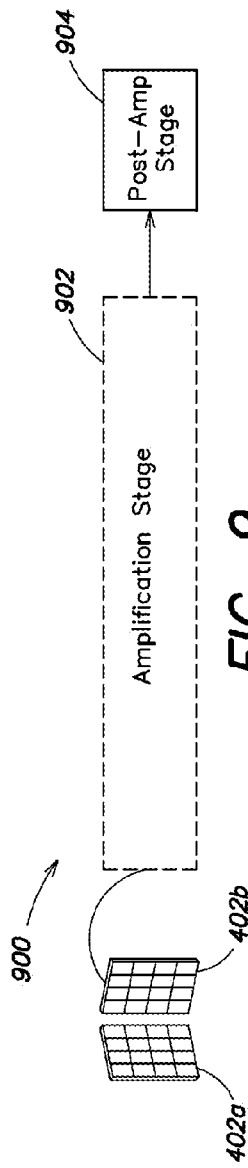
FIG. 9 illustrates a block diagram of a signal receiver as may be implemented in a system in accordance with one or more embodiments of the present application.

FIG. 9 illustrates a non-limiting example of a signal receive chain (also referred to as a receiver) as may be implemented by systems according to one or more aspects of the present application (e.g., the systems of FIGS. 2 and 4-6 or any other suitable systems). For example, the illustrated signal receive chain may represent the receiver 412 of FIGS. 4 and 6, though the receiver 412 may take alternative forms in other embodiments. The signal chain may be linear in some embodiments.

As shown, the signal receive chain 900 of FIG. 9 comprises an amplification stage 902 (e.g., coupled to the array 402b) and configured to receive signals detected by the ultrasound elements of the array 402b configured as sensors. The signal receive chain 900 further comprises a post-amplification stage 904 which may take various forms, non-limiting examples of which are illustrated in FIGS. 11A-11D and described below.

The amplification stage 902 may be any suitable amplification stage and may comprise any suitable circuitry for amplifying signals received by the elements of the array 402b. The amplification stage 902 may also perform additional functions, such as filtering the received signals. According to a non-limiting embodiment, the amplification stage 902 includes only a single amplifier and/or filter. Alternatively, the amplification stage 902 may include multiple amplifiers and/or filters. A non-limiting example is illustrated in FIG. 10.

Figure 10:
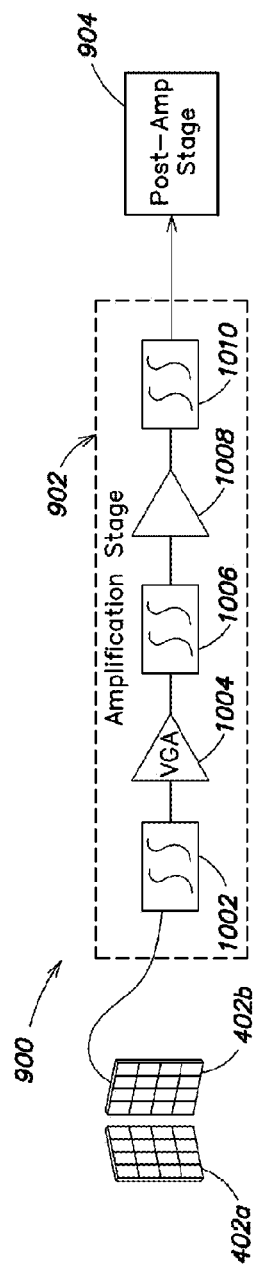
FIG. 10 illustrates a more detailed example of the signal receiver of FIG. 9, according to a non-limiting embodiment.

As shown in FIG. 10, the amplification stage 902 may include multiple amplifiers 1004 and 1008. The amplifiers 1004 and 1008 may be any suitable types of amplifiers, and one or both may be a linear amplifier. The amplifier 1004 may be a variable gain amplifier in the non-limiting embodiment illustrated.

The amplification stage 902 may also include filters 1002, 1006, and 1010, which may be any suitable filters. For example, any one of the filters 1002, 1006, and 1010 may be a low pass filter or a high pass filter having any suitable cutoff frequency to pass the signals of interest. In some non-limiting embodiments, one of the filters 1002, 1006, and 1010 may be a high pass filter to separate out signals used for imaging from signals used for HIFU. As another example, any of filters 1002, 1006, and 1010 may be a notch filter or any other suitable type of filter for filtering out unwanted narrowband or other signal components, respectively.

The ordering of components illustrated in FIG. 10 is non-limiting, and it should be appreciated that various alternative orderings may be implemented. Also, it should be appreciated from the foregoing description of signal transmit chains and signal receive chains that both types of signal chains may be linear according to one or more embodiments of the present application.

Figure 11A:
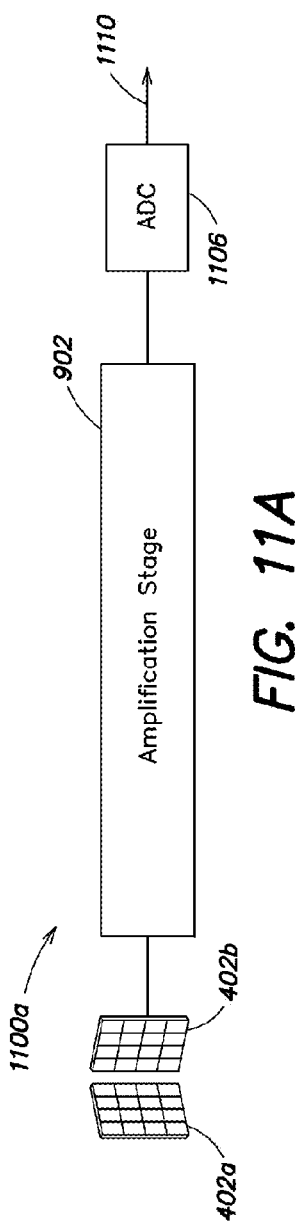

FIGS. 11A-11D illustrate non-limiting examples of the post-amplification stage 904 of signal receive chain 900. FIG. 11A illustrates an alternative in which the signal receive chain 1100a is configured so that the output of the amplification stage 902 is provided directly to the ADC 1106. The ADC 1106 then provides a digital output signal 1110. The output signal 1110 represents a raw received waveform, in this non-limiting embodiment. The waveform may be analyzed to determine characteristics of interest such as amplitude, phase, and/or frequency, which may be used to determine properties of interest of a subject such as index of refraction, speed of sound in the subject, attenuation in the subject, density, and/or other properties.

FIG. 11B illustrates another embodiment of a signal receive chain 1100b, providing a further alternative for the post-amplification stage 904. The signal receive chain 1100b comprises analog pulse compression stage 1116 coupled to the amplification stage 902 and configured to receive an output signal from the amplification stage 902. The analog pulse compression stage 1116 provides an output signal 1118. The analog pulse compression stage 1116 may apply a pulse compression filter to the received signal. To this end, in some embodiments, the received signal may be correlated with the transmitted signal to produce a correlated signal. The correlated signal may be digitized by an analog to digital converter to produce output signal 1118.

FIG. 11C illustrates another embodiment of a signal receive chain providing a further alternative for the post-amplification stage 904. In the signal receive chain 1100c, the output of the amplification stage 902 is provided to a detector 1112. In some embodiments, detector 1112 may be a square law detector, a logarithmic amplifier detector, a linear detector, a phase detector, a frequency detector, or any other suitable signal detector, as aspects of the present application are not limited in this respect. In some embodiments, the detector may be used to identify the location of a peak of the received signal, which, may be provided as output signal 1114. The output signal, in turn, may be used to obtain one or more measurements of the subject being imaged (e.g., attenuation measurements).

FIG. 11D illustrates yet another alternative embodiment of a signal receive chain including a post-amplification stage 904. According to the non-limiting embodiment of FIG. 11D, the signal receive chain 1100d includes a post-amplification stage comprising circuitry configured to perform a heterodyning-type function. The post-amplification stage comprises circuitry including a mixer 1102, a filter 1104 and the analog-to-digital converter (ADC) 1106.

The mixer 1102 obtains a reference signal as well as an output signal of the amplification stage 902, and combines the output signal with the reference signal to produce a combined signal. The reference signal may be obtained in any suitable way. As one illustrative non-limiting example, the reference signal may be a transmission signal obtained from transmit circuitry of the system (e.g., from transmitter 408 or any other suitable transmitter). As another illustrative non-limiting example, the reference signal may be generated by processing circuitry in the post-amplification stage (and/or by any other suitable processing circuitry). The processing circuitry may be configured to generate the reference signal at least in part by using a local oscillator. The reference signal may be a chirp, a pulse, a pulse train, a sinusoid, and/or any other suitable waveform.

In some embodiments, the mixer 1102 may combine the output signal with the reference signal by multiplying the signals and may output the product of the two received signals to a filter 1104, which may be a low pass filter or any other suitable filter. The filtered output of the filter 1104 is provided to the ADC 1106, which produces a digital output signal 1108 suitable for further processing. Examples of such further processing are described further below.

In embodiments where the transmitted waveform is a linear FM waveform having a pulse length greater than the time it takes for a signal to propagate from array 402a to array 402b, the output signal of the ADC 1106 may be a tone representing a frequency difference between the transmitted signal (e.g., from transmitter 408) and the signal received by the ultrasound element of the array 402b and output by the amplification stage 902. For example, in some embodiments the data received by the ADC represents the Fourier transform of the time of flight data. The transmissive component of such data may be the largest tonal contributor. As such, performing a Fourier transform of the received data may yield a time-domain signal representing the pulse-compressed data—thus, the transmissive component will likely represent a peak in this signal. Therefore, the time-of-flight (TOF) may provide information about the speed of sound in a subject, index of refraction in the subject, and/or information about other properties of the subject. The amplitude of the tone represented by the output signal 1108 may be used to determine attenuation of a signal transmitted from an ultrasound element of the array 402a, which therefore may provide information about attenuation within a subject.

The output signals provided by the signal receive chains of FIGS. 9, 10, and 11A-11D may be further processed in some embodiments, for example by pre-processing circuitry 414 and/or any other suitable processing circuitry. For example, further processing may be performed to measure amplitude, phase, and/or frequency of a signal, among other potential signal characteristics of interest. Such pre-processing may be an end result in some embodiments, or may lead to further analysis of the measured values in other embodiments, for example to determine properties of a subject such as density, speed of sound, and/or index of refraction. Furthermore, as previously described (e.g., with respect to FIG. 3), one or more volumetric images may optionally be reconstructed illustrating properties of the subject or any other suitable data of interest. The type of processing performed by pre-processing circuitry (e.g., pre-processing circuitry 414) may depend, at least in part, on the manner of operation of the system and the types of signals transmitted by the opposed arrays. Thus, a description of modes of operation of systems of the type described herein is now provided.

According to an embodiment, signals received by ultrasound elements of an arrangement of the types described herein may be separated by frequency (or frequency band) for further processing. As described previously, the ultrasound signals transmitted by an arrangement of ultrasound elements may contain multiple frequencies, for example being wideband signals. The different frequencies of the transmitted signal may interact differently with the subject, for example in terms of attenuation and refraction, among other possible differences. Thus, according to an aspect of the present application, receiving circuitry may process received signals to determine information with respect to specific frequencies, for example by separating received wideband signals into frequency components and analyzing those frequency components. In such cases, suitable circuitry may be provided at any point in a signal receive chain (e.g., in the signal receive chains of FIGS. 11A-11D or at any other suitable location within a system) to separate out frequencies of interest and separately process the different frequency components of a received signal.

Moreover, in such embodiments, separate images may be generated for separate frequencies. For example, multiple images of index of refraction of a subject may be generated, with each image corresponding to a different frequency (or frequency band). Thus, additional data may be provided beyond what may be achieved by considering only a single frequency (or frequency band).

As previously described, according to some embodiments of the present application, a system may be configured to distinguish or discriminate among multiple ultrasound signals received by an ultrasound sensor from multiple ultrasound sources. As also described previously, according to some embodiments of the present application, a system may be configured to distinguish or discriminate among multiple ultrasound signals transmitted from ultrasound elements arranged in at least two dimensions and received by a single ultrasound element configured as a sensor. Multiple modes of operation of systems of the types described herein may be employed to achieve such results, including code division multiple access (CDMA), time division multiple access (TDMA) modes, frequency division multiplexing (FDM) modes, as well as combinations of any of two or more of these modes. Non-limiting examples are described below.

The use of CDMA according to an aspect of the present application is described in the context of system 400 of FIG. 4, for purposes of illustration. It should be appreciated that CDMA may similarly be employed in systems of other types described herein as well.

According to an embodiment in which CDMA is implemented by the system 400, the ultrasound elements of the array 402a configured as sources may transmit distinct ultrasound signals concurrently or substantially simultaneously. The distinct ultrasound signals may be obtained by using one or more codes to encode a waveform. For example, in some embodiments, a waveform to be transmitted by multiple ultrasound sources (e.g., a wideband waveform such as a chirp) may be coded, prior to being transmitted by an ultrasound source, by using a code associated with that ultrasound source. As such, multiple ultrasound sources may transmit distinct waveforms obtained by coding the same underlying waveform by using CDMA codes corresponding to the ultrasound sources.

A waveform may be coded by using a CDMA code in any of numerous ways. In some non-limiting embodiments, an underlying waveform (or a sequence of waveforms) may be coded using a so-called intrinsic CDMA coding scheme in which the CDMA code may be used to modulate the underlying waveform directly (e.g., by computing an exclusive-or between the CDMA code and the waveform) to produce a coded waveform. The coded waveform may then be transmitted. Alternatively, an underlying waveform may be coded using a so-called extrinsic CDMA coding scheme in which the CDMA code may be used to modulate a waveform indirectly. In this case, the coded waveform, for a particular ultrasound source, may be obtained by sequentially joining multiple copies of the underlying waveform, with each copy being phase modulated in accordance with the CDMA code corresponding to that ultrasound source. Since the phase modulation of the set of copies of the underlying waveform depends on the CDMA code corresponding to the ultrasound source to transmit the coded waveform, distinct coded waveforms will be obtained for each of the ultrasound sources. These waveforms may then be transmitted. It should be appreciated that the number of copies of the underlying waveform depends on the length of the CDMA code. For example, if a binary CDMA code of length 10 is used (e.g., to distinguish among $2^{10}=1024$ ultrasound sources), the coded waveform may comprise 1024 phase modulated copies of the underlying waveform.

Non-limiting examples of suitable CDMA codes include Hadamard codes, Walsh functions, Golay codes, pseudo-random codes (e.g., LML codes) and poly-phase sequences, among others.

The ultrasound elements of array 402b configured as sensors may be active substantially simultaneously, and thus may receive the ultrasound signals transmitted by the ultrasound elements of the array 402a. The front-end circuitry such as receiver 412 and/or pre-processing circuitry 414 may distinguish (or discriminate between), for each of the ultrasound elements of the array 402b, each of the received ultrasound signals from each of the ultrasound elements of the array 402a by decoding the signals (e.g., using matched filtering, or in any other suitable manner). In this manner, a large number of distinct measurements (e.g., on the order of $N^4$ in some embodiments, as previously explained with respect to FIG. 1A) may be made by the system in a relatively short time period since all the ultrasound signals are transmitted concurrently or substantially simultaneously.

Figure 12:
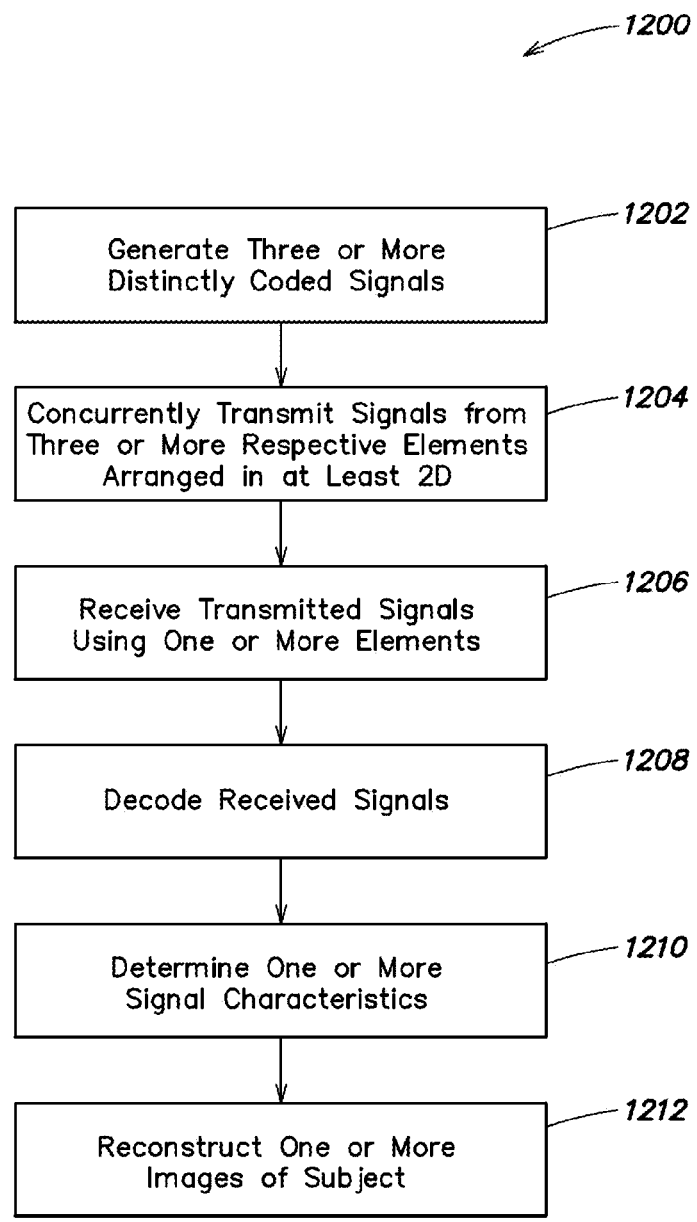
FIG. 12 is a flowchart of a method of implementing code division multiple access (CDMA) processing, according to a non-limiting embodiment.

While the use of CDMA according to an embodiment of the present application may involve transmitting respective coded signals from each ultrasound element of the array 402a and receiving each of the respective coded signals with each of the ultrasound elements of the array 402b, it should be appreciated that alternative implementations of CDMA according to one or more aspects of the present application are also possible. For example, in some embodiments distinctly coded signals may be concurrently transmitted by two or more ultrasound elements of the array 402a configured as sources and arranged in one or more dimensions. In some embodiments, distinctly coded signals may be concurrently transmitted by three or more ultrasound elements of the array 402a configured as sources and arranged in at least two dimensions. The ultrasound elements of array 402b configured as sensors may receive the distinctly coded signals, which may be decoded and processed in any suitable manner (e.g., to form a volumetric image). FIG. 12 illustrates a non-limiting process flow of such operation.

As shown, the method 1200 comprises generating three or more distinctly coded signals at 1202. The coded signals may be generated in any suitable manner, for example using a waveform generator (e.g., waveform generator 702).

The distinctly coded signals may then be transmitted from three or more respective elements of an array of ultrasound elements at 1204, such as array 402a as a non-limiting example. The three or more respective elements may be arranged in at least two dimensions. For example, referring to FIG. 1A, three or more distinctly coded signals may be transmitted from ultrasound elements 110, 112, and 114, respectively. The distinctly coded signals may be transmitted concurrently or according to any other suitable timing.

At 1206, the three or more distinctly coded signals may be received by an element of an array (e.g., array 402b) configured as a sensor. As a non-limiting example, the element 108 of array 102b in FIG. 1A may receive the distinctly coded signals sent from elements 110, 112, and 114 of array 102a. Thus, it should be appreciated that the element receiving the three or more distinctly coded signals may, in this non-limiting embodiment, receive three or more distinctly coded signals sourced (or transmitted) by ultrasound elements arranged in at least two dimensions. In some embodiments, multiple elements of an array (e.g., array 402b) configured as sensors may receive, concurrently, distinctly coded signals sourced by elements of an array arranged in at least two dimensions.

At 1208, the received signals may be decoded in any suitable manner. For example, as will be described further below, matched filtering techniques may be applied to decode the received signals. According to a non-limiting embodiment, each element of an array of ultrasound elements configured as sensors may have a number of decoders associated therewith. The number of decoders may, in an embodiment, equal a number of potential codes to be used in transmitting signals to the elements of the array. For example, if 1,024 distinct codes may potentially be used for transmitting signals, the element configured as a sensor may have 1,024 decoders (e.g., implementing matched filtering) associated therewith. It should be appreciated that any suitable number of codes may be used and therefore any suitable number of decoders may be implemented on the receiving end of the system.

In some embodiments, where extrinsic CDMA coding may be used to encode the signals, the signals may be decoded at least in part by averaging combinations of the received signals. Advantageously, such averaging may improve the SNR of the received signals. An example of such operation is now described.

In some embodiments in which extrinsic CDMA coding is used, each extrinsically coded signal that is received is multiplied by multiplying each pulse of the received signal by the corresponding phase factor for the transmitter/source being decoded. Then, the resulting multiplied signal is added into an accumulator for each successive pulse of the received signal. Many such multiply-accumulate circuits can operate in parallel to decode multiple transmitters from a single receiver. The result, after accumulation, may be an averaged signal for the desired transmitter, which, ignoring possible distortions, will have an improved SNR due to averaging. However, other manners of performing CDMA with extrinsically coded signals are possible.

At 1210, one or more signal characteristics of the received and decoded signals may be determined. For example, as described previously, characteristics of interest may include amplitude, phase, and/or frequency, as non-limiting examples.

Further processing may be performed as desired for a given use of the data determined from 1210. For example, at 1212, one or more volumetric images may be reconstructed. Alternatively, the method may end with determination of the signal characteristics at 1210.

Figure 13:
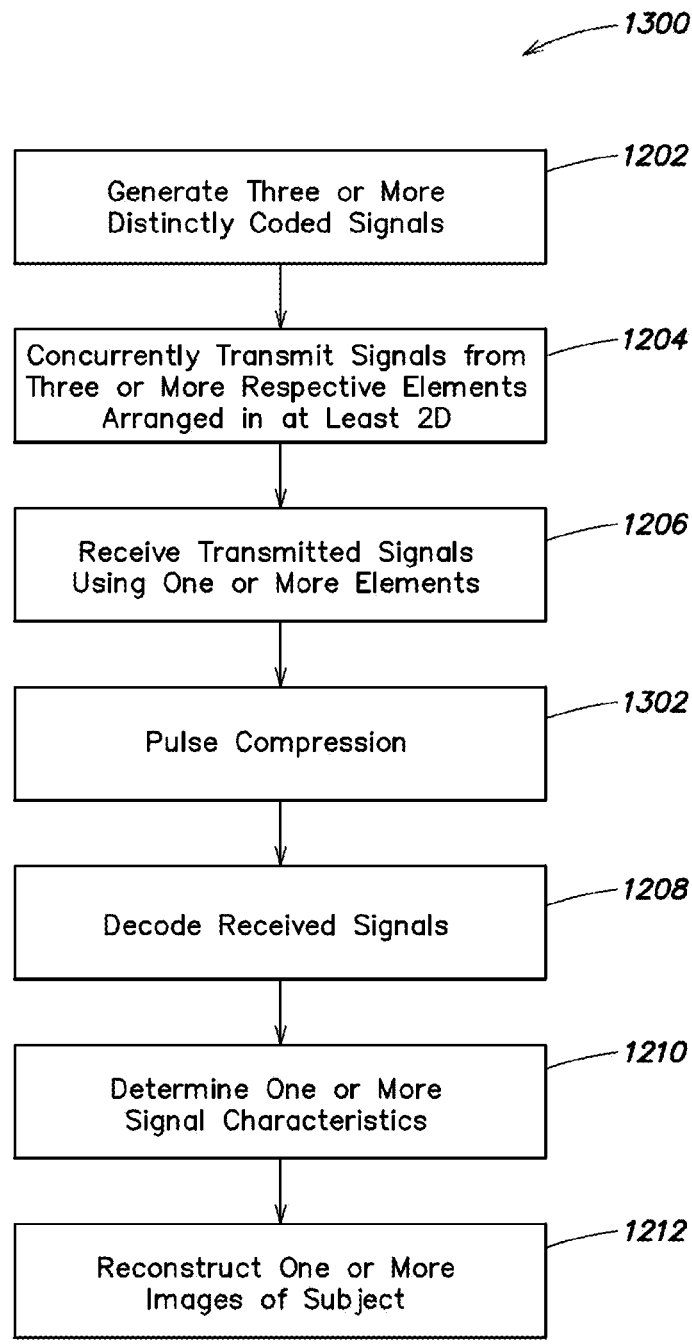
FIG. 13 is a flowchart of an alternative to the methodology of FIG. 12, adding further processing, according to a non-limiting embodiment.

It should be appreciated that the method 1200 of FIG. 12 is a non-limiting example, and that alternatives are possible. For example, one or more processing steps of the received signals may be performed prior to decoding at 1208, such as amplifying, filtering, digitizing, smoothing, and/or any other processing. Any suitable form of linear processing may be performed, as the various aspects described herein are not limited in this respect. A non-limiting example is illustrated in FIG. 13.

As shown, the method 1300 expands upon the method 1200 of FIG. 12 by the inclusion of a pulse-compression step 1302, in which a pulse compression filter may be applied. As previously described, in some embodiments, where pulse compression is used, the received signals may be processed by applying a pulse compression filter to the received signals. Applying the pulse compression filter may comprise correlating the received signals with a copy of the transmitted signals—a form of matched filtering. For example, in some embodiments, where pulse compression is used one or more ultrasound sources may transmit a chirp. The received chirp may be correlated with the transmitted chirp. The correlation may be performed in the time domain or in the frequency domain, as aspects of the present application are not limited in this respect. The correlation may be performed by any suitable circuitry, including a processor, one or more parallel field-programmable gate arrays (FPGA), and/or any other suitable circuitry.

Although not shown, further optional processing may additionally be performed in the method 1300. For example, decimation of the signals received at 1206 may be performed prior to the pulse compression step 1302 or at any other suitable time. Decimation may comprise a low-pass filter operation and down-sampling the received signals to a Nyquist frequency, for example, to minimize the number of computations performed with subsequent processing. Furthermore, a complex analytic transformation (e.g., a Hilbert transform) may be applied to the received signal to obtain the magnitude information of the received signal (e.g., envelope of the signal) and/or the phase information of the received signal. The complex analytic transformation may be performed after the pulse compression at 1302 and prior to decoding the received signals at 1208, according to a non-limiting embodiment.

Figure 14:
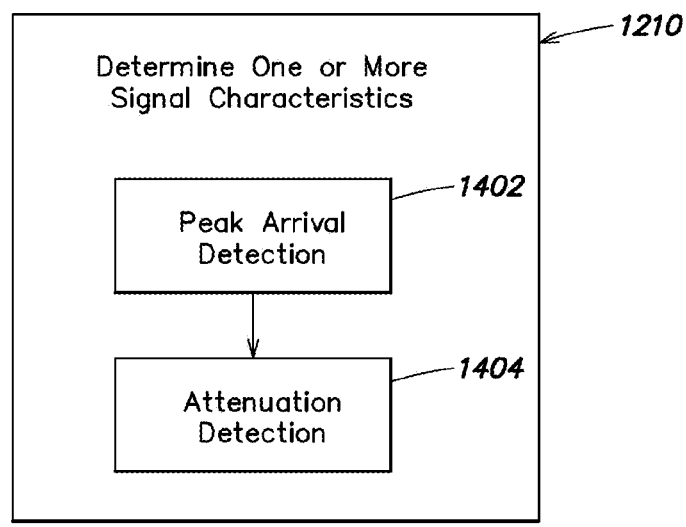
FIG. 14 illustrates a non-limiting example of an implementation of a portion of the methods of FIGS. 12 and 13.

FIG. 14 illustrates a non-limiting example of processing which may be used to determine one or more signal characteristics at 1210. As shown, determination of one or more signal characteristics may comprise performing peak arrival detection at 1402 and attenuation detection at 1404, as non-limiting examples. Detection of a signal peak itself ("peak detection") may be performed together with attenuation detection, or may be performed as a separate step in some non-limiting embodiments. The order of processing need not be the same as that illustrated, as, for example, the order may be reversed from that shown in FIG. 14.

In some embodiments, peak detection may be performed at least in part by identifying a portion of the received signal that may contain at least one peak. The process of identifying a portion of the signal that may contain the peak is referred to as a "peak arrival detection" process. Peak arrival detection may be performed using any of various suitable methods. As one non-limiting example, peak arrival detection may be performed by using a statistical model to detect a change in characteristics of the received signal. One non-limiting example of such a model is any model in the family of so-called autoregressive models, which includes, but is not limited to, autoregressive models, noise-compensated autoregressive models, lattice models, autoregressive moving average models, etc. Accordingly, in some embodiments, peak arrival detection may be performed by fitting a model in the family of autoregressive models to at least a portion of the received signal. This may be done in any suitable way and, for example, may be done by using least-squares techniques such as the Yule-Walker algorithm, Burg algorithm, covariance method, correlation method, etc. An information criterion (e.g., Akaike information criterion) may be used to select model order. Though, it should be appreciated that any other statistical model may be used to detect a change in characteristics of the received signal, as aspects of the present application are not limited in this respect. Further, any other techniques may be used such as techniques based on detecting a percentage of a maximum value. Again, other techniques may also suitably be used, as these represent non-limiting examples.

In some embodiments, after the portion of a received signal containing a peak is identified using a peak arrival detection step, the location of a peak may be identified using any suitable peak detection technique. Non-limiting examples of suitable peak detection methods include techniques based on group delay processing, sinc interpolation, parabolic processing, detecting a maximum value, and/or cubic interpolation, among others. Though, it should be appreciated that, in some embodiments, the location of a peak may be identified without a peak arrival detection step. For example, any of the above-identified peak detection methods may be applied directly to the received signal.

Any suitable techniques for performing attenuation detection may be implemented. In some embodiments, an amount of attenuation may be determined by using one or more amplitudes of the received signal and one or more reference amplitudes. The amount of attenuation may be determined by computing a ratio (or a log of the ratio) between the amplitude(s) of the received signal and the reference amplitude(s) and comparing the obtained ratio (or a logarithm of the ratio) with a threshold. An amplitude of the received signal may be an amplitude of the received signal at a specific location, such as at a location of a peak (i.e., the amplitude of the peak). An amplitude of the received signal may be an average absolute amplitude computed for a set of locations, such as over a portion of a signal corresponding to a pulse (e.g., the portion identified by a peak arrival detection technique or any other suitable portion). The reference amplitude(s) may be computed from a reference signal in a same manner as amplitude(s) of the received signal are computed. The reference signal may be the transmitted signal or, in some embodiments, may be a reference signal obtained by transmitting a signal from an ultrasound source to an ultrasound sensor when the imaging device is not imaging a subject. Though, it should be appreciated that an amount of attenuation may be determined using other techniques and, in some embodiments, may be determined by computing a ratio of a function of the amplitude(s) of the received signal and a function of the reference amplitude(s). Any suitable function of the amplitude(s) may be used (e.g., square of the magnitude, cube of the magnitude, logarithm of the magnitude, etc.), as aspects of the invention described herein are not limited in this respect. In other embodiments, an amount of attenuation may be determined by using one or more power values of the received signal and one or more reference power values of a reference signal.

Figure 15:
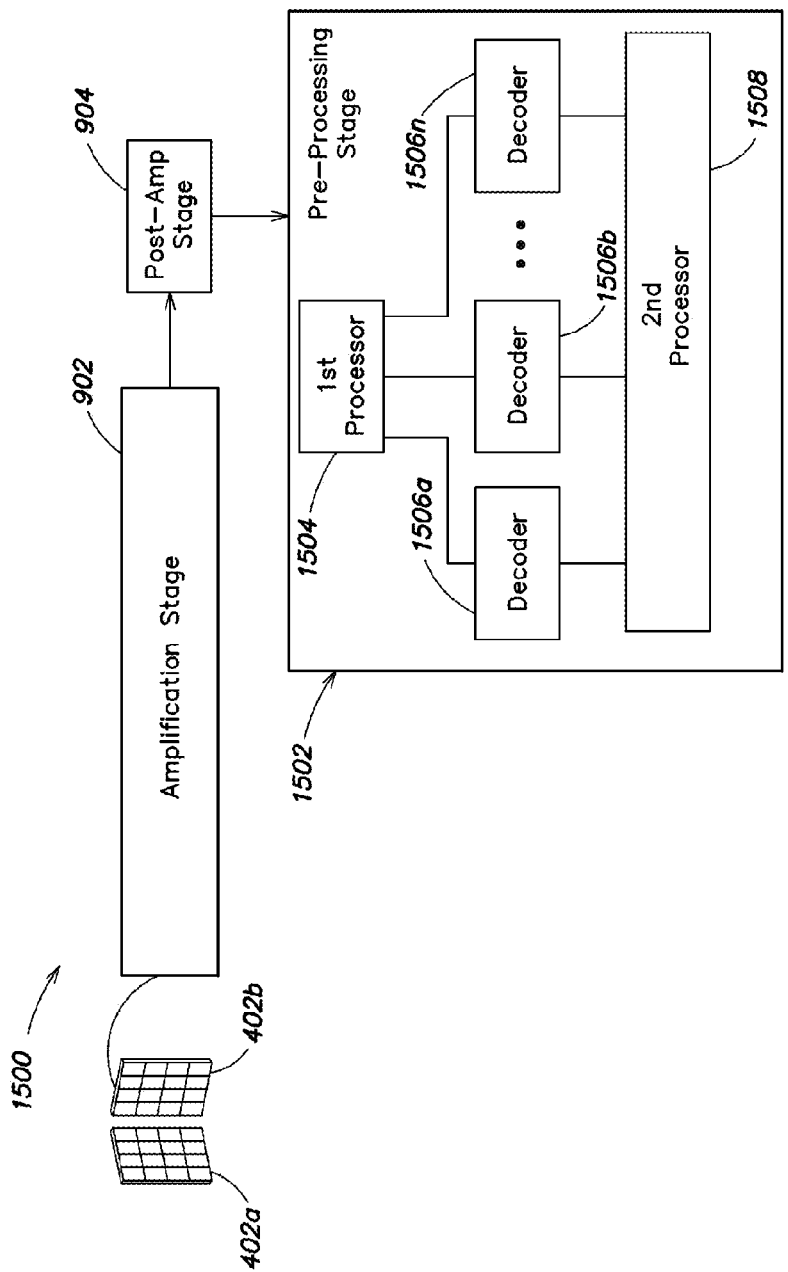
FIG. 15 illustrates in block diagram form a signal receiver suitable for performing CDMA processing, according to a non-limiting embodiment.

The processing illustrated in FIGS. 13 and 14 may be performed by any suitable computer or hardware. As a non-limiting example, pre-processing circuitry coupled to a receiver or otherwise configured as part of a signal receive chain may implement one or more of the processes illustrated. A non-limiting example is illustrated in FIG. 15, which expands upon the signal receive chain 900 of FIG. 9. As illustrated, the signal receive chain 1500 comprises, in addition to those components of the signal receive chain 900, a pre-processing stage 1502. The pre-processing stage 1502 in this non-limiting example comprises a first processor 1504, decoders 1506a, 1506b, . . . , 1506n, and a second processor 1508. In this non-limiting example, the first processor 1504 may perform operations such as matched filtering, decimation, Hilbert transforms, linear processing and/or any other suitable processing. In a non-limiting embodiment, the processor 1504 may be a digital signal processor (DSP). Non-limiting alternatives include one or more FPGA boards, each of which may process signals from one or more signal receive chains.

The decoders 1506a-1506n may decode signals in a CDMA context. Thus, the decoders 1506a-1506n may be any suitable type of decoders. Additionally, the number of decoders 1506a-1506n may depend on the number of potential codes used in transmission of signals within the system. For example, as a non-limiting illustration, the number of decoders 1506a-1506n may correspond to the number of elements (e.g., of array 402a) configured to transmit ultrasound signals. As a non-limiting example, if an array of ultrasound elements includes 32 ultrasound elements, there may be 32 decoders 1506a-1506n.

The decoders 1506a-1506n may decode signals and provide their outputs to a second processor 1508, which may perform functions such as those previously described with respect to peak detection, peak arrival detection, and/or attenuation detection, among others. The processor 1508 may be any suitable type of processor, including a DSP, a plurality of processing boards, one or more FPGAs, and/or any other suitable processor. Also, it should be appreciated that the circuitry of pre-processing stage 1502 may, in some non-limiting embodiments, be implemented with a single processor (e.g., a single DSP).

Thus, in view of the foregoing description, it should be appreciated that implementing CDMA represents one manner in which a large number of distinct signals may be sent and received by a system of the types described herein in a relatively short time. The use of CDMA may therefore allow for a large number of measurements of a subject within a relatively short period of time, and may allow for rapid reconstruction of volumetric images of the subject. In some embodiments where CDMA techniques are implemented, a frame rate of up to 5 frames per second, a frame rate of up to 10 frames per second, a frame rate of up to 25 frames per second, a frame rate of up to 50 frames per second, a frame rate of up to 75 frames per second, a frame rate of up to 100 frames per second, a frame rate of up to 125 frames per second may be achieved.

CDMA, however, is not the only manner in which a large number of distinct measurements may be made of a subject using systems of the type described herein in a relatively short time. As an alternative or in addition to CDMA, one or more time division multiple access (TDMA) techniques may be implemented. According to some embodiments of the present application, TDMA may be implemented with a system including opposed arrays of ultrasound elements (e.g., a system of the type illustrated in FIG. 1A), by activating a single ultrasound element configured as a sensor (or, in other embodiments, multiple ultrasound elements configured as sensors), and then sequentially transmitting signals from the ultrasound elements of the apparatus configured as sources. A non-limiting example is illustrated with respect to FIG. 16.

Figure 16:
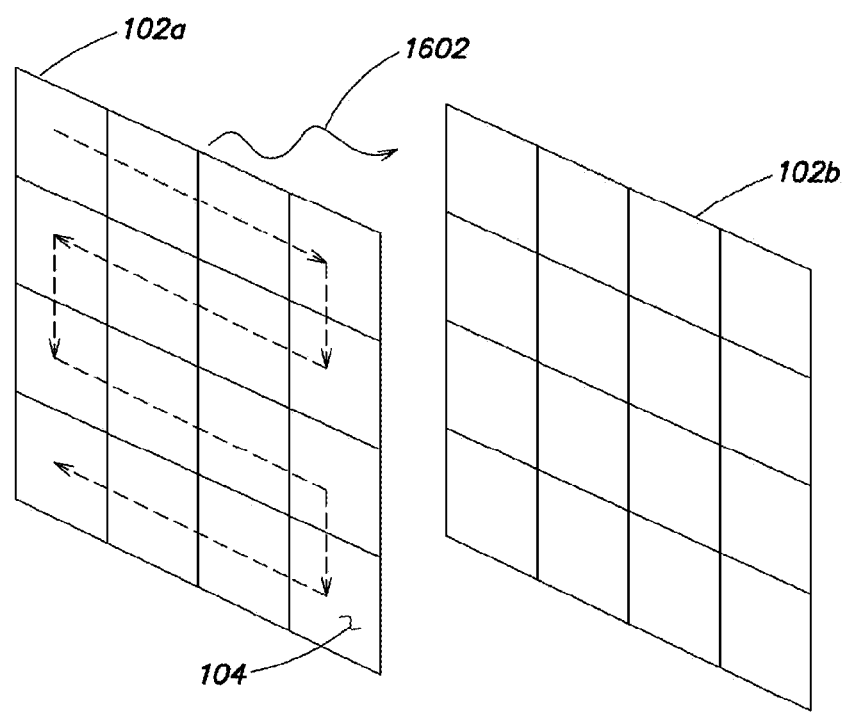
FIG. 16 illustrates a system configuration for performing time division multiple access (TDMA) processing according to an embodiment of the present application.

As shown, the two arrays 102a and 102b are arranged in an opposing configuration. At any given time, one or more of the elements of the array 102b may be activated and configured as sensors to receive signals 1602 transmitted from the elements of the array 102a. While that sensor is activated, a scan of the elements of the array 102a may be performed, whereby each of the elements in the scan sequence transmits one or more waveforms that the activated sensor may be configured to receive. Elements 104 of array 102a may be scanned in any suitable way. In some embodiments, the elements may be scanned using a raster scan pattern, whereby the scan sequence comprises groups of neighboring elements. FIG. 16 illustrates a non-limiting example of scanning the elements 104 of the array 102a using a raster scan pattern, in which the raster scan pattern is illustrated by the dashed arrows. A signal is sent sequentially from each of the elements of the array 102a in the non-limiting embodiment shown. However, elements may be scanned using any suitable scan pattern, as embodiments of the application described herein are not limited in this respect. For example, in some embodiments, elements may be scanned by using a scan pattern, whereby the scan sequence comprises non-neighboring elements so that after one element transmits a signal, another element, not adjacent to the first element, transmits the next signal. Such embodiments may be used to keep power deposition levels within specified requirements.

In some embodiments in which TDMA is employed, after an ultrasound source has finished transmitting a waveform, there may be a period of time before any other ultrasound source begins to transmit another waveform. Thus, there may be no ultrasound source transmitting during this period of time. The period of time may be any suitable period of time and may be determined based at least in part on the geometry of the sources and sensors in the imaging device. As an illustrative example, the period of time may be sufficiently long such that a waveform transmitted from an ultrasound source may be received by an ultrasound sensor without interference.

The following example may be used as a guide to determining a suitable temporal spacing of signals in a TDMA context to avoid interference of the signals. Assuming for purposes of this example that the volume being imaged is a medium with minimum speed of sound of $c_{min}$ and maximum speed of sound $c_{max}$, then for an imaging system with arrays separated by a distance l and with physical dimensions w and h, the temporal gap $\Delta t$ between successive pulses to ensure no overlap of the pulses (i.e., the time between transmission of the tail end of one pulse and the start of the next pulse) is approximately $\Delta t > [\text{sqrt}(l^2+w^2+h^2)/c_{min} - l/c_{max}]$. If the pulse length is given by T, then the period of the pulse train may be $T+\Delta t$. Thus, as an example, for an imaging system in which an array of ultrasound sources is separated from an array of ultrasound sensors by 20 cm, and in which each of the arrays has dimensions of 10 cm×10 cm, the temporal gap for typical tissue speeds (1600 m/s maximum) is about 30 μs. In such an embodiment, it may be preferable to use a temporal gap of approximately 50 μs to ensure no overlap of transmitted signals.

It should be appreciated that the formula provided above for determining a suitable time delay $\Delta t$ is a non-limiting example. For example, a more conservative approach is to ignore the last term ($l/c_{max}$) of the above-noted formula, and instead use $\Delta t > [\text{sqrt}(l^2+w^2+h^2)/c_{min}]$.

In general, when TDMA is employed, the transmitted signals may be transmitted at any suitable times with respect to each other. As described, one option is to transmit signals sequentially, though not all embodiments are limited in that respect. In such embodiments, signals to be transmitted sequentially may be separated in time by approximately 1-2 times the time necessary to avoid interference among sequentially transmitted waveforms. For example, if a transmitted waveform has a duration of approximately 80 microseconds, a total "window" time allotted to each ultrasound source may be approximately 200 microseconds. In other words, the beginning of a waveform sent by a first ultrasound source may be sent approximately 200 microseconds prior to the beginning of a waveform sent by a second ultrasound source. Other timing scenarios are also possible, as that described is a non-limiting example.

In the non-limiting embodiment of FIG. 16, each element 104 of the array 102a may transmit substantially the same signal as the other elements of the array 102a. However, due to the sequential nature of the transmission, a determination may be made upon receipt of the signals (e.g., by suitable front-end circuitry) as to which element of the array 102a transmitted a particular signal, i.e., a received signal may be discriminated from another received signal. After all the elements of the array 102a have transmitted a signal, a new element of the array 102b may be activated and configured as a sensor to receive signals transmitted from the array 102a, while the initially activated element of array 102b may be deactivated (e.g., using a demultiplexer or any other suitable circuitry). Then, another scan of the elements of array 102a may be performed. A non-limiting example of this type of operation is illustrated with respect to the flowchart of FIG. 17A.

As shown, the method 1700 may comprise activating a sensor element at 1702. The sensor element may be an element of array 102b, configured to receive ultrasound signals transmitted from elements of an array 102a configured as ultrasound sources. At 1704, signals may be transmitted sequentially from three or more elements of an array arranged in at least two dimensions. The transmitted signals may be received at 1706 by the activated sensor element. The sensor element may be deactivated at 1708 after all the transmitted signals have been detected. At 1710 a decision may be made as to whether the activated sensor element was the last sensor element. If not, the method may proceed back to 1702, at which the next sensor element of the array 102*b* may be activated, and the method may be repeated. After the last sensor element has been deactivated (i.e., when the answer to the question at 1710 is "yes"), further processing of the received signals may be performed, such as the previously described pulse compression at 1302, determination of one or more signal characteristics at 1210, and reconstruction of one or more images of a subject at 1212.

Figure 17A:
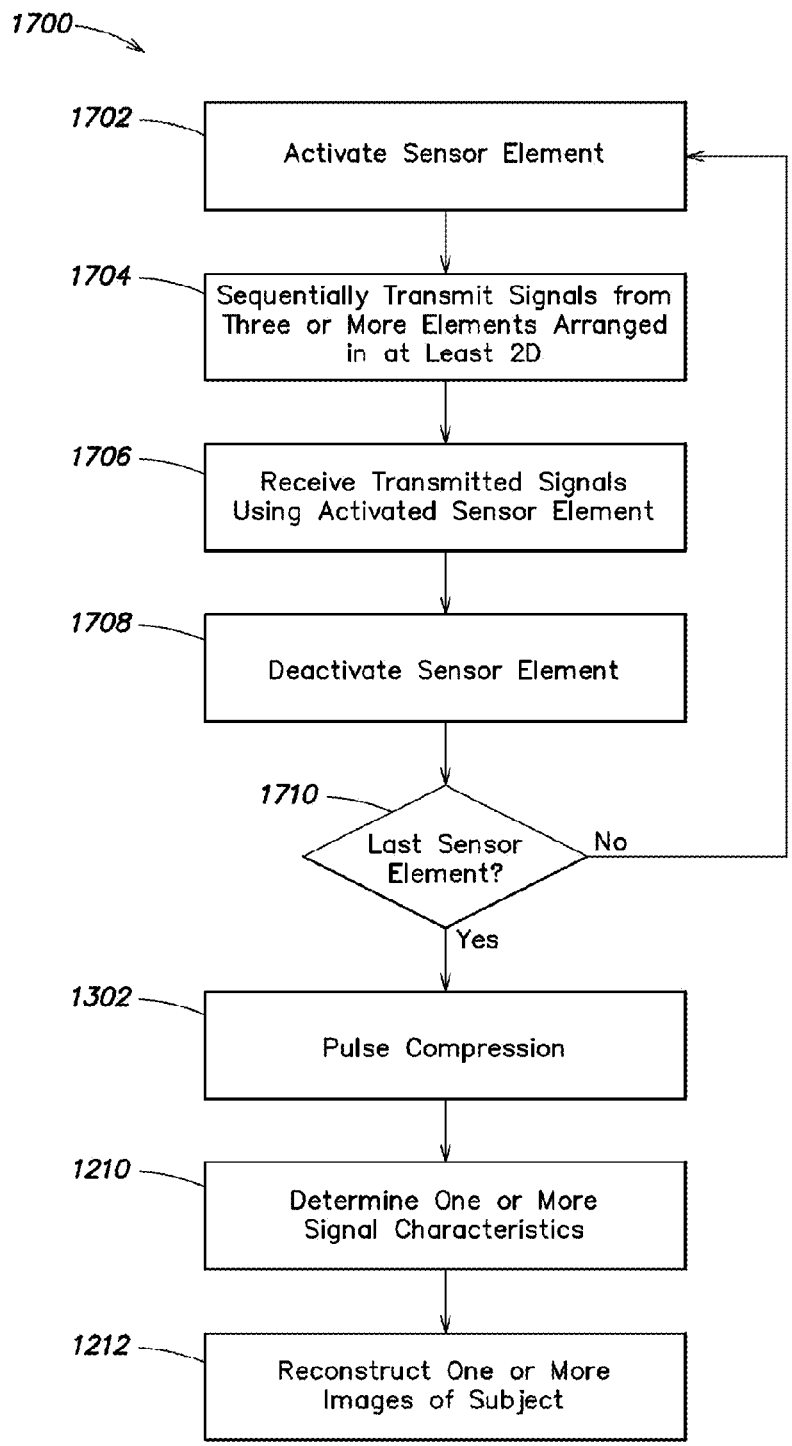
FIGS. 17A and 17B are flowcharts a methods of implementing TDMA processing, according to non-limiting embodiments.

It should be appreciated that FIG. 17A illustrates a non-limiting embodiment, and that variations of the methodology are possible. For example, performance of further processing such as application of a pulse compression filter, determination of one or more signal characteristics, and/or reconstruction of one or more images need not necessarily wait until the last of the sensor elements has been activated and received the transmitted signals. Rather, processing of received signals may occur in parallel to receipt of further transmitted signals by other activated sensor elements. Other variations on the relative timing of receipt of signals and processing of the signals are also possible.

Moreover, processing of received signals (e.g., linear processing of the types described herein) may be performed by circuitry positioned in front of any demultiplexing circuitry connected to the elements of the receiving array. For example, a demultiplexer may be coupled to the ultrasound elements to provide the time-varying activation of the elements as sensors. However, linear processing circuitry positioned prior to the demultiplexer may perform linear processing on received signals prior to them reaching the demultiplexer. In this manner, the amount of linear processing circuitry may be reduced in some embodiments.

Figure 17B:
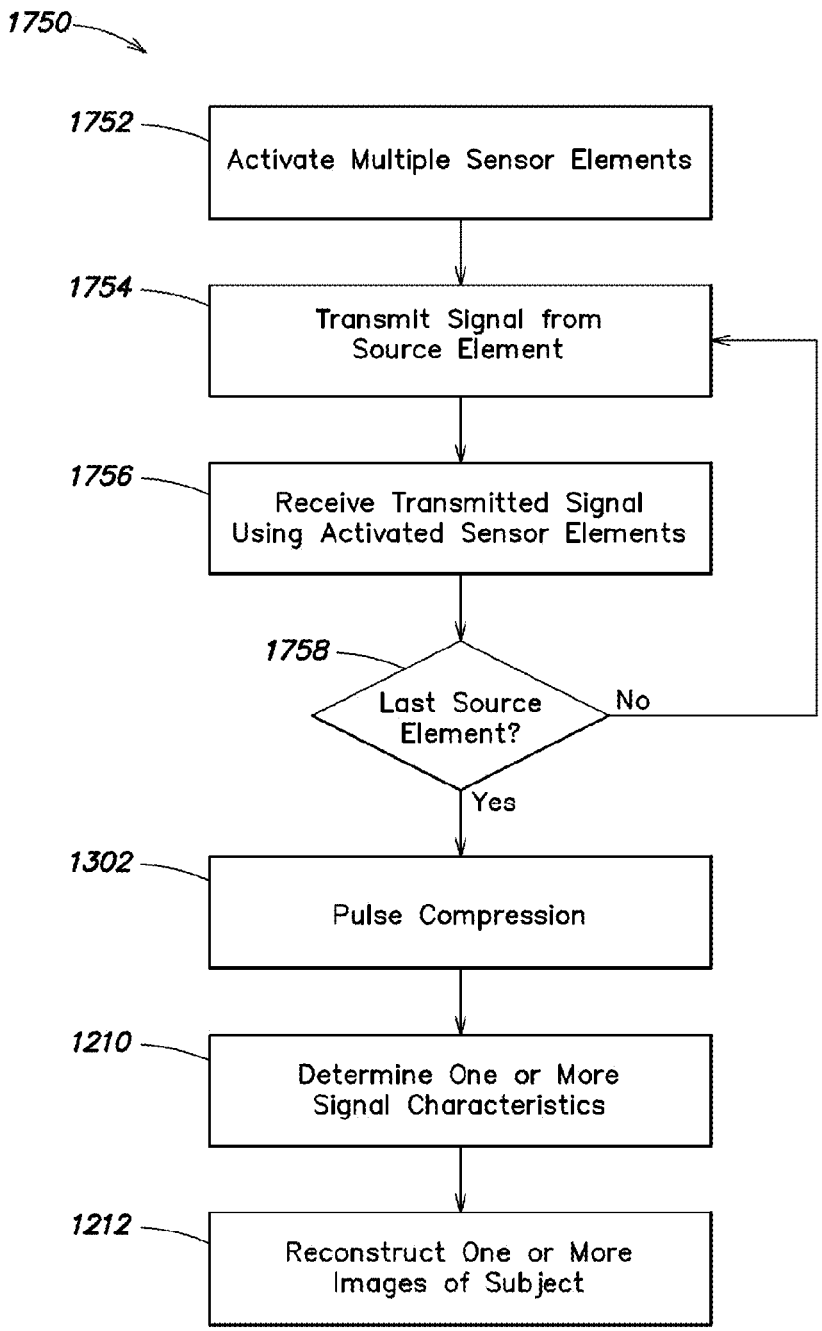

FIG. 17B illustrates an alternative implementation of TDMA according to an embodiment. The illustrated method 1750 may be the preferred manner of implementing TDMA in some embodiments. The method 1750 differs from the method 1700 of FIG. 17A in that, rather than activating a single sensor element at a time as in the method 1700, multiple sensors elements may be activated simultaneously and thus may receive signals from source elements simultaneously. In a non-limiting embodiment, all sensor elements of an apparatus may be activated simultaneously, though not all implementations of the method 1750 are limited in this respect.

As shown, the method 1750 begins at 1752 with the activation of multiple sensor elements, for example two or more sensor elements. In some embodiments, all sensors elements of an arrangement may be activated simultaneously at 1752. A signal may be transmitted from a source element at 1754. The transmitted signal may be received at 1756 by all the activated sensor elements, i.e., by all the sensor elements activated in 1752.

A determination may then be made at 1758 whether the source element from which the signal was transmitted was the last source element to be used. If the answer is "No", then the method may return to 1754 to transmit a signal from a different source element. In this manner, the method 1750 may be iterative, and may implement any suitable number of iterations.

If, however, a determination is made at 1758 that the source element from which the signal was transmitted was the last source element to be used, i.e., if the answer is "Yes", then the method 1750 may proceed to 1302, 1210, and 1212 as shown in FIG. 17B and as previously described in connection with FIG. 17A.

When the method 1750 follows the iteration path from 1758 back to 1754, any suitable source element may be used upon returning to 1754 to transmit the next signal. In some embodiments, the source element may be a neighboring element to that used during the previous occurrence of 1754. In some embodiments, the method may loop back to reactivate the first source element of the arrangement of elements, for example, after a complete scan has been performed. Alternatively, as previous described, any suitable subset of source elements of an arrangement of elements may be activated in any desired order as part of a scan pattern. Thus, when the method loops back from 1758 to 1754, any suitable source element may be used to transmit the subsequent signal.

As with the method 1700 of FIG. 17A, it should be appreciated that the method 1750 of FIG. 17B is also non-limiting, and that alternatives are possible. For example, performance of further processing such as application of a pulse compression filter, determination of one or more signal characteristics, and/or reconstruction of one or more images need not necessarily wait until the last of the source elements has been used to transmit a signal and the signal has been received by the activated sensor elements. Rather, processing of received signals may occur in parallel to receipt of further transmitted signals transmitted by subsequent source elements. Other variations on the relative timing of receipt of signals and processing of the signals are also possible.

As with the previously described CDMA scheme, it should be appreciated that according to the present aspect of the application, TDMA may be used suitably to provide distinct measurements of a subject via communication between pairs of source elements and sensor elements with multiple source elements arranged in at least two dimensions, i.e., the signals received by sensor elements may be discriminated to determine from which source element the signals were emitted. Thus, either the CDMA previously described or the TDMA according to the present aspect may be used to provide volumetric imaging of a subject, according to non-limiting embodiments.

It should also be appreciated that TDMA may be applied without transmitting signals from all elements of an arrangement of elements configured as sources and/or without receiving signals with all elements of an arrangement of ultrasound elements configured as sensors. Rather, any desired number and arrangement of elements configured as sources may be used to transmit signals at different times from each other, and any desired number and arrangement of ultrasound elements configured as sensors may be used to receive the transmitted signals. For example, in some embodiments it may be desirable to transmit signals only from a subset of an array of ultrasound elements configured as sources. Use of only a subset of sources and/or a subset of sensors may provide higher speed operation in some embodiments. Thus, the aspects described herein are not limited to using all sources and sensors of an arrangement of sources and/or sensors.

Furthermore, according to an aspect of the present application, a combination of CDMA and TDMA techniques may be employed. As a non-limiting example, multiple subsets of ultrasound elements of an array of ultrasound elements may be sequentially activated (or otherwise activated at different times) to transmit ultrasound signals. The ultrasound elements within each subset may transmit distinctly coded signals, while elements of a subsequently activated subset of elements configured as sources may utilize the same or different codes as those utilized by a previously activated subset, but at a different time. In this manner, a combination of the benefits achieved via CDMA and TDMA techniques may be obtained. For example, CDMA techniques may provide faster transmission and collection of data than that of TDMA, for example, because according to an aspect in which CDMA techniques are employed, ultrasound signals from multiple elements configured as sources may be transmitted concurrently and multiple ultrasound elements configured as sensors may concurrently receive signals. However, the circuitry and systems utilized to implement CDMA operations may be more complex than that of TDMA, for example, because of the complexity of decoding involved. By contrast, TDMA may provide relatively slower operation than that of CDMA (e.g., lower frame rates), but may provide benefits in terms of simplicity of system design. Implementing a combination of TDMA and CDMA as explained above may allow for achieving a beneficial intersection between speed of operation and complexity of circuit design.

It should be appreciated that operation of a system according to TDMA principles may be achieved using any suitable circuitry, non-limiting examples of which have been previously described. For example, signal transmit chains such as those illustrated in FIGS. 7A-7C may be employed. Signal receive chains such as those of FIGS. 9, 10, and 11A-11D may be employed. The signal receive chain of FIG. 15 may be altered in a TDMA context, for example, by removal of the decoders 1506a-1506n. In such a scenario, the pre-processing stage 1502 may comprise at least one processor (e.g., processors 1504 and 1508 may be combined) or any suitable hardware configuration for performing the functions previously described absent decoding of the type performed by decoders 1506a-1506n. Thus, the various aspects in which TDMA techniques are employed are not limited to the specific circuitry used.

Frequency division multiplexing is a further manner of operation, which may be implemented according to an aspect of the present application. Frequency division multiplexing may be implemented in any suitable manner. For example, sources (e.g., of array 102a) may first transmit signals in a first band having a first center frequency and subsequently transmit signals in a second band having a second center frequency. Alternatively, different subsets of an arrangement of ultrasound elements may transmit at different bands of frequencies. A band of frequencies may consist of only one frequency or have multiple frequencies. Thus, those aspects described herein in which frequency division techniques are used are not limited to the particular manner in which frequency division operation is achieved.

Moreover, frequency division techniques may be employed in combination with CDMA and/or TDMA in any suitable manner. As one non-limiting example, a frequency hopping code division multiple access (FH-CDMA) technique may be used. In some embodiments, orthogonal frequency division multiple access (OFDMA) may be implemented, which is a technique of having different transmitters occupying different sets of frequencies at different times. That is, for one pulse, a single transmitter (or group of transmitters) may occupy a certain set of frequencies, while another transmitter (or group of transmitters) occupies a different (orthogonal) set of frequencies. The occupied frequencies then change on the next pulse according to a predetermined code sequence.

Systems and methods of the types described herein may provide for rapid collection of large amounts of data regarding a volume or 3D subject of interest. As also described previously, high resolution volumetric images may be generated rapidly. Also, in at least some embodiments, the circuitry implemented by systems of the types described herein may have beneficial characteristics. For example, the signal chains described herein may be linear (e.g., a linear signal transmit chain and/or linear signal receive chain), which may allow for rapid and efficient signal processing and robust operation. Other benefits may also be achieved.

Reconstructed images, such as those produced as part of the methods of FIGS. 12, 13, 17A and 17B may be used for any suitable purpose(s), examples of which are described. In some embodiments, one or more images (e.g., one or more volumetric images) of a subject may be used to classify the subject or a portion of the subject. For example, imaged subjects may be classified as a type of tissue, a type of organ (e.g., kidney, liver, etc.), or may be classified according to any desired classes. Classification, when performed, may be based on detected shape in some embodiments (e.g., by looking at coefficients of spherical norms, shape metrics, shape descriptors (e.g., spherical harmonics), or any features characterizing shape, as examples). In some embodiments, classification may be performed based on collected data values (e.g., time-of-flight values, attenuation values, speed-of-sound values, dispersion coefficients, etc.). In some embodiments, classification may be based on changes in (e.g., gradients) these types of data values. Other manners of classification are also possible.

Various aspects of the present application have been described with respect to opposed arrays of ultrasound elements. However, it should be appreciated that various aspects of the present application are not limited to use with opposed arrays of ultrasound elements. Rather, various alterations are possible. Several are now described.

Figure 18A:
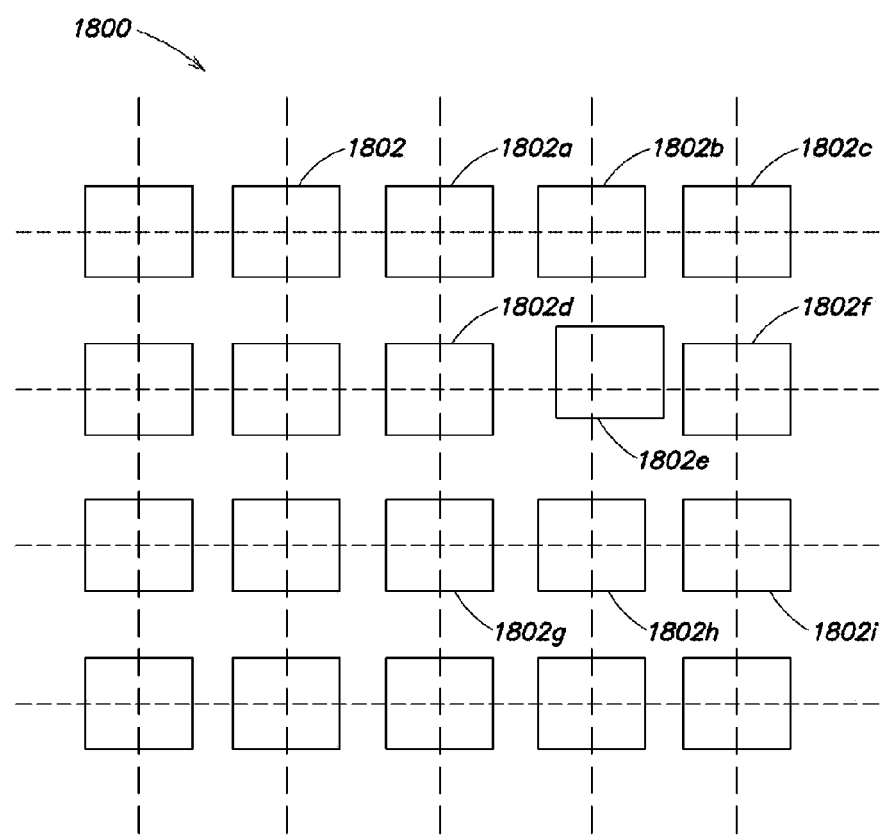
FIGS. 18A-18D illustrate irregular arrangements of radiation (e.g., ultrasound) elements, according to non-limiting embodiments.

As has been explained, for example, with respect to FIG. 1A, one or more aspects of the present application may apply to systems including opposed arrangements of ultrasound elements forming arrays. However, arrays represent a non-limiting configuration. For instance, the ultrasound elements need not be arranged in an array of evenly (or uniformly) spaced elements, but rather may assume practically any arrangement in which the elements are arranged in at least two dimensions. A first non-limiting alternative example is illustrated in FIG. 18A, in which the ultrasound elements of a single arrangement are arranged irregularly, i.e., not all the ultrasound elements are spaced at regular (uniform in some embodiments) intervals with respect to neighboring ultrasound elements. As shown, the arrangement 1800 of ultrasound elements 1802 includes, among others, ultrasound elements 1802a-1802i. Uniformly spaced dashed grid lines are also illustrated. As shown, ultrasound element 1802e is not spaced at a regular distance from its neighboring ultrasound elements 1802a-1802d and 1802f-1802i. Rather, in the non-limiting embodiment illustrated, ultrasound element 1802e is disposed more closely to ultrasound elements 1802b, 1802c, and 1802f than it is, for example, to ultrasound elements 1802d, 1802g, and 1802h. As shown, while the other ultrasound elements of the illustrated arrangement 1800 are centered on grid lines, ultrasound element 1802e is not. Although the majority of the ultrasound elements of the arrangement 1800 may be regularly spaced, the displacement of ultrasound element 1802e from a regular spacing means that the arrangement 1800 is an irregular arrangement.

In some embodiments, positions of elements in an arrangement of irregularly-spaced elements may be derived from positions of regularly-arranged points in a higher-dimensional space. The positions of elements may be derived from the positions of regularly-arranged points by mapping or projecting the positions of the regularly-arranged points to the lower-dimensional space of the arrangement of irregularly-spaced elements. In some embodiments, for example, the spacing of elements in an arrangement of irregularly-spaced elements may be obtained at least in part by arranging, regularly, a set of points on a three-dimensional object (e.g. a sphere, a cylinder, an ellipsoid, etc.) and projecting this set of points onto a plane to obtain a set of positions for elements in the arrangement of irregularly-spaced elements. A set of points may be regularly arranged on a three-dimensional object in any suitable way. As a non-limiting example, a set of points may be regularly arranged on a sphere by being placed with uniform spacing along one or more great circles of the sphere, by being placed at points of intersection between the sphere and a polygon (e.g., icosahedron), being regularly placed with respect to solid angles of the sphere, and/or in any other suitable way. Though, it should be appreciated that the set of points is not limited to being regularly arranged on a three-dimensional object and may be regularly arranged on a higher-dimensional object of any suitable dimension (e.g., a hypersphere of any suitable dimension greater than or equal to three). The set of points may be projected using a stereographic projection, a linear projection, or any other suitable projection technique or techniques, as aspects of the disclosure provided herein are not limited in this respect. It should be appreciated that a projection of regularly arranged points from a higher-dimensional space (e.g., from three-dimensional space) to a lower-dimensional space (e.g., a plane) may be irregular.

In some embodiments, an irregular arrangement of ultrasound elements may conform to a Penrose tiling scheme. In some embodiments, an irregular arrangement of ultrasound elements may exhibit varying spacing of elements within the arrangement, such as greater spacing of elements toward the center of the arrangement and closer spacing of elements toward the edges (perimeter) of the arrangement.

In the non-limiting embodiment of FIG. 18A, only one ultrasound element (i.e., ultrasound element 1802*e*) is disposed at an irregular spacing with respect to the other ultrasound elements of the arrangement. However, it should be appreciated that irregular spacing does not require any particular number or percentage of ultrasound elements of an arrangement to be irregularly spaced with respect to the other ultrasound elements. Rather, an arrangement of ultrasound elements may be irregular if any one or more ultrasound elements of the arrangement are irregularly spaced from neighboring elements. In some embodiments, a substantial percentage of ultrasound elements of an ultrasound element arrangement (configured as sources or sensors) may be regularly spaced with respect to neighboring ultrasound elements. By contrast, in some embodiments a substantial percentage of ultrasound elements of an ultrasound element arrangement (configured as sources or sensors) may be irregularly spaced with respect to neighboring ultrasound elements. In some embodiments, a majority of ultrasound elements of an ultrasound element arrangement (configured as sources or sensors) may be irregularly spaced with respect to neighboring ultrasound elements.

Figure 18B:
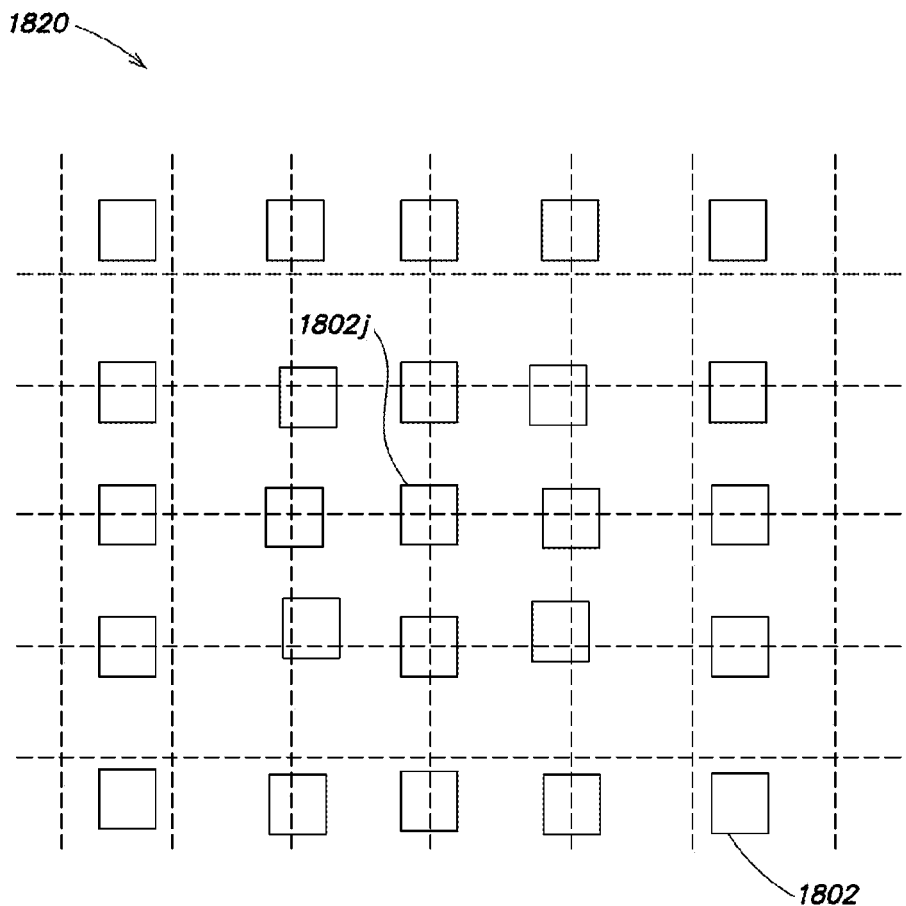
Figure 18C:
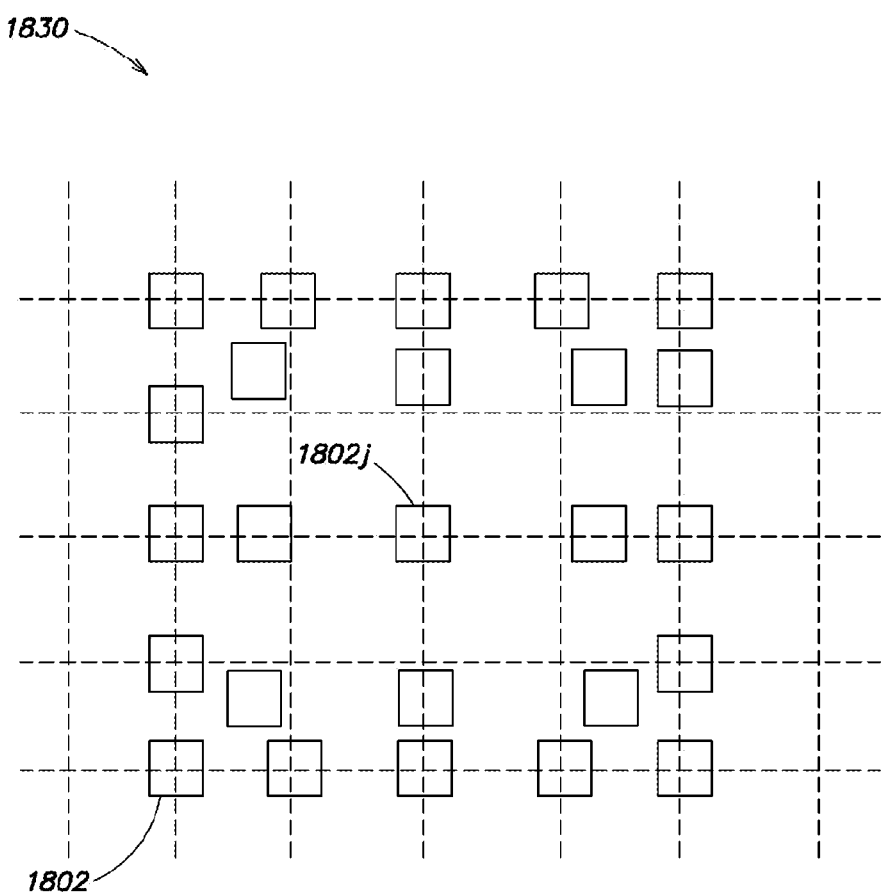

FIGS. 18B and 18C illustrate alternative irregular arrangements to that of FIG. 18A, with each figure including a grid defined by uniformly spaced grid lines for purposes of illustration. The arrangement 1820 of FIG. 18B includes ultrasound elements 1802 that are spaced more closely together toward the center of the arrangement (i.e., toward element 1802*j* in the center of the arrangement 1820) and more widely apart toward the edges of the arrangement. Thus, as shown, the spacing between neighboring ultrasound elements of the arrangement 1820 increases moving outwardly from the center of the arrangement.

FIG. 18C illustrates an irregular arrangement 1830 of ultrasound elements 1802 that are spaced more closely together toward the edges of the arrangement and more widely apart toward the center of the arrangement (i.e., toward ultrasound element 1802*j*).

Figure 18D:
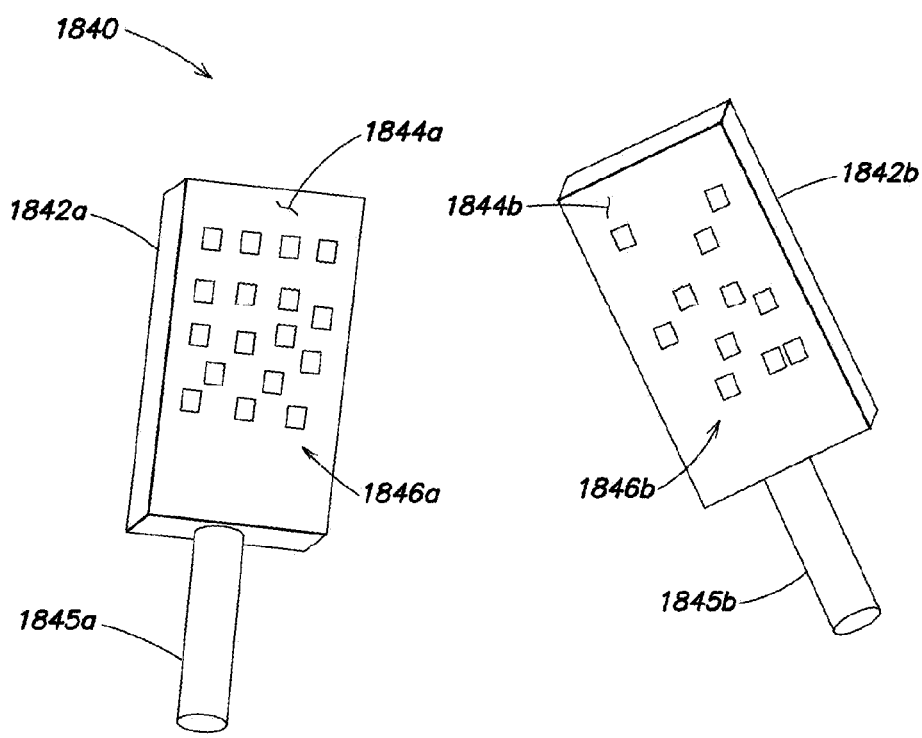

According to an embodiment of the present application, arrangements of ultrasound elements used in combination, for example for transmissive ultrasound imaging, may be irregular and need not have identical layouts. FIG. 18D illustrates a non-limiting example. The system 1840 includes a first paddle 1842*a* and a second paddle 1842*b*, each including a respective support 1844*a* and 1844*b* and a respective handle 1845*a* and 1845*b*. Each of the paddles also includes a respective arrangement 1846*a* and 1846*b* of ultrasound elements. The arrangements may be configured to operate in combination in a transmissive ultrasound imaging modality. Yet, as shown, each of the two arrangements is irregular and they are not irregular in the same manner, i.e., the arrangements do not exhibit identical element layout to each other. As illustrated, the two arrangements 1846*a* and 1846*b* also have different numbers of ultrasound elements than each other. Even so, using one or more of the operating techniques described herein, the arrangements 1846*a* and 1846*b* may be used in combination for ultrasound imaging (e.g., with the arrangement 1846*a* including ultrasound elements configured as ultrasound sources and the arrangement 1846*b* including ultrasound elements configured as ultrasound sensors) or other suitable purposes.

A further potential alternative to use of arrays of ultrasound elements is to use a random arrangement of ultrasound elements. As used herein, a random arrangement is one in which there is no generally discernible regular spacing between elements of the arrangement, irrespective of whether the elements are arranged in a mathematically random manner. Thus, a random arrangement, as that term is used herein, represents one example of an irregular arrangement, but not all irregular arrangements are random arrangements.

Moreover, it should be appreciated that an irregular (e.g., random) arrangement of ultrasound elements may be effectively created by operating only a subset of ultrasound elements of an arrangement, wherein the subset of elements constitutes a random arrangement even while the overall arrangement may not constitute a random arrangement.

Figure 19:
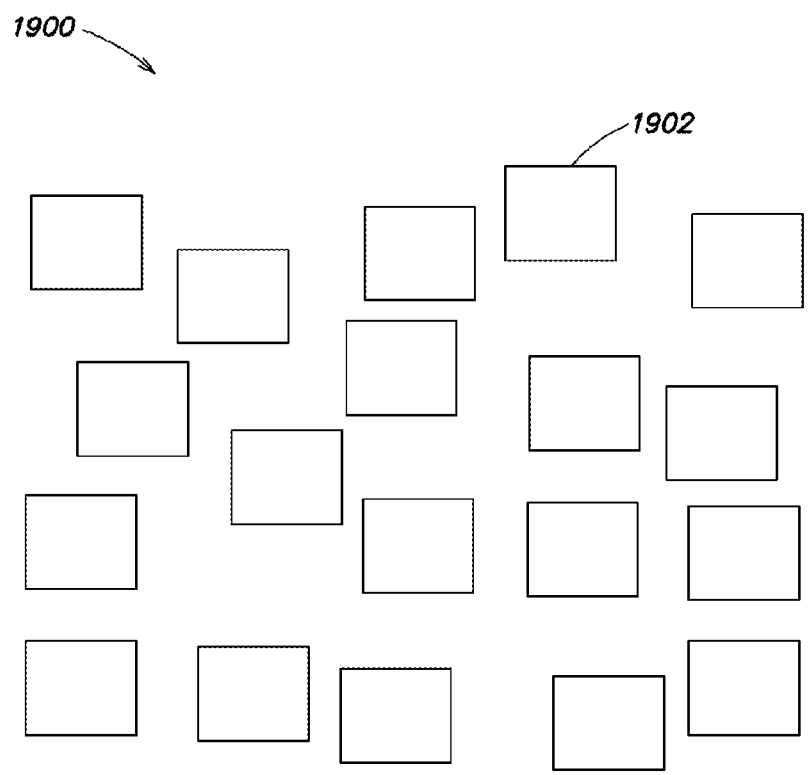
FIG. 19 illustrates a random arrangement of radiation elements, according to a non-limiting embodiment.

A non-limiting example of a random arrangement of ultrasound elements is illustrated in FIG. 19 as arrangement 1900. As shown, there is no generally discernible regular spacing between the ultrasound elements 1902 of the arrangement 1900. As with the foregoing explanation of an irregular arrangement, according to an aspect of the present application simply knowing the relative positions of the ultrasound elements 1902 may be sufficient to allow for suitable discriminate and processing of data collected by the arrangement.

The irregular and random arrangements of FIGS. 18A-18D and 19 may provide one or more benefits. For example, the ability to use such arrangements of ultrasound elements while collecting 3D data may relax design constraints and manufacturing tolerances with respect to construction of the arrangements of ultrasound elements (and therefore the devices in which such arrangements may be embodied). As another example, the irregular spacing of ultrasound sources and/or sensors may lead to fewer artifacts in images calculated from measurements obtained by using ultrasound sources/sensors so spaced. The irregular spacing may lead to fewer artifacts that ordinarily result from symmetry in regular sensor arrangements.

As will be described further below, it may be desirable to know the relative positions of ultrasound elements of an arrangement, for example, in interpreting data collected by the arrangement and producing images. Utilizing an arrangement of ultrasound elements regularly spaced (e.g., an array as in FIG. 1A) may simplify analysis of data collected by the arrangement, but is not a necessity in all aspects of the present application. Rather, as will be described further below, knowing the relative positions of ultrasound elements of an arrangement, whether or not those positions represent a regular spacing, may be sufficient to allow for suitable discrimination and analysis of data collected by the arrangement. Thus, knowing the relative positions of ultrasound elements of irregular arrangements such as those of FIGS. 18A-18D may be sufficient in some embodiments to allow for suitable discrimination and analysis of data collected by such arrangements for imaging or other purposes.

Figure 20:
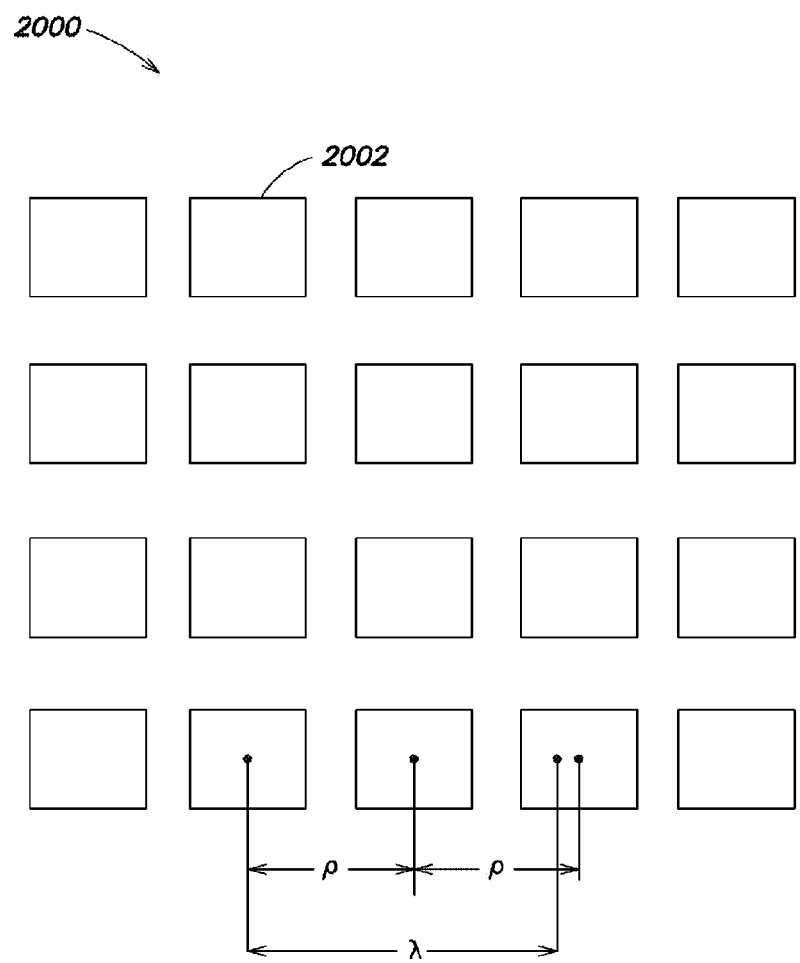
FIG. 20 illustrates a sparse arrangement of radiation elements, according to a non-limiting embodiment.

According to an aspect of the present application, an arrangement of ultrasound elements in two or more dimensions may be a sparse arrangement. Sparsity, in this context, may relate to a wavelength of signals transmitted between pairs of ultrasound elements arranged as sources and sensors. In some embodiments, sparsity of an arrangement, whether an arrangement of sources or sensors, may be defined with respect to a wavelength of radiation as transmitted by sources. However, in some cases, sparsity may be defined with respect a received wavelength. As previously described, signals transmitted by ultrasound elements configured as sources may have a given frequency or, in the case of broadband signals, may have a center frequency. The frequency, or center frequency as the case may be, has a corresponding wavelength $\lambda$. The arrangement of ultrasound elements may be sparse in that $\lambda/2$ may be smaller than the spacing between neighboring ultrasound elements of the arrangement. For example, as shown in the non-limiting embodiment of FIG. 20, which illustrates a single arrangement 2000 of ultrasound elements 2002, the ultrasound elements of a row of the arrangement may be spaced from each other by a distance p, such that the distance 2p may be greater than $\lambda$ of the transmitted or received signals operated on by the arrangement 2000 (stated another way, p>$\lambda/2$). In some embodiments, the distance p may be greater than $3/4\lambda$, greater than $\lambda$, greater than $2\lambda$, greater than $3\lambda$, or take any other suitable value greater than $\lambda/2$. Despite the sparse spacing of ultrasound elements of the arrangement 2000, accurate collection of data providing sufficient resolution of a subject may be provided by using the techniques described further below with respect to volumetric image construction.

It should be appreciated that a sparse arrangement as that term is used herein need not require the distance between every pair of neighboring ultrasound elements of the arrangement to be greater than $\lambda/2$. Rather, a subset of ultrasound elements may be separated from their respective nearest neighbors by a distance p greater than $\lambda/2$. In some embodiments, a sparse arrangement may be formed with respect to active elements of an arrangement (e.g., active sources and/or active sensors), even if the arrangement includes additional elements. A sparse arrangement does not require uniform pitch of ultrasound elements, but rather may have a non-uniform pitch. According to an embodiment, a sparse arrangement may have a non-uniform pitch and may be characterized by a minimum pitch of the arrangement that is greater than $\lambda/2$. In some embodiments, more than approximately 95% of the elements have a spacing greater than $\lambda/2$, or more than approximately 90%, more than approximately 80%, more than approximately 70%, more than approximately 60%, more than approximately 50%, or more than approximately 40% have a spacing greater than $\lambda/2$.

As will be described further below, one or more benefits may be achieved using sparse arrangements of the types described above in connection with FIG. 20. For example, the ability to use a sparse arrangement of ultrasound elements may allow for a reduction in the total number of ultrasound elements needed to achieve particular imaging performance criteria, such as resolution. Thus, cost and design of an ultrasound arrangement may be reduced. In addition, as will be described further below, the ability to use the sparse arrangement of ultrasound elements may allow for provision of additional elements of a different type or serving a different purpose to be positioned among the ultrasound elements configured to operate as sources and sensors in an imaging modality. For example, use of a sparse arrangement of ultrasound elements configured to operate in an imaging modality may facilitate placement of high intensity focused ultrasound (HIFU) elements among the elements configured for imaging. Thus, use of a sparse arrangement of ultrasound elements configured to operate in an imaging modality may facilitate use of a collection of ultrasound elements as a dual- or multi-mode device.

The above-described embodiments relating to irregular and sparse arrays may be used in combination in one or more embodiments. In some embodiments, an arrangement of ultrasound elements may be both sparse and irregular, though alternatives are possible. For example, an arrangement of ultrasound elements may be a sparse arrangement but may also exhibit regular spacing of all the ultrasound elements from their neighbors. In a further embodiments, an arrangement of ultrasound elements may be irregular but not sparse. In some embodiments, an arrangement may be neither sparse nor irregular.

Figure 21:
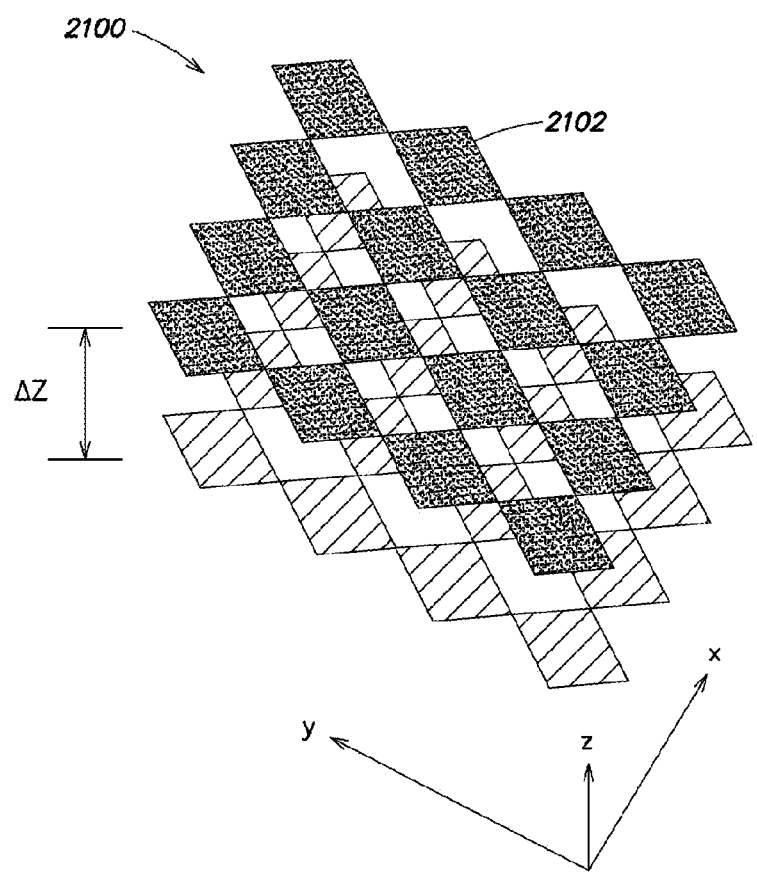
FIG. 21 illustrates a three-dimensional arrangement of radiation elements according to a non-limiting embodiment.

As a further alternative to those embodiments illustrated thus far, it should be appreciated that ultrasound elements of an arrangement may be arranged in three dimensions. While FIG. 1A, among others, has illustrated substantially planar arrangements of ultrasound elements, the various aspects of the present application are not limited in this respect. Referring to FIG. 21, an arrangement 2100 of ultrasound elements 2102 is illustrated. As shown, the ultrasound elements 2102 are arranged along three dimensions, not just two, assuming different positions in the x, y, and z-axes. Some of the ultrasound elements are separated along the z-axis by a distance $\Delta z$, which may have any suitable value, ranging from, for example, a few millimeters to a several inches or more. The illustrated arrangement 2100 may represent a first arrangement of ultrasound elements, and according to some embodiments a second arrangement of ultrasound elements may be provided which may operate in connection with the illustrated arrangement. For example, a second arrangement of ultrasound elements may be disposed in a substantially opposed position with respect to the arrangement 2100 of FIG. 21. The first arrangement may operate as a collection of ultrasound sources, while the second arrangement (not shown) may operate as a collection of ultrasound sensors, as a non-limiting example. Thus, according to a non-limiting embodiment, substantially opposed three-dimensional arrangements of ultrasound elements may be provided.

Furthermore, in those embodiments in which three-dimensional arrangements of ultrasound elements are provided, it should be appreciated that the arrangements may take any suitable form and the elements may have any suitable spacing therebetween. For example, the arrangements of ultrasound elements in three dimensions may be regular arrangements, irregular arrangements, and/or sparse arrangements, among others.

Figure 22A:
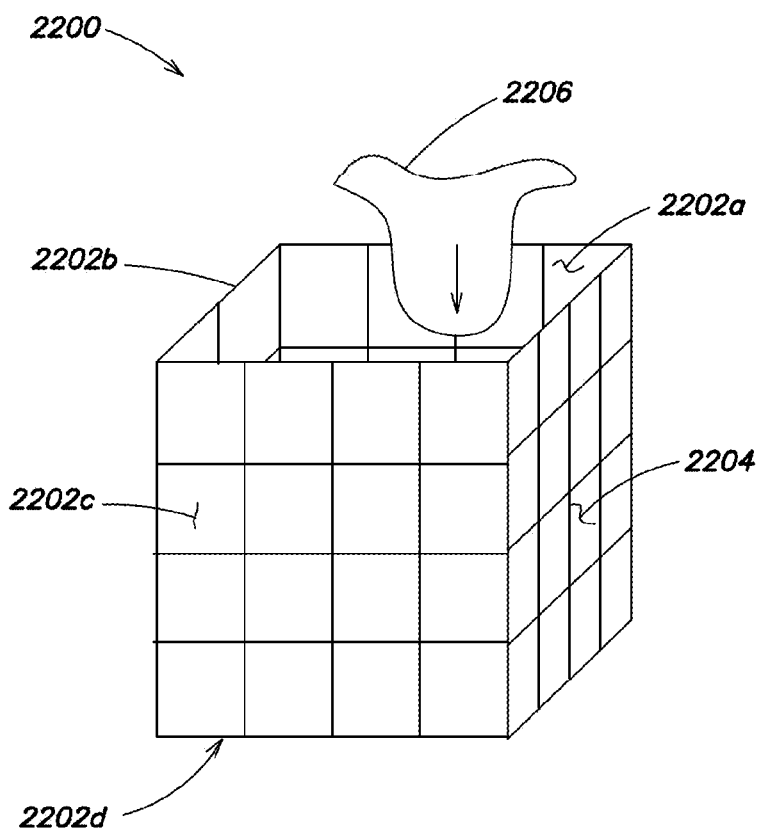
FIGS. 22A-22C illustrate imaging systems of sources and sensors, according to a non-limiting embodiment.

FIG. 22A illustrates a non-limiting example of an arrangement of ultrasound elements configured as sources and sensors, and which may be suitable for receiving a subject for imaging of the subject. As shown, the system 2200 includes a substantially cube-shaped (or box shaped) arrangement of ultrasound elements. In particular, in the non-limiting embodiment shown, the system 2200 includes ultrasound elements configured as sides 2202a-2202d of a cubic structure, with such ultrasound elements being configured as ultrasound sources. In the non-limiting embodiment shown, 2202d may represent the bottom of the cubic structure, but may generally be referred to as a side. The system 2200 further comprises ultrasound elements arranged on a side 2204 and configured to operate as ultrasound sensors. The cubic structure illustrated may have an open top, such that a subject 2206 may be inserted into the volume between the ultrasound elements configured as sources and those configured as sensors. The subject may be any type of subject, such as a medical patient (e.g., breast, a head, a hand, or any other suitable portion of a patient) or other subject of interest. It should be appreciated that use of a configuration such as that shown in FIG. 22A may allow for volumetric imaging of the subject 2206, for example, because ultrasound signals may be sourced from multiple angles with respect to the subject 2206.

In the configuration of FIG. 22A, the sides 2202a-2202d may be considered distinct arrangements of ultrasound elements, such that the non-limiting embodiment illustrated includes four distinct arrangements of ultrasound elements configured as ultrasound sources. More generally, embodiments of the present application provide for two or more distinct arrangements of ultrasound elements configured as sources, with some embodiments consisting of two distinct arrays of ultrasound elements configured as sources. The two or more distinct arrangements, in combination with one or more arrangements of ultrasound elements configured as sensors may substantially surround a subject. According to a non-limiting embodiment involving the configuration of FIG. 22A, one or more of the ultrasound elements of side 2204 configured to operate as ultrasound sensors may receive respective signals from at least one ultrasound element of any two or more of the sides 2202a-2202d (and in some cases from all of the sides 2202a-2202d). Such signals may be discriminated in any suitable manner, such as any of those described elsewhere herein.

Figure 22B:
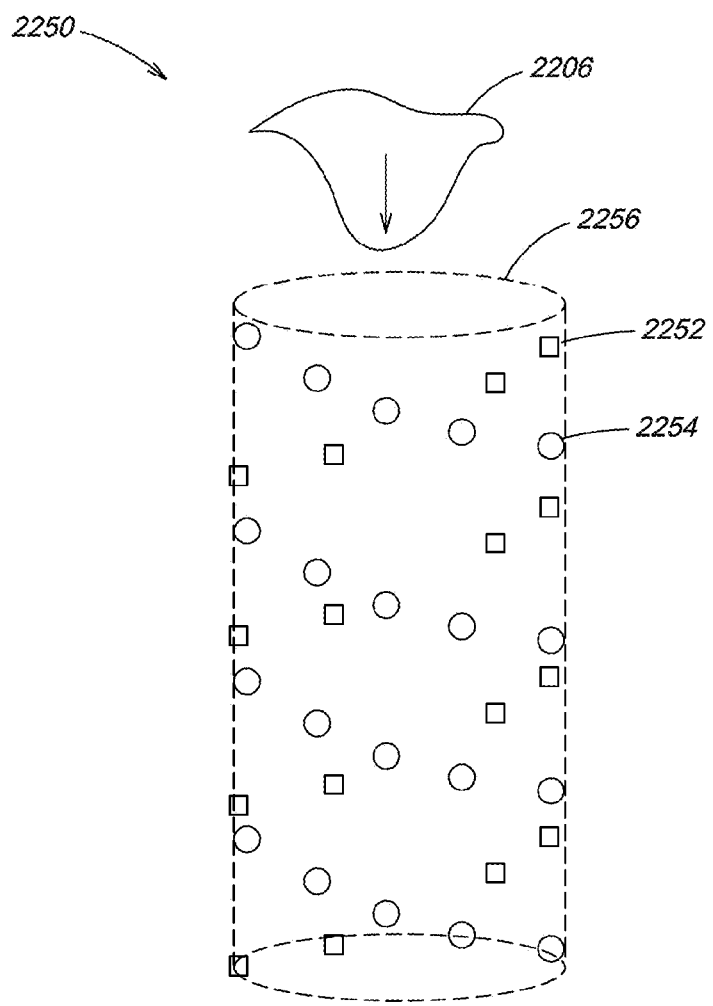

FIG. 22B illustrates an alternative arrangement to that of FIG. 22A. As shown, the system 2250 includes ultrasound elements 2252 configured as ultrasound sources and indicated by boxes, together with ultrasound elements 2254 configured as ultrasound sensors and indicated by circles. The ultrasound elements 2252 and 2254 may be disposed in a substantially helical pattern (or other cylindrical configuration), as shown. In some embodiments, the ultrasound elements 2252 and/or 2254 may be configured on a support 2256, which may accommodate insertion of the subject 2206 for imaging or other investigation. In some embodiments, an arrangement of ultrasound elements like that shown in FIG. 22B may be a sparse arrangement and/or an irregular arrangement. The helical pattern may comprise one or multiple helices, as aspects of the disclosure provided herein are not limited in this respect.

Figure 22C:
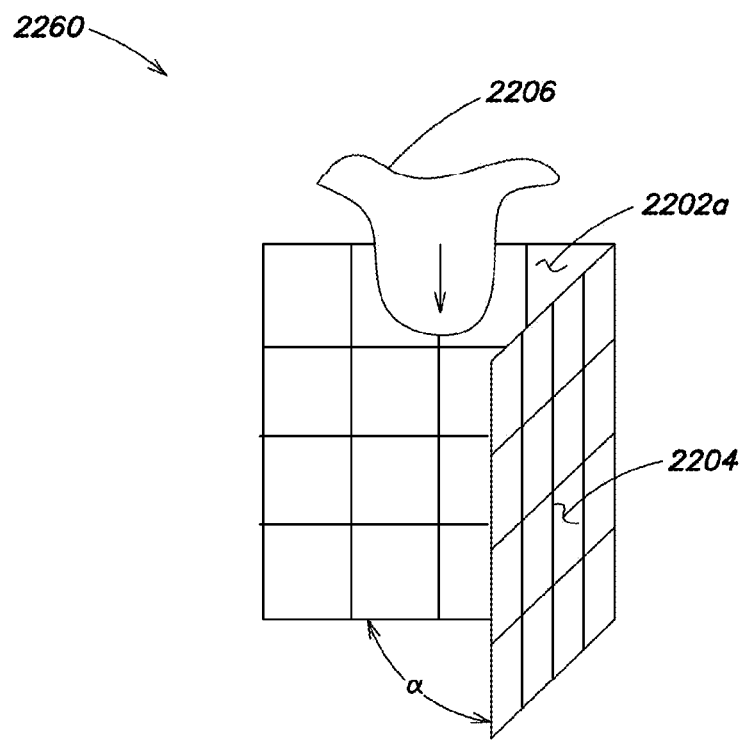

FIG. 22C illustrates a variation on the apparatus of FIG. 22A. Namely, FIG. 22C illustrates an apparatus 2260 similar to that of FIG. 22A but without the sides 2202b, 2202c and 2202d. The apparatus 2260 therefore includes ultrasound elements configured as side 2202a and ultrasound elements arranged on a side 2204 and configured to operate as ultrasound sensors. The angle α between sides 2202a and 2204 may take any suitable value in this non-limiting embodiment, such as being between zero degrees and forty-five degrees, between ten degrees and sixty degrees, between forty degrees and ninety degrees, or having any other suitable value. Thus, it should be appreciated that embodiments of the present application provide arrangements of ultrasound elements tilted with respect to each other (e.g., tilted by any of the angles previously described or by any other suitable angle). In some embodiments, an arrangement of ultrasound elements configured as ultrasound sources may be tilted relative to an arrangement of ultrasound elements configured as ultrasound sensors. In some embodiments, an arrangement of ultrasound elements configured as ultrasound sources may be tilted relative to another arrangement of ultrasound elements configured as ultrasound sources. In some embodiments, an arrangement of ultrasound elements configured as ultrasound sensors may be tilted relative to another arrangement of ultrasound elements configured as ultrasound sensors.

It should be appreciated that the arrangements of ultrasound elements described herein may take any suitable dimensions. As previously described, the arrangements may comprise any suitable number of ultrasound elements, for example to provide a desired resolution. The ultrasound elements may be arranged in a manner sufficient to image subjects of interest, such as a patient's head, breast, hand, or other subjects of interest. Thus, arrangements of ultrasound elements as described herein may occupy distances ranging from centimeters up to several inches or more. As a non-limiting example, an arrangement of ultrasound elements may be approximately 15 cm×15 cm, less than approximately 100 cm×100 cm, or any other suitable size.

Various aspects of the present application have been described in which one or more ultrasound elements are implemented. It should be appreciated that the various aspects implementing ultrasound elements are not limited in the type of ultrasound elements used. Any suitable type of ultrasound elements may be implemented, and in certain applications the type of ultrasound element used may be selected based on considerations such as size, power, and material, among others. For example, conventional piezoelectric ultrasound elements may be used, and/or capacitive micromachined ultrasound transducers (CMUT) may be used, though other types are also possible. In one embodiment, CMUT elements may be used to form an array of ultrasound elements configured as sources to transmit ultrasound radiation. CMUT elements may be used for both imaging and HIFU functionality, and therefore may simplify design of an array of ultrasound elements in some embodiments. In some embodiments, it may be desirable to perform ultrasound imaging in combination with MRI, such that it may be preferred for the ultrasound elements to be formed of a material suitable for operation in the presence of strong magnetic fields.

Non-limiting examples of ultrasound elements which may be used in any of the embodiments described herein include CMUT, lead zirconate titanate (PZT) elements, lead magnesium niobate-lead titanate (PMN-PT) elements, polyvinylidene difluoride (PVDF) elements, high power ("hard") ceramics such as those designated as PZT-4 ceramics, or any other suitable elements. Materials designated as PZT-8 materials may be preferable for use as HIFU elements in some embodiments. In some embodiments, ultrasound elements configured as sources may be of a first type while ultrasound elements configured as sensors may be of a second type. For example, according to an embodiment, PZT elements may be used to form an array of ultrasound elements configured as sources, while PVDF elements may be used to form an array of ultrasound elements configured as sensors. Such a configuration may be implemented for any purpose(s). In some embodiments, PVDF elements may be more efficient in terms of receiving signals, but may be characterized by an undefined output impedance. Thus, it may be desirable to couple such PVDF elements to high impedance low noise amplifiers (LNAs), which may be best suited for receipt of ultrasound signals rather than sourcing ultrasound signals. PZT elements, on the other hand, may be better suited in some embodiments to operate as ultrasound sources. Thus, embodiments of the present application provide for suitable mixing of radiation element types as sources and sensors to provide desired operation.

It should be appreciated from the foregoing that according to some embodiments of the present application an ultrasound system suitable for performing volumetric imaging of a subject may be provided in which the arrangements of ultrasound elements do not enclose the subject. The ability to collect volumetric data of a subject without the need to enclose or substantially enclose the subject may facilitate operation of the system, for example, by facilitating arrangement of the ultrasound elements with respect to the subject. Various configurations of ultrasound elements suitable for performing volumetric imaging of a subject without substantially enclosing the subject are possible.

For example, referring to FIG. 1A, it should be appreciated that the arrays 102a and 102b of ultrasound elements define a volume therebetween, and that the arrays do not substantially enclose the volume. Thus, a subject disposed within the volume will not be substantially enclosed by the arrays of ultrasound elements. For example, there may be no part of the system that forms a closed loop around the subject or even a substantially closed loop.

As a further non-limiting example, reference is made again to FIG. 4 in which, similar to FIG. 1A, it should be appreciated that the arrays 402a and 402b of ultrasound elements define a volume 418 therebetween, but do not substantially enclose the volume. Thus, the subject 410 is not substantially enclosed by the arrays 402a and 402b. Nonetheless, even with leaving the arrays 402a and 402b in static locations, volumetric imaging of the subject 410 may be achieved as described previously.

While FIGS. 1 and 4 illustrate non-limiting examples in which arrangements of ultrasound sources and sensors do not substantially enclose a subject, it should be appreciated that the arrangements need not be substantially planar. For example, arrangements of ultrasound elements may be curved while still not substantially enclosing the subject. For example, arrangements of ultrasound elements may be formed on flexible supports such as those of FIG. 28, and curved to conform to a patient without substantially enclosing the patient. Whether or not an arrangement of ultrasound elements substantially encloses a subject may depend on the context. In some embodiments, an arrangement does not substantially enclose a subject if the arrangement does not form any closed contour around the subject (see, e.g., FIGS. 4-6). In some embodiments, an arrangement does not substantially enclose a subject if two or more sides of the subject are accessible.

Figure 47:
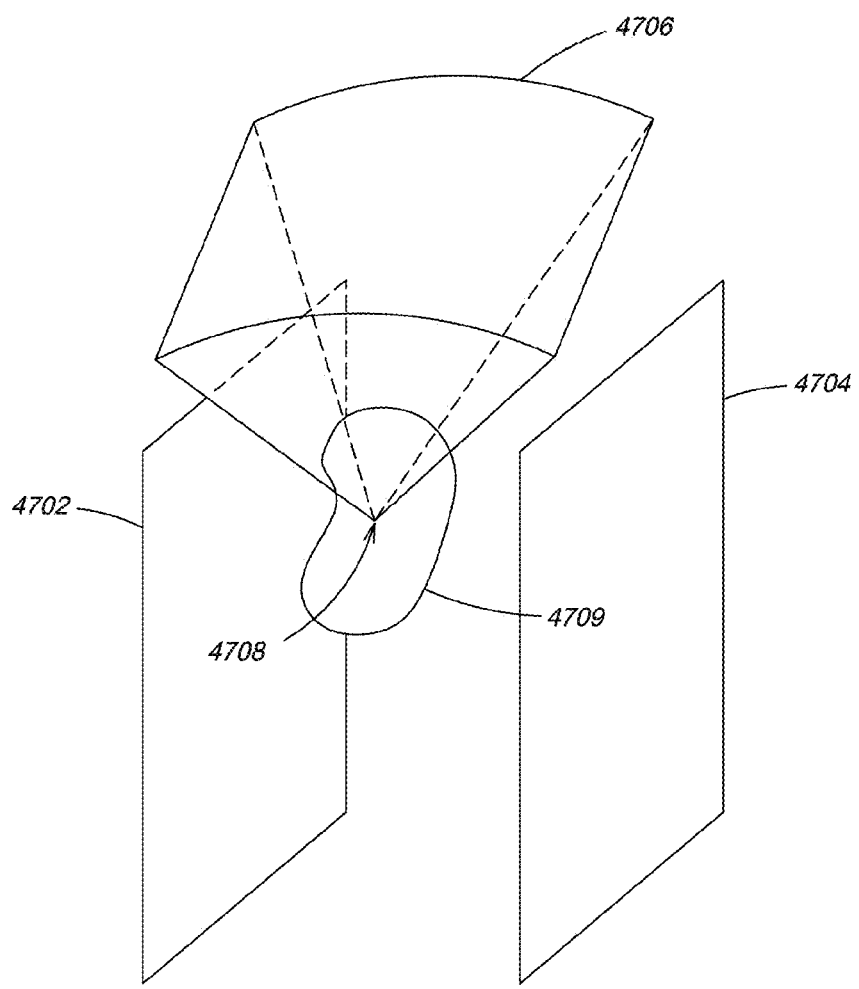
FIG. 47 illustrates an embodiment in which an arrangement of radiation elements (e.g., ultrasound elements) does not occupy a substantial solid angle having its vertex located at the position of a subject.

In some embodiments, a system comprising two or more arrangements of ultrasound elements may be said to not substantially enclose a subject if there is a gap separating the arrangements. In some embodiments, the gap may be at least five inches, at least 10 inches, at least one foot, at least several feet, or more. In some embodiments, the gap may be between approximately 6 inches and 18 inches. In some embodiments, the gap may be sufficiently large to allow access to the subject while the system is in operation (e.g., to allow a doctor to touch the subject). An arrangement of ultrasound elements may be said to not substantially enclose a subject in some embodiments if the subject may be inserted into and/or removed from the arrangement without needing to substantially alter the position of the arrangement. An arrangement of ultrasound elements may be said to not substantially enclose a subject in some embodiments if there is a substantial solid angle, defined with its vertex corresponding to the subject, which is not occupied by sources or sensors. For example, non-ring shaped arrangements and non-cylindrical arrangements may be said to not substantially enclose a subject in some embodiments. FIG. 47 illustrates an example, in which an arrangement of radiation elements (e.g., ultrasound elements) 4702 is configured to operate in combination with an arrangement of radiation elements (e.g., ultrasound elements) 4704 to image a subject 4709. A solid angle 4706 defined with respect to the subject (i.e., having its vertex 4708 located at the position of the subject) is free from any ultrasound elements. The solid angle may assume any suitable value depending on the context. For example, the solid angle 4706 may be at least at least $\pi/5$ steradians, at least $\pi/4$ steradians, at least $\pi/2$ steradians, at least $\pi$ steradians, at least $2\pi$ steradians, between approximately $\pi/10$ and $3\pi$ steradians, between approximately $\pi/5$ and $3\pi$ steradians, between approximately $\pi$ and $3\pi$ steradians or any other suitable non-zero solid angle. In some embodiments, such a configuration of ultrasound elements may be said to not substantially enclose the subject.

It should also be appreciated from the foregoing description that, according to an aspect of the present application, a system may comprise an arrangement of ultrasound elements configured to operate as ultrasound sources, which is separated from an arrangement of ultrasound elements configured to operate as ultrasound sensors. For example, again referring to FIG. 1A, it should be appreciated that the array 102a may include ultrasound elements 104 configured to operate as ultrasound sources, and that those ultrasound elements are separated in the non-limiting embodiment illustrated from the ultrasound elements 104 of array 102b arranged to operate as ultrasound sensors. The distance of separation is not limiting. For example, referring to FIG. 1A, the array 102a may be separated from the array 102b by any suitable distance, such as one inch, two inches, between two and six inches, between one and ten inches, between 1-30 centimeters, between 10-50 centimeters, or any other suitable distance. Furthermore, the distance of separation need not be the same for all pairs of ultrasound elements of the array 102a with respect to those of the array 102b. For example, as has been described, arrangements of ultrasound elements that are not strictly planar may be implemented according to one or more aspects of the present application (see, e.g., FIG. 21), and thus the distances between pairs of ultrasound elements configured as sources and those configured as sensors of an opposing arrangement may not be the same. Also, as will be described further below, arrangements of ultrasound elements may be formed on curved, flexible, and/or deformable surfaces, such that the distance between one portion of a first arrangement and a second arrangement may differ from the distance between a second portion of the first arrangement and second arrangement.

Figure 23:
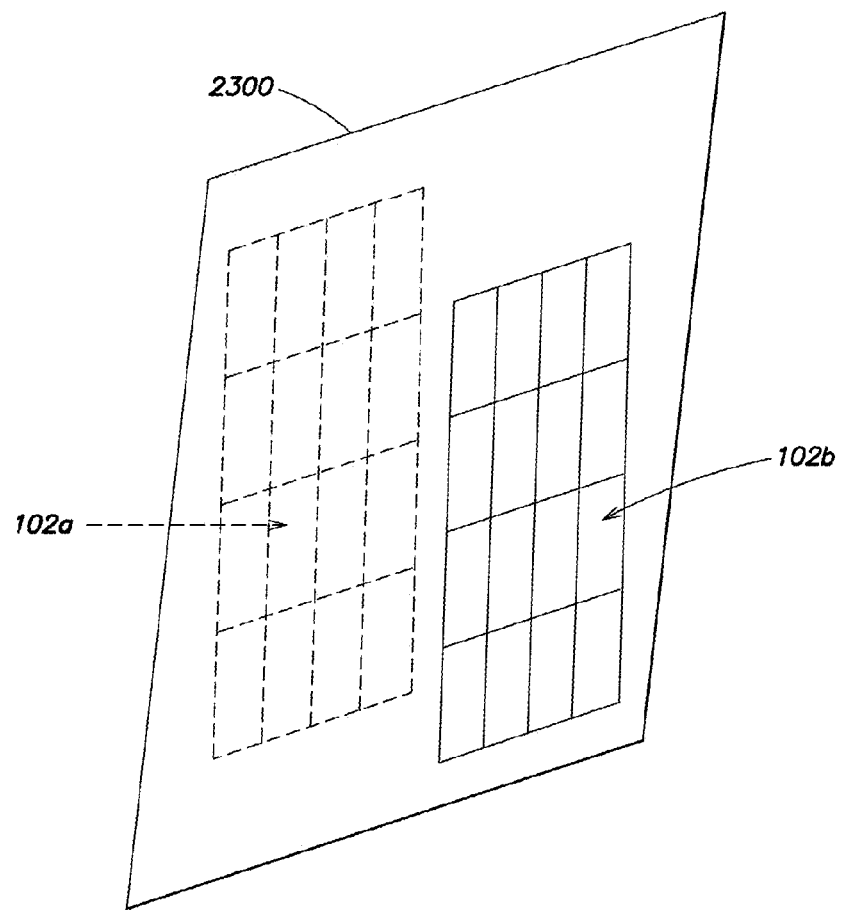
FIG. 23 illustrates two arrangements of radiation elements separated by a plane, according to a non-limiting embodiment.

Referring to FIG. 23, according to an embodiment of the present application, an arrangement of ultrasound elements configured to operate as ultrasound sources may be separated from an arrangement of ultrasound elements configured to operate as ultrasound sensors by a plane. As shown, the plane 2300 may separate the array 102a of ultrasound elements from the array 102b of ultrasound elements. In some embodiments, all of the ultrasound elements configured to operate as ultrasound sources may be on one side of the plane 2300, while all the ultrasound elements configured to operate as sensors may be on the opposite side of the plane 2300. In other embodiments, each of arrays 102a and 102b may include both sensors and sources.

It should be appreciated that the ultrasound elements of an arrangement need not be limited to performing only one function. For example, referring again to FIG. 23, the ultrasound elements of the array 102a may be configured to operate for a first period of time as ultrasound sources, but at a later period of time as ultrasound sensors. Similarly, the ultrasound elements of arrangement 102b may be configured to operate at different times as ultrasound sources and sensors. According to an embodiment, arrangements of ultrasound elements disposed in an opposed relationship with respect to each other may be configured to alternate their mode of operation. For example, the ultrasound elements of array 102a may be configured to operate as ultrasound sources while the ultrasound elements of array 102b may be configured to operate as ultrasound sensors, and then the respective functions of the ultrasound elements of the two arrays may be alternated over time.

Figure 24:
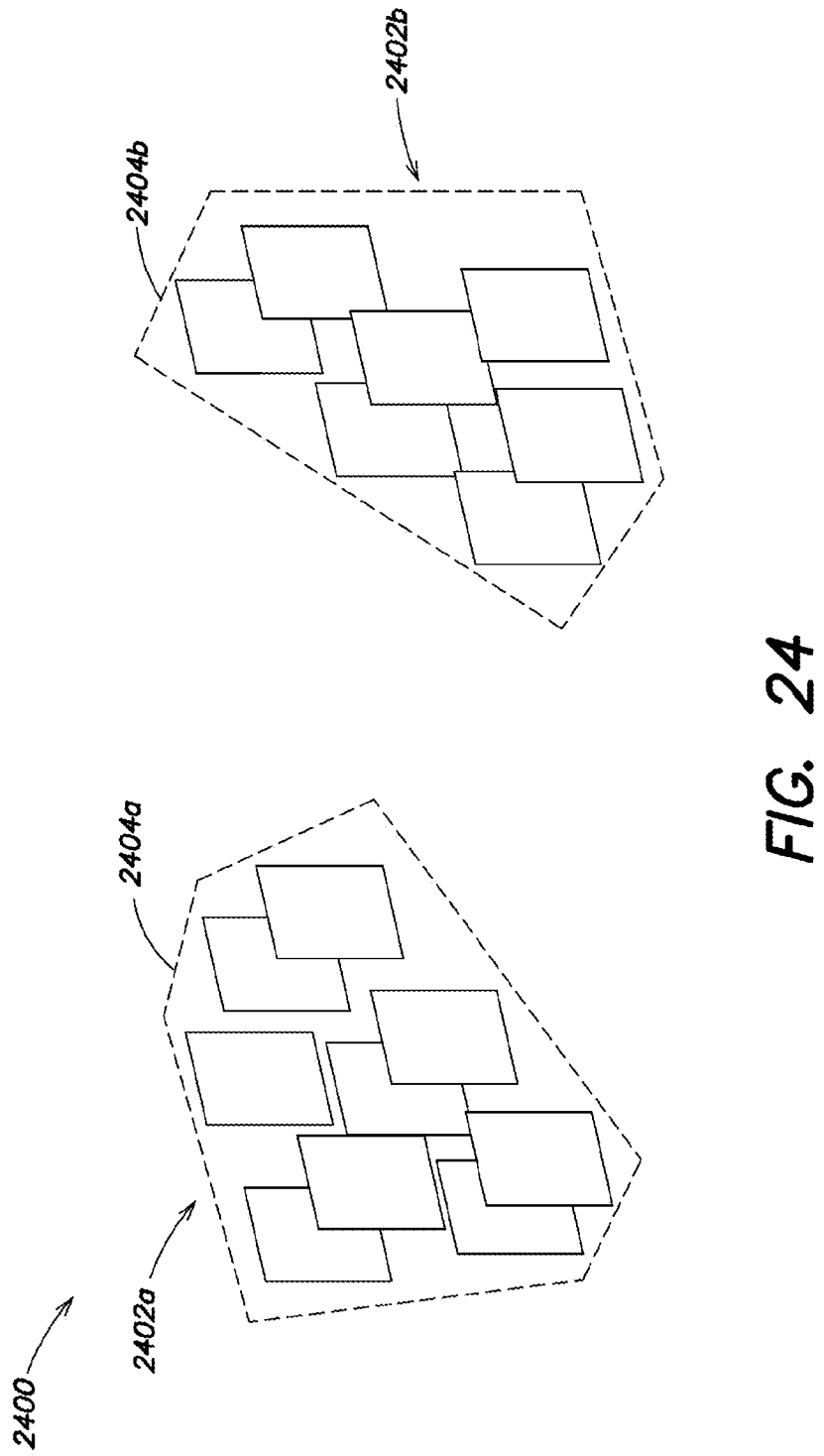
FIG. 24 illustrates two arrangements of radiation elements separated in space, according to a non-limiting embodiment.

FIG. 24 illustrates another non-limiting example of a manner in which arrangements of ultrasound elements configured as ultrasound sources may be separated in space from ultrasound elements configured as ultrasound sensors. As shown, the system 2400 includes an arrangement of ultrasound elements 2402a and a second arrangement of ultrasound elements 2402b. For purposes of illustration, the ultrasound elements of the arrangement 2402a may be configured to operate as ultrasound sources, whereas the ultrasound elements of arrangement 2402b may be configured to operate as ultrasound sensors. The convex surface (i.e., convex hull (the smallest convex surface) or any other convex surface) enclosing the arrangement 2402a is identified by 2404a. Similarly, the smallest convex hull enclosing the arrangement 2402b of ultrasound elements is identified by 2404b. As seen, the convex hull 2404a does not intersect the convex hull 2404b, and thus the arrangement 2402a of ultrasound elements may be considered separated in multiple dimensions in space from the arrangement 2402b of ultrasound elements.

Figure 25:
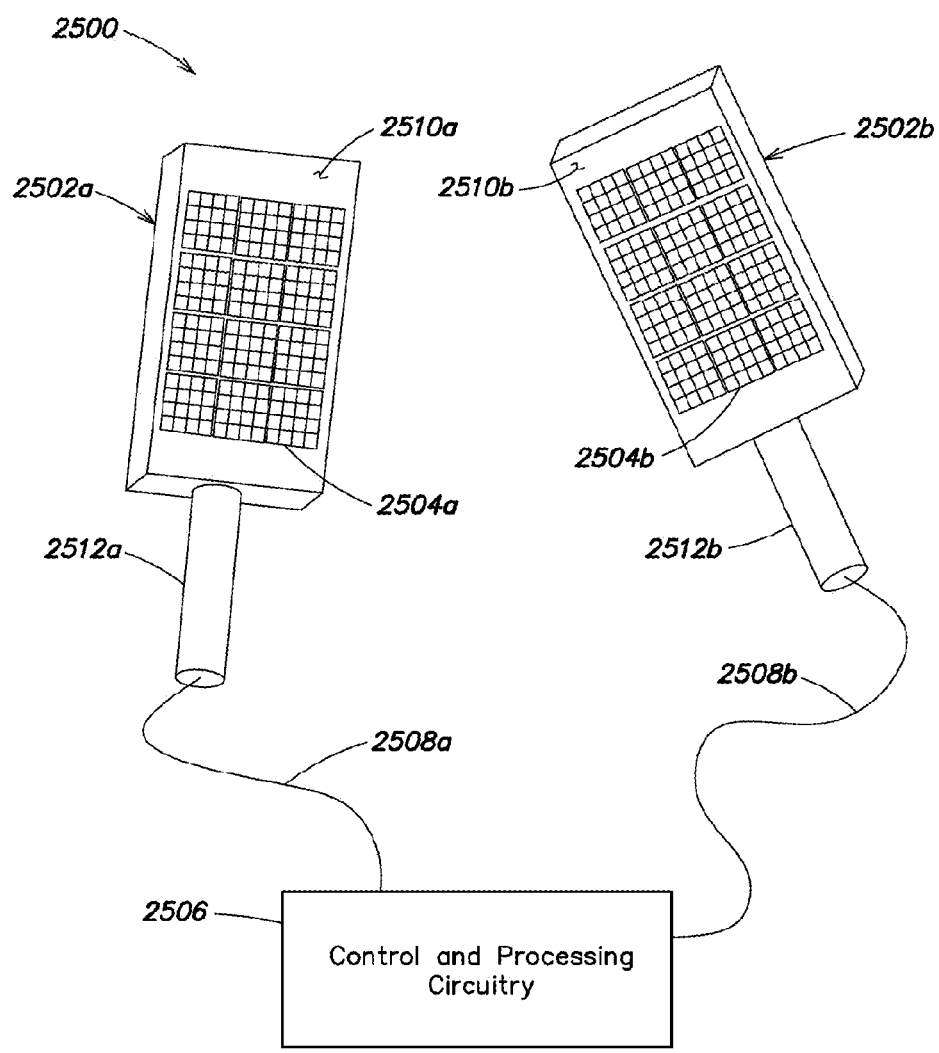
FIG. 25 illustrates a plurality of movable supports including arrangements of radiation elements, according to a non-limiting embodiment.

Arrangements of ultrasound elements according to one or more aspects of the present application may take any suitable form. According to one aspect, arrangements of ultrasound elements are configured on a support, and/or shaped substantially as paddles. A non-limiting example is illustrated in FIG. 25. As shown, the system 2500 includes a first paddle 2502a and a second paddle 2502b, each of which includes a respective arrangement of ultrasound elements 2504a and 2504b on a respective support 2510a and 2510b (also referred to herein as substrates or mounts). Each paddle is connected to control and processing circuitry 2506 by a respective connection 2508a and 2508b (wired, wireless, and/or assuming any suitable form). The ultrasound elements of paddle 2502a may communicate with those of paddle 2502b in the manner previously described with respect to substantially opposed arrangements of ultrasound elements.

The supports 2510a and 2510b may be any suitable supports. They may be rigid in some embodiments, and flexible in others. They may have any sizes suitable for accommodating the arrays 2504a and 2504b. The supports may be formed of any suitable material, such as plastic, rubberized materials, metal, and/or any other suitable material or materials. In some embodiments it may be desirable to use the paddles 2502a and 2502b in combination with MRI technology (e.g., within an MRI machine), and thus it may be preferred in some embodiments for the supports to be formed of non-magnetic material.

Constructing arrangements of ultrasound elements in the form of paddles, as shown in FIG. 25, may provide various benefits. For example, the paddles may be movable and thus may facilitate positioning with respect to a patient or other subject of interest. For example, the paddles may be handheld in some embodiments (e.g., using handles 2512a and 2512b) and therefore easily manipulated by a user. Furthermore, the paddles may be portable, allowing for transport between locations (e.g., from room to room in a hospital, or between other locations) and therefore providing convenient access to imaging technology.

The control and processing circuitry 2506 may be any suitable circuitry for controlling operation and collection of data from the paddles 2502a and 2502b. For example, the control and processing circuitry 2506 may embody any of the circuitry previously described herein, and may take any suitable form.

Figure 26:
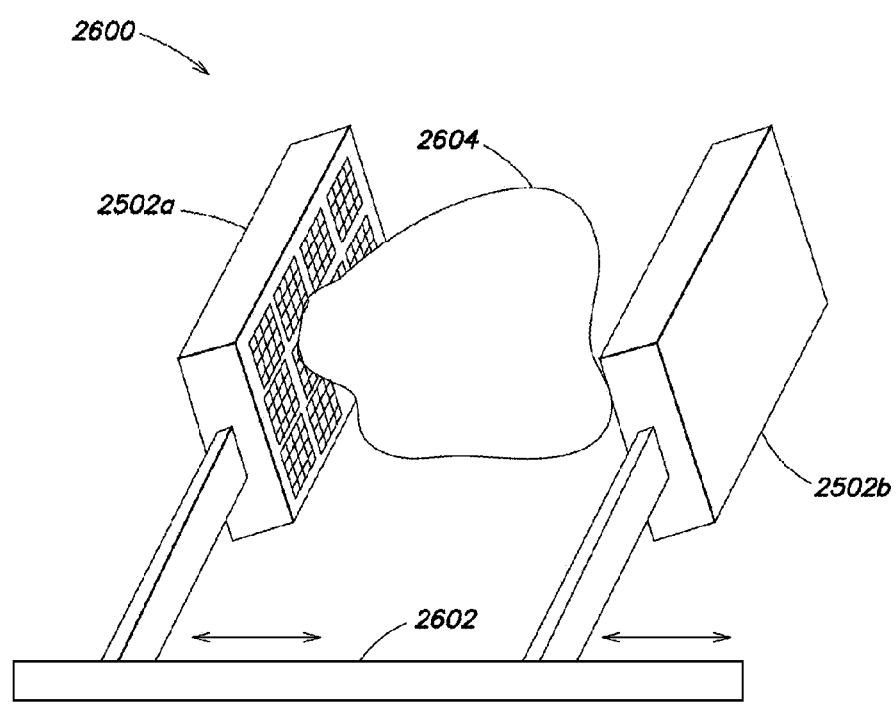
FIG. 26 illustrates an alternative to that of FIG. 25, in which the movable supports are coupled together by a rigid connector, according to a non-limiting embodiment.

FIG. 26 illustrates an alternative configuration of paddles to that of FIG. 25. As shown, in the system 2600 the paddles are connected to a rigid support 2602. The rigid support may facilitate maintaining the paddles in a fixed relationship with respect to each other during operation, which may be desirable in some embodiments. The rigid support 2602 may allow for movement of the paddles relative to each other, for example in the direction of the arrows, as may be desired to reposition the paddles when transitioning between analyzing different subjects or during investigation of a single subject. The rigid support may take any suitable form, and may be formed of any suitable material.

Adjustment of the positions of the paddles 2502a and 2502b along the rigid support may be performed in any suitable manner, such as via a slide mount, or any other suitable manner. According to a non-limiting embodiment, the rigid support 2602 may provide a force inwardly directed toward the subject 2604, for example, to allow for a compression fit of the subject between the paddles 2502a and 2502b.

Figure 27:
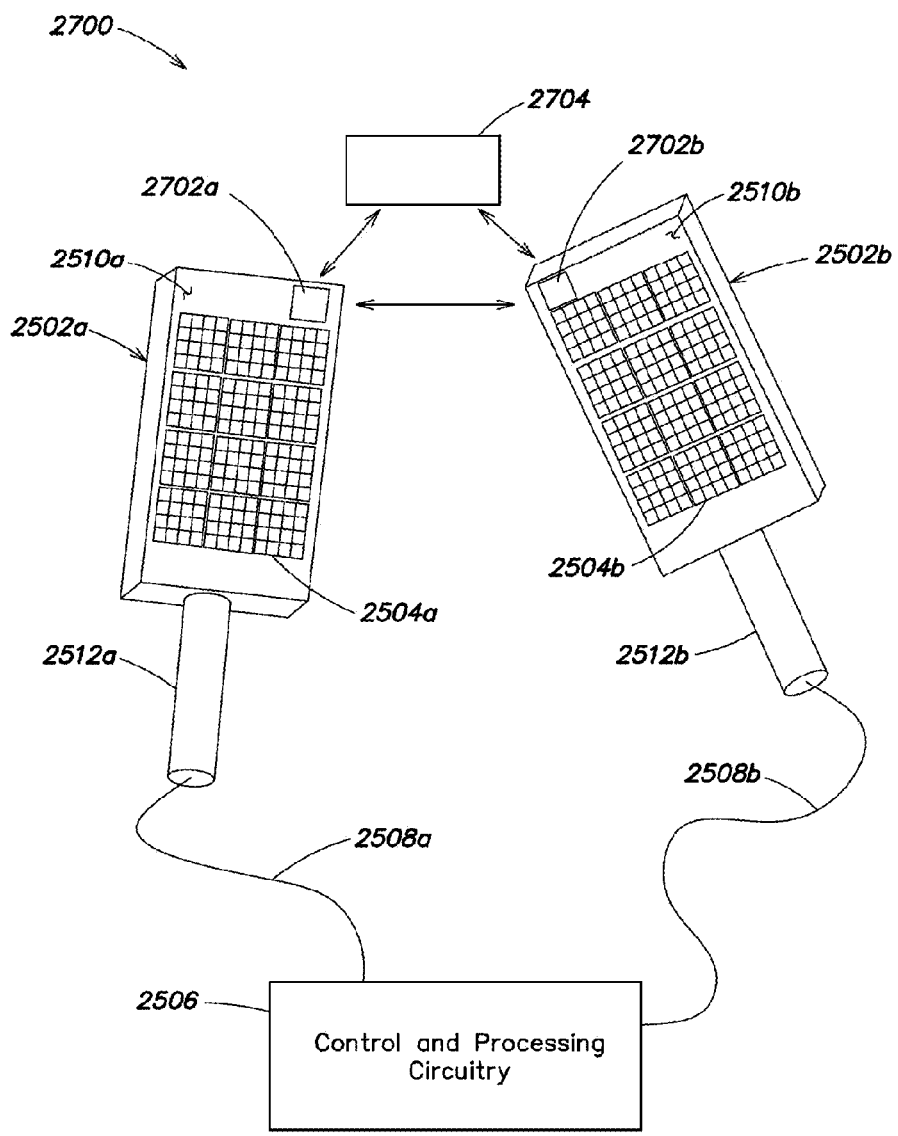
FIG. 27 illustrates an expansion on the system of FIG. 25 in which the movable supports may communicate with each other and/or with a remote device to determine orientation and/or position information, according to a non-limiting embodiment.

FIG. 27 illustrates a further embodiment in which communication between paddles 2502a and 2502b is provided. As previously described, it may be desirable in some settings to determine a relative orientation and/or position of the arrays 2504a and 2504b with respect to each other. For example, knowledge of the relative (and/or absolute) orientation and/or position of the arrays may facilitate processing of data signals collected by the elements of the arrays. In some embodiments, the relative orientation and/or position may be detected dynamically. FIG. 27 illustrates multiple non-limiting examples of how the relative orientation and/or position of the arrays may be determined.

According to a non-limiting embodiment, each of the paddles 2502a and 2502b may include a respective one or more sensor(s) (or detector(s)) 2702a and 2702b. The sensors may operate to detect the relative orientation and/or position of the respective paddle, in some cases dynamically. Additionally or alternatively, the sensors 2702a and 2702b may detect an absolute orientation and/or position, in some cases dynamically. Non-limiting examples of suitable sensors include gyroscopes, accelerometers, inclinometers, range finders, inertial navigation systems, lasers, infrared sensors, ultrasonic sensors, electromagnetic sensors, any other suitable sensors, or any combination of two or more such sensors. In some embodiments, one or more of the sensors may be integrated with the ultrasound elements (e.g., configured as ultrasound sources or ultrasound sensors) on a substrate. The sensor(s) may be integrated on the substrate, for example by flip-chip bonding, flex-circuit bonding, solder bump bonding, monolithic integration, or in any other suitable manner. In some embodiments, the ultrasound elements may be on a flexible support together with one or more of the sensors.

According to a non-limiting embodiment, the sensors 2702a and 2702b may communicate with each other, for example, to transmit signals to each other indicative of orientation and/or position, or to transmit signals from which relative orientation and/or position of the paddles may be determined. Communication between the sensors 2702a and 2702b may be performed wirelessly, using any suitable wireless communication protocol.

Alternatively or additionally, the sensors 2702a and 2702b may communicate with a remote device 2704, which may process signals from the sensor 2702a and/or 2702b to determine relative and/or absolute orientation and/or position of one or both of the paddles. Communication between the sensors 2702a and/or 2702b and the remote device 2704 may be performed wirelessly, using any suitable wireless protocol, or may be performed in any other suitable manner.

The remote device 2704 may be any suitable device, such as a general-purpose processor. The remote device 2704 may be remote in the sense that it is distinct from the paddles 2502a and 2502b, but need not necessarily be at a separate geographic location. For example, according to an embodiment, a system such as system 2700 may be employed in a medical office. The remote device 2704 may be, for example, disposed at a fixed location within the office, and the paddles 2502a and 2502b may be moved within the office as needed to position them relative to a patient being examined. The remote device 2704 may communicate with one or both of the paddles 2502a and 2502b via the sensors 2702a and 2702b, or in any other suitable manner (e.g., via transmitters distinct from the sensors, via wired connections, or in any other suitable manner). As shown, the remote device 2704 may not only receive signals from the sensors 2702a and/or 2702b, but also may actively transmit signals to the sensors.

While FIG. 27 illustrates an embodiment in which both control and processing circuitry 2506 and a remote device 2704 are provided, not all embodiments are limited in this respect. According to an alternative embodiment, the control and processing circuitry 2506 may perform the functionality of the remote device 2704. Thus, the remote device is optional and may not be included in all embodiments.

According to an alternative embodiment, determination of relative orientation and/or position of the paddles 2502a and 2502b may be performed without the need for sensors 2702a and/or 2702b. For example, suitable processing of ultrasound signals detected by the ultrasound elements of arrays 2504a and/or 2504b may provide the same or similar information. For example, suitable processing of such signals may indicate distance between the arrays 2504a and/or 2504b and may also be used to detect relative angles of the arrays, thus providing relative orientation.

Thus, it should be appreciated that there are various manners in which absolute and/or relative orientation and/or position of multiple arrays of ultrasound elements, whether arranged in the form of paddles or not, may be determined. The various aspects described herein in which detection of relative orientation and/or position of arrangements of ultrasound elements is performed are not limited in the manner in which the orientation and/or position are determined.

Figure 28:
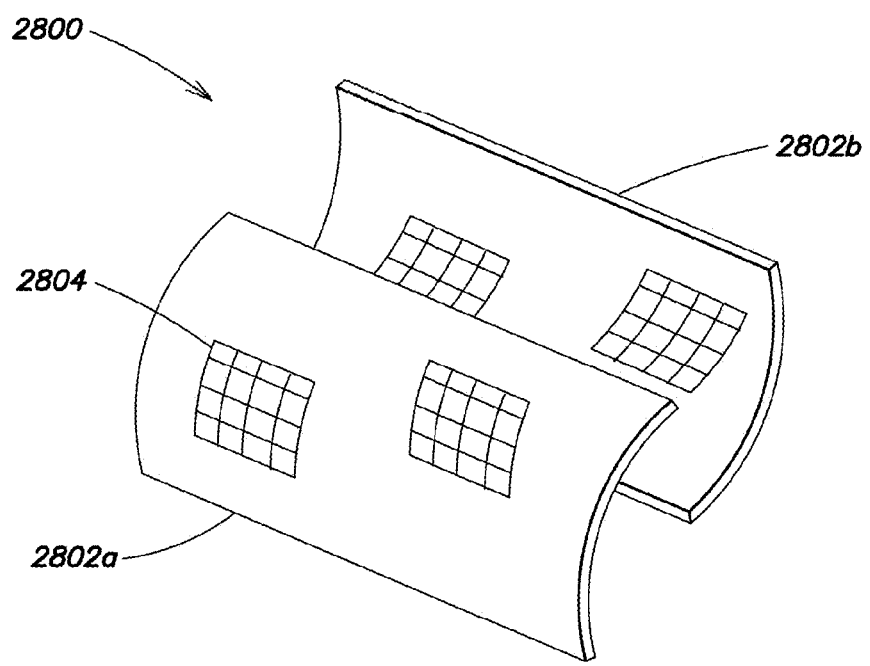
FIG. 28 illustrates an apparatus utilizing flexible supports on which arrangements of ultrasound elements may be disposed, according to a non-limiting embodiment.

According to an alternative non-limiting embodiment, an arrangement of ultrasound elements may be disposed on a flexible support. FIG. 28 illustrates a non-limiting example, showing a system 2800 comprising a first flexible support 2802a and a second flexible support 2802b. Each of the flexible supports may have disposed thereon an arrangement 2804 of ultrasound elements (e.g., the arrangement 2804 may be an array such as 102a and 102b, or any other suitable arrangement of the types described herein). The supports may be formed of any suitable material providing a desired level of flexibility, such as flexible plastic, a rubberized material, or any other suitable material. Again, it may be desirable for the supports 2802a and 2802b to be formed of a material which is non-magnetic, for example, to facilitate use of the system 2800 in combination with MRI techniques.

Use of flexible supports such as those illustrated in FIG. 28 may provide various benefits. For example, use of flexible supports may allow for positioning of arrangements of ultrasound elements which conform to a subject, such as a patient's body. Thus, various imaging geometries may be accommodated where use of a rigid support may not be adequate. As will be appreciated, the relative position between ultrasound elements of an arrangement disposed on a flexible support, such as on support 2802a, may change as the support is flexed. For example, some ultrasound elements of an arrangement disposed on support 2802a may become closer to each other when the substrate is flexed in a first direction, or alternatively may become farther from each other if the substrate is flexed in a different direction. Thus, in processing data collected from arrangements of ultrasound elements implemented on flexible supports, use of a suitable process which may account for such variation in the positioning among ultrasound elements may be preferred. Non-limiting examples of suitable processes are described further below.

As one non-limiting example, a compressive sensing image reconstruction process may account for variation in the positioning among ultrasound elements when generating one or more volumetric images, as described in more detail below. In some embodiments, a calibration procedure may be used to calibrate a system having arrays arranged on flexible supports. For instance, time of flight data collected using such a configuration of ultrasound elements as that shown in FIG. 28 may be fit to the geometry of the supports using a second order polynomial (or other suitable fitting technique) in the absence of a subject between the elements. The resulting fit may be treated as a baseline (or background) for operation of the system. Then, when data is collected of a subject of interest using substantially the same configuration, the background data may be subtracted out.

According to an alternative embodiment, sensors which detect flexing may be implemented in a system like that shown in FIG. 28. For example, variable resistance resistors whose resistance changes in response to flexing may be implemented on the supports 2802a and 2802b. When the supports are flexed, the resistance value of such resistors may provide an indication of the flexed geometry of the substrates, and therefore the positioning (relative or absolute) of ultrasound elements disposed on the substrates. Other techniques for monitoring changes in geometry of arrangements of ultrasound elements on flexible supports may also be used.

In embodiments in which flexible supports are used, an array of ultrasound elements may be concave depending on the curvature of the support(s). In some embodiments, use of concave arrays of ultrasound elements as sources and/or sensors may be desirable for purposes independent of having the array conform to a subject. Ultrasound elements located near the edge of an array of such elements may produce wasted energy in that the some of the energy produced by such elements may radiate in directions not focused toward the subject. Thus, by orientating (e.g., angling) ultrasound elements located at the edges of an array such that they are directed inward (toward the subject), energy efficiency gains may be realized. Accordingly, some embodiments of the present application provide concave arrays of ultrasound elements, whether achieved through suitable flexing of a flexible substrate on which the arrays are formed or through manufacture of a (rigid) concave substrate. Various manners of achieving a concave array of ultrasound elements are possible.

As previously described, in some embodiments, an ultrasound-imaging device having multiple ultrasound sources and multiple ultrasound sensors may be used to obtain measurements of a subject being imaged. In turn, an image reconstruction process may be used to generate one or more volumetric images of the subject from the obtained measurements.

Illustrative, non-limiting examples of image reconstruction processes that may be used in accordance with embodiments of the present application are described in greater detail below. In one embodiment, a compressive sensing image reconstruction process may be used to calculate a volumetric image of the subject from measurements obtained by an ultrasound imaging device.

In some embodiments, an image reconstruction process may be used to obtain a volumetric image of a subject by using measurements obtained when the ultrasound imaging device is operated in a transmissive modality. In these embodiments, as previously described, the ultrasound sensors are configured to receive ultrasound signals which may be transmitted through the subject being imaged by multiple ultrasound sources. The ultrasound sources may be disposed in an opposing arrangement to the ultrasound sensors, though the sources and sensors may be disposed in any of the arrangements described herein as aspects of the present application are not limited in this respect.

By measuring characteristics (e.g., amplitudes, frequencies, and/or phases) of the ultrasound signals (or changes thereof) that pass through the subject being imaged, information related to the subject may be obtained to form a volumetric image of the subject. Such information may be contained in measurements derived from the measured characteristics. Such measurements include, but are not limited to, attenuation measurements and time-of-flight measurements. Indeed, as previously described, the amplitude of a received ultrasound signal may be used to obtain a value indicative of an amount of attenuation of that ultrasound signal as result of its passing through the subject being imaged. Phase of a received ultrasound signal may be used to obtain a value indicative of the time-of-flight of the signal from the source that transmitted the ultrasound signal to the ultrasound sensor that received it.

It should be appreciated that an image reconstruction process used to obtain a volumetric image of a subject is not limited to using measurements obtained when the ultrasound imaging device is operated in a transmissive modality. For example, in some embodiments, the image reconstruction process may use measurements obtained at least in part based on scattered radiation such as back-scattered radiation and/or forward-scattered radiation.

In some embodiments, an image reconstruction process may be applied to all the measurements obtained by the ultrasound imaging device within a period of time. The period of time may be set in any of numerous ways and, for example, may be set to be sufficiently long so that a signal transmitted from each of the ultrasound sources may be received by at least one (or all) of the ultrasound sensors in the ultrasound imaging device. Though, it should be recognized that in some embodiments the image reconstruction process may be applied to some, but not all, the measurements obtained by the ultrasound imaging device within a period of time, as aspects of the present application are not limited in this respect. This may be done for numerous reasons, for instance, when a volumetric image of only a portion of the subject being imaged is desired.

In some embodiments, an image reconstruction process may take into account the geometry of the sources and sensors in the ultrasound imaging device to calculate a volumetric image of the subject from measurements obtained by the imaging device. To this end, the image reconstruction process may utilize information about the geometry of the sources and sensors and such information may be obtained for use in the image reconstruction process in addition to (and, in some embodiments, independently of) the measurements obtained from the signals received by the ultrasound sensors. Though, in some embodiments, an image reconstruction process may be applied to measurements to obtain a volumetric image without using any additional information about the geometry of the sources and sensors used to obtain such measurements, as aspects of the present application are not limited in this respect.

Although any of numerous types of image reconstruction processes may be used, in some embodiments, a compressive sensing (CS) image reconstruction process may be used to calculate a volumetric image of the subject from measurements obtained by an imaging device. A CS image reconstruction technique may comprise calculating a volumetric image of the subject at least in part by identifying a solution to a system of linear equations relating a plurality of measurements (e.g., time-of-flight measurements, attenuation measurements, etc.) to a property of the subject being imaged (e.g., index of refraction, etc.). The system of linear equations may represent a linear approximation to the forward operator of a three-dimensional wave propagation equation or equations. Accordingly, applying a CS image reconstruction technique comprises identifying a solution to a system of linear equations, subject to suitable constraints, rather than numerically solving a wave-propagation equation in three dimensions, which is more computationally demanding and time consuming. A CS image reconstruction process may calculate a volumetric image of the subject, at least in part, by using a domain (e.g., a basis) in which the image may be sparse. Such a domain is herein referred to as a "sparsity domain" (e.g., a sparsity basis; though the domain need not be a basis and, for example, may be an overcomplete representation such as a frame of a vector space). An image may be sparse in a sparsity basis if it may be adequately represented by a subset of coefficients in that basis. Reconstruction processes taking into account the geometry of an imaging system may utilize any suitable algorithms, examples of which may include diffraction-based algorithms. Others are also possible.

Figure 29:
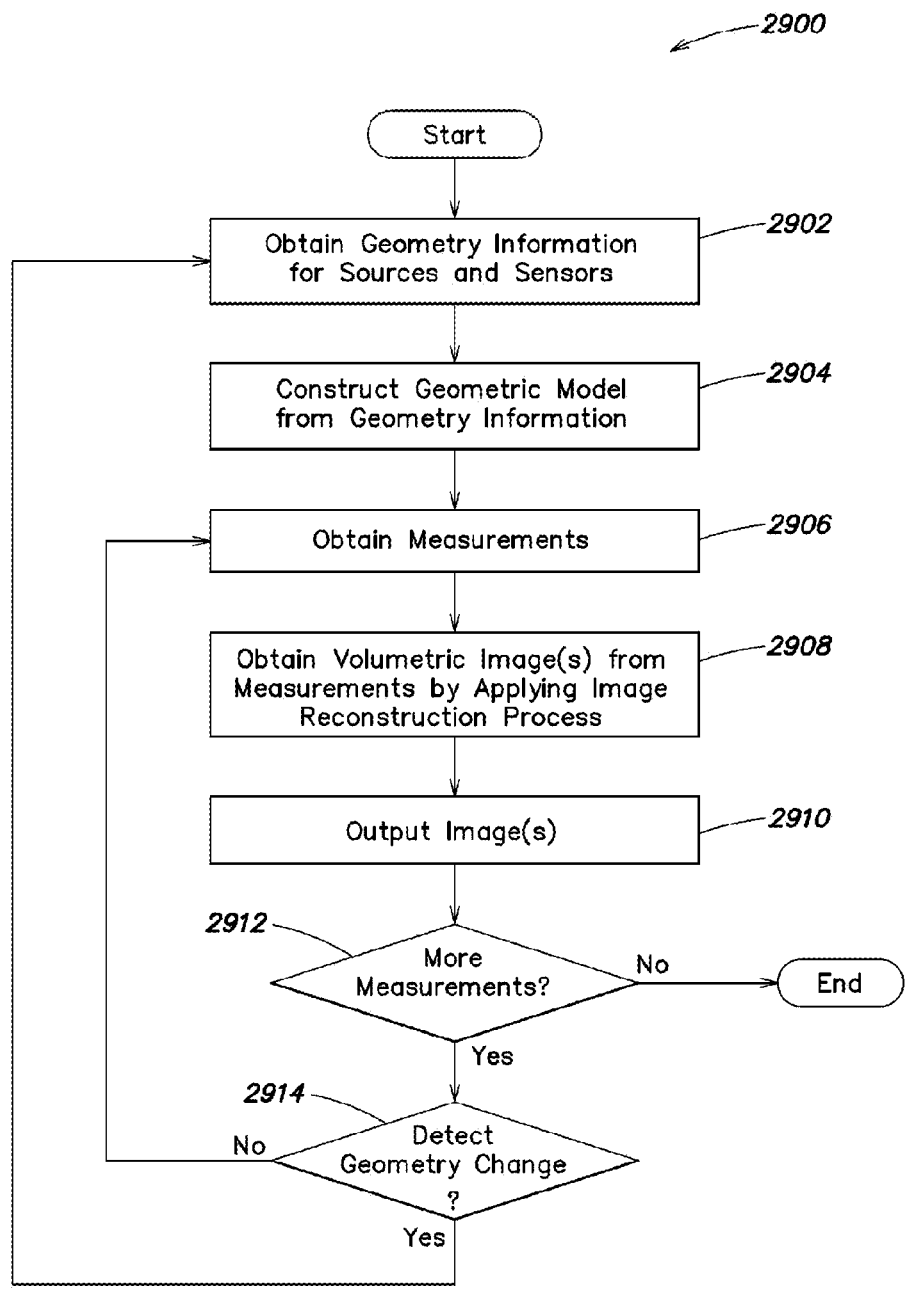
FIG. 29 illustrates a flowchart of a process for generating one or more volumetric images of a subject, according to a non-limiting embodiment.

Some embodiments, where an image reconstruction process may take into account the geometry of sources and sensors of the ultrasound imaging device, are described below with reference to FIG. 29. FIG. 29 illustrates a non-limiting process 2900 for obtaining one or more volumetric images from multiple measurements of a subject being imaged, in accordance with some embodiments. Process 2900 may be performed by any suitable processor or processors. For example, process 2900 may be performed by the reconstruction computer described with reference to FIG. 4.

Process 2900 begins at stage 2902, where the information about the geometry of sources and sensors in the ultrasound imaging device is obtained. In some instances, such geometry information may comprise information about the location of one or more ultrasound sources and/or one or more sensors in the ultrasound imaging device. The location information may comprise any information from which a location of one or more sources and/or sensors in three-dimensional space may be obtained and, as such, may comprise absolute location information for one or more sources and/or sensors, relative location information for one or more sources and/or sensors, or both absolute information and relative information. Absolute location information may indicate the location of one or more sources and/or sensors without reference to location of other objects (e.g., sources, sensors, other components of the ultrasound imaging device, etc.) and, for example, may include coordinates (e.g., Cartesian, spherical, etc.) indicating the location of one or more sources and/or sensors in three-dimensional space. Relative location information may indicate the location of one or more sources and/or sensors with reference to the location of other objects and, for example, may indicate the location of one or more sources and/or sensors relative to one or more other sources and/or sensors.

In some instances, when the ultrasound imaging device has one or more arrays of sources and/or sensors, the geometry information may comprise information about the location and/or orientation of each such array in three-dimensional space. As one non-limiting example, in embodiments where the ultrasound imaging device comprises sources and sensors disposed on moveable supports (e.g., a pair of hand-held paddles as in FIG. 25), the geometry information may comprise information about the location and/or orientation of one or more of the moveable supports. The location information may comprise absolute location information for one or more arrangements, relative location information for one or more arrangements, or any suitable combination thereof. Absolute location information may indicate the location and/or orientation of an arrangement without reference to location of other objects (e.g., any other arrays or components of the ultrasound imaging device) and, for example, may include coordinates indicating the location and/or orientation of the arrangement in three-dimensional space. Relative location information may indicate the location and/or orientation of an arrangement relative to that of another array or component of the ultrasound imaging device.

Geometry information may be obtained at 2902 in any of numerous ways. As described in more detail below, the geometry information may be obtained by using one or more sensors (e.g., accelerometer, gyroscope, inclinometer, inertial navigation system, etc.) in the ultrasound imaging device or outside the ultrasound imaging device. Moreover, as described in more detail below, geometry information may be obtained, additionally or alternatively, by operating the ultrasound imaging device in a transmissive modality to obtain the geometry information from characteristics of the signals received by the sensors of the imaging device. This may be done before the ultrasound imaging device is used to image a subject, but may be done, additionally or alternatively, while the ultrasound imaging device is being used to image the subject (e.g., dynamically during operation of the ultrasound imaging device).

Regardless of the manner in which geometry information is obtained in 2902, process 2900 next proceeds to 2904, where a geometric model is constructed based, at least in part, on the obtained geometry information. The constructed geometric model represents the obtained geometry information and, in some instances, may represent the geometry information so that it may be used by one or more image reconstruction processes.

Figure 30:
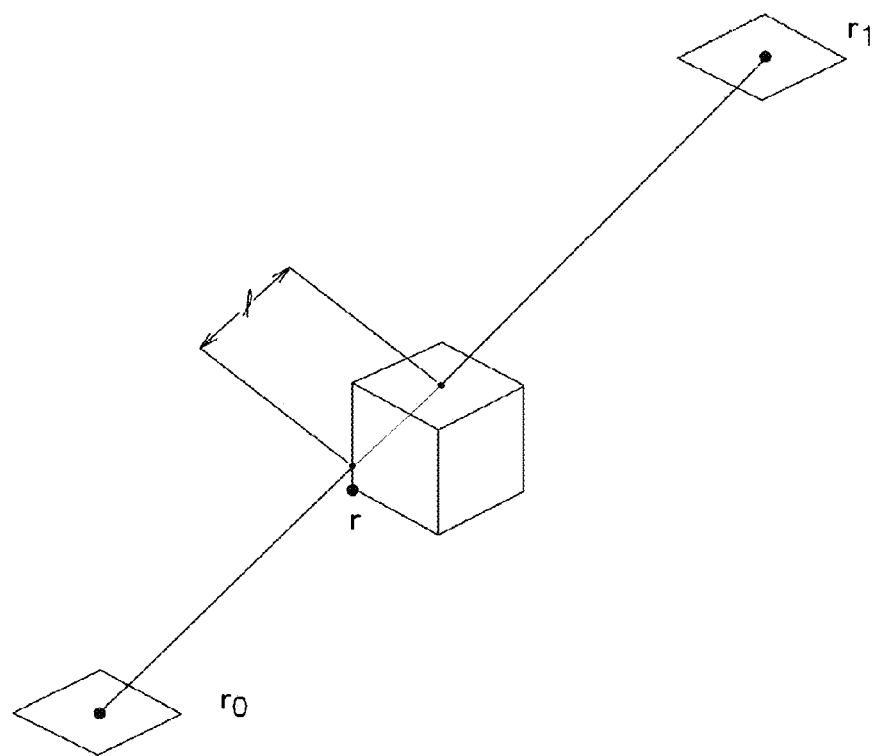
FIG. 30 illustrates a line segment, from one ultrasound element to another ultrasound element, which intersects a voxel in a volume to be imaged, according to a non-limiting embodiment.

In some embodiments, the geometric model may comprise path length information for one or more pairs of ultrasound sources and sensors. For an ultrasound source-sensor pair, a line segment between (positions of) the ultrasound source and the ultrasound sensor may intersect one or more voxels in the volume being imaged. For each of one or more such voxels, the path length information may comprise a value indicative of a length of the portion of the line segment that intersects the voxel. For example, as shown in FIG. 30, a voxel r lies along a line segment from source $r_0$ to sensor $r_1$. The length of the portion of the line segment intersecting the voxel r is shown to be l. As such, in this illustrative example, the path length information may comprise the value l. Additionally or alternatively, the path length information may identify one or more voxels of the volume being imaged, which intersect a line segment from the ultrasound source and to the ultrasound sensor.

In some embodiments, the path length information may comprise values indicative of the lengths of portions of a line segment between an ultrasound source and the ultrasound sensor for every source-sensor pair (i.e., every pair of an ultrasound source and an ultrasound sensor in which the ultrasound sensor may detect a signal transmitted by the ultrasound source). The values may include a value for each of one or more voxels intersecting the corresponding line segment.

The path length information may be calculated based at least in part on the geometry information obtained in 2902. In some embodiments, a value indicative of a length of the portion of the line segment that intersects a voxel may be calculated based, at least in part, on the geometry information obtained in 2902. The distance may be computed based on location information, absolute and/or relative, of the ultrasound source, the ultrasound sensor, and the voxel. As a non-limiting example, this distance may be computed by using coordinates (in any suitable coordinate system) specifying the locations of the ultrasound source, ultrasound sensor and the voxel.

Values included in path length information may be organized in any suitable way for accessing and using those values for subsequent processing. To this end, in some embodiments, the values may be encoded in a data structure. The data structure encoding such values may be stored on any tangible computer-readable storage medium (e.g., a computer hard drive, a CD, a flash memory, EEPROM, magnetic tape, disk, static RAM, dynamic RAM, or any other suitable medium). The listed types of computer-readable storage media are non-limiting examples of non-transitory storage media, and thus it should be appreciated that non-transitory storage media may be used in some embodiments. The computer-readable storage medium may be accessed by any physical computing device that may use the values encoded in the data structure.

By way of an illustrative non-limiting example, path-length information may be encoded in a matrix data structure, commonly referred to as a matrix. The matrix may have an entry for each value, included in path length information, which is indicative of a length of a line segment through a voxel in a volume being imaged. For example, the matrix may have a row (or column) storing values for each ultrasound source-sensor pair. In embodiments, where the ultrasound device has a source array having N×N ($N^2$) elements and a sensor array having N×N ($N^2$) elements, the matrix may have up to $N^4$ rows (or columns) as there are up to $N^4$ source-sensor pairs in such an arrangement. It should be appreciated that the source array is not limited to having a square-like N×N arrangement of elements, and may have $N_{tx} \times N_{ty}$ array of sources and an $N_{rx} \times N_{ry}$ array of sensors. In this case, the matrix may have up to $N_{tx} \times N_{ty} \times N_{rx} \times N_{ry}$ rows (or columns) as there up to $N_{tx} \times N_{ty} \times N_{rx} \times N_{ry}$ source-sensor pairs. For ease of presentation we denote this matrix by the symbol A.

Each row (or column) of the matrix A may comprise values indicative of the lengths of the portions of a line segment, between the source and sensor in the source-sensor pair associated with the row, through the voxels corresponding to each entry in the row. As a specific example, in a case when a volume being imaged comprises a volume composed of $M_x \times M_y \times M_z$ voxels, each row (or column) of matrix A may have $M_x \times M_y \times M_z$ entries (or $M^3$ entries when $M_x = M_y = M_z$). As such, in this illustrative non-limiting example, the geometric model constructed in act 2904 from obtained geometry information may comprise path length information, which may be encoded in an $N^4 \times M^3$ matrix A whose entry at (ijkl)'th row (i.e., the row associated with source (i,j) and sensor (k,l)) and (xyz)'th column (i.e., the column associated with voxel at coordinate (x,y,z) in the volume being imaged) corresponds to a value indicating the length of a path up through voxel (x,y,z) of a ray going from source (i,j) to receiver (k,l).

Entries of the matrix A may be computed in any of numerous ways. As one illustrative non-limiting example, a length of a portion of a line segment (from a source to a sensor in a source-sensor pair) through a voxel may be iteratively computed (in serial or in parallel) for each of multiple voxels in a volume being imaged and for each of multiple ultrasound source-sensor pairs. In some cases, a length of a portion of a line segment may be computed for each voxel in a volume being imaged and for each ultrasound source-sensor pair in the ultrasound imaging device. In some embodiments, such a computation may be performed by (1) iterating over all voxels in the volume being imaged and, for each voxel in the volume, (2) iterating over all ultrasound source-sensor pairs and, for each pair, (3) checking whether a line segment between the source and the sensor in the pair intersects the voxel, and, if it does, then (4) computing a length of the portion of the line segment that intersects the voxel.

The computational complexity of an approach in which the length of a line segment through a voxel is computed may scale linearly with the product of the number of source-sensor pairs and voxels in the volume being imaged. For example, in a case when a volume being imaged is composed of $O(M^3)$ voxels and there are $O(N^4)$ source-sensor pairs, the computational complexity of such an approach is $O(N^4 M^3)$ operations. Here, the "O(.)" notation is the standard "big O" notation, as is known in the art. It should be recognized that numerous other approaches to calculating entries of the matrix A are possible and, as described in more detail in Appendix A below, some of these other approaches may have better computational complexity. For instance, in one such illustrative approach described in Appendix A, entries of the matrix A may be computed by using a process whose computational complexity is $O(N^4 M)$ rather than $O(N^4 M^3)$ as the case may be for the above-described calculation technique.

Moreover, in some embodiments, construction of the geometric model at 2904 may take into account various physical phenomena. For example, scattering (e.g., back-scattered radiation, forward-scattered radiation), dispersion, diffraction, and/or refraction may be taken into account as desired. For example, dispersion may be modeled as a Taylor expansion series, and may be accounted for in speed of sound and attenuation measurements. Accounting for such phenomena may provide more accurate geometric models and therefore more accurate images. However, not all embodiments require consideration of such phenomena.

In some embodiments in which line segment lengths are computed, such computation may take into account refraction. Doing so may improve the accuracy of a reconstructed image, for example by reducing smearing in the image. In many embodiments, assuming a straight line from a source to a sensor represents an approximation. In practice, the path from source to sensor may deviate from a straight line due to refraction. One manner of accounting for the impact of refraction is to utilize an iterative reconstruction process.

A volumetric image may be reconstructed initially assuming straight paths from sources to sensors of an imaging system. Refracted paths may then be computed in any suitable manner. According to some embodiments, refracted paths may be computed using Fermat's principle, for example by formulating a suitable differential equation based on the principle and obtaining a solution to the differential equation. The differential equation may be formulated to represent optic ray propagation in two or three dimensions. The different equation may be formulated at least in part based on the Euler-Lagrange equations. The computed refracted paths may then be used to calculate another volumetric image of the subject.

Accordingly, in some embodiments, an iterative reconstruction process may comprise accessing measurements of a subject; calculating a first volumetric image of the subject from the accessed measurements and using first path length information obtained by assuming straight paths from sources to sensors of the ultrasound imaging device used to obtain the measurements (e.g., in a transmissive modality); computing refractive paths and using the refractive paths to calculate second path length information; and calculating a second volumetric image of the subject from the measurements and the second path length information.

In some embodiments, where a compressive sensing image reconstruction technique is used to calculate volumetric images of the subject, and the technique includes identifying a solution to a system of linear equations relating measurements of the subject to a property of the subject being imaged, the system of linear equations may be modified to account for the computed refracted paths. As one non-limiting example, the above-described matrix A (representing the system of linear equations) may be modified to account for the refracted paths. The resulting updated system of linear equations may be used to calculate another volumetric image of the subject. As desired, the method may be iterated (e.g., by again calculating the refracted paths and again updating the matrix A) as many times as needed to provide a desired level of accuracy of the reconstructed image.

As mentioned, path lengths, as well as path shapes, may be calculated in any suitable manner. In some embodiments, the path lengths and/or path shapes may be calculated over a discretized grid by using Dijkstra's algorithm, Floyd-Warshall algorithm, and/or Johnson's algorithm may be used. In other embodiments, ray-tracing (e.g., ray-bending) techniques may be used. Other techniques are also possible.

Regardless of how the geometric model is constructed from geometry information at 2904, process 2900 proceeds to 2906, where measurements of a subject being imaged are obtained. Measurements of the subject may be obtained in any suitable way. In some embodiments, the measurements may be accessed after having been obtained by using an ultrasound imaging device (e.g., operating in a transmissive modality) and made available for subsequent access. Additionally or alternatively, the measurements may be obtained by using the ultrasound imaging device as part of act 2906. In some embodiments, the measurements may be obtained based at least in part on energy forward scattered from the subject and detected by the ultrasound imaging device.

Any of the numerous types of measurements previously described herein or any other measurements may be obtained including, but not limited to, amplitude of the received ultrasound signals, phase of the received ultrasound signals, frequency of the ultrasound signals as well as any measurements (e.g., attenuation, time-of-flight, speed of sound, temperature, etc.) derived from these quantities. The measurements may be received for some or all of the ultrasound sensors in an ultrasound imaging device.

Since one or multiple of the above-described types of measurements may be obtained as a result of the operation of an ultrasound imaging device, one or multiple volumetric images may be obtained by applying an image reconstruction process to these measurements. In some embodiments, a volumetric image of the subject being imaged may be calculated from each of one or more of the above-described types of measurements. For example, a volumetric image of the subject being imaged may be calculated based at least in part on time-of-flight measurements. In some instances, such a volumetric image may be a volumetric image of the index of refraction of the subject being imaged, herein referred to as a volumetric index of refraction image. Additionally or alternatively, a volumetric image may be calculated based, at least in part, on the attenuation measurements, herein referred to as a volumetric attenuation image. Additionally or alternatively, a volumetric image may be calculated based, at least in part, on the speed-of-sound measurements, herein referred to as a volumetric speed-of-sound image. Additionally or alternatively, a volumetric image of the subject being imaged may be formed based, at least in part, on temperature measurements, herein referred to as a volumetric temperature image. Any suitable number of volumetric images may be calculated from the obtained measurements, as aspects of the present application are not limited in this respect.

After measurements are obtained, process 2900 proceeds to 2908, where an image reconstruction process may be used to generate one or more volumetric images from the obtained measurements. Any suitable image reconstruction process may be used. In some embodiments, an image reconstruction process that takes into account the geometry information (obtained at 2902) and/or the geometric model (constructed at 2904) may be used. The image reconstruction process may use the geometry information and/or the geometric model to calculate a property of the subject being imaged from the measurements obtained at 2906 and, in some embodiments, may calculate a value associated with the property for each of one or more voxels in a volume being imaged in order to calculate a volumetric image. For example, in some embodiments, a geometric model comprising path length information may be used to compute an index of refraction for each of one or more voxels in a volume being imaged from time-of-flight measurements only, from attenuation measurements only, or from both time-of-flight measurements and attenuation measurements. In embodiments where both time-of-flight and attenuation measurements are used to compute an index of refraction, the calculation may be done at least in part by using Kramers-Kronig relations and/or power law calculations to relate attenuation measurements with time-of-flight measurements. As another example, in some embodiments, an image reconstruction process may use a geometric model comprising path length information to compute a scattering and/or absorption value for each of one or more voxels in a volume being imaged from the attenuation measurements only, time-of flight measurements only, or from both time-of-flight measurements and attenuation measurements.

A geometric model comprising path length information may be used to relate measurements to a property of the subject being imaged in any of numerous ways. In some embodiments, the path length information may be used to construct a functional relationship (i.e., a mapping) between the measurements and the property of interest. This may be accomplished in any of numerous ways. As an illustrative non-limiting example, the path length information may be used to construct a mapping between the time-of-flight measurements and indices of refraction of voxels in an volume being imaged by using the above-described matrix A. In particular, suppose that the matrix A has $N^4$ rows, with each row corresponding to an ultrasound source-sensor pair (for opposed rectangular arrays of dimension N×N), and $M^3$ columns, with each column corresponding to a voxel being imaged (for a cubic volume of dimension M×M×M). Additionally, let x be an $M^3 \times 1$ vector of index of refraction values for each of the voxels in the volume being imaged, and let y be an $N^4 \times 1$ vector of time-of-flight measurements (with each measurement obtained from a source-sensor pair). Then the measurements may be related to the index of refraction values according to the relationship given by:

$$Ax=y, \quad (1)$$

Thus, the linear relationship of (1) may be used to calculate a volumetric image by obtaining the measurements y and using (1) to estimate x, which contains the values of one or more voxels of the volumetric image. It should be appreciated that a relationship analogous to that of (1) may be constructed for any of the above-described types of measurements and properties. It should also be appreciated that the dimensions of the above matrices and vectors are illustrative and non-limiting, as the precise dimensions of the vectors and matrices may depend on the number of source-sensor pairs used to obtain measurements as well as the number of voxels for which a value of the property of interest is to be calculated. It should also be appreciated that the relationship between properties of the subject being imaged is not limited to being represented in a form such as (1) and, in some embodiments, may be represented in any other suitable way.

Any of numerous image reconstruction processes may be used to calculate a volumetric image by using the measurements obtained at 2906 and a geometric model comprising path length information. For example, any image reconstruction process that may be used to calculate a volumetric image based, at least in part, on the relationship (1) may be used. In some embodiments, a compressive sensing (CS) image reconstruction process may be used to generate a volumetric image by using a geometric model comprising path length information and the measurements obtained at 2906 and, for example, based, at least in part, on the relationship (1).

Compressed sensing or compressive sampling refers to a set of signal processing techniques (e.g., image processing techniques) premised on the assumption that the signals to which they are applied are sparse in some sparsifying domain. That is, the energy of these signals may be concentrated in a small subset of the sparsifying domain. For example, images may be sparse (and as a result may be amenable to being compressed) in certain domains A typical photograph, for instance, may be sparse in the Discrete Cosine Transform (DCT) domain because most of the energy in the DCT coefficients is concentrated in a small subset of the DCT coefficients representing the photograph in the transform domain, while the other coefficients are either zero or very small with respect to the largest coefficients. Thus, the DCT is a "sparsifying" transform for natural images—which is one reason that it is the technique underlying JPEG compression.

Another sparsifying transform is the CDF Wavelet Transform, which is the technique underlying JPEG 2000 compression.

Figure 31:
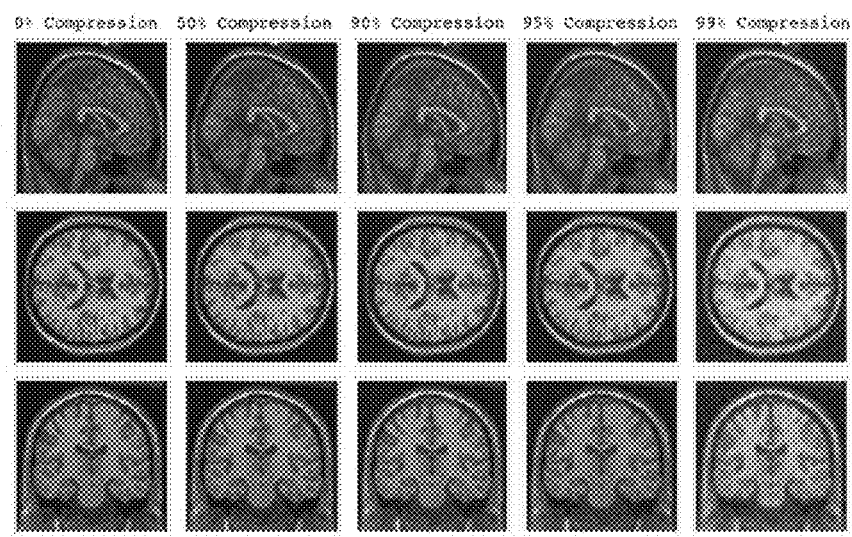
FIG. 31 illustrates medical images at various levels of compression in the discrete cosine transform domain.

As another example, medical images may be sparse in the DCT domain FIG. 31 shows how images of the brain may be compressed by discarding data corresponding to, e.g., the smallest N % DCT coefficients, where N is any number between 0 and 100. As an illustrative example, FIG. 31 shows images of the brain at various levels of "compression" in the DCT domain. To obtain the images shown in a particular column of images shown in FIG. 31, the original brain images are transformed to the DCT domain, all N % (where N is indicated at the top of the column) of the DCT coefficients representing the transformed images are discarded, and the images shown in FIG. 31 are reconstructed from the remaining DCT coefficients. Note how similar the images are across columns even as large percentages of coefficients are discarded. Indeed, many of the important features in the images are still discernible even when 99% of the coefficients are discarded, demonstrating that medical images may be sparse in the DCT domain.

Accordingly, a compressive sensing image reconstruction process utilizing a sparsity domain to generate the volumetric image from the obtained measurements may be used at 2908. The sparsity domain may be any suitable domain in which the volumetric image may be sparse. In some embodiments the sparsity domain may be a representation such as a basis, a frame of a vector space, an overcomplete representation, etc., in which the volumetric image may be sparse. For example, the sparsity domain may be a three-dimensional basis including, but not limited to, a three-dimensional generalization of any type of discrete cosine basis, discrete sine basis, wavelet basis, or any other type of sparsifying domain known in the art. As a particular non-limiting example, the three-dimensional discrete cosine transform, which is the three-dimensional generalization of the DCT-II, or $D_3$ for short, is given according to:

$$(D_3 x)_k = \sum_{n=0}^{N-1} a_n \cos\frac{\pi k}{N} n + \frac{1}{2} x_n,$$

where $$a_n = \begin{cases} \frac{1}{\sqrt{N}} & n = 0 \\ \frac{1}{\sqrt{2N}} & n > 0. \end{cases}$$

A compressive sensing image reconstruction process may generate a volumetric image based, at least in part, on the measurements (e.g., obtained at 2906), geometric model (e.g., calculated at 2904), and the sparsity basis. This may be done in any suitable way. In some embodiments, a compressive sensing image reconstruction process may calculate a volumetric image by using a mapping between the measurements (e.g., time-of-flight measurements) and a property of the subject being imaged (e.g., indices of refraction). As an illustrative example, a CS image reconstruction process may use the relationship (1) together with a sparsity basis to calculate a volumetric image. In some embodiments, a CS image reconstruction process may calculate a volumetric image at least in part by solving an optimization problem comprising a sparsity constraint. In one illustrative, non-limiting embodiment this may be done, at least in part, by solving:

$$\min\|x\|_{l_1}, \text{ subject to the constraint of } (AD_3^{-1})x = y, \qquad (2)$$

and return $x^* = D_3^{-1}x$ as the vector of values corresponding to the volumetric image, where the matrix A and the vectors x and y, were previously described with reference to (1). This formulation of compressive sensing is sometimes called the basis pursuit method and comprises optimizing an $l_1$ norm subject to an equality constraint. It should be appreciated that a CS image reconstruction process may be used to calculate a volumetric image at least in part by solving optimization problems different from that of (2), corresponding to different formulations of compressive sensing. For example, a CS image reconstruction process may calculate a volumetric image at least in part by optimizing an $l_1$ norm subject to an inequality constraint (e.g., minimize $\|x\|_{l_1}$ subject to $\|AD_3^{-1}x - y\|_2 < \lambda$ for some small $\lambda > 0$, where $\|\ \|_2$ is the Euclidean norm, and where $\|\ \|_{l_1}$ is the $l_1$ norm). As another example, a CS image reconstruction process may calculate a volumetric image at least in part by using the Dantzig selector approach (e.g., minimize $\|x\|_{l_1}$ subject to $\|A^*(AD_3^{-1}x - y)\|_\infty < \lambda$, where $A^*$ is the Hermitian conjugate of A and $\|\ \|_\infty$ is the $1\infty$ norm). As yet another example, a CS image reconstruction process may calculate a volumetric image at least in part by using an objective function comprising a total-variation norm (e.g., minimize $\|x\|_{l_1} + \alpha\|x\|_{TV}$ subject to $\|AD_3^{-1}x - y\|_2 < \lambda$, for some small $\lambda > 0$, for some $\alpha > 0$, where $\|\ \|_{TV}$ is the total variation norm suitably generalized to three dimensions). As yet another example, a CS image reconstruction process may calculate a volumetric image at least in part by using a LASSO algorithm (e.g., minimize $\|AD_3^{-1}x - y\|_2$ subject to $\|x\|_{l_1} < \lambda$, for some small $\lambda > 0$). As yet another example, a CS image reconstruction process may calculate a volumetric image at least in part by using an objective function comprising a re-weighted $l_1$ norm subject to any of the above-described constraints or any other suitable constraints. Other examples of compressive sensing techniques that may be used as part of a CS image reconstruction process include, but are not limited to, soft thresholding, hard thresholding, matching pursuit, and iterative greedy pursuit. Thus, it should be appreciated that the formulation of (2) is an illustrative and non-limiting example.

It should be appreciated that solving (2) may be considered a proxy for reconstructing the unknown volumetric image x from a set of measurements y, such that x is the sparsest signal consistent with the measurements. Indeed, under certain conditions, minimizing the $l_1$ norm subject to a constraint by solving:

$$\min\|\Psi x\|_{l_1}, \ s \cdot t \cdot Ax = y, \qquad (2a)$$

where $\|x\|_{l_1} = \sum_{i=1}^n |x_i|$ and $\Psi$ is a sparsity basis (e.g., DCT), is equivalent to solving:

$$\min\|\Psi x\|_{l_0}, \ s \cdot t \cdot Ax = y,$$

where the $l_0$ norm, is equal to the number of non-zero elements in x. The formulation in (2a) may also be generalized according to alternative CS formulations (e.g., $l_1$ norm subject to inequality constraints, the Dantzig selector, LASSO, etc.) as described with respect to equation (2). As such, it should be appreciated that the calculated volumetric images may be sparse in the sparsity domain defined by $\Psi$. Note that the latter problem, is a combinatorial optimization problem that is computationally infeasible, whereas the former (i.e., the optimization problem defined by (2a)) may be solved using any of numerous linear programming techniques as described in more detail below.

A CS image reconstruction process may utilize a suitable numerical technique or techniques to calculate a volumetric image. In some embodiments, any suitable convex optimization techniques may be used. For example, linear programming techniques may be used. As another example, "first-order" methods such as Nesterov methods may be used. As yet another example, interior point methods may be used. Such convex optimization methods may be implemented at least in part by using "matrix-free" solvers such as a conjugate-gradient process, which may be advantageous in a setting where it may be more efficient to operate on rows or columns of the matrix ($AD_3^{-1}$) than on the entire matrix, which may be the case when A is sparse and/or the sparsifying transform (e.g., the DCT transform) may be efficiently computed using the fast Fourier transform. It should be appreciated that techniques from sparse linear algebra may be applied as well since the matrix A may be sparse. Indeed, the number of voxels intersecting a straight line through a cubic volume V is O($\sqrt[3]{V}$), so that each row (representing a single measurement), may be largely filled with zeros.

Accordingly, a CS image reconstruction process may utilize one or more software packages implementing the above-described numerical techniques. For example, a CS image reconstruction process may use one or more compressive sensing software packages, numerical linear algebra software packages, or other suitable software. In addition, a CS image reconstruction process may be parallelized. An interior point method may comprise performing multiple iterations of solving a particular linear equation, which may be done at least in part by using the conjugate gradient (CG) algorithm or any other least squares solver. Such a CG algorithm may be parallelized and may be performed by multiple processors and/or by a graphical processing unit or units. In some embodiments, a truncated CG technique may be used.

It should be recognized that a volumetric image may be calculated using image reconstruction processes other than compressive sensing image reconstruction processes, as aspects of the present application are not limited in this respect. For example, in some embodiments, a least-squares type technique may be used. A least-squares type technique may be used with or without regularization. A least-squares type technique may be used to calculate a volumetric image at least in part by finding the solution x that minimizes the $l_2$ error (i.e., the squared error) of the measurements according to:

$$\min \|Ax-y\|_{l_2}. \quad (3).$$

The relation (3) may be solved using any of numerous processes including, but not limited to, processes for iteratively solving linear equations such as the conjugate gradient process, LSQR process, etc. Though, it should be appreciated that the applicability of such a technique may depend on whether the system of linear equations represented by (1) is solvable. The relation (1) is one that may comprise $O(N^4)$ equations in $O(M^3)$ variables and, depending on the values of M and N in a particular embodiment, may be over-constrained.

The inventors have appreciated that, in some instances, the solution to (3) may not be unique. That is, calculating a volumetric image by using (3) to compute x may be an ill-posed problem. Accordingly, in some embodiments, the least-squares criterion of (3) may be used together with a regularization technique to identify a solution from among the set of non-unique solutions such that the identified solution satisfies a suitable regularity criterion. Any of numerous regularization techniques (e.g., Tikhonov regularization, truncated SVD, total variation, edge preserving total variation, etc.) may be used, as aspects of the present application are not limited in this respect.

Regardless of the type of image reconstruction process used at 2908, process 2900 next proceeds to 2910 where the volumetric image(s) calculated at 2908 may be output. This may be done in any suitable way. In some embodiments, the calculated images may be presented for viewing by a user or users using one or more display screens or any other device for visualizing the images (e.g., a doctor viewing medical images). Additionally or alternatively, the calculated images may be stored (e.g., in a memory or any other suitable computer-readable storage medium) so that they may be accessed later and presented for viewing by a user or users.

Once an image is generated, the image may optionally be manipulated. For instance, a viewer (e.g., a doctor) may desire to enlarge an image, shrink an image, move an image from side to side, and/or rotate an image (in 3D or otherwise), as non-limiting examples. Such manipulation may be performed in any suitable manner, as the aspects described herein in which manipulation of an image is provided are not limited to the manner in which the manipulation is performed.

For instance, an image may be manipulated via a user interface or other device. A keyboard may be implemented, a mouse, a remote control, or a 3D detection mechanism detecting movements of the viewer (e.g., hand movements) suggestive of the viewer's desired manipulation of the image. A non-limiting example of such 3D detection mechanisms is the Leap, available from Leap Motion of San Francisco, Calif. Such technology may allow the viewer to control the image by pointing, waving, or using other natural hand gestures within a detection space located above the Leap device.

Manipulation of images, performed in any suitable manner, may facilitate various functions to be performed by a user. For example, a doctor viewing such images may more easily be able to diagnose a patient based on what is shown by suitable manipulation of the image. The doctor may be able to plan a surgical path based on the image, or identify a position of a patient at which to apply HIFU (described further below). Thus, various benefits may be achieved by allowing for viewing and manipulation of images.

Next, process 2900 proceeds to decision block 2912, where it may be determined whether there are more measurements to be processed. In some embodiments, the ultrasound imaging device may obtain or may have already obtained more measurements to use for forming one or more additional volumetric images. This may occur in numerous scenarios such as when the imaging device is operated to obtain multiple volumetric images of a subject being imaged. If it is determined, in decision block 2912, that there are no additional measurements to be processed, process 2900 completes.

On the other hand, if it is determined, in decision block 2912, that there are additional measurements to be processed, process 2900 proceeds, via the YES branch, to decision block 2914, where it is determined whether the geometry of sources and/or sensors in the ultrasound imaging device changed. In particular, it may be determined whether the relative position and/or orientation of the ultrasound sources and sensors changed. This may be done in any suitable way and, for example, may be done based at least in part on information gathered by one or more sensors configured to detect changes in the relative position and/or orientation of ultrasound sources and sensors (e.g., see FIG. 27). Such sensors may be external to or onboard the ultrasound imaging device, or at any other suitable locations.

If no change in the geometry of the sources and/or sensors is detected, process 2900 loops back, via the NO branch, to 2906 and 2906-2912 may be repeated. On the other hand, if a change in the geometry of the sources and/or sensors is detected, process 2900 loops back, via the YES branch, to 2902, where updated geometry information for sources and/or sensors may be obtained.

It should be appreciated that process 2900 is illustrative and many variations of this process are possible. For example, in the illustrated embodiment, process 2900 comprises obtaining geometry information and calculating a geometric model based at least in part on the obtained geometry information. However, in other embodiments, a geometric model may have been pre-computed and saved in a memory or any other suitable computer-readable storage medium prior to the start of process 2900. In these embodiments, the pre-computed geometric model may be loaded rather than calculated as part of process 2900. Other variations are also possible.

In some embodiments in which compressive sensing techniques are used, the A matrix may be stored in memory. In some embodiments, the A matrix may be stored in cache. In some embodiments, the A matrix may be computed dynamically, for example by computing a kernel as a starting point. Thus, those embodiments utilizing compressive sensing techniques are not limited in the manner in which the A matrix is obtained.

The physical process that takes place when a signal is transmitted from a radiation source to a radiation sensor may be modeled in any of numerous ways. For example, infinite wavelength approximations, such as the straight ray approximation described earlier may be used. Higher-order approximations incorporating scattering and diffraction phenomena may also be used. For example, fat beams, Fresnel zone beams, Gaussian beams, banana-donut beams, and combinations of those types of beams may be implemented in the image reconstruction process to model the measurement process. As has been previously described, beamforming may be implemented according to embodiments of the present application. Information about the beam may be used in the reconstruction process. For example, the beam type may impact the geometry of the system, and therefore the above-described A matrix. Accordingly, in some embodiments, the A matrix may be computed to reflect the type of beam chosen for image reconstruction.

Compressive sensing is one technique which may be used to form images according to embodiments of the present application, as described above. However, other techniques may be used as well. As one example, one or more algebraic reconstruction techniques (e.g., simultaneous algebraic reconstruction techniques (SART), filtered backprojection, etc.) may be used to form images. As another example, in some embodiments imaging configurations may be modeled as a forward scattering problem and volumetric images may be calculated by using one or more inverse scattering techniques (e.g., inverse scattering techniques using a Born approximation(s), Rytov approximation(s), hybrid Rytov approximation(s), series solutions, iterated solutions, and/or any suitable combination thereof). The forward scattering problem may be evaluated numerically or analytically, and does not require use of an A matrix. In some embodiments, modeling the system as a forward scattering problem may allow for measuring the spatial frequencies of the index of refraction of a subject. For example, a value representing the gradient of the index of refraction may be obtained for one or more voxels within an imaged volume, thus providing an indication of the object susceptibility or scattering potential of the object. As another example, in some embodiments, volumetric images may be calculated by using one or more wave-propagation techniques for propagating waves in three dimensions. For example, backpropagation techniques may be used. As another example, linearized backpropagation techniques (e.g., in the Fourier domain), iterative propagation techniques, pre-condition wave propagation techniques, techniques utilizing Frechet derivative(s) of a forward operator, and/or time-reversed wave propagation techniques may be used.

Various aspects of the present application have been described in the context of imaging, and more specifically in the context of medical imaging. For example, aspects of the present application may be used in the diagnosis, monitoring, and/or treatment of patients. Detection of various patient conditions, such as the presence of tumors, may be facilitated using one or more aspects of the present application.

However, it should be appreciated that medical imaging represents a non-limiting example of an application of the aspects described herein.

Moreover, techniques for ultrasound imaging described herein may be implemented in combination with other medical imaging modalities. As previously alluded to, another common imaging modality is MRI. MRI is typically characterized by drawbacks such as expense and geometry constraints. MRI machines are conventionally large, and not easily adapted to a subject under investigation. In some scenarios, it may be desirable to provide an additional imaging modality in combination with MRI. One or more aspects of the present application may facilitate such combination of imaging modalities. For example, use of arrangements of ultrasound elements in the form of paddles (e.g., see FIGS. 25 and 26) may be used in combination with MRI. The paddles may be disposed in a suitable location with respect to a patient inside an MRI machine. The data collected by the arrangement of ultrasound elements and any images developed therefrom may supplement MRI images.

It should be appreciated, however, that medical imaging represents a non-limiting field in which aspects of the present application may be applied. For example, aspects of the present application may also be applied to materials investigation, geologic investigation, and other fields in which it is desired to determine properties of a subject of interest non-invasively.

Moreover, it should be appreciated that while various non-limiting embodiments have been described in the context of ultrasound, various aspects of the present application are not limited in this respect. For example, some of the aspects of the present application may apply to other types of signals, such as X-ray techniques and optical transmission techniques, among others. Thus, it should be appreciated that arrangements of elements as described herein are not necessarily limited to the elements being ultrasound elements, and the transmission and reception of signals by arrangements of elements is not limited to such signals being ultrasound signals.

Figure 32:
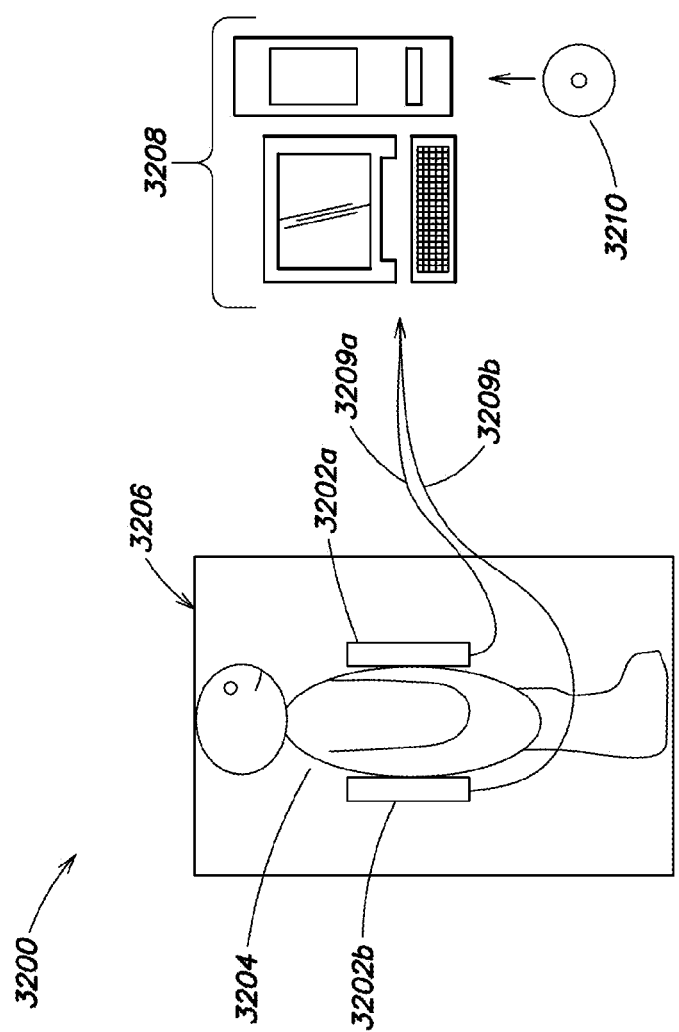
FIG. 32 illustrates an imaging system, which may be used to image a patient, according to a non-limiting embodiment.

FIG. 32 illustrates a non-limiting example of a system 3200 as may be used according to one or more aspects of the present application for imaging of a patient. As shown, the system 3200 includes arrangements of ultrasound elements 3202*a* and 3202*b*, which may be configured as paddles (e.g., of the type previously illustrated with respect to FIGS. 25 and 26, or any other suitable type), though not all embodiments are limited in this respect. The arrangements of ultrasound elements 3202*a* and 3202*b* may be disposed in a desired position with respect to a patient 3204 on a table 3206. The arrangements of ultrasound elements 3202*a* and 3202*b* may be coupled via respective connections 3209*a* and 3209*b* to a processing system 3208, which may be any suitable processing system, such as any of those previously described herein, for controlling operation of the arrangements of ultrasound elements. According to an embodiment, the processing system 3208 may further be configured to reconstruct one or more images. As shown, the processing system 3208 may be configured to receive a digital video disc (DVD) or compact disc (CD) 3210, which may, in some non-limiting embodiments, store instructions which may be executed by the processing system 3208 to control operation of the arrangements of ultrasound elements 3202a and 3202b. The processing system 3208 may itself include memory, for example, random access memory (RAM), read-only memory (ROM), or any other suitable memory. The memory may store instructions which may be executed by the processor 3208 to control operation of the arrangements of ultrasound elements and/or to reconstruct one or more images of the subject 3204.

Figures 33A, 33B:
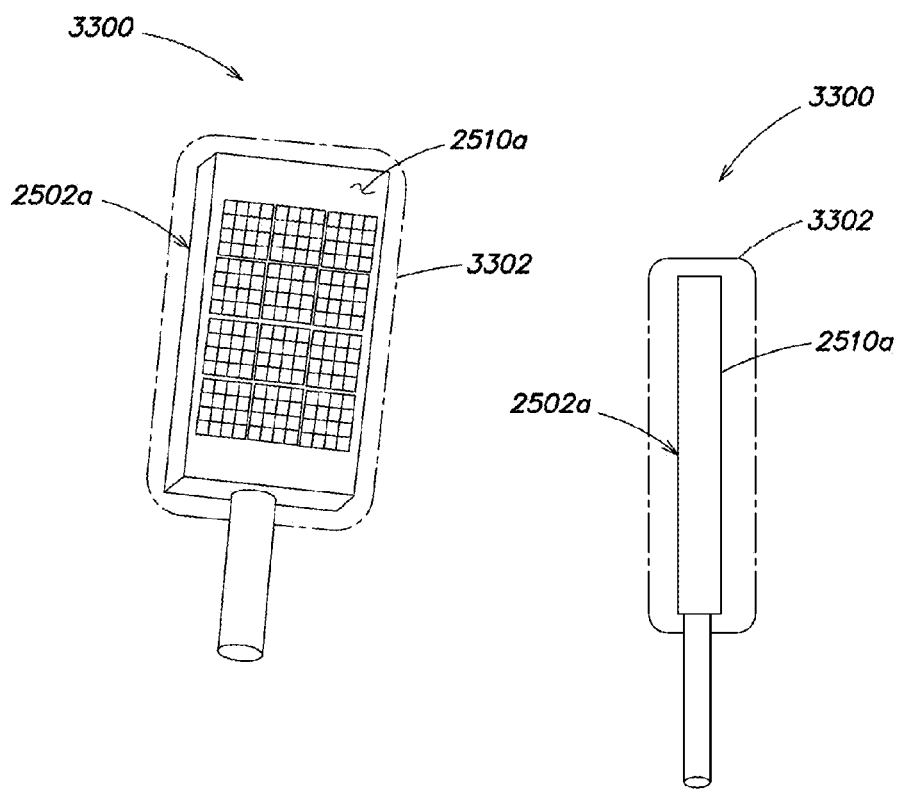
FIGS. 33A and 33B provide alternate views of an apparatus comprising an arrangement of ultrasound elements and an impedance matching component, according to a non-limiting embodiment.

In some embodiments, it may be desirable to provide for an acoustic impedance matching condition of the ultrasound device. For example, an acoustic impedance matching component may be positioned between an arrangement of ultrasound elements and a subject (e.g., a patient). FIGS. 33A and 33B illustrate a non-limiting example expanding upon the construction of paddle 2502a of FIG. 25.

As shown, the device 3300 includes the paddle 2502a of FIG. 25 with the addition of a bolus 3302. The bolus 3302 may be formed of any suitable material to provide desired impedance matching when the paddle 2502a is brought into contact with a subject to be imaged. For example, if the subject is a human patient, the bolus 3302 may include a material having substantially the same impedance as that of human tissue. The bolus 3302 may include an outer bag filled with a gel, liquid, or other suitable material, and may be attached or otherwise coupled to the paddle 2502a in any suitable manner. In some embodiments, the bolus may not be attached to the paddle, but may be positioned between the subject and the arrangement of ultrasound elements in any suitable manner.

According to some embodiments of the present application, an apparatus for performing HIFU is provided. The apparatus may comprise an arrangement of ultrasound elements configured to operate as HIFU elements, and which in some non-limiting embodiments may be arranged (or distributed) among ultrasound elements configured to operate as ultrasound imaging elements. In this manner, a single apparatus may perform both HIFU and ultrasound imaging, and therefore may be considered a dual- or multi-modal apparatus.

In some embodiments in which an apparatus is provided including both ultrasound imaging elements and HIFU elements, one or more of the imaging and HIFU elements may be the same as each other. However, in alternative embodiments, the two types of elements may differ. For example, the center frequency, bandwidth, size and/or power specifications may differ for the ultrasound elements configured as imaging elements as compared to those configured as HIFU elements. The types of waveforms transmitted may also differ between the different types of elements. In some embodiments, the ultrasound elements configured as imaging elements may be coupled to different types of circuitry than those configured as HIFU elements.

HIFU elements, as used herein, are ultrasound elements which may be used to induce a temperature change in a subject. The temperature change may be up to approximately 30 degrees Celsius or more, and may be sufficient in some embodiments to cauterize tissue. However, HIFU elements need not achieve cauterization. For example, less energy than that required for cauterization may be applied. In some embodiments, HIFU elements may be used to achieve heat shock or cause apoptosis (programmed cell death). Achieving such results typically requires less energy than that required to achieve cauterization, but may still be useful in some embodiments. Typically, HIFU elements deposit more power in a subject than conventional ultrasound imaging elements.

According to an embodiment, an apparatus may be provided comprising a first plurality of ultrasound imaging elements and a first plurality of high intensity focused ultrasound (HIFU) elements. The first plurality of ultrasound imaging elements and the first plurality of HIFU elements may be physically coupled to a first support. At least some elements of the first plurality of ultrasound imaging elements are disposed among at least some elements of the first plurality of HIFU elements. As described, the relative arrangement of ultrasound elements configured as HIFU elements and those configured as ultrasound imaging elements may take any of various suitable forms.

According to an embodiment, the ultrasound elements configured as HIFU elements may be interspersed (placed at intervals) among the ultrasound elements configured as imaging elements. The ultrasound elements configured as HIFU elements may be interspersed in a patterned or substantially non-patterned manner. As a non-limiting example, the ultrasound elements configured as HIFU elements may, in combination with the ultrasound elements configured as imaging elements, form a checkerboard pattern, a non-limiting example of which is described below in connection with FIG. 34B.

According to an embodiment, the ultrasound elements configured as HIFU elements may be arranged between ultrasound elements configured as imaging elements. For example, referring to FIG. 34A, which illustrates an apparatus 3400 comprising elements configured as HIFU elements 3402 and elements configured as imaging elements 3404, one or more of the HIFU elements 3402 may be between two or more of the imaging element 3404. In the embodiment shown, the HIFU elements are larger than the imaging elements, but the present aspect is not limited in this respect.

Figure 34A:
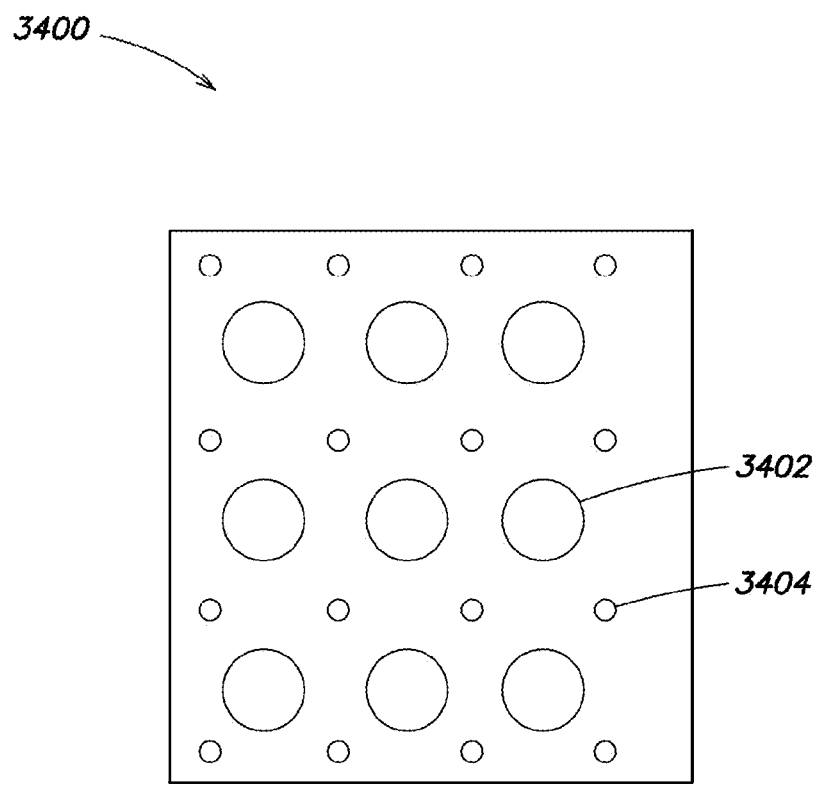
FIGS. 34A, 34B, and 35A-35I illustrate examples of apparatus including arrangements of ultrasound elements configured to perform HIFU and radiation (e.g., ultrasound) elements configured to perform imaging (e.g., ultrasound imaging), according to two non-limiting embodiments.

According to an embodiment, the ultrasound elements configured as HIFU elements may be interleaved with (i.e., arranged in an alternating manner) the ultrasound elements configured as imaging elements. The configuration of FIG. 34A illustrates a non-limiting example. In the illustrated device 3400, the HIFU elements 3402 are arranged in rows interleaved with rows of imaging elements 3404. Alternatively, it may be considered that in the illustrated device 3400 the HIFU elements 3402 are arranged in columns interleaved with columns of the imaging elements 3404.

Figure 34B:
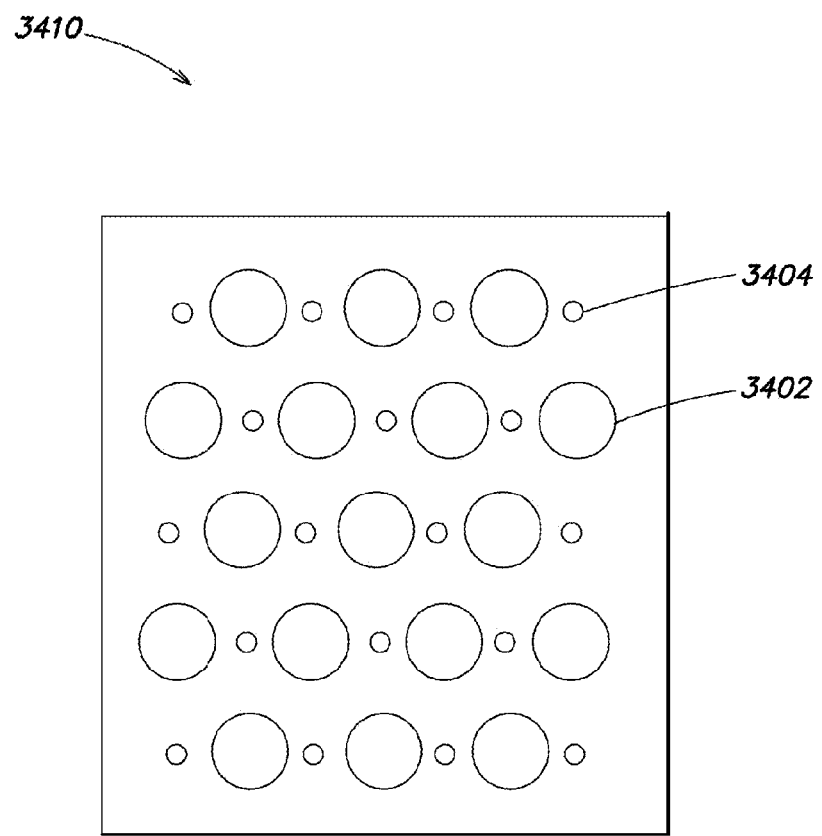

FIG. 34B illustrates an alternative configuration to that of FIG. 34A in which apparatus 3410 comprises the elements configured as HIFU elements 3402 and the elements configured as imaging elements 3404 arranged in a checkerboard pattern. Further alternative layouts are also possible.

In embodiments in which ultrasound elements configured as imaging elements (e.g., in an imaging array) are used in combination with ultrasound elements configured as HIFU elements (e.g., in a HIFU array), the arrangements of elements may take any suitable spacing. For example, the arrangements of ultrasound elements configured as imaging elements may be a sparse arrangement. Additionally or alternatively, the arrangement of ultrasound elements configured as HIFU elements may be a sparse arrangement. In some embodiments, the arrangement of ultrasound elements configured as imaging elements may be a sparse arrangement, while the arrangement of ultrasound elements configured as HIFU elements may not be sparse (i.e., may be densely positioned with respect to each other).

Figure 35A:
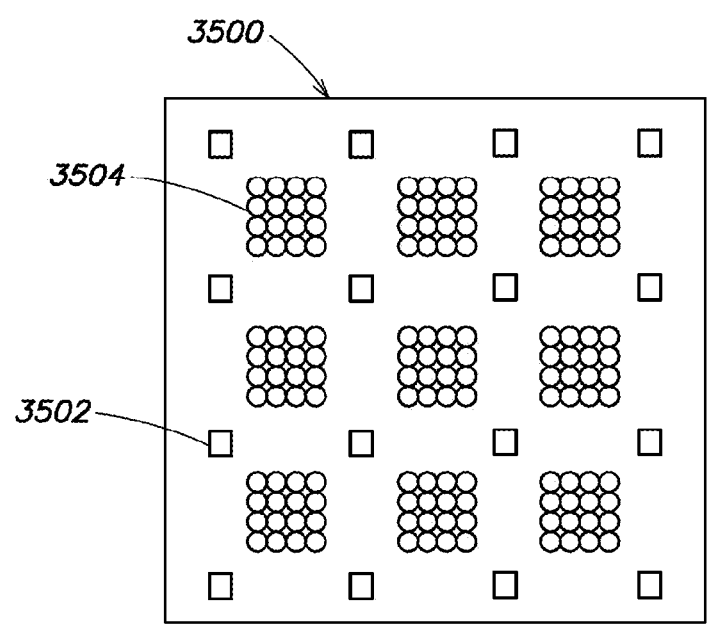

Configurations combining ultrasound elements configured as imaging elements with those configured as HIFU elements may also utilize subarrays of elements configured as one type or another. FIG. 35A illustrates a non-limiting example. As shown, the configuration 3500 includes subarrays 3504 of ultrasound elements configured as HIFU elements disposed among ultrasound elements configured as ultrasound imaging elements 3502.

Figure 35B:
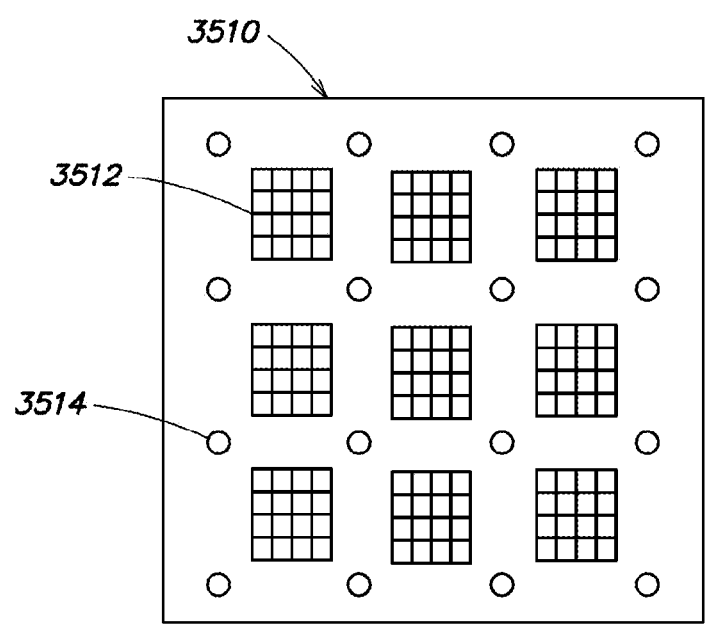

FIG. 35B illustrates an alternative using subarrays of ultrasound elements configured as imaging elements disposed among ultrasound elements configured as HIFU elements. Namely, the configuration 3510 illustrates subarrays 3512 of ultrasound elements configured as imaging elements disposed among ultrasound elements 3514 configured as HIFU elements.

Figure 35C:
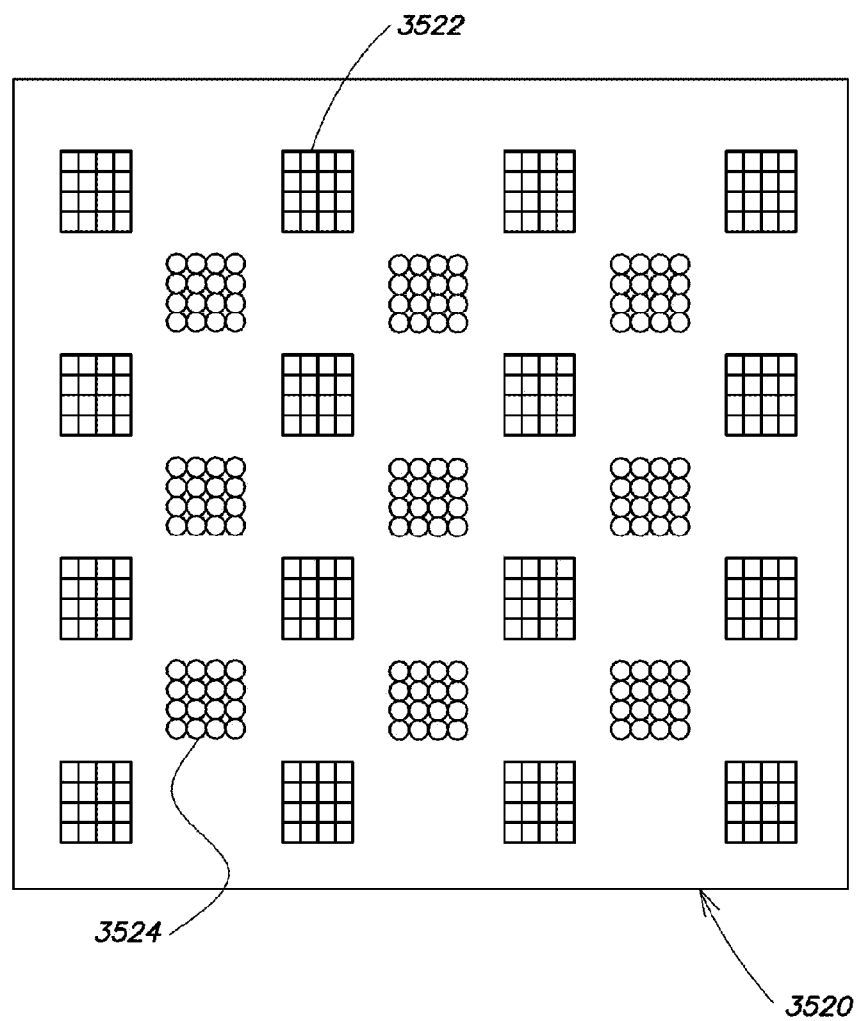

FIG. 35C illustrates a further embodiment in which subarrays of ultrasound elements configured as imaging elements are disposed among subarrays of ultrasound elements configured as HIFU elements. Namely, the configured 3520 illustrates subarrays 3522 of ultrasound elements configured as imaging elements disposed among subarrays 3524 of ultrasound elements configured as HIFU elements. Variations on the illustrated configuration are possible, for example regarding the uniformity of spacing between subarrays and the number of elements in each subarray, as examples.

Figure 35D:
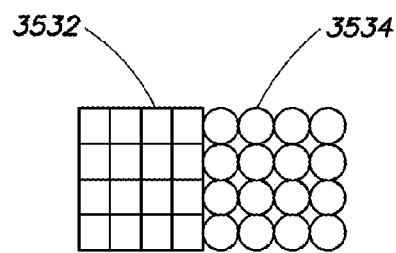

According to some embodiments, an array of ultrasound elements configured as HIFU elements may be disposed relative to an array of ultrasound elements configured as imaging elements such that the two arrays are substantially distinct. FIGS. 35D-35G illustrate non-limiting embodiments. In FIG. 35D, an array 3532 of ultrasound elements configured as imaging elements is disposed next to an array 3534 of ultrasound elements configured as HIFU elements. Here, the array 3532 is to the left of array 3534.

Figure 35E:
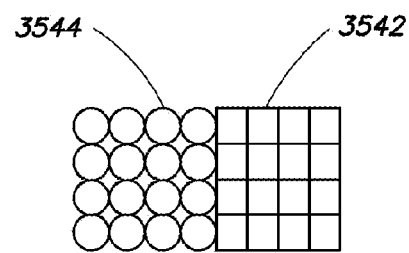

FIG. 35E illustrates a similar configuration utilizing an array 3542 of ultrasound elements configured as imaging elements disposed next to an array 3544 of ultrasound elements configured as HIFU elements. Here, the array 3542 is to the right of the array 3544.

Figure 35F:
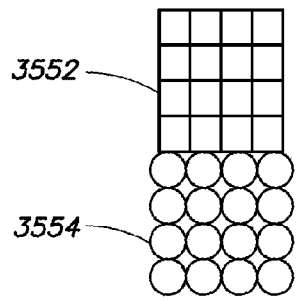

FIG. 35F illustrates a further alternative embodiment in which an array 3552 of ultrasound elements configured as ultrasound imaging elements is positioned above an array 3554 of ultrasound elements configured as HIFU elements.

Figure 35G:
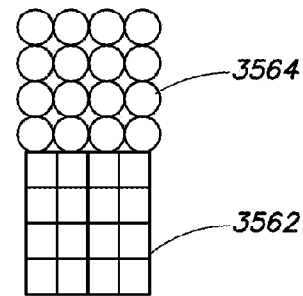

FIG. 35G illustrates a further embodiment in which an array 3562 of ultrasound elements configured as imaging elements is positioned below an array 3564 of ultrasound elements configured as HIFU elements.

Figure 35H:
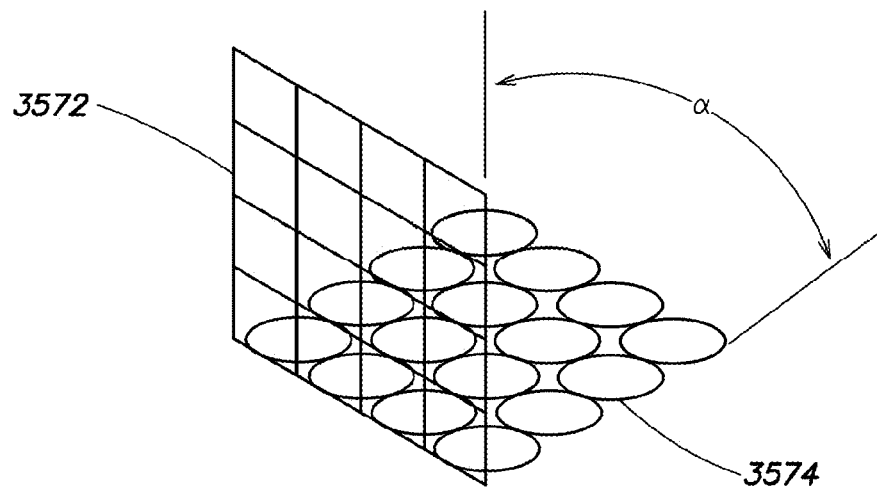
Figure 35I:
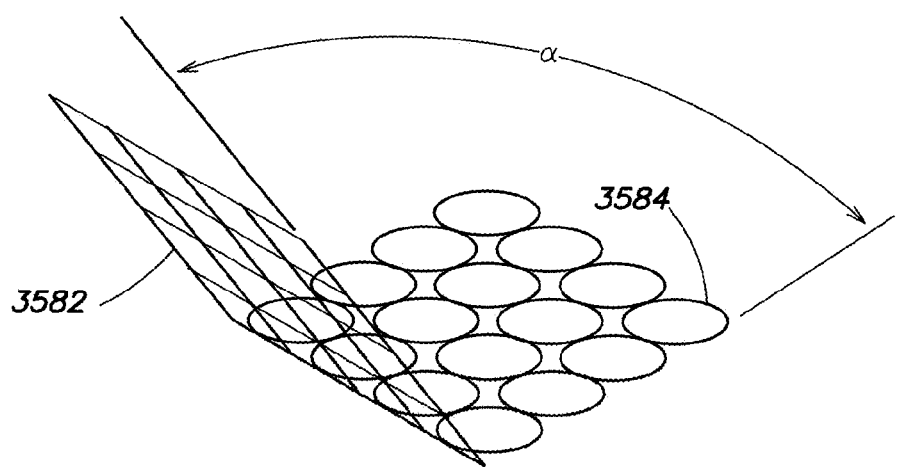

In those embodiments in which an array of ultrasound elements configured as imaging elements is used in combination with an array of ultrasound elements configured as HIFU elements, the arrays may have any orientation with respect to each other. For example, in some embodiments, the arrays may be in the same plane as each other (e.g., FIGS. 35D-35G). However, in alternative embodiments, the arrays may be oriented at an angle with respect to each other. FIGS. 35H and 35I illustrate non-limiting examples.

In FIG. 35H, an array 3572 of ultrasound elements configured as imaging elements is angled relative to an array 3574 of ultrasound elements configured as HIFU elements by an angle $\alpha$. The angle may be ninety degrees (a right angle) or less than ninety degrees. In FIG. 35I, an array 3582 of ultrasound elements configured as imaging element may also be angled relative to an array 3584 of ultrasound elements configured as HIFU elements, with the angle $\alpha$ being greater than ninety degrees.

In some embodiments in which one or more arrays of ultrasound elements configured as imaging elements are used in combination with one or more arrays of ultrasound elements configured as HIFU elements (e.g., the embodiments of FIGS. 35D-35I), the arrays of imaging elements may be separate from the arrays of HIFU elements. For example, the arrays of imaging elements may be formed on a separate substrate from the arrays of HIFU elements, may be movable independent of the arrays of imaging elements, and may be electrically separated (e.g., separate power supplies, separate communication inputs and outputs, etc.). However, in some embodiments, arrays of imaging elements may be disposed on the same substrate as arrays of HIFU elements and/or may share electronics and/or may be movable together as a unified entity. In some such embodiments, the substrate may be acoustically insulating, and thus formed of any suitable acoustically insulating material.

Figure 36A:
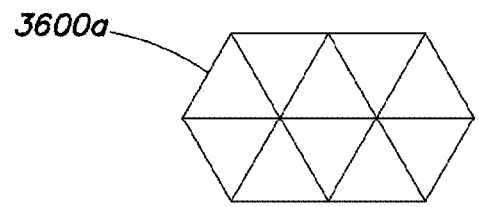
FIGS. 36A, 36B, 37 and 38 illustrate alternative configurations of radiation elements that may be used in an apparatus to perform high intensity focused ultrasound (HIFU) and ultrasound imaging, according to non-limiting embodiments.
Figure 36B:
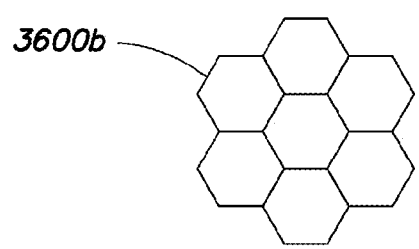

FIGS. 36A and 36B illustrate examples alternative subarray configurations to that of the rectangular subarrays of FIG. 35. As shown in FIG. 36A, the subarrays 3600a of ultrasound elements configured as HIFU elements may have a trigonal structure. FIG. 36B illustrates a further alternative, in which the subarrays 3600b may have a hexagonal structure. Further alternatives are possible.

In any of the foregoing embodiments in which a device includes ultrasound elements configured as HIFU elements and ultrasound elements configured as imaging elements, the elements may be in a fixed relation with respect to each other. Maintaining such a fixed relation may facilitate processing of imaging data and control over a location at which HIFU is performed relative to the imaged subject. Even so, it should be appreciated that the elements may be placed on a flexible substrate (e.g., of the types previously described with respect to FIG. 28) and maintain suitable operation.

It should be appreciated that the embodiments illustrated and described above in which configurations of ultrasound elements includes those configured as HIFU elements in addition to those configured as imaging elements may have any suitable spacing of elements. For example, the elements configured as HIFU elements may be spaced at any suitable distances from elements configured as imaging elements. According to an embodiment, the pitch between HIFU elements may be approximately the same as the pitch between imaging elements. For example, the pitch between both types of elements may be between approximately 2 mm and 10 mm (e.g., 3 mm, 5 mm, etc.). Moreover, one or both types of elements may have a regular spacing, irregular spacing, or random spacing, according to various embodiments. As described previously, utilizing a sparse arrangement of ultrasound elements configured as imaging elements may facilitate accommodation of ultrasound elements configured as HIFU elements within the illustrated configurations. Namely, the ability to perform ultrasound imaging utilizing a sparse array of ultrasound elements may allow for ultrasound elements configured as HIFU elements to be positioned among (e.g., disposed between, interspersed with, interleaved with, etc.) the ultrasound elements configured as ultrasound imaging elements.

According to an aspect of the present application, one or both of the arrangements of HIFU elements and imaging elements may be sparse. It should be appreciated that sparsity may be different for the two types of arrangements since sparsity may relate to a frequency of operation and, as described previously, the frequencies of operation of the imaging elements may differ from those of the HIFU elements. Thus, it should be appreciated that the pitch of the two types of elements may be the same even though only one of the two types may be arranged sparsely, according to a non-limiting embodiment.

Figure 37:
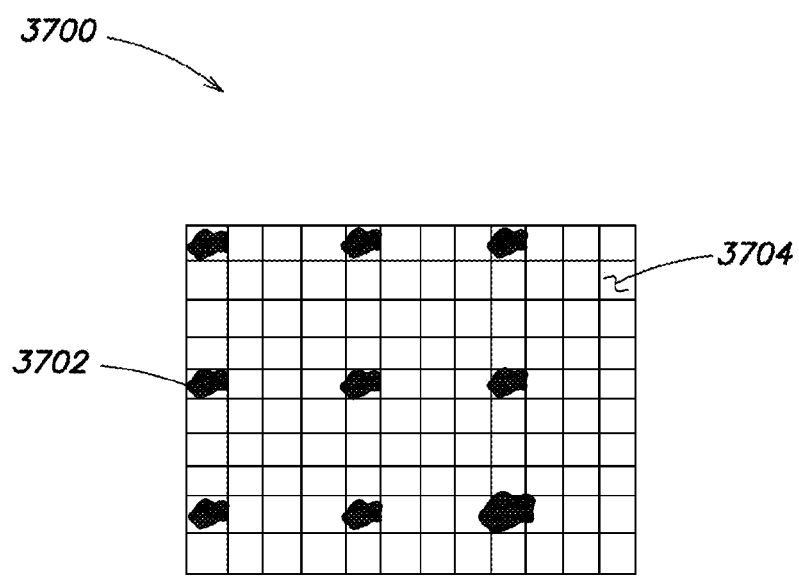
Figure 38:
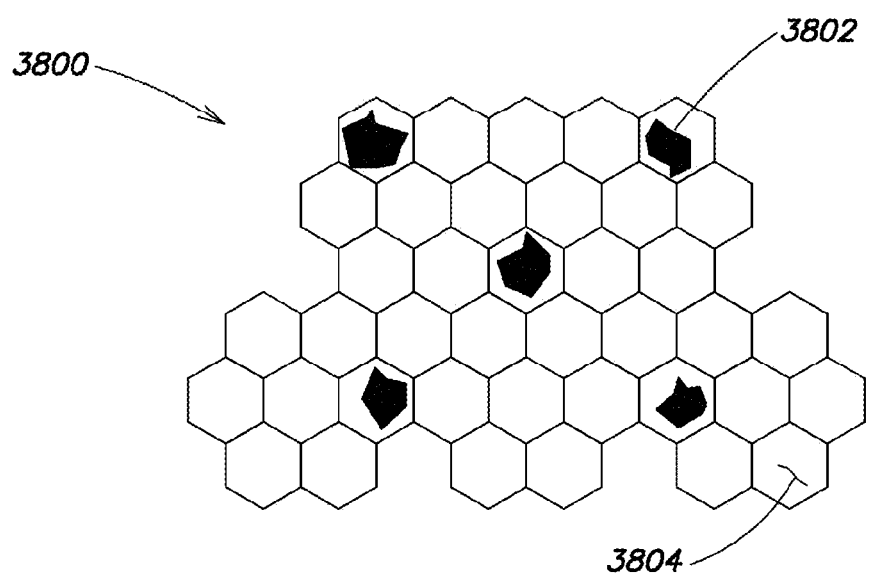

FIGS. 37 and 38 illustrate further non-limiting examples of suitable configurations implementing ultrasound elements configured as HIFU elements in addition to ultrasound elements configured as imaging elements. In FIG. 37, the configuration 3700 includes ultrasound elements configured as imaging elements 3702 and ultrasound elements configured as HIFU elements 3704. In FIG. 38, the configuration 3800 includes ultrasound elements configured as imaging elements 3802 and ultrasound elements configured as HIFU elements 3804.

In those embodiments in which arrays or subarrays of ultrasound elements configured as HIFU elements are used, the arrays or subarrays may exhibit any one or more of the characteristics of arrangements of ultrasound imaging elements described herein. For example, in some embodiments, sparse arrays of ultrasound elements configured as HIFU elements may be used. In some embodiments, irregular arrangements of ultrasound elements configured as HIFU elements may be used.

In some embodiments, arrangements of ultrasound elements configured as imaging elements and/or HIFU elements may be operated in a manner to provide a desired effective arrangement. For example, a densely populated arrangement of ultrasound elements configured as imaging elements may be operated as a sparse arrangement by activating only a suitable subset of the elements. The same may be true for arrangements of HIFU elements. In the same manner, subsets of an arrangement may be operated in a manner to provide an effective irregular arrangement (whether for imaging or HIFU). More generally, embodiments according to the present application provide for operation of subsets of arrangements of radiation elements to provide desired characteristics of the arrangements, such as any of those characteristics described herein.

Those aspects of the present application in which HIFU is performed may provide for focusing of the HIFU signal (or beam) in any suitable manner. Thus, beamforming may be performed, in any of the manners previously described herein with respect to imaging or in any other suitable manner. In some embodiments, time reversal beamforming may be used. Also, any suitable type of beam (e.g., a pencil beam, a fan beam, etc.) may be formed. The type of beam formed may depend, in some embodiments, on the geometry of the HIFU configuration. For example, depending on the shape of the subject being targeted with HIFU and the configuration of ultrasound elements, a particular beam type may be chosen.

According to an aspect, the HIFU beam may be focused by suitable excitation of the HIFU elements of a device, and thus any such device may be referred to as an electronically scanned HIFU array, to be distinguished from geometric focusing systems. Moreover, any desired depth of focus may be provided. In some embodiments, a HIFU focal length may be movable in two or three dimensions, for example by suitable excitation of HIFU elements. In some embodiments, the device(s) may be a near field HIFU device. The larger the arrangement of HIFU elements, the greater the depth of focus which may be provided. Moreover, it should be appreciated that devices according to the aspects described herein in which HIFU elements are used may provide the capability to focus the HIFU beam in three dimensions (e.g., in x, y, and z-directions). Thus, precise control over location of HIFU deposition may be provided. In some embodiments, one or more HIFU elements may be located on one of the arrays (e.g., array 102a). In some embodiments, one or more HIFU elements may be located on each of the arrays (e.g., arrays 102a and 102b).

Also, according to an embodiment, ultrasound elements of an arrangement may be configured to exhibit time-varying operation as HIFU elements or imaging elements. For example, referring to the configuration 3700 of FIG. 37, the ultrasound elements 3702 may be configured to operate as imaging elements during a first time period and as HIFU elements during a second time period. Similarly, the behavior of elements 3704 may alternate between functioning as HIFU elements and imaging elements.

The various aspects described herein relating to configurations of ultrasound elements including those configured as HIFU elements and those configured as imaging elements are not limited to two-dimensional (2D) arrangements. Rather, the elements configured as HIFU elements may be arranged in two or more dimensions and/or the elements configured as imaging elements may be arranged in two or more dimensions. In some embodiments, the HIFU elements may be coplanar and/or the imaging elements may be coplanar. Again, though, not all embodiments are limited in this respect.

According to an aspect of the present application, an apparatus comprising ultrasound elements configured as HIFU elements and ultrasound elements configured as imaging elements is configured such that the two types of elements operate at different frequencies. Thus, HIFU and imaging may be provided at the same time, without the imaging functionality being negatively impacted by the HIFU. The elements configured as HIFU elements may be configured to operate in a first frequency range while the elements configured as imaging elements may be configured to operate in a second frequency range. The first and second frequency ranges may be entirely distinct (e.g., being separated by at least 3 MHz, at least 5 MHz, or any other suitable frequency separation), or may have some overlap in some embodiments. As non-limiting examples, the elements configured as HIFU elements may be configured to operate in a range from approximately 100 KHz-5 MHz, while the elements configured as imaging elements may be configured to operate in a range from approximately 1-40 MHz Other ranges are also possible.

Furthermore, in some embodiments, an array of ultrasound elements configured as HIFU elements may include ultrasound elements operating at different frequencies. For example, a HIFU array may include one or more HIFU elements configured to operate at a first frequency and one or more HIFU elements configured to operate at a second frequency. The first and second frequencies may take any suitable values and may have any suitable relationship with respect to each other.

In those embodiments in which a device comprises ultrasound elements configured as imaging elements in addition to those configured as HIFU elements, the elements may be physically supported in any suitable manner. For example, according to an embodiment, the elements configured as HIFU elements and those configured as imaging elements may be coupled to a common support (e.g., of the type shown in FIG. 25 or any other suitable type). Alternatively, the two types of elements may be coupled to distinct supports, which themselves may be coupled together.

According to an embodiment, an arrangement of HIFU elements and imaging elements may be formed into an apparatus which may be handheld. For example, a paddle of the type shown in FIG. 25 may be implemented, with the addition of elements configured as HIFU elements. Moreover, multiple such apparatus may be provided. Thus, according to an embodiment, two paddles may be provided, one or both of which may include HIFU elements and imaging elements. A non-limiting example is illustrated in FIG. 39.

The apparatus 3900 includes several of the components previously illustrated and described with respect to FIG. 27. However, the paddles 3902a and 3902b both include ultrasound elements configured as imaging elements and ultrasound elements configured as HIFU elements. As a non-limiting example, paddles 3902a and 3902b may include respective arrangements 3904a and 3904b of the type previously illustrated in FIG. 34A including HIFU elements 3402 and imaging elements 3404. Other configurations of imaging elements and HIFU elements are also possible. In some embodiments, for either or both of the paddles, the HIFU elements and imaging elements may be in a substantially fixed relationship with respect to each other. In some embodiments, the paddles may include flexible supports, for example as previously described herein.

Transmissive ultrasound imaging may be performed using the two arrangements of ultrasound elements configured as imaging elements, in the manner previously described herein. Additionally, or alternatively, both paddles (e.g., paddles 3902a and 3902b) may provide HIFU functionality, thus allowing for HIFU to be directed at a subject from multiple angles (e.g., from opposing sides of the subject). Such operation may allow for each of the HIFU arrangements individually to use less power (e.g., approximately half the amount of power) to achieve the same HIFU operation as would be needed if only a single arrangement of HIFU was used.

Figure 39:
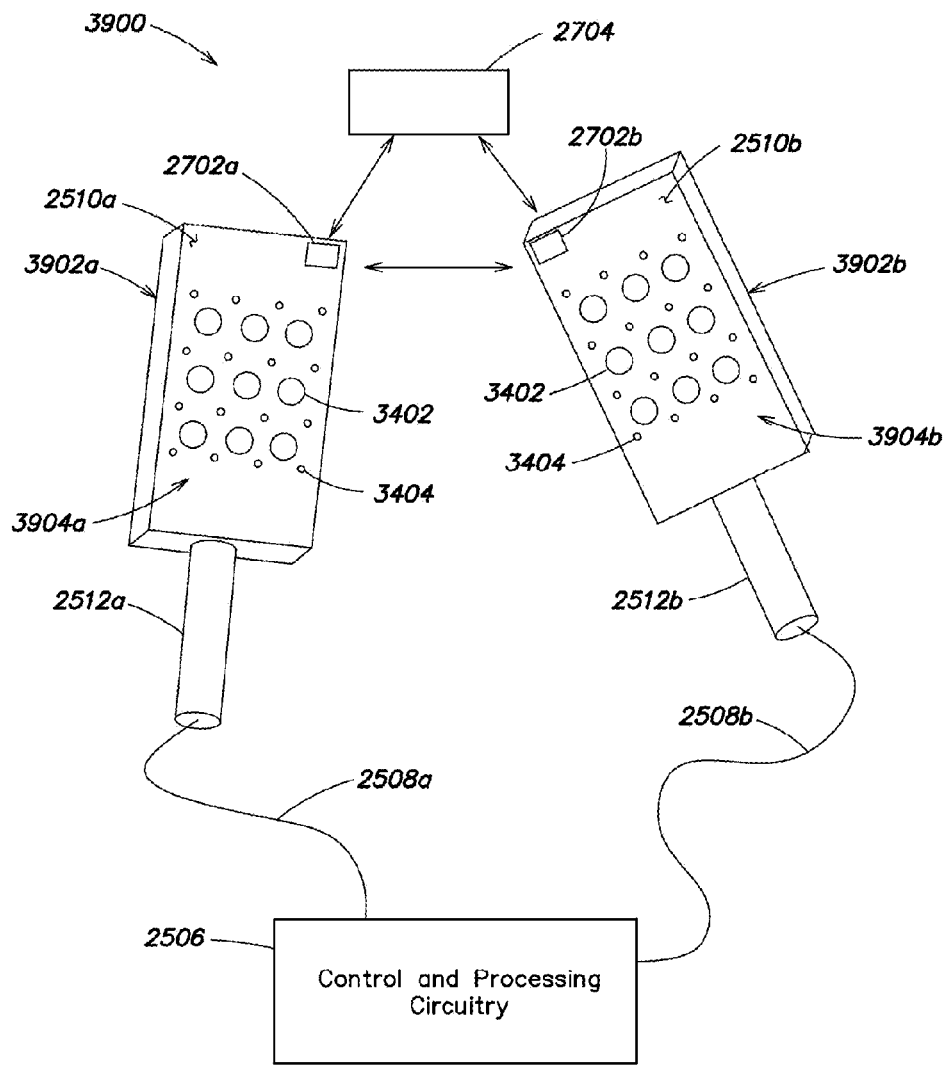
FIG. 39 illustrates a system including two movable supports including ultrasound elements configured as imaging elements and ultrasound elements configured as HIFU elements, according to a non-limiting embodiment.

Thus, it should be appreciated by reference to, for example, FIGS. 34A, 34B, and 39 (among others), that embodiments of the present application provides an apparatus comprising a support, a first plurality of ultrasound elements configured as ultrasound imaging elements, and a second plurality of ultrasound elements configured as high intensity focused ultrasound (HIFU) elements. The first plurality and second plurality of ultrasound elements may be physically coupled to the first support, and at least some elements of the first plurality of ultrasound elements are arranged among at least some elements of the second plurality of ultrasound elements. In some such embodiments, two or more such apparatus may be provided (e.g., two paddles of the types illustrated in FIG. 39). In some embodiments, each of the first plurality of ultrasound imaging elements is configured to perform at least one of emission of a radiation source signal incident upon a volume to be imaged three-dimensionally or detection of such a radiation source signal.

In those embodiments in which multiple arrangements of imaging elements are provided with one or more arrangements of HIFU elements, the relative orientation and/or position of the arrangements (e.g., of the imaging arrangements with respect to each other) may be determined to facilitate combined operation. For example, the relative orientation and/or position may be determined in any manner previously described herein, such as those described with respect to FIG. 27.

According to an aspect of the present application, an apparatus of the types described herein may be used to perform thermometry. Temperature measurements may be based on several types of data. According to some embodiments, the speed of sound in a material (e.g., human tissue) may depend on the temperature of the tissue. As has been described previously, the speed of sound in a subject may be determined using various aspects described herein (e.g., the apparatus of FIGS. 1-6, as non-limiting examples). For example, by detecting changes in the speed of sound through a subject, changes in temperature of the subject may be determined. As another example, by detecting the speed of sound at a location within a subject being imaged, the temperature at the location may be determined.

According to an embodiment, thermometry may be performed based on the index of refraction of a subject. Thus, using any of the systems described herein suitable for detecting index of refraction of a subject may be used to also determine temperature of the subject using any suitable processing techniques.

According to another embodiment, TOF data collected by ultrasound source-sensor pairs may provide an indication of temperature of a subject. Thus, as an example, operation of a system like that of FIG. 4, 5 or 6 may be used to collect TOF data. The TOF data may be processed using any suitable techniques to determine temperature of the subject.

In some embodiments, raw waveforms collected by ultrasound sensors operating in combination with ultrasound sources in a transmissive modality may be analyzed for changes (e.g., changes in amplitude, phase, etc.). Such changes may be indicative of changes in temperature of a subject. Thus, for example, systems like those in FIGS. 4, 5 and 6 may be used to collect raw waveforms which may be processed using any suitable techniques to determine temperature of a subject.

In those embodiments in which raw waveforms are used to detect changes in temperature, principles of coherence may be utilized. For instance, in some embodiments a change in temperature may be detected when a waveform de-coheres from its previous form. Waveforms representing sound speed and attenuation may be analyzed individually or in combination for such de-coherence. According to some embodiments, coherence of the raw waveform of a chirp may be analyzed and any de-coherence in the received chirp waveform may be used to determine a change in temperature of the subject. In some embodiments, absolute temperature may also be determined in addition to or as an alternative to temperature changes.

According to an embodiment of the present application, a three-dimensional (3D) temperature profile may be constructed based at least partially on data collected using apparatus of type described herein. Temperature values or changes in temperature may be determined in any of the manners described herein. In some embodiments, a temperature value or change in temperature may be determined for a plurality of voxels corresponding to a volume to be characterized (e.g., subject 410 of FIG. 4). The temperature-related values of the voxels may therefore be used to construct a temperature profile of the volume. Because the voxels may be arranged in three-dimensions in some embodiments, a 3D temperature profile of the volume may be constructed. FIG. 40 illustrates a non-limiting example.

The temperature profile 4002 includes a plurality of temperature-related values corresponding to voxels 4004 associated with the subject of interest. In this non-limiting embodiment, the temperature-related values represent absolute temperature in degrees Fahrenheit. The profile may be displayed or otherwise presented to a user in any suitable manner, including via a 2D display, a 3D display, or in any other suitable manner.

The performance of thermometry may be combined with other operations described herein. For example, according to an embodiment, an apparatus may be configured as a multi-mode apparatus to perform ultrasound imaging, HIFU, and thermometry, or any combination of those functions. The performance of thermometry may be used in combination with HIFU to monitor the temperature of a subject undergoing HIFU treatment, as a non-limiting example.

In some embodiments, thermometry may be used for classifying an imaged subject. For example, tissue type may be determined based, at least partially, on the temperature behavior of the tissue. Other thermal classification is also possible.

As previously mentioned, in some embodiments, a volumetric image or images generated according to any of the previously-described techniques (e.g., the techniques described with reference to FIG. 29), may be output to a viewer (e.g., a doctor) for viewing and/or manipulation. Volumetric image(s) may be output to the viewer in any suitable way. In some embodiments, volumetric image(s) may be output to the viewer via a conventional two-dimensional display of a computing device (e.g., the screen of a computer monitor). The viewer may view the image(s) on the two-dimensional display and manipulate the image(s) on the computer screen by using a mouse, a touch screen, or a keyboard. However, in some embodiments, described in greater detail below, a user interface may use a three-dimensional (3D) display configured to present a volumetric image or images to the viewer in three-dimensional (3D) space. Additionally, the user interface may allow the viewer to manipulate a presented volumetric image in 3D space. In some embodiments, such manipulation may be performed by the user via a controller (e.g., a wired or wireless stylus, a wired or wireless remote control, a wired or wireless mouse, an inertial navigation system (e.g., 3-axis accelerometer and/or 3-axis gyroscope) or with motion (e.g., hand motion).

The inventors have appreciated that various benefits may be achieved by utilizing a user interface configured to present volumetric images to a viewer via a 3D display and, optionally, allow the viewer to manipulate the presented images in three dimensions. For example, a doctor viewing such images via a 3D display may view a 3D image corresponding to an organ (or a subsection of the 3D image corresponding to a portion of the organ), enlarge it, shrink it, tilt it, rotate it, and/or manipulate it in any other suitable way to help diagnose a patient and/or plan a surgical path for applying HIFU to the organ, for performing other surgical procedures, or simply to alter viewing conditions of the image. The user may want to view only a portion of an image, or multiple portions in sequence, and may be able to do so by a suitable user-selection tool (e.g., an option on a computer user interface, a mouse, etc.).

Figure 41:
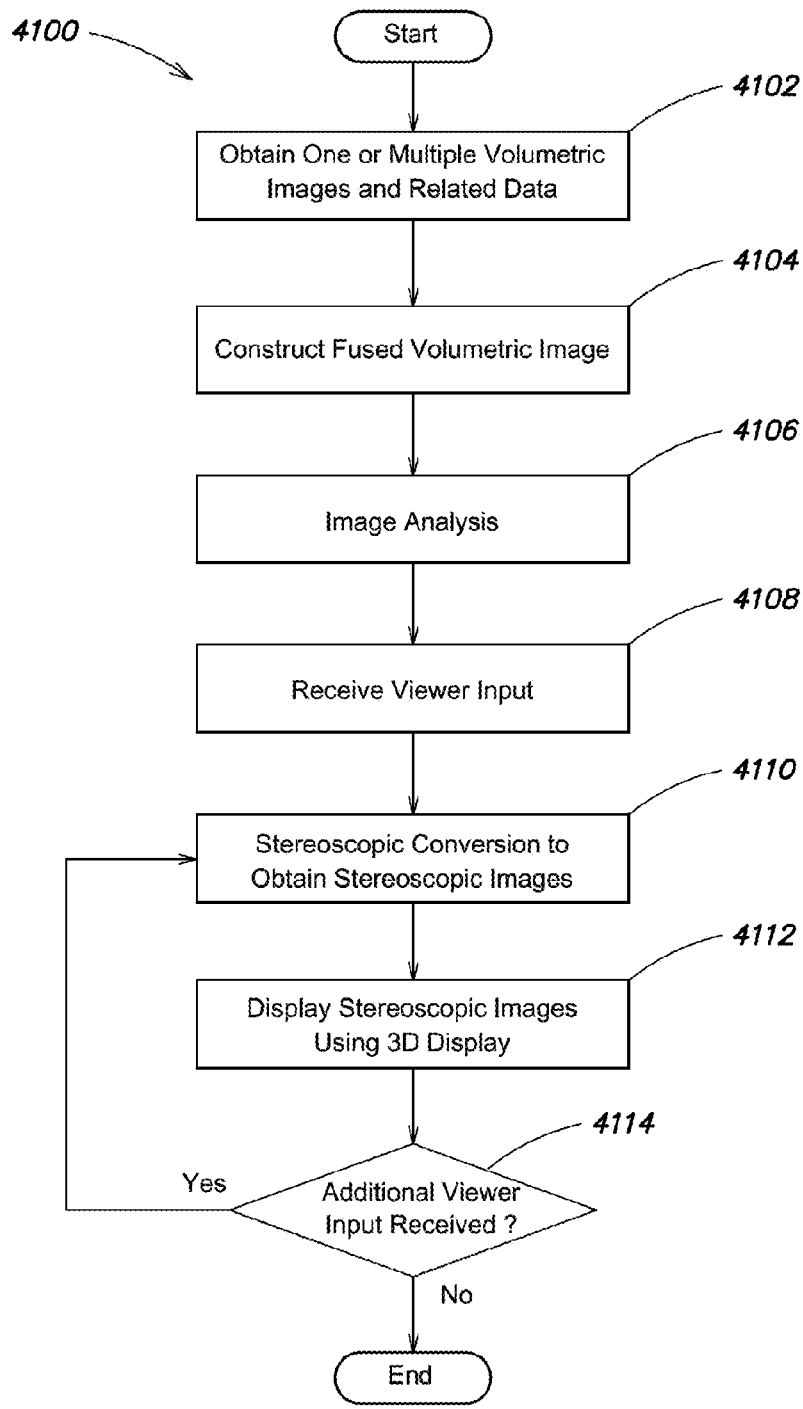
FIG. 41 is a flowchart of a process for presenting one or more volumetric images to a viewer using a three-dimensional (3D) display, according to some non-limiting embodiments.

Illustrative embodiments of the operation of a user interface configured to present one or more volumetric images to a viewer via a 3D display are described below with reference to FIG. 41, which is a flow chart of process 4100. Process 4100 may be performed by any suitable hardware and, for example, may be performed, at least in part, by using system 400 (as a non-limiting example), previously described with reference to FIG. 4. In some embodiments, one or more hardware components of the system may be configured to implement a three-dimensional display and/or to receive input from a user as described in greater detail below.

Process 4100 begins at act 4102, where one or more volumetric images of a subject being imaged may be obtained. The volumetric image(s) may be obtained in any suitable way. In some embodiments, the volumetric image(s) may be accessed after having been obtained by using an imaging device and made available for subsequent access (e.g., by storing the image(s) on at least one non-transitory computer-readable storage medium) during act 4102. Additionally or alternatively, the volumetric image(s) may be obtained by using an imaging device as part of act 4102.

The volumetric image(s) may be obtained by any suitable imaging device in any suitable way. For example, the volumetric image(s) may be obtained by collecting imaging related data using an imaging device comprising arrays of sources and sensors in any suitable way (e.g., using an ultrasound imaging device operating in a transmissive modality), examples of which were previously described with reference to process 2900 in FIG. 29. Each volumetric image obtained at act 4102 may be of any suitable type and may comprise one or more values of the corresponding type for each voxel in the volumetric image. Examples of volumetric images that may be obtained include, but are not limited to, volumetric images comprising for each voxel (or each of two or more voxels, but not necessarily all voxels in some embodiments) one or more time-of-flight values, one or more attenuation values, one or more speed of sound values, one or more index of refraction values, one or more scattering potential values, one or more absorption values, one or more temperature values, one or more values indicative of energy power being applied to the voxel, one or more susceptibility values, one or more Doppler values, one or more spectral attenuation values, one or more values obtained via a two-pulse coherent change detection technique, one or more values obtained via a two-pulse incoherent change detection technique, one or more values obtained via an elastography technique, or any other suitable types of values. Any number of images may be obtained, and they need not all represent the same type of data. As a specific non-limiting example, two volumetric images may be obtained at act 4102 with the first volumetric image comprising one or more index of refraction values for each voxel and the second volumetric image comprising one or more temperature values for each voxel in the image. Though, it should be appreciated that any suitable number of volumetric images of any suitable type may be obtained.

In some embodiments, other data comprising measurements of the subject being imaged may be obtained in addition to one or more volumetric images. Examples of such data include, but are not limited to, electrocardiogram (ECG/EKG) data, electroencephalography (EEG) data, blood pressure data, and any other suitable data comprising measurements of the subject being imaged.

After one or more volumetric images of the subject being imaged are obtained, process 4100 proceeds to act 4104, where, if multiple volumetric images were obtained at act 4102, the volumetric images are combined to form a single fused volumetric image so that the single fused volumetric image may be subsequently presented to the viewer via a 3D display. If only one volumetric image was obtained at act 4102, then process 4102 simply proceeds to act 4106, but for ease of explanation such a volumetric image is also referred to as a fused volumetric image in the remainder of the description of process 4100.

Volumetric images may be fused in any suitable way. In some embodiments, volumetric images may be fused at a voxel level by associating a unique visual cue to each of the values in the fused image that originate from a single volumetric image obtained at act 4102. Any suitable type of visual cue may be used including, but not limited to, color, transparency, and/or shading. When the fused volumetric image is subsequently displayed via the 3D display, the visual cues may help the viewer compare various aspects of the subject being imaged on the same image.

As a non-limiting illustrative example, a volumetric image comprising an index of refraction value for each voxel and a volumetric image comprising a temperature value for each voxel may be used to construct a fused volumetric image in which each voxel may be associated with an index of refraction value and/or a temperature value, as well as one visual cue (e.g., one color map mapping values to colors) associated with the index of refraction values and a different visual cue (another color map mapping values to colors in a different way) associated with the temperature values. Accordingly, when the fused image is subsequently displayed via the 3D display, the visual cues may help the viewer compare various aspects of the subject being imaged (e.g., index of refraction vs. temperature) on the same image. In some embodiments, a voxel may be displayed by using a mixture of the colors associated with the voxel.

Next, process 4100 proceeds to act 4106, where one or more image analysis techniques may be applied to the fused volumetric image. Image analysis techniques may be applied to obtain image features that may, in some embodiments, be used to automatically detect one or more problems (e.g., an area of diseased tissue) in the subject being imaged, and/or automatically identify the types of problem(s) detected (e.g., the detected area of diseased tissue is cancer).

In some embodiments, image analysis techniques may be applied to the fused volumetric image to automatically identify at least one shape in the fused volumetric image. The image analysis techniques may be used to obtain information about the one or more identified shapes in the fused volumetric image. The obtained shape information may, in turn, be used to automatically detect and classify problems in the subject being imaged. Information about a shape may comprise information about the size of the shape, volume of the shape, orientation of the shape, density of a volume bound by the shape, crinkliness of an object, and one or more values representing the shape itself. For example, the shape may be represented by multiple coefficients in a three-dimensional basis (e.g., spherical harmonic coefficients, wavelet coefficients, etc.) and information about the shape may include such coefficients.

In some embodiments, features obtained from the fused volumetric image (including, but not limited to, information about one or more shapes in the image) may be used to automatically detect and classify one or more problems in the subject being imaged, to categorize the imaged subject (e.g., as a particular type of subject, as a particular type of tissue, etc.), or may be used for any other desired purpose. For example, the features may be used to automatically detect the presence of cancer, kidney stones, cysts, fluid-filled cavities, foreign objects, broken bones, or any other problems within the body. The detection and classification of problems in the subject being imaged based on one or more features obtained from the fused volumetric image may be done in any suitable way using any suitable techniques and tools including, but not limited to, machine learning techniques (classifiers, Bayesian networks, support vector machines, neural networks, decision trees, hidden Markov models, graphical models, clustering (e.g., binning or histograms as examples), etc.), statistical inference (e.g., Bayesian inference, maximum likelihood estimation, etc.), and tracking techniques (target tracking, scene tracking, volume tracking, etc.). In those embodiments in which images are analyzed to categorize or classify the imaged subject, such categorization or classification may be performed in any suitable manner. In some embodiments, an image of a subject may be compared against a template image (or, more generally, template data) to aid the classification or categorization.

In some embodiments, the fused volumetric image may be updated to show any of the information obtained as part of act 4106. For example, the fused volumetric image may be updated to show one or more identified shapes, when displayed. As another example, the fused volumetric image may be updated to indicate how a shape or an area of the subject being imaged was classified, when displayed.

After image analysis techniques are applied at act 4106, process 4100 proceeds to act 4108, where viewer input, at least partially specifying how the fused volumetric image is to be presented to the viewer, is received. The viewer input may specify a position where the fused volumetric image is to be displayed, an orientation for the displayed image, and a size for the displayed image. Additionally or alternatively, the viewer input may identify a portion of the image to be displayed to the viewer. The viewer may provide these and/or any other suitable inputs in any suitable way including, but not limited to, by using a stylus pen, a mouse pad, a keyboard, a remote control, and/or a detection mechanism configured to detect movements of the viewer (e.g., leg movements, arm movements, hand movements, finger movements, eye movements, etc.) suggestive of the viewer's desired presentation of the image. A non-limiting example of such 3D detection mechanisms is the Leap device, available from Leap Motion of San Francisco, Calif. Such technology may allow the viewer to control the image by pointing, waving, and/or using other natural gestures (e.g., hand gestures) within a detection space monitored by the Leap device.

Next, the process 4100 proceeds to act 4110, where the fused volumetric image obtained in acts 4102-4106 is further processed to prepare the fused volumetric image for subsequent presentation to the viewer via a 3D display. This may be done in any suitable way. In some embodiments, a stereoscopic conversion algorithm may be applied to the fused volumetric image to produce two stereoscopic images, each of which will be presented to a different eye of the viewer via the 3D display. The stereoscopic conversion algorithm may produce the two stereoscopic images based at least in part on the viewer input provided at act 4108.

Figure 42:
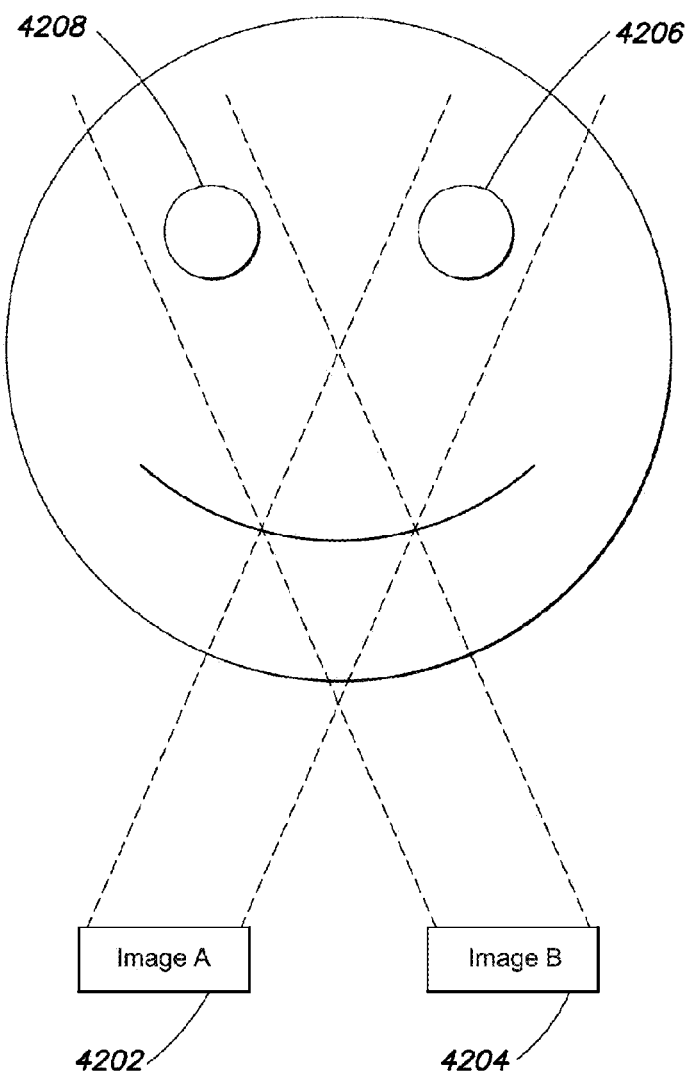
FIG. 42 illustrates an example of displaying stereoscopic images, obtained from a volumetric image, by using a 3D display, according to some non-limiting embodiments.

Next, process 4100 proceeds to act 4112, where the images produced by the stereoscopic conversion process are presented to the viewer via the 3D display. This is illustrated in FIG. 42, which illustrates displaying images 4202 (Image A) and 4204 (Image B) obtained from a fused volumetric image to the viewer by displaying the image 4202 onto eye 4206 and image 4204 onto eye 4208. Images A and B may be 2D projections in some embodiments, representing a rendering of a scene from two different perspectives.

Any suitable type of 3D display may be used to present the images to the user. For example, in some embodiments, a 3D display such as the zSpace display available from Infinite Z, Inc.® may be used. In other embodiments, any suitable lenticular display may be used. In other embodiments, "active" 3D technologies may be used which provide a 3D display at least in part by actively switching shutters on the left and right eye. In other embodiments, the images may be presented as red/blue images to a user wearing "3D glasses," presented as polarized images having different polarizations, presented as time-gated alternating images, or may be presented in any other suitable way. In some embodiments, a 3D display may be a heads-up display similar to the displays presented to pilots operating aircraft. In some embodiments, additional information about the subject being imaged (e.g., ECG information obtained at act 4102) may be presented to the viewer as part of the image or concurrently with the image.

Figure 43:
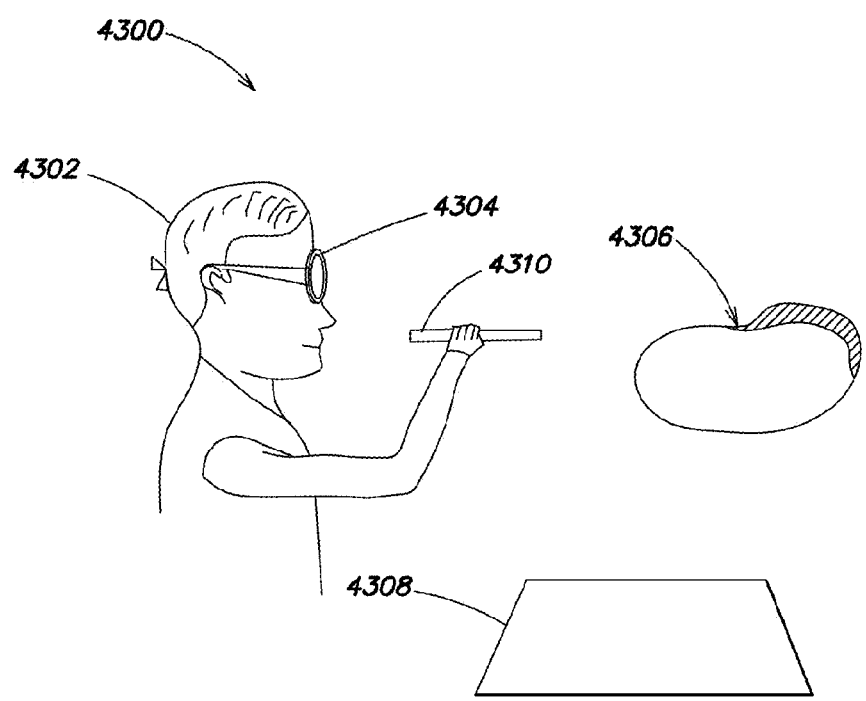
FIG. 43 illustrates a system in which a user may view and manipulate a 3D image, according to a non-limiting embodiment.

Next, process 4100 proceeds to decision block 4114, where it is determined whether additional viewer input is received. Such input may be any input provided by the viewer to specify an update to how the fused volumetric image is displayed to the viewer. For example, the input may specify to update the fused volumetric image by rotating the image, shrinking the image, enlarging the image, viewing one or more desired portions of the image, mapping the underlying data of the image to a new coordinate system, etc.). A non-limiting example is illustrated in FIG. 43.

The system 4300 allows a user 4302 to view a 3D image 4306 (e.g., produced at act 4112 in FIG. 41), for example by wearing 3D glasses 4304 or in any other suitable manner. The 3D image may be generated by a 3D display device 4308. The user may use a device 4310 (e.g., a stylus pen or other device)

to manipulate the 3D image 4306 or to otherwise provide input (e.g., identifying a point of interest in the image).

If it is determined at act 4114 that additional viewer input is provided, process 4100 returns to acts 4110-4112, where the way in which the fused volumetric image is displayed to the viewer, via the 3D display, is updated. If no such input is provided at act 4114 (e.g., after a predetermined period of time), process 4100 completes.

It should be appreciated that process 4100 is illustrative and that variations of process 4100 are possible. For example, although in the illustrated embodiment a single fused volumetric image is presented to the user via a 3D display, in other embodiments multiple fused volumetric images may be presented to the user via the 3D display. In such embodiments, process 4100 may be applied to each of multiple fused volumetric images, one or more of which may have been obtained from volumetric images taken at different points in time. In some such embodiments, the multiple fused volumetric images may be displayed to the user in a time-dependent manner, in real time or in accordance with any other suitable timing. In this manner, a movie of the volumetric images may be presented. The passage of time may represent a fourth dimension and therefore some embodiments of the present application provide four-dimensional (4D) imaging.

The inventors have appreciated that it may be desirable to present volumetric images to a viewer from different points of view, via a 3D display or any other suitable type of display. Accordingly, in some embodiments, a user interface may be configured to present, to a viewer, any volumetric image from one or more points of view (i.e., from the perspective of a viewer located at the point(s) of view) external to the volumetric image. This way a volumetric image of a subject being imaged may be presented to the viewer from any point of view external to or outside of the subject. For example, a volumetric image of an organ (e.g., heart, kidney, etc.) may be presented to the viewer from any point of view external to the organ. Additionally or alternatively, in some embodiments described in more detail below, the user interface may be configured to present any volumetric image from one or more points of view within the volumetric image. For example, a volumetric image of a body cavity may be presented to the viewer from any point of view within the body cavity. In this respect, the user interface may provide the viewer with the type of images that may be obtained by inserting a device (e.g., an endoscope, a tube, a needle (e.g., a biopsy needle)) inside of the subject being imaged (e.g., inside of a body cavity) to capture images of the subject from points of view within the subject, but without the need for such a device. Accordingly, such a user interface may be referred to as a "virtual" endoscope. The user may view the imaged subject from points internal to the subject at any desired angle (e.g., looking up from within the subject, looking down, etc.). Such viewing may be static in some embodiments such that a static image from within the subject is presented. In other embodiments, such viewing may be dynamic, for example allowing the viewer to see the subject as the view "travels" along a path through the subject (e.g., as an endoscope or other device might).

Thus, the user interface is not limited to presenting a volumetric image from a single point of view, regardless of whether the point of view is within or external to the subject being imaged, and may be configured to present the volumetric image from multiple points of view. For example, in some embodiments, the user interface may be configured to present the volumetric image from each of multiple points of view that lie along a path. The path may lie entirely within the subject being imaged (in analogy to a path a physical endoscope would follow through a body being imaged), entirely external to the subject being imaged, or at least one point on the path may lie inside the subject being imaged and at least another point on the path may lie outside of the subject being imaged.

Figure 44:
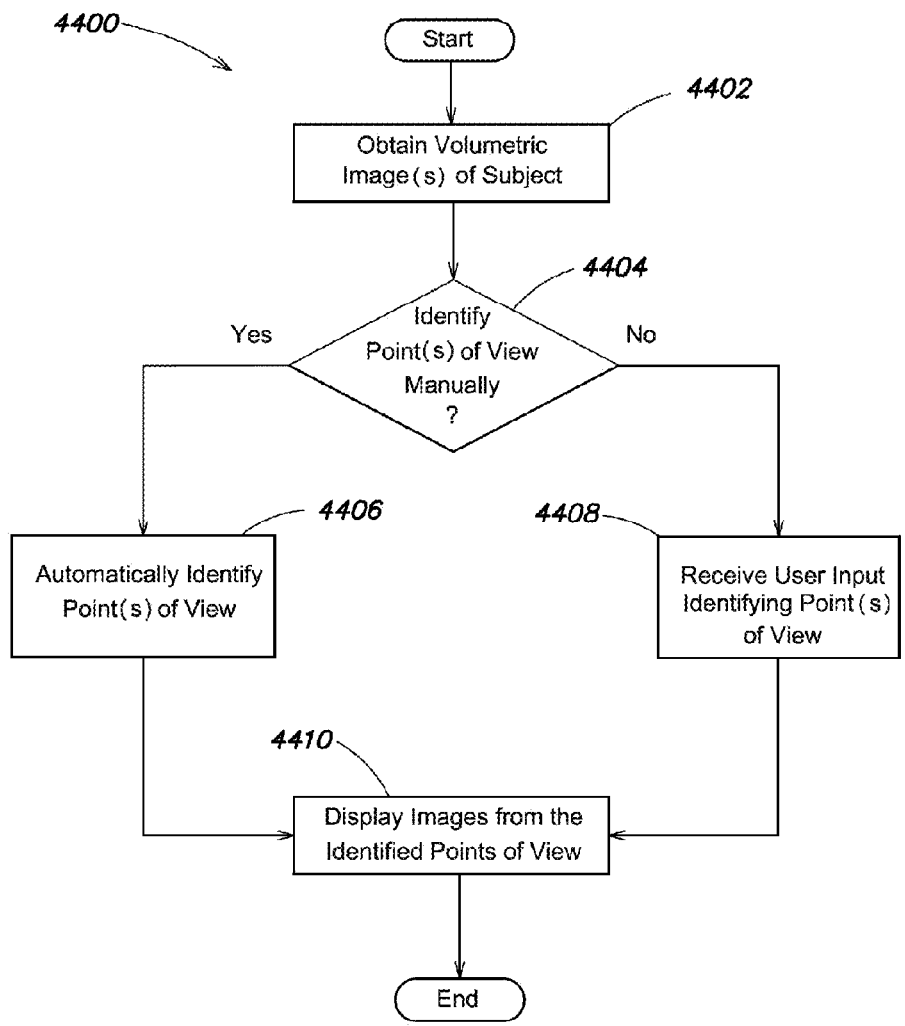
FIG. 44 is a flowchart of a process for displaying images from multiple points of view within the subject being imaged, according to some non-limiting embodiments.

FIG. 44 illustrates a flowchart of process 4400 for displaying one or more images to a viewer from one or more points of view within the subject being imaged. Process 4400 may be performed by any suitable hardware and, for example, may be performed, at least in part, by using system 400, previously described with reference to FIG. 4.

Process 4400 begins at act 4402, where one or multiple volumetric images of a subject may be obtained for subsequent presentation to the viewer from one or multiple points of view within the volumetric image. The volumetric image may be obtained in any suitable way and be of any suitable type, as previously described with reference to act 4102 of process 4100. For example, the volumetric image may be accessed after having been previously obtained.

Next, process 4400 proceeds to decision block 4404, where it may be determined whether one or more points of view from which the received volumetric image(s) are to be presented are to be identified manually or automatically. This determination may be made in any suitable way and, for example, may be made based on input from a user (e.g., a viewer or any other user) indicating whether the user will manually identify the point(s) of view. Identifying a point of view may involve identifying a location within the subject and an angle (or direction) from the identified location. In some embodiments, multiple points of view (and therefore multiple locations and angles) may be identified and images may be displayed to a viewer from the multiple points of view, for example in a time-based sequence as a non-limiting example. In some embodiments, multiple images may be presented to a user corresponding to multiple points of view in a sequence corresponding to an ordering of multiple locations along a path identified by a user or determined automatically.

Regardless of how such a determination is made at decision block 4404, when it is determined that a user will manually identify the point(s) of view, process 4400 proceeds to act 4408, where user input identifying the point(s) of view is received. For each identified point of view, the user input may specify a location of the point of view and/or one or more viewing angles. A user may provide input to identify the desired points of view in any suitable way. For example, in some embodiments, the user may provide input specifying a path through a volumetric image obtained at act 4402 using a configuration like that of FIG. 43 (e.g., by drawing a path in the volumetric image by using a stylus pen, a mouse pad, a remote control, and/or a detection mechanism configured to detect movements of the viewer (examples of which were previously described)). In some embodiments, the user may provide such input while being presented with the image. For example, the user may be viewing a volumetric image via a 3D display and draw a path through the displayed volumetric image by moving a pointing device, a finger, or any other suitable object along the path the user desires to draw (e.g., as may be done with the system 4300 of FIG. 43). The path indicated by the motion may be detected via the aforementioned detection mechanism and provided to the user interface.

On the other hand, when it is determined at decision block 4404 that a user will not specify the point(s) of view manually, process 4400 proceeds to act 4406, where the point(s) of view are identified automatically. This may be done in any suitable way. The point(s) of view may lie along one or more paths through the subject being imaged and the point(s) of view may be identified at least in part by identifying one or more paths through the subject. For example, in some embodiments, one or more paths through the subject being imaged may be identified by using image analysis techniques (e.g., computer vision techniques), examples of which were previously described with reference to FIG. 41. For instance, image analysis techniques may be applied to the volumetric image obtained at act 4402 to identify one or more physical paths in the subject being imaged (e.g., paths through arteries, veins, body cavities, etc. when a human subject is being imaged). To this end, image analysis techniques including, but not limited to, image segmentation techniques, shape-fitting techniques, least-squares methods, and tracking techniques may be used.

In some embodiments, a path through the subject being imaged may be identified using computer vision routines for understanding content of an image or images of the subject. As an example, features of an imaged subject, such as boundaries, circular canals or cavities, may be identified by using segmentation techniques (e.g., based on changes in image intensity) and then fitting shapes such as ovals in 2D cross-sectional slices, or fitting piece-wise cylinders and/or ellipsoids in 3D volumes. In another embodiment, a least-squares solution and/or a probabilistic solution to analyzing an image may be used to determine the path. Moreover, a path may be updated in real time, for example using a tracking technique such as, but not limited to, Kalman filtering. Other techniques for determining a path are also possible.

After at least one point of view (e.g., along a path through a volumetric image) is specified, manually or automatically, process 4400 proceeds to act 4410, where multiple images are presented to the viewer such that each of the images is presented from the identified point(s) of view. In some embodiments, when the points of view lie along a path, the images may be presented to the user sequentially such that the sequence of images presented corresponds to an ordering of the points of view along the path. In this way, the user may feel as though he is viewing images produced by a moving "virtual" endoscope. Also, presentation of multiple 3D images in this manner may function to effectively provide 4D imaging of a subject, for example with time (i.e., the passage of time related to traveling along the path) serving as the fourth dimension, and with the images be presented according to any desired timing scheme (e.g., in real time, with a desired time delay, or in accordance with any other suitable timing scheme). Thus, it should be appreciated that in some embodiments real time display of 3D real time imagery may be provided.

The images may be presented using any suitable display including any of the previously-described 3D displays. Images of a path through a subject may be displayed together with volumetric images of the subject in some embodiments.

In some embodiments, the viewer may manipulate any of the presented images. For example, for each image, the viewer may change the point of view for the image (e.g., by providing input to pan and tilt the image, move the image from side to side, and/or up and down).

In some embodiments, images produced at act 4410 may be displayed to one or more remote users (e.g., over the Internet and/or any other suitable network). Such functionality may be desirable in numerous types of applications such as telemedicine. For example, a doctor located remotely from an operating room in which a medical procedure is taking place and in which the subject of the medical procedure is being imaged may be able to view the images and provide input to a surgeon (or other personnel) or a device (e.g., a surgical robot) performing the medical procedure.

The inventors have further appreciated that it may be desirable not only to present a viewer with images of a subject being imaged from multiple points of view that lie along a path, at least partially intersecting the subject, but also to apply HIFU along the path. The purpose of the HIFU may be to heat tissue along the path, cauterize tissue along the path, ablate tissue along the path, and/or for any other suitable purpose.

Figure 45:
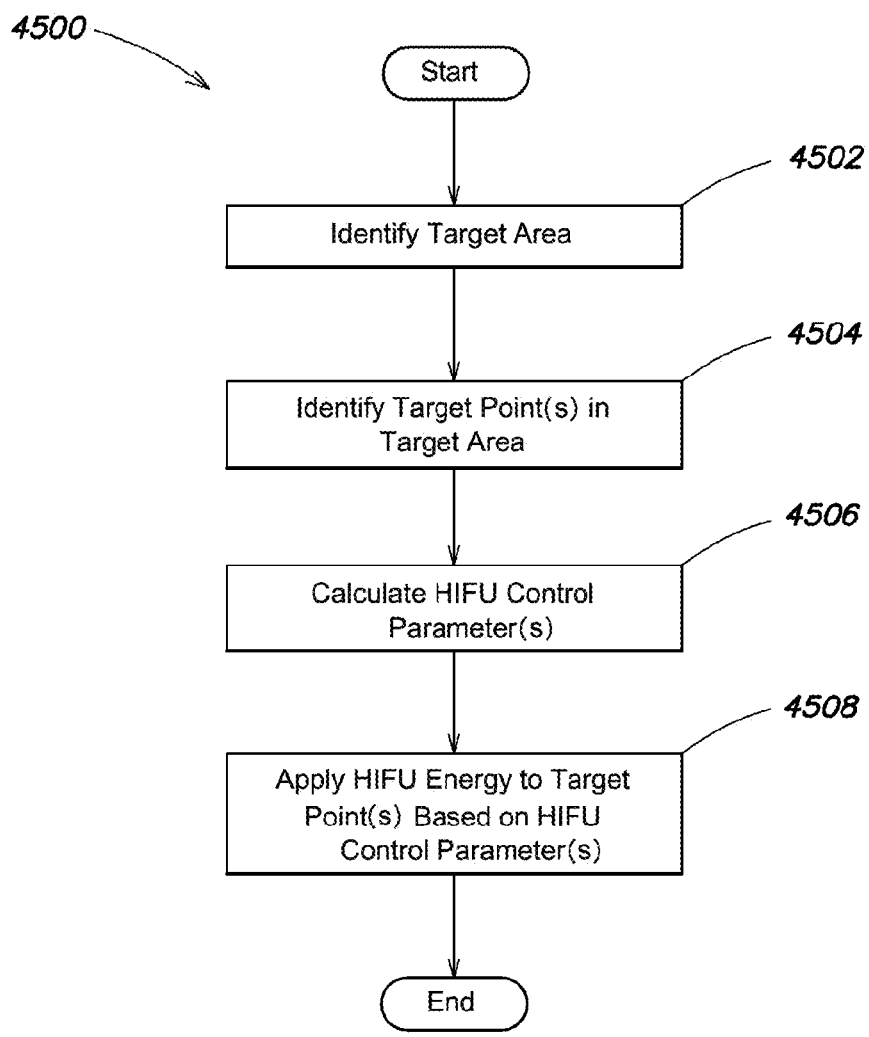
FIG. 45 is a flowchart of a process for identifying a path at least partially intersecting a subject being imaged and applying HIFU along the identified path, according to some non-limiting embodiments.

Accordingly, in some embodiments, a path at least partially intersecting the subject being imaged may be identified and HIFU may be applied to the subject along one or more points in the path. This may be done in any suitable way, an illustrative example of which is described below with reference to FIG. 45, which shows illustrative process 4500 for identifying a path at least partially intersecting a subject being imaged and applying HIFU along the path. Process 4500 may be performed by any suitable system configured to image a subject and apply HIFU to the subject, an example of which is system 400 described with reference to FIG. 4.

Process 4500 begins at act 4502, where a target area in the subject being imaged is identified for subsequent treatment by the application of at least one HIFU beam. This may be done in any suitable way. For example, the target area may be identified automatically by using image analysis algorithms, examples of which were previously described with reference to FIG. 41. Alternatively, the target area may be identified manually by a user providing any suitable type of input, examples of which were previously described with reference to act 4408 of FIG. 44. In some embodiments, the target area may be identified by a user viewing an image of the subject (e.g., any of the types of images previously described herein) and identifying the target area from the image. For example, the user may view a 3D image of a subject, manipulate the image (e.g., rotate the image, enlarge the image, etc.) and thereby locate the target area within the image. Regardless of how a target area is identified, the target area may be any suitable type of target area. For example, in medical applications, the target area may comprise tissue that is to be treated or destroyed by the application of HIFU.

After the target area is identified, the process 4500 proceeds to act 4504, where one or more target points in the target area are identified. In some embodiments, the target points may lie along a path at least partially intersecting the target area. The identified path may be used to determine how HIFU is to be applied to the target area identified at act 4502. The path at least partially intersecting the target area may be identified in any suitable way. In some embodiments, the path may be identified automatically, for example, by using techniques described with reference to act 4406 and FIG. 44. In other embodiments, the path may be identified based, at least in part, on input from a user, for example, as previously described with reference to act 4408 and FIG. 44. For example, the user may specify a path at least partially intersecting the target area, while viewing a volumetric image of the target area (using a 3D display or any other suitable type of display), by drawing a path through the displayed target by moving a pointing device, a finger, or any other suitable object. The path indicated by the motion may be detected via the aforementioned detection mechanism and used to provide the specified path to the system executing process 4500.

In some embodiments, after the target point(s) have been specified, the system executing process 4500 may display the target point(s) together with the target area (e.g., by overlaying a path containing the target point(s) on the target area) to the viewer via a 3D display. The viewer, in turn, may edit the displayed path by manipulating the displayed path. The viewer may manipulate the displayed path using any suitable type of input including, but not limited, to the above-described types of input from manually specifying paths.

The path at least partially intersecting the target area may be any suitable type of path. As previously described, the path may indicate a sequence of target points along which HIFU (e.g., at least one focused HIFU beam) is to be applied. The target points in the sequence may be ordered in any suitable way and, for example, may be ordered in accordance with a raster scan of the target area, as a non-limiting embodiment.

After the path for the application of HIFU is identified, the process 4500 proceeds to act 4506, where one or more HIFU control parameters used for applying HIFU along the path are calculated. The following description assumes the HIFU control parameters are calculated, though they may be determined in other manners in other embodiments. The HIFU control parameters are calculated in such a way that when the system executing process 4500 applies HIFU to the target area based on the calculated HIFU parameters, HIFU is applied along points in the identified path using at least one HIFU beam. In some embodiments, the HIFU control parameters are calculated based at least in part on user input specifying how much energy and/or power to apply to each point along the path. For example, such input may specify different energy and/or power levels depending on whether HIFU is used to heat, cauterize, or ablate the tissue along the path of a HIFU beam.

In some embodiments, the HIFU control parameters specify how an array of ultrasound elements (e.g., array 402*a*) may transmit signals to form the focused HIFU beam. In such embodiments, the HIFU parameters may be calculated by using a beamforming technique (e.g., spherically converging wave front beamforming), a focusing technique (e.g., time reversal focusing), and/or any other suitable technique. In some embodiments, the beamforming and/or focusing techniques may take into account speed of wave propagation in the medium to which the HIFU is applied and/or refraction.

After HIFU parameters are calculated in act 4506, the process 4500 proceeds to act 4508, where at least one HIFU beam is applied to the target area based at least in part on the calculated HIFU parameters. After the HIFU is applied, process 4500 completes.

It should be appreciated that process 4500 is illustrative and that there are variations of process 4500. For example, in some embodiments, instead of calculating a path at least partially intersecting a target area, it may be determined (e.g., based on user input or automatically) that HIFU is to be applied to the entire target area or a shell around the target area. In such embodiments, HIFU parameters are determined such that HIFU is applied by spreading HIFU energy along the entire target area or the shell around the target area.

As a non-limiting example of the operation of process 4500, a user may identify the target area of a subject at act 4502 by viewing a 3D image of the subject. The user may extract a 3D subvolume of the 3D image (e.g., extract a portion of an imaged kidney) and plan the HIFU path through the subvolume. In considering the path, the viewer may manipulate the subvolume, for instance by rotating the image of the subvolume, enlarging the image of the subvolume, or manipulating the image of the subvolume in any other suitable manner. The view may then identify the locations of interest within the subvolume that are to make up the HIFU path. A system (e.g., a computer system) being used to perform the process 4500 may record the points making up the desired HIFU path identified by the viewer. In some embodiments, registration between a subvolume of a 3D image extracted from a larger 3D image may be maintained by the system, such that if a surgical path (e.g., a path along which a focused HIFU beam may be applied) is planned with respect to the extracted subvolume, the path may be accurately translated to the larger 3D image. Such processing (including viewing of the 3D image and any extracted subvolume) may proceed in real time in some embodiments.

The inventors have appreciated that it may be useful to adjust the way in which HIFU is applied to a subject in response to motion of the subject. For example, when a HIFU beam is applied to heat, cauterize, and/or ablate a target area of tissue in a subject and the subject moves causing the target area of tissue to move from one position to another position, the HIFU beam may need to be adjusted so that it is still applied to the target area after the patient movement. This way, the HIFU beam may be applied only to a target area of tissue (e.g., diseased tissue) to which the application of a HIFU beam is planned, herein referred to as a planned target area, and may not be applied, inadvertently, to other areas of tissue (e.g., healthy tissue) as a result of the subject's motion.

Figure 46:
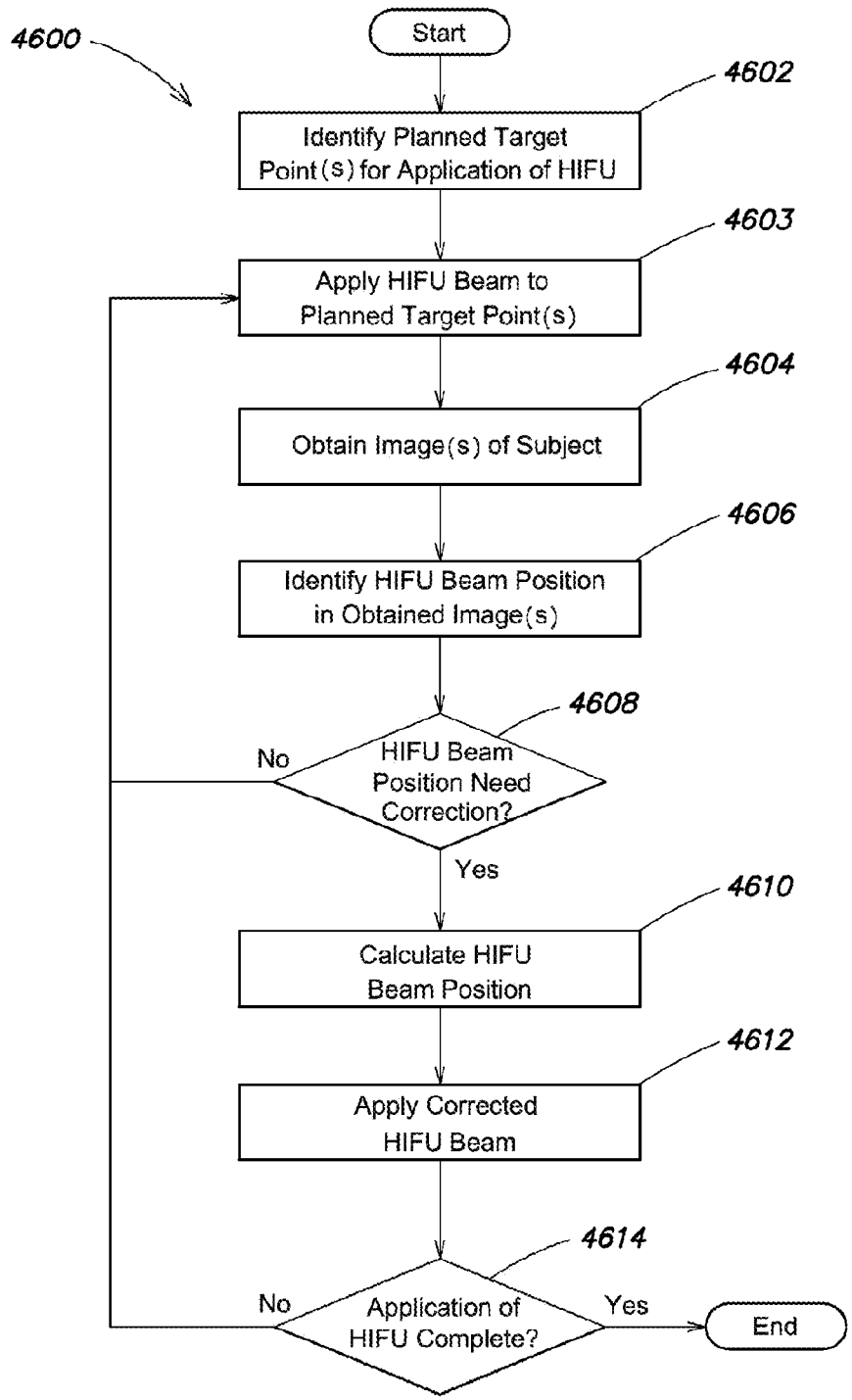
FIG. 46 is a flowchart of a process for correcting how HIFU is applied to a subject based on one or more volumetric images of the subject, according to some non-limiting embodiments.

The inventors have further appreciated that one or more images of a subject, obtained while HIFU energy is being applied to the subject, may be used to adjust the way in which HIFU is being applied to the subject. Such image(s) of the subject may be used to detect whether HIFU is being applied to a planned target area or areas in the subject (e.g., as determined by a doctor and/or in any other suitable way) or is being applied to other areas in the subject (e.g., due to motion of the subject). This may be done in any suitable way. For example, in some embodiments, image(s) of the subject may be used to identify an area to which the HIFU beam has been applied. The position of the identified area may be compared with the position of a planned target area, and the manner in which the HIFU beam is applied to the subject may be adjusted based on results of the comparison. For example, the HIFU beam may be adjusted to apply energy to one or more different positions in the subject to maintain the focus of the HIFU beam on a planned target area in the subject, even as the subject moves. These and other embodiments are described in more detail below with reference to FIG. 46, which shows an illustrative process 4600 for adjusting application of a HIFU beam to a subject based on one or more images of the subject. Process 4600 may be performed by any suitable controller configured to control HIFU beams produced by one or more ultrasound arrays, an example of which is control system 406 described with reference to FIG. 4. As previously described, control system 406 is configured to control one or more HIFU beams produced by opposed arrays 402*a* and 402*b*.

It should be appreciated that image(s) of the subject may be used to adjust the way in which HIFU is being applied to the subject in other ways. For example, image(s) of the subject may be used to determine whether HIFU is being applied to an appropriately sized area of the subject. For example, the image(s) may be used to determine whether the HIFU beam is applied to a larger area of the subject than planned and/or a smaller area of the subject than planned.

Process 4600 begins at act 4602, where one or more multiple target points for application of HIFU in a subject are identified. The target point(s) may be identified in any suitable way and, for example, may be obtained in the manner previously described with reference to act 4504 in FIG. 45. In some embodiments, a volumetric image of a subject may be displayed (e.g., with a 3D display) and a user may identify target points using the displayed volumetric image, for example using hand motions, a point device (e.g., stylus pen), or in another suitable manner, examples of which have been described herein. In some embodiments, the target points may be identified automatically. This may be done in any suitable way. For example, target points may be identified automatically by using any suitable computer vision and/or image understanding techniques including, but not limited to, segmentation, boundary estimation, ellipsoid fitting, and detection with shape descriptor metrics. In some embodiments, target points may be identified automatically by using one or more other sensors. The target point(s) may lie along a path through the subject.

After the target point(s) for application of HIFU are identified, process 4600 proceeds to act 4603, where HIFU energy is applied to one or more of the identified target points. This may be done in any suitable way and, for example, may be done as described with reference to acts 4506 and 4508 of process 4500. That is, for example, one or more HIFU control parameters may be calculated and HIFU energy may be applied to the identified target point(s) based on the HIFU control parameter(s).

Next, process 4600 proceeds to act 4604, where one or more images of the subject are obtained. In some embodiments, one or more volumetric images of the subject may be obtained. The volumetric image(s) may be obtained in any suitable way, examples of which were previously described with reference to process 2900 in FIG. 29. The volumetric images(s) of any suitable type may be obtained including, but not limited to, one or more volumetric images computed from only time-of-flight measurements, only attenuation measurements, or any suitable combination thereof. Some embodiments described herein are not limited to obtaining only volumetric images of the subject as part of act 4604, and other types of images (e.g., two-dimensional images, B-scan images, etc.) of the subject may be obtained in addition to or instead of volumetric images of the subject.

In some embodiments, the volumetric image(s) obtained at act 4604 may be computed from measurements obtained, at least in part, by the same array or arrays that generate the HIFU beam in process 4600. For example, arrays 402a and 402b, described with reference to FIG. 4, may be used to image the subject as well as to generate and apply a HIFU beam to the subject. However, in other embodiments, different arrays may be used for imaging a subject and generating and applying a HIFU beam to the subject.

In some embodiments, one or more image shape analysis techniques may be applied to each image of the subject obtained in act 4604. Any suitable image shape analysis technique may be applied, examples of which were previously described with reference to act 4106 of process 4100. The image shape analysis techniques may be applied to image(s) of the subject before or the after the images(s) are obtained at act 4604.

After one or more images of the subject are obtained at act 4604, the process 4600 proceeds to act 4606, where the image(s) are used to identify one or more positions in the subject to which HIFU energy (e.g., a HIFU beam) has been applied. Each image obtained in act 4604 may be processed on its own to identify one or more positions to which a HIFU beam has been applied. This may be done in any suitable way, for example, by detecting features in the image indicative of the application of the HIFU beam and tracking the path of these features through the image. When multiple images are obtained in act 4604, the images may be jointly processed to identify the positions, in each of the multiple images, to which a HIFU beam has been applied.

Regardless of whether a single or multiple images are processed as part of act 4606, any suitable techniques may be used to process the image(s) to detect and/or track positions in the subject to which a HIFU beam has been applied. In some embodiments, statistical inference techniques may be used to detect and/or track the positions including, but not limited to, least-squares fitting, Kalman filtering, extended Kalman filtering, unscented Kalman filtering, particle filtering, tracking as inference, and/or any other suitable technique.

After one or more positions to which a HIFU beam has been applied are identified by processing the images obtained in act 4604, the process 4600 proceeds to decision block 4608, where it is determined whether the position(s) to which the HIFU beam is being applied should be corrected. This determination may be made in any suitable way, and may be automatic. For example, in some embodiments, the positions identified from imaging data in act 4604 may be compared with positions in the planned path of positions obtained in act 4602. The comparison may be performed by calculating the difference between the identified and planned positions, the ratio between the identified and planned positions, or in any other suitable way. When it is determined that the identified positions do not significantly deviate from the planned positions (e.g., when the difference between the identified and planned positions is below a threshold), it may be determined that the HIFU beam need not be adjusted. Accordingly, parameters controlling the positions to which the HIFU beam is to be applied are left unchanged and HIFU energy may continue to be applied to the same target point(s) to which HIFU energy has been applied. Process 4600 returns to act 4603 and acts 4603-4606 are repeated. In this way, process 4600 continues to monitor the subject, by using images of the subject, to determine whether any adjustments should be made to the HIFU beam.

On the other hand, when it is determined, at decision block 4608, that the identified positions deviate from the planned positions (e.g., when the difference between the identified and planned positions of the HIFU beam is above a threshold), it may be determined that the HIFU beam is to be adjusted (e.g., by adjusting the positions to which the HIFU beam is to be applied). For example, when a subject moves while a HIFU beam is being applied to the subject, images of the subject may indicate that the HIFU beam has been applied to one or more positions that deviate from the planned positions. This may provide an indication that the HIFU beam should be adjusted to compensate for the subject's motion.

If it is determined that the HIFU beam should be corrected (e.g., because the location to which the HIFU beam was being applied (which may be referred to as a target point) does not match the desired location (which may be referred to as a planned point) for application of the HIFU), process 4600 proceeds to act 4610, where a HIFU beam correction may be determined (e.g., calculated). This may be done in any suitable way. In some embodiments, differences between the identified and planned positions of the HIFU beam may be used to adjust one or more HIFU control parameters that control the position(s) to which the HIFU beam is being applied or the position(s) to which the HIFU beam is to be applied. For example, differences between the identified and planned positions of the HIFU beam may be used to calculate a HIFU steering vector which, in turn, may be used to adjust the position(s) to which the HIFU beam is being applied. In some embodiments, the difference between the identified and planned positions of the HIFU beam may be processed (e.g., by integrating and/or smoothing changes over time) to stabilize the way in which the HIFU beam is controlled so that adjustments to the HIFU beam are not made in response to fluctuations due to noise or other spurious anomalies in the imaging data.

After the HIFU beam correction has been computed, at act 4610, process 4600 proceeds to act 4612, where the HIFU beam correction is used to adjust one or more parameters controlling the positions to which the HIFU beam is applied. In turn, the corrected HIFU beam may be applied to the subject.

Next, process 4600 proceeds to decision block 4614, where it is determined whether the HIFU beam has been applied along the entirety of the planned HIFU path obtained at act 4602. This determination may be made in any suitable way and, for example, may be made by comparing the positions to which the HIFU beam has been applied with the positions in the planned HIFU path. If the HIFU beam has been applied to all the positions of the planned path, process 4600 completes. Otherwise, process 4600 returns to act 4603.

Processes 4500 and 4600 may utilize various levels of automation. For example, one or more acts in each process may be automated. In some embodiments, process 4500 and/or 4600 may be fully automated. Automatic HIFU control (e.g., automatic focusing of a HIFU beam, automatic tracking of a HIFU beam, automatic identification of one or more target points to which HIFU energy has been applied (e.g., via a HIFU beam)) may therefore be provided according to some embodiments described herein.

The timing of the processes illustrated in FIGS. 41 and 44-46 may conform to any desired timing schemes. In some embodiments, real time imaging and image manipulation may be desired. Thus, according to some aspects, one or more acts shown in FIGS. 41 and 44-46 may be performed in real time. In some embodiments, in-situ real time image guided surgery with HIFU may be provided. Alternative timings are also possible.

Having thus described several aspects and embodiments of the technology described in the application, it is to be appreciated that various alterations, modifications, and improvements will readily occur to those skilled in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present application involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

APPENDIX A

As previously described with reference to process 2900, a geometric model may be constructed by computing path length information. Path length information may be computed by using any suitable techniques including, but not limited to, any of the techniques previously described with reference to process 2900. In this Appendix, additional techniques for computing path length information are described.

The techniques for computing path length information which are described below are explained with reference to a matrix data structure that may be used to encode path length information. Though, it should be appreciated that this is done only for clarity of exposition as path length information may be encoded and/or stored in any suitable way.

I. First Technique

Geometric Considerations

Path length information may be computed, at least in part, by determining for a line segment from an ultrasound source to an ultrasound sensor (e.g., from ultrasound source (i,j) to ultrasound sensor (k,l)), which voxels (if any) of a volume being imaged are intersected by the line segment. For each voxel that is intersected by the line segment, a value indicative of the length of the portion of the line segment that intersects the voxel may be computed. In some embodiments, the computed value may be encoded using a data structure such as, but not limited to, a matrix. For example, a value for a voxel intersecting the line segment from ultrasound source (i,j) to ultrasound sensor (k,l) may be encoded in the (ijkl) row of matrix A, and may be encoded in a column corresponding to the voxel (e.g., column (xyz) corresponding to voxel located at coordinates (x,y,z) in the volume being imaged).

Initially, note that the bounding planes of a voxel (i.e., planes demarcating the faces of the voxel) may be represented simply when the planes are aligned with Cartesian coordinates. As a result, the planar intersections between the line segment from an ultrasound source located at Cartesian coordinates $r_0 = (x_0, y_0, z_0)^T$ to an ultrasound sensor located at Cartesian coordinates $r_1 = (x_1, y_1, z_1)^T$ and the plane demarcating each face of the voxel may be computed as described below. Let $r = (x,y,z)^T$ be the lowermost corner (lowest in Cartesian components) of a voxel in a volume being imaged. Any point $v_\eta$ along the above-described line segment may be represented according to:

$$v_\eta = r_0 + \eta(r_1 - r_0), 0 \leq \eta \leq 1, \quad (A.1)$$

where the interpolation parameter, $\eta$, indicates how far along the line segment the point $v_\eta$ lies. Since the interpolation parameter $\eta$ uniquely determines the location of point $v_\eta$ along given line segment, the point $v_\eta$ and the interpolation parameter $\eta$ are referred to interchangeably.

The intersection point between the line segment from $r_0$ to $r_1$ and the x-y plane at offset Z, may be computed by solving (A.1) in the z-component to find $\eta$ according to:

$$\eta = \frac{z - z_0}{z_1 - z_0}. \quad (A.2)$$

The other components of the intersection point $v_\eta$ may then be computed using (A.1). Note that the form of equation A.2 remains the same for planes in the other two mutually orthogonal orientations (i.e., the x-z plane and the y-z plane).

Also note that the length of the sub-segment from two points represented at least in part by interpolation parameters $\eta_1$ and $\eta_2$ is given according to:

$$|v_{\eta_2} - v_{\eta_1}| = |[r_0 + \eta_2(r_1 - r_0)] - [r_0 + \eta_1(r_1 - r_0)]| \quad (A.3)$$
$$= (\eta_2 - \eta_1)(r_1 - r_0).$$

Thus, if the interpolation parameters of each intersection point between a line segment and a voxel are computed, the intersection segment length (and e.g., the corresponding entry of the matrix A) may be computed.

Illustrative Process for Constructing Geometry Model

A technique for constructing a geometry model including path length information is now described below. The technique relies on the above-described geometric principles. Consider a line segment from an ultrasound source positioned at $r_0 = (x_0, y_0, z_0)^t$ to an ultrasound sensor positioned at $r_1 = (x_1, y_1, z_1)^t$. To compute the lengths of portions of a line segment (from the ultrasound source to the ultrasound sensor) intersecting each voxel along the line segment (e.g., to compute the entries of the row of the matrix A that corresponds to the above-identified source-sensor pair), the technique comprises computing interpolation parameters, $\eta$, for the intersections of the line segment with all of the planes defining the voxel boundaries. For example, to compute the interpolation parameters of the intersections of the x-y planes with the line segment at offsets $z_i$, equation A.2 may be used to compute:

$$\eta_{z_i} = \frac{z_i - z_0}{z_1 - z_0}. \quad (A.4)$$

Similarly, equation A.2 may be used to compute the interpolation parameters of the intersections of the x-z planes with the line segment at offsets $y_i$, and the interpolation parameters of the intersections of the y-z planes with the line segment at offsets $x_i$, for all voxel boundary planes. If the computed interpolation parameter of an intersection point is less than 0 or is greater than 1, then such an intersection point is not within the extents of the line segment (i.e., it intersects the continuation of the line segment), and the intersection point is discarded from further consideration. It should be appreciated that the above-described computation may be vectorized, for example, by storing the offsets $\{x_i\}$, $\{y_i\}$, and $\{z_i\}$ in machine vectors and using vector operations to compute equation A.4 and its analogues. Furthermore, if the offsets $\{x_i\}$, $\{y_i\}$, and $\{z_i\}$ are sorted prior to computing equation A.4, then the resulting vector of interpolation parameters will also be sorted.

The three sets of interpolation parameters $\{\eta_{x_i}\}$, $\{\eta_{y_i}\}$, and $\{\eta_{z_i}\}$ are then merged into an ordered set $(\eta_i)$ and sorted from smallest to largest. If the three sets of parameters are already ordered, then the merge and sort operations may be performed in linear time (e.g., similarly to the "merge" step of the "merge-sort" algorithm, which is known in the art). Note that if the interpolation parameters $\eta_i$ and $\eta_{i+1}$ are distinct, then there are no intersection points $\eta$ strictly between them, so the line segment from $\eta_i$ to $\eta_{i+1}$ describes an intersecting line sub-segment within a single voxel. Thus, the desired lengths may be obtained by iterating through $(\eta_i)$ and computing the desired lengths with equation A.3 according to:

$$l_i = (\eta_{i+1} - \eta_i)|r_0 - r_1|. \quad (A.5)$$

When the lengths are stored in the row of the matrix A (the row corresponding to the above-identified source-sensor pair), a determination is made of how to assign the lengths computed using (A.5) to the appropriate columns within that row. This may be done iteratively by attaching information to the intersection points $\eta_i$ before they merged and sorted. Each voxel can be described by a position vector $s \in Z^3$, that indexes the position of the voxel within the three-dimensional Cartesian integer lattice. When the process starts, the first length computed, $l_0$, corresponds to the voxel $s_0$, describing the voxel containing $r_0$. The index of the next voxel, $s_1$, corresponding to the next length computed, $l_1$, may be inferred from the orientation of the plane of intersection described by the intersection point $\eta_1$. If it were an x-y plane, then the next voxel is positioned at $s_0 \pm (0,0,1)^t = s_0 \pm e_3$ (with the sign being determined by the corresponding component of the vector $r_1 - r_0$). To facilitate this step of the computation, the vector $\pm e_3$ may be associated to each of the $\eta_{z_i}$ as they are being computed, and similarly for $\eta_{x_i}$ (attaching $\pm e_1$) and $\eta_{y_i}$ (attaching $\pm e_2$). Hence, instead of sets $\{\eta_i\}$, sets of tuples $b_i = (\eta_i, \delta_i)$ are stored, where $\delta_i$ describes the voxel index displacement vector corresponding to the intersection plane orientation. The $b_i$ may then be merged and sorted, with $\eta_i$ used as the sort key. Thus, after the length $l_i$ is computed, it may be stored in the column of the matrix A corresponding to the voxel index given according to: $s_i = s_{i-1} + \delta_i$.

The above-described technique may be summarized as follows:

1. Given position vectors $r_0$ and $r_1$ of an ultrasound source-sensor pair, compute the interpolation parameters $\{\eta_{x_i}\}$, $\{\eta_{y_i}\}$, and $\{\eta_{z_i}\}$, from the plane offsets $\{x_i\}$, $\{y_i\}$, and $\{z_i\}$, respectively, using equation A.4. Associated with each interpolation parameter, the corresponding displacement vector $\delta$ ($\pm e_1$ for each $\eta_{x_i}$, $\pm e_2$ for each $\eta_{y_i}$, and $\pm e_3$ for each $\eta_{z_i}$, where the sign is taken from the corresponding component of $(r_1 - r_0)$), forming tuples $\{b_{x_i}\}$, $\{b_{y_i}\}$, and $\{b_{z_i}\}$.

2. Merge and sort $\{b_{x_i}\}$, $\{b_{y_i}\}$, and $\{b_{z_i}\}$, into an ordered set $(b_i)$ using $\eta_i$ as the sort key (from smallest to largest).

3. For each i, compute $l_i$ from $b_i$ and $b_{i+1}$ according to (A.5) and assign it to voxel $s_i$ where $s_i = s_{i-1} + \delta_i$, and $s_0$ is the index of the voxel containing $r_0$.

To compute path length information and, in particular, to compute entries of the matrix A, in some embodiments, the above-described process may be used to calculate entries for one or more (or all) row in the matrix A. Specifically, the above-described process may be used to calculate entries for the (ijkl)th row of the matrix A corresponding to a pair of an ultrasound source (i,j) and sensor (k,l).

Computational Complexity

The computational complexity of the above-described technique for computing path length information is analyzed below. Consider an embodiment where an ultrasound imaging device has an $N_{tx} \times N_{ty}$ array of sensors and an $N_{rx} \times N_{ry}$ array of sources configured to image an $M_x \times M_y \times M_z$ volume of voxels. The computational complexity of the first step in the above described sequence of three steps is linear in each of the dimensions of the volume being imaged—i.e., the computational complexity is $O(M_x + M_y + M_z)$. As previously described, the sets, $\{b_{x_i}\}$, $\{b_{y_i}\}$, and $\{b_{z_i}\}$, may be sorted, in which case the computational complexity of step 2 in the above-described sequence is also linear in each of the dimensions of the volume being imaged—i.e., the computational complexity is $O(M_x + M_y + M_z)$. Finally, the computational complexity of step 3 is also $O(M_x + M_y + M_z)$, since an $O(1)$ calculation is performed for each $b_i$.

Since the above process may be run for each of the $N_{rx} N_{ry} N_{tx} N_{tz}$ line segments associated with the source-sensor pairs, the computational complexity of computing path length information for all source sensor pairs, using this approach, is $O(N_{rx}N_{ry}N_{tx}N_{tz}(M_x+M_y+M_z))$. If N were to represent the largest dimension of either array (in number of elements) and M represents the largest dimension of the volume (in number of voxels), then the computational complexity would be $O(N^4M)$.

It should be appreciated that although the above-described technique was described with reference to a rectangular array of sources, a rectangular array of sensors, and a regular volume of voxels, the technique may be applied in a more general setting, as aspects of the present application are not limited in this respect. For example, the locations of the sources and sensors may be arbitrary, for the purposes of calculating path length information, since all that is needed is a parameterization of a line segment between a source and a sensor in a source-sensor pair. Thus, the above-described technique for computing path length information is not limited to being applied to any particular configuration of sources and sensors (e.g., opposing two-dimensional arrays of sources and sensors). Furthermore, voxels need not be defined by regularly spaced planes. If the planes bounding the voxels are in mutually orthogonal orientations, then the computational complexity may be given in more general terms as $O(N_{linesegments} N_{voxelboundaryplanes})$.

It should also be appreciated that the above-described process, as well as any of the processes for computing path length information described herein, may be parallelized. Calculations performed for each source-sensor pair (i.e., line segment) may be performed in parallel. As such, such processing may be performed by multiple parallel and/or distributed processors, graphical processing units, etc. As such, the computation of path-length information may be computed in real time.

II. Second Technique: Generalization to Arbitrary Voxelizations

In the above-described process for computing a geometric model by computing path length information, each of the voxels in a volume to be imaged was assumed to be characterized by the same set of boundary planes and that each of the boundary planes lies in one of three mutually orthogonal orientations. The technique described below applies in a more general setting, where the voxels may be adjacent polyhedra, such that there are no gaps among them. As an illustrative, non-limiting example, such voxels may arise if a volume being imaged is subdivided into voxels by means of a tessellation, such as a Voronoi tessellation.

For the purposes of described the technique, assume that each voxel $v_i$, in a volume being imaged may be described by a set of boundary planes $P_i$. In addition, let the graph $G=(V,E)$, where the vertices in the set of vertices V, correspond the voxels and an edge $e=v_i, v_j \in E$ if and only if the voxels $v_i$ and $v_j$ are adjacent (i.e., there exist unique planes $p \in P_i$ and $q \in P_j$ such that p and q are co-planar and overlap on the boundaries of the vertices $v_i$ and $v_j$). Thus, each bounding plane, $p_j$, has a non-empty set of associated edges, $E_j \subset E$. The dual graph G comprises a unique vertex $v_{out} \in V$ corresponding to the "outside" of the volume, so that the bounding planes on the exterior of the volume have corresponding edges as well.

Geometric Considerations

Note that a plane may be defined with a point $p_0$, in the plane, and a vector n, normal to the plane, according to:

$$(v-p_0) \cdot n = 0.$$

Substituting (A.1) into the above equation, yields:

$$(r_0 + \eta_i(r_1 - r_0) - p_0) \cdot n = 0,$$

which may be solved for $\eta_i$ to obtain:

$$\eta_i = \frac{(p_0 - r_0) \cdot n}{(r_1 - r_0) \cdot n}, \quad (A.6)$$

which is a generalization of (A.4).

Equation A.6 may be used to calculate the intersection points of a line segment (from a source to a sensor) with the bounding planes of a given voxel, $v_j$. Initially, an intersection point $\eta_i$ may be found for each $p_k \in P_j$ by using equation A.6.

For a point $\eta_i$ to be an intersection point of $v_j$, it must lie on the line segment and within the voxel (i.e., in the interior or on the boundary of the voxel as voxels are considered to be closed sets). The intersection point lies on the line segment, when the $0 \le \eta_i \le 1$. Let the bounding planes $p_k \in P_j$ of voxel $v_j$ each be defined a point $p_k$ and a normal vector $n_k$, where the normal vector points to the interior of the voxel. A determination as to whether an arbitrary point, v, is within voxel $v_j$ may be made by computing:

$$w_k = (v - p_k) \cdot n_k \quad (A.7)$$

for each plane $p_k \in P_j$. Intuitively, this is the distance that v lies "above" the plane $p_k$, where positive values are "above" in the direction of the interior of the voxel. Hence, if $w_k$ is negative for any k, then the point is not within the voxel, otherwise it is within the voxel (in the interior if all positive, or on the boundary otherwise). Thus, the criteria for a point $\eta_i$ to be a valid intersection point of $v_j$ are given by:

$$0 \le \eta_i \le 1 \text{ and} \quad (A.8)$$

$$(v_{\eta_i} - p_k) \cdot n_k \ge 0, \forall p_k \in P_j. \quad (A.9)$$

Another Illustrative Process for Constructing Geometry Model

Another illustrative technique for constructing a geometry model including path length information is now described below. The technique relies on the above-described geometric principles. Once again, consider a line segment from an ultrasound source positioned at $r_0 = (x_0, y_0, z_0)^t$ to an ultrasound sensor positioned at $r_1 = (x_1, y_i, z_1)^t$. The process may be formulated as a "walk" from $r_0$ to $r_1$ through the voxels. To this end, the dual graph G will be used to iterate over the voxels.

Let $s_0$, the initial voxel, be the voxel enclosing $r_0$. Next, the nearest point at which the line segment from $r_0$ to $r_1$ leaves the initial voxel $s_0$ is determined. This may be done by computing the intersection points $\eta_i$ between the line segment and planes in the set $P_0$ of boundary planes of voxel $s_0$ by using equation A.6. Those intersection points which do not satisfy the criteria of (A.8) and (A.9) are eliminated. If the voxel $s_0$ is convex, then there will be exactly one such point (unless we hit a "corner," as described below). Otherwise, the smallest such $\eta_i$ will be the unique exiting point, $\eta^{(1)}$.

Suppose that the exiting point, $\eta^{(1)}$, lies on the plane $p_j \in P_0$. If the exiting point is not a corner of the voxel, which may be a point at which multiple planes intersect, then the plane $p_j$ is unique. The edges $E_j$ corresponding to $p_j$ may be identified by using the dual graph G. The next voxel, $s_1$, will be the voxel incident with the other end of the edge $e = (s_0, v) \in E_j$ such that the intersection point $\eta^{(1)}$ lies within voxel v. Often, there will be only one edge in $E_j$, but in some instances, $E_j$ may comprise multiple edges, an ambiguity which may occur in the limit as two bounding planes become co-planar. Repeating the process, the existing point $\eta^{(2)}$ of $s_1$ may be determined, and so on. When determining the exiting point of the i'th voxel, care should be taken to ensure that that $\eta^{(i)}$ be monotonic so that the entrance point (i.e., $\eta^{(i-1)}$) is not selected as the exiting point. The iterations proceed until the point $r_1$ is reached. This may be detected in any of numerous ways including by detecting that the only $\eta$ that satisfies (A.8) is the entrance point. At each iteration i, the length $$l_i = \eta^{(i+1)} - \eta^{(i)} |r_1 - r_0|, \tag{A.10}$$

may be added to the matrix A to the row corresponding to the source-sensor pair positioned at $r_0 = (x_0, y_0, z_0)^t$, $r_1 = (x_1, y_1, z_1)^t$ and the voxel $s_i$, where $\eta^{(0)} = 0$ and $\eta^{(final+1)} = 1$. If the voxel $s_i$ is convex, the addition will be equivalent to assignment, but non-convex voxels can be entered more than once.

The above-described technique may be summarized as follows:

1. Let $s_0$ be the voxel containing $r_0$ and let $\eta^{(0)} = 0$.
2. For each i,
   (a) Compute $\eta_j$ for each $p_j \in P_i$, and let $\eta^{(i+1)}$ be the smallest $\eta_j$ that satisfies (A.8) and (A.9) and is strictly greater than $\eta^{(i)1}$.
   (b) If there is no such point, then terminate the process after the next step is performed with $\eta^{(i+1)} = 1$.
   (c) Add the length $l_i$, computed according to (A.10), to the entry of A corresponding to $s_i$.
   (d) Let $E_j \subset E$ be the edges of the dual graph G corresponding to the plane $p \in P_i$ containing the exiting point $\eta^{(i+1)}$, and find the edge $e = s_i$, $v \in E_j$ such that the exiting point $\eta^{(i+1)}$ is within v as per (A.8) and (A.9).
   (e) Let $s_{i+1} = v$ and repeat.

It should be appreciated that in the corner case, the exiting point lies on the intersection of two or more bounding planes $p_j \in P_i$ of $s_i$. In that case, associated with each $p_j$ is a voxel $s_{i,j}$, which is the "next" voxel according to that plane. In such a corner case, the exiting point $\eta_{i,j}$ may be computed as follows. If the candidate exiting points are distinct, then the smallest one is the next voxel (this may occur if the voxels are not convex). Otherwise, all the candidate exiting points coincide with the entrance point, and any such point may be used. However, in this case, the constraint that no voxel is visited twice during the search for the "next" voxel should be enforced in this case.

Computational Complexity

To analyze the computational complexity of the second technique, let $N_l$ be the number of line segments (equal to $N^4$ for opposed rectangular arrays of dimension N×N), |V| be the number of voxels (equal to $M^3$ for a cubic volume of dimension M×M×M), and d be the average degree of the vertices in V. Also observe that the computational complexity of Step 1 is O(1), so that the running time is determined by Step 2. The computational complexity of step 2a is $O(d^2)$ steps, since (on average) a point is computed for each of d planes, that each need to be checked against the d planes. The worst case in Step 2d is O(d), corresponding to an ambiguous plane with d neighbors, which can be discerned by an O(1) computation. Finally, in the worst-case scenario, Step 2 is repeated |V| times. Thus, the computational complexity of the second technique is given by $O(N_l|V|d^2)$. It should be appreciated that for most voxelizations, step 2 is actually executed $O(\sqrt[3]{\sqrt{|V|}})$ times, for a computational complexity of $O(N_l|V|^{1/3}d^2)$. In the parameters of the rectangular array and cuboidal voxelization, this is $O(N^4M)$, where d=6 is a constant factor. Hence, asymptotically, the computational complexity of the second technique is the same as that of the first. However, the first technique incurs a smaller storage cost (only O(M) planes must be stored instead of $O(dM^3)$), a smaller constant factor, and uses a simpler implementation.

Finding $s_0$

In the above description, it was assumed that the voxel $s_0$ that contains $r_0$ is known a priori. If this is not the case, $s_0$ is to be identified. One approach involves checking every voxel until one was found with an entrance point $\eta_0$ and an exit point $\eta_1$ satisfying $\eta_0 \leq 0 \leq \eta_1$. However, the computational complexity of such an approach is $O(|V|d^2)$ in the worst case. Another approach may be to use a variation of the above-described generalized process. That is, to first locate a point preceding $r_0$ (i.e., $\eta < 0$) that is known to be within $v_{out}$. For example, if we know that the greatest distance between any two points in the volume is W, then $$\eta = -\frac{W}{|r_1 - r_0|}, \tag{A.11}$$

will describe such a point. Then the generalized process may be applied with $r_0 \mapsto v_\eta$ (given by (A.11)) and $r_1 \mapsto r_0$. When the process terminates, found $s_0$ (the voxel containing $r_0$, which is the endpoint in the re-mapped problem) will have been identified.

What is claimed is:

1. An apparatus, comprising:
   a plurality of radiation sources comprising a first radiation source, a second radiation source, and a third radiation source;
   a plurality of radiation sensors configured to receive radiation of wavelength $\lambda$ emitted by one or more of the first, second, or third radiation sources, the plurality of radiation sensors including a first radiation sensor and a second radiation sensor, wherein the plurality of radiation sensors is sparsely arranged such that a spacing between the first radiation sensor and its nearest neighboring radiation sensor of the plurality of radiation sensors is greater than $\lambda/2$; and
   processing circuitry coupled to the first radiation sensor and the second radiation sensor and configured to receive and discriminate between, for each of the first and second radiation sensors, respective source signals emitted by the first, second, and third radiation sources,
   wherein the first radiation source, the second radiation source, and the first radiation sensor lie in a first plane, and
   wherein the second radiation source, the third radiation source, and the second radiation sensor lie in a second plane different than the first plane.

2. The apparatus of claim 1, wherein the first radiation source is an ultrasound source.

3. The apparatus of claim 2, wherein the first radiation sensor and the second radiation sensor are ultrasound radiation sensors.

4. The apparatus of claim 1, wherein the processing circuitry is configured to receive and discriminate between, for each of the first and second radiation sensors, the respective source signals emitted by at least ten radiation sources of the plurality of radiation sources.

5. The apparatus of claim 4, wherein the processing circuitry is configured to receive and discriminate between, for each of the first and second radiation sensors, the respective source signals emitted by at least 100 radiation sources of the plurality of radiation sources.

6. The apparatus of claim 5, wherein the processing circuitry is configured to receive and discriminate between, for each of the first and second radiation sensors, the respective source signals emitted by at least 1,000 radiation sources of the plurality of radiation sources.

7. The apparatus of claim 4, wherein the processing circuitry is configured to receive and discriminate between, for each of the first and second radiation sensors, the respective source signals emitted by between ten radiation sources and 10,000 radiation sources of the plurality of radiation sources.

8. The apparatus of claim 1, wherein the processing circuitry is configured to receive and discriminate between, for each of the first and second radiation sensors, the respective source signals emitted by at least 1% of the radiation sources of the plurality of radiation sources.

9. The apparatus of claim 8, wherein the processing circuitry is configured to receive and discriminate between, for each of the first and second radiation sensors, the respective source signals emitted by at least 10% of the radiation sources of the plurality of radiation sources.

10. The apparatus of claim 9, wherein the processing circuitry is configured to receive and discriminate between, for each of the first and second radiation sensors, the respective source signals emitted by at least 25% of the radiation sources of the plurality of radiation sources.

11. The apparatus of claim 10, wherein the processing circuitry is configured to receive and discriminate between, for each of the first and second radiation sensors, the respective source signals emitted by at least 50% of the radiation sources of the plurality of radiation sources.

12. The apparatus of claim 11, wherein the processing circuitry is configured to receive and discriminate between, for each of the first and second radiation sensors, the respective source signals emitted by at least 75% of the radiation sources of the plurality of radiation sources.

13. The apparatus of claim 12, wherein the processing circuitry is configured to receive and discriminate between, for each of the first and second radiation sensors, the respective source signals emitted by at least 90% of the radiation sources of the plurality of radiation sources.

14. The apparatus of claim 13, wherein the processing circuitry is configured to receive and discriminate between, for each of the first and second radiation sensors, the respective source signals emitted by all radiation sources of the apparatus.

15. The apparatus of claim 14, wherein the plurality of radiation sources comprises at least fifty radiation sources.

16. The apparatus of claim 1, wherein the plurality of radiation sources is arranged in three dimensions.

17. The apparatus of claim 1, wherein the plurality of radiation sources forms an array of at least two dimensions in which the plurality of radiation sources adopts a regular spacing.

18. The apparatus of claim 17, wherein the plurality of radiation sources is arranged in three dimensions.

19. The apparatus of claim 1, wherein the plurality of radiation sensors is arranged in at least two dimensions.

20. The apparatus of claim 19, wherein the plurality of radiation sensors is arranged in three dimensions.

21. The apparatus of claim 19, wherein the plurality of radiation sensors forms an array of at least two dimensions in which the plurality of radiation sensors adopts a regular spacing.

22. The apparatus of claim 19, wherein the plurality of radiation sensors forms an array of at least two dimensions, and wherein the plurality of radiation sensors forms an array of at least two dimensions.

23. The apparatus of claim 1, wherein the plurality of radiation sources and the first and second radiation sensors are configured to remain static during operation.

24. The apparatus of claim 1, wherein at least some radiation sources of the plurality of radiation sources are not spaced at regular intervals with respect to neighboring radiation sources.

25. The apparatus of claim 1, wherein at least some radiation sensors of the plurality of radiation sensors are not spaced at regular intervals with respect to neighboring radiation sensors.

26. The apparatus of claim 1, wherein the plurality of radiation sources are physically coupled to a first mount and wherein the first and second radiation sensors are physically coupled to a second mount.

27. The apparatus of claim 26, wherein the first mount is flexible.

28. The apparatus of claim 26, wherein the first and second mounts are configured to be independently movable.

29. The apparatus of claim 28, further comprising a detector configured to detect an orientation and/or position of one or more of the plurality of radiation sources relative to one or both of the first and second radiation sensors.

30. The apparatus of claim 1, wherein the first and second radiation sensors are disposed on a first side of a plane and wherein the plurality of radiation sources are disposed on a second side of the plane.

31. The apparatus of claim 1, wherein the first, second, and third radiation sources and the first and second radiation sensors are collectively configured to operate in a transmissive modality.

32. The apparatus of claim 1, wherein directivity vectors of the first, second, and third radiation sources are incident upon the first and second radiation sensors.

33. The apparatus of claim 1, wherein at least one of the first, second, and third radiation sources is configured to alternately operate as a radiation source and a radiation sensor.

34. The apparatus of claim 33, wherein the first, second, and third radiation sources are coupled to the processing circuitry via parallel transmit and receive signal paths, and wherein the apparatus further comprises a switch for switchably coupling the first, second, and third radiation sources to either the transmit signal path or the receive signal path.

35. The apparatus of claim 1, wherein the plurality of radiation sources comprises at least two distinct arrays of radiation sources.

36. The apparatus of claim 35, wherein the at least two distinct arrays of radiation sources comprises three or more distinct arrays of radiation sources.

37. The apparatus of claim 36, wherein the processing circuitry coupled to the first radiation sensor and the second radiation sensor is configured to receive and discriminate between, for each of the first and second radiation sensors, respective source signals emitted by at least one radiation source in each of three distinct arrays of the three or more distinct arrays of radiation sources.

38. The apparatus of claim 1, wherein the processing circuitry is configured to perform a heterodyning function to receive and discriminate between the respective source signals emitted by the first, second, and third radiation sources.

39. The apparatus of claim 38, wherein the processing circuitry comprises a multiplier configured to receive an output signal from the first radiation sensor and a transmission signal to be emitted from the first radiation source, and wherein the multiplier is configured to provide an output signal to an analog-to-digital converter.

40. The apparatus of claim 1, wherein the processing circuitry comprises analog pulse compression circuitry configured to perform analog pulse compression on the respective source signals emitted by the first, second, and third radiation sources and received by the first and second radiation sensors.

41. The apparatus of claim 1, wherein the processing circuitry comprises an amplification stage coupled directly to a detector.

42. The apparatus of claim 1, wherein the processing circuitry comprises an amplification stage coupled to an input of an analog-to-digital converter (ADC).

43. The apparatus of claim 1, wherein the plurality of radiation sources and the first and second radiation sensors are configured to characterize a volume, and wherein the apparatus comprises a processor configured to construct a three-dimensional (3D) image of the volume based at least partially on the respective source signals emitted by the first, second, and third radiation sources and received by the first and second radiation sensors.

44. The apparatus of claim 43, wherein the processor comprises the processing circuitry.

45. The apparatus of claim 43, wherein the at least one processor is configured to construct the 3D image of the volume by:
generating a 3D image of the volume from a plurality of measurements by using a compressive sensing image reconstruction process, the plurality of measurements obtained based at least partially on the respective source signals.

46. The apparatus of claim 45, wherein using the compressive sensing image reconstruction process comprises identifying a solution to a system of linear equations relating the plurality of measurements to a property of the volume being imaged.

47. The apparatus of claim 46, wherein the system of linear equations represents a linear approximation to a forward operator of a three-dimensional wave propagation equation.

48. The apparatus of claim 1, wherein the plurality of radiation sources and the first and second radiation sensors are configured to characterize a volume, and wherein the apparatus comprises a processor configured to construct a three-dimensional (3D) temperature profile of the volume based at least partially on the respective source signals emitted by the first, second, and third radiation sources.

49. The apparatus of claim 48, wherein the processor comprises the processing circuitry.

50. The apparatus of claim 1, wherein the plurality of radiation sources and the plurality of radiation sensors collectively form a structure into which a subject may be inserted.

51. The apparatus of claim 50, wherein the structure is substantially a box with an open side via which the subject may be inserted, and wherein the plurality of radiation sensors form a side of the box.

52. The apparatus of claim 1, further comprising a plurality of ultrasound elements configured as high intensity focused ultrasound (HIFU) elements configured to apply HIFU.

53. The apparatus of claim 52, further comprising a support on which the plurality of radiation sources and the HIFU elements are disposed.

54. The apparatus of claim 1, wherein the first radiation source and the first radiation sensor are formed of different materials.

55. The apparatus of claim 54, wherein the first radiation source is an ultrasound source comprising lead zirconate titanate (PZT) and wherein the first radiation sensor is an ultrasound sensor comprising polyvinylidene difluoride (PVDF).

56. The apparatus of claim 1, wherein the spacing between the first radiation sensor and its nearest neighboring radiation sensor of the plurality of radiation sensors is greater than $\lambda$.

57. The apparatus of claim 1, wherein the spacing between the first radiation sensor and its nearest neighboring radiation sensor of the plurality of radiation sensors is greater than $2\lambda$.

58. The apparatus of claim 1, wherein the spacing between the first radiation sensor and its nearest neighboring radiation sensor of the plurality of radiation sensors is greater than $3\lambda$.

59. The apparatus of claim 1, wherein the spacing between any radiation sensor in the plurality of radiation sensors and its nearest neighboring radiation sensor of the plurality of radiation sensors is greater than $\lambda/2$.

60. The apparatus of claim 1, wherein the spacing between any radiation sensor in the plurality of radiation sensors and its nearest neighboring radiation sensor of the plurality of radiation sensors is greater than $\lambda$.

61. The apparatus of claim 1, wherein the spacing between any radiation sensor in the plurality of radiation sensors and its nearest neighboring radiation sensor of the plurality of radiation sensors is greater than $2\lambda$.

62. The apparatus of claim 1, wherein the spacing between any radiation sensor in the plurality of radiation sensors and its nearest neighboring radiation sensor of the plurality of radiation sensors is greater than $3\lambda$.

63. The apparatus of claim 1, wherein the spacing between any radiation sensor in the plurality of radiation sensors and its nearest neighboring radiation sensor of the plurality of radiation sensors is greater than $\lambda/2$ and less than or equal to $3\lambda$.

64. The apparatus of claim 1, further comprising a plurality of ultrasound elements disposed on a same substrate as the plurality of radiation sensors, the plurality of ultrasound elements being different than the plurality of radiation sensors, the plurality of ultrasound elements being configured as high intensity focused ultrasound elements.

65. An apparatus, comprising:
a plurality of radiation sources configured to emit respective source radiation signals incident upon a volume to be characterized, the volume spanning orthogonal X, Y, and Z axes, the plurality of radiation sources occupying multiple locations in the X direction and multiple locations in the Y direction;
a plurality of radiation sensors, including a first radiation sensor, separated from the plurality of radiation sources along the Z direction and configured to sense the respective source radiation signals emitted by the plurality of radiation sources, the plurality of radiation sensors occupying multiple locations in the X direction and multiple locations in the Y direction, the plurality of radiation sensors configured to receive radiation of wavelength $\lambda$ emitted by one or more of the plurality of radiation sources, wherein the plurality of radiation sensors is sparsely arranged such that a spacing between the first radiation sensor and its nearest neighboring radiation sensor of the plurality of radiation sensors is greater than $\lambda/2$; and
processing circuitry coupled to the plurality of radiation sensors and configured to receive and discriminate between, for each of the plurality of radiation sensors, the respective source signals of the plurality of radiation sources.

66. The apparatus of claim 65, wherein the apparatus further comprises at least one additional radiation sensor in addition to the plurality of radiation sensors.

67. An apparatus, comprising:
a plurality of radiation sources configured to emit respective source radiation signals directed to be incident across a surface area of a subject;

a plurality of radiation sensors configured to receive radiation of wavelength λ emitted by one or more of the plurality of radiation sources, the plurality of radiation sensors including first and second radiation sensors each configured to sense the respective source radiation signals, wherein the plurality of radiation sensors is sparsely arranged such that a spacing between the first radiation sensor and its nearest neighboring radiation sensor of the plurality of radiation sensors is greater than λ/2; and processing circuitry coupled to the first and second radiation sensors and configured to receive and discriminate between, for each of the first and second radiation sensors, the respective source radiation signals emitted by the plurality of radiation sources.

68. The apparatus of claim 67, wherein a first radiation source of the plurality of radiation sources is an ultrasound source.

69. The apparatus of claim 68, wherein the first radiation sensor and the second radiation sensor are ultrasound radiation sensors.

70. The apparatus of claim 67, wherein the plurality of radiation sources comprises at least ten radiation sources.

71. The apparatus of claim 70, wherein the plurality of radiation sources comprises at least 100 radiation sources.

72. The apparatus of claim 71, wherein the plurality of radiation sources comprises at least 1,000 radiation sources.

73. The apparatus of claim 70, wherein the plurality of radiation sources comprises between ten radiation sources and 10,000 radiation sources.

74. The apparatus of claim 67, wherein the plurality of radiation sources is arranged in three dimensions.

75. The apparatus of claim 67, wherein the plurality of radiation sources forms an array of at least two dimensions in which the plurality of radiation sources adopts a regular spacing.

76. The apparatus of claim 75, wherein the plurality of radiation sources is arranged in three dimensions.

77. The apparatus of claim 67, wherein the plurality of radiation sensors is arranged in at least two dimensions.

78. The apparatus of claim 77, wherein the plurality of radiation sensors is arranged in three dimensions.

79. The apparatus of claim 77, wherein the plurality of radiation sensors forms an array of at least two dimensions in which the plurality of radiation sensors adopts a regular spacing.

80. The apparatus of claim 77, wherein the plurality of radiation sources forms an array of at least two dimensions, and wherein the plurality of radiation sensors forms an array of at least two dimensions.

81. The apparatus of claim 67, wherein the plurality of radiation sources and the first and second radiation sensors are configured to remain static during operation.

82. The apparatus of claim 67, wherein at least some radiation sources of the plurality of radiation sources are not spaced at regular intervals with respect to neighboring radiation sources.

83. The apparatus of claim 67, wherein at least some radiation sensors of the plurality of radiation sensors are not spaced at regular intervals with respect to neighboring radiation sensors.

84. The apparatus of claim 67, wherein the plurality of radiation sources are physically coupled to a first mount and wherein the first and second radiation sensors are physically coupled to a second mount.

85. The apparatus of claim 84, wherein the first mount is flexible.

86. The apparatus of claim 84, wherein the first and second mounts are configured to be independently movable.

87. The apparatus of claim 86, further comprising a detector configured to detect an orientation and/or position of the plurality of radiation sources relative to the first and second radiation sensors.

88. The apparatus of claim 67, wherein the first and second radiation sensors are disposed on a first side of a plane and wherein the plurality of radiation sources are disposed on a second side of the plane.

89. The apparatus of claim 67, wherein the plurality of radiation sources and the first and second radiation sensors are collectively configured to operate in a transmissive modality.

90. The apparatus of claim 67, wherein directivity vectors of first, second, and third radiation sources of the plurality of radiation sources are incident upon the first and second radiation sensors.

91. The apparatus of claim 67, wherein at least one radiation source of the plurality of radiation sources is configurable to alternately operate as a radiation source and a radiation sensor.

92. The apparatus of claim 91, wherein the at least one radiation source is coupled to the processing circuitry via parallel transmit and receive signal paths, and wherein the apparatus further comprises a switch for switchably coupling the at least one radiation source to either the transmit signal path or the receive signal path.

93. The apparatus of claim 67, wherein the plurality of radiation sources comprises at least two distinct arrays of radiation sources.

94. The apparatus of claim 93, wherein the at least two distinct arrays of radiation sources comprises three or more distinct arrays of radiation sources.

95. The apparatus of claim 94, wherein the processing circuitry coupled to the first radiation sensor and the second radiation sensor is configured to receive and discriminate between, for each of the first and second radiation sensors, respective source signals emitted by at least one radiation source in each of three distinct arrays of the three or more distinct arrays of radiation sources.

96. The apparatus of claim 67, wherein the processing circuitry is configured to perform a heterodyning function to detect and discriminate the respective source signals.

97. The apparatus of claim 96, wherein the processing circuitry comprises a multiplier configured to receive an output signal from the first radiation sensor and a transmission signal to be emitted from a first radiation source of the plurality of radiation sources, and wherein the multiplier is configured to provide an output signal to an analog-to-digital converter.

98. The apparatus of claim 67, wherein the processing circuitry comprises analog pulse compression circuitry configured to perform analog pulse compression on the respective source signals.

99. The apparatus of claim 67, wherein the processing circuitry comprises an amplification stage coupled directly to a detector.

100. The apparatus of claim 67, wherein the processing circuitry comprises an amplification stage coupled to an input of an analog-to-digital converter (ADC).

101. The apparatus of claim 67, wherein the plurality of radiation sources and the first and second radiation sensors are configured to characterize at least part of the subject, and wherein the apparatus comprises a processor configured to construct a three-dimensional (3D) image of the part of the subject based at least partially on the respective source signals.

102. The apparatus of claim 101, wherein the processor comprises the processing circuitry.

103. The apparatus of claim 67, wherein the plurality of radiation sources and the first and second radiation sensors are configured to characterize at least part of the subject, and wherein the apparatus comprises a processor configured to construct a three-dimensional (3D) temperature profile of the part of the subject based at least partially on the respective source signals.

104. The apparatus of claim 103, wherein the processor comprises the processing circuitry.

105. The apparatus of claim 67, wherein the surface area is between approximately 1 cm$^2$ and approximately 100 cm$^2$.

106. The apparatus of claim 105, wherein the surface area is between approximately 50 cm$^2$ and approximately 100 cm$^2$.

107. An apparatus, comprising:
three radiation sources arranged in a multi-dimensional, non-linear arrangement and configured to produce respective source signals;
a plurality of radiation sensors, including a first radiation sensor, configured to receive radiation of wavelength $\lambda$ emitted by one or more of the three radiation sources, wherein the plurality of radiation sensors is sparsely arranged such that a spacing between the first radiation sensor and its nearest neighboring radiation sensor of the plurality of radiation sensors is greater than $\lambda/2$; and
processing circuitry coupled to the plurality of radiation sensors and configured to receive and discriminate between, for at least one radiation sensor of the plurality of radiation sensors, the respective source signals produced by the three radiation sources.

108. The apparatus of claim 107, wherein a first radiation source of the three radiation sources is an ultrasound source.

109. The apparatus of claim 108, wherein the at least one radiation sensor is an ultrasound radiation sensor.

110. The apparatus of claim 107, further comprising a plurality of radiation sources including the three radiation sources, and wherein the processing circuitry is configured to receive and discriminate between, for the at least one radiation sensor, the respective source signals emitted by at least ten radiation sources of the plurality of radiation sources.

111. The apparatus of claim 110, wherein the processing circuitry is configured to receive and discriminate between, for the at least one radiation sensor, the respective source signals emitted by at least 100 radiation sources of the plurality of radiation sources.

112. The apparatus of claim 111, wherein the processing circuitry is configured to receive and discriminate between, for the at least one radiation sensor, the respective source signals emitted by at least 1,000 radiation sources of the plurality of radiation sources.

113. The apparatus of claim 110, wherein the processing circuitry is configured to receive and discriminate between, for the at least one radiation sensor, the respective source signals emitted by between ten radiation sources and 10,000 radiation sources of the plurality of radiation sources.

114. The apparatus of claim 107, further comprising a plurality of radiation sources including the three radiation sources, and wherein the processing circuitry is configured to receive and discriminate between, for the at least one radiation sensor, the respective source signals emitted by at least 1% of the radiation sources of the plurality of radiation sources.

115. The apparatus of claim 114, wherein the processing circuitry is configured to receive and discriminate between, for the at least one radiation sensor, the respective source signals emitted by at least 10% of the radiation sources of the plurality of radiation sources.

116. The apparatus of claim 115, wherein the processing circuitry is configured to receive and discriminate between, for the at least one radiation sensor, the respective source signals emitted by at least 25% of the radiation sources of the plurality of radiation sources.

117. The apparatus of claim 116, wherein the processing circuitry is configured to receive and discriminate between, for the at least one radiation sensor, the respective source signals emitted by at least 50% of the radiation sources of the plurality of radiation sources.

118. The apparatus of claim 117, wherein the processing circuitry is configured to receive and discriminate between, for the at least one radiation sensor, the respective source signals emitted by at least 75% of the radiation sources of the plurality of radiation sources.

119. The apparatus of claim 118, wherein the processing circuitry is configured to receive and discriminate between, for the at least one radiation sensor, the respective source signals emitted by at least 90% of the radiation sources of the plurality of radiation sources.

120. The apparatus of claim 119, wherein the processing circuitry is configured to receive and discriminate between, for the at least one radiation sensor, the respective source signals emitted by all radiation sources of the apparatus.

121. The apparatus of claim 120, wherein the plurality of radiation sources comprises at least fifty radiation sources.

122. The apparatus of claim 107, further comprising a fourth radiation source, wherein the four radiation sources are arranged in three dimensions.

123. The apparatus of claim 107, comprising a plurality of radiation sources including the three radiation sources, wherein the plurality of radiation sources forms an array of at least two dimensions in which the plurality of radiation sources adopts a regular spacing.

124. The apparatus of claim 123, wherein the plurality of radiation sources is arranged in three dimensions.

125. The apparatus of claim 107, wherein the plurality of radiation sensors is arranged in at least two dimensions.

126. The apparatus of claim 125, wherein the plurality of radiation sensors is arranged in three dimensions.

127. The apparatus of claim 125, wherein the plurality of radiation sensors forms an array of at least two dimensions in which the plurality of radiation sensors adopts a regular spacing.

128. The apparatus of claim 125, comprising a plurality of radiation sources including the three radiation sources, wherein the plurality of radiation sources forms an array of at least two dimensions, and wherein the plurality of radiation sensors forms an array of at least two dimensions.

129. The apparatus of claim 107, wherein the three radiation sources and the plurality of radiation sensors are configured to remain static during operation.

130. The apparatus of claim 107, comprising a plurality of radiation sources including the three radiation sources, wherein at least some radiation sources of the plurality of radiation sources are not spaced at regular intervals with respect to neighboring radiation sources.

131. The apparatus of claim 107, wherein at least some radiation sensors of the plurality of radiation sensors are not spaced at regular intervals with respect to neighboring radiation sensors.

132. The apparatus of claim 107, wherein the three radiation sources are physically coupled to a first mount and wherein the plurality of radiation sensors are physically coupled to a second mount.

133. The apparatus of claim 132, wherein the first mount is flexible.

134. The apparatus of claim 132, wherein the first and second mounts are configured to be independently movable.

135. The apparatus of claim 134, further comprising a detector configured to detect an orientation and/or position of the three radiation sources relative to the plurality of radiation sensors.

136. The apparatus of claim 107, wherein the plurality of radiation sensors are disposed on a first side of a plane and wherein the three radiation sources are disposed on a second side of the plane.

137. The apparatus of claim 107, wherein the three radiation sources and the plurality of radiation sensors are collectively configured to operate in a transmissive modality.

138. The apparatus of claim 107, wherein directivity vectors of the three radiation sources are incident upon first and second radiation sensors of the plurality of radiation sensors.

139. The apparatus of claim 107, wherein at least one radiation source of the three radiation sources is configurable to alternately operate as a radiation source and a radiation sensor.

140. The apparatus of claim 139, wherein the at least one radiation source is coupled to the processing circuitry via parallel transmit and receive signal paths, and wherein the apparatus further comprises a switch for switchably coupling the at least one radiation source to either the transmit signal path or the receive signal path.

141. The apparatus of claim 107, wherein the apparatus comprises at least two distinct arrays of radiation sources, and wherein each of the three radiation sources belongs to at least one of the at least two distinct arrays.

142. The apparatus of claim 141, wherein the at least two distinct arrays of radiation sources comprises three or more distinct arrays of radiation sources.

143. The apparatus of claim 142, wherein the processing circuitry coupled to the plurality of radiation sensors is configured to receive and discriminate between, for the at least one radiation sensor, respective source signals emitted by at least one radiation source in each of three distinct arrays of the three or more distinct arrays of radiation sources.

144. The apparatus of claim 107, wherein the processing circuitry is configured to perform a heterodyning function to detect and discriminate the respective source signals.

145. The apparatus of claim 107, wherein the processing circuitry comprises a multiplier configured to receive an output signal from the first radiation sensor of the plurality of radiation sensors and a transmission signal to be emitted from a first radiation source of the three radiation sources, and wherein the multiplier is configured to provide an output signal to an analog-to-digital converter.

146. The apparatus of claim 107, wherein the processing circuitry comprises analog pulse compression circuitry configured to perform analog pulse compression on the respective source signals.

147. The apparatus of claim 107, wherein the processing circuitry comprises an amplification stage coupled directly to a detector.

148. The apparatus of claim 107, wherein the processing circuitry comprises an amplification stage coupled to an input of an analog-to-digital converter (ADC).

149. The apparatus of claim 107, wherein the three radiation sources and the plurality of radiation sensors are configured to characterize at least part of a subject, and wherein the apparatus comprises a processor configured to construct a three-dimensional (3D) image of the part of the subject based at least partially on the respective source signals.

150. The apparatus of claim 149, wherein the processor comprises the processing circuitry.

151. The apparatus of claim 107, wherein the three radiation sources and the plurality of radiation sensors are configured to characterize at least part of a subject, and wherein the apparatus comprises a processor configured to construct a three-dimensional (3D) temperature profile of the part of the subject based at least partially on the respective source signals.

152. The apparatus of claim 151, wherein the processor comprises the processing circuitry.

153. An apparatus, comprising:
a plurality of radiation sources arranged nonlinearly in a first plane or three-dimensional space and configured to emit respective source signals through a volume to be characterized;
a plurality of radiation sensors, including a first radiation sensor, arranged nonlinearly in a second plane or three-dimensional space and configured to oppose the first plane or three-dimensional space, and the volume, wherein each of the plurality of radiation sensors is configured to sense the source signals emitted by each of the plurality of radiation sources after the source signals pass through the volume, wherein each of the plurality of radiation sensors is configured to receive radiation of wavelength $\lambda$ emitted by one or more of the plurality of radiation sources, wherein the plurality of radiation sensors is sparsely arranged such that a spacing between the first radiation sensor and its nearest neighboring radiation sensor of the plurality of radiation sensors is greater than $\lambda/2$; and
processing circuitry coupled to the plurality of radiation sensors and configured to receive and discriminate between the source signals sensed by the plurality of radiation sensors, the received signals being indicative of at least one characteristic of the volume.

154. The apparatus of claim 153, wherein the plurality of radiation sources is arranged nonlinearly in a plane.

155. The apparatus of claim 154, wherein the plane is the first plane, and wherein the plurality of radiation sensors is arranged nonlinearly in the second plane.

156. The apparatus of claim 154, wherein the plurality of radiation sensors is arranged nonlinearly in a three-dimensional space.

157. The apparatus of claim 153, wherein the plurality of radiation sources is arranged nonlinearly in a three-dimensional space.

158. The apparatus of claim 157, wherein the plurality of radiation sensors is arranged nonlinearly in a plane.

159. The apparatus of claim 157, wherein the three-dimensional space is a first three-dimensional space, and wherein the plurality of radiation sensors is arranged nonlinearly in a second three-dimensional space.

160. The apparatus of claim 153, wherein:
the received signals are indicative of the appearance of the volume; and
the apparatus further comprises image processing circuitry configured to generate a three-dimensional image of the volume based on the received signals.

161. The apparatus of claim 153, wherein the at least one characteristic of the volume is a density of the volume.

162. The apparatus of claim 153, wherein the at least one characteristic of the volume is a refractive index of the volume.

163. The apparatus of claim 153, wherein the plurality of radiation sources includes between ten and 10,000 radiation sources.

164. The apparatus of claim 153, wherein the plurality of radiation sensors includes between ten and 10,000 radiation sensors.

165. The apparatus of claim 153, wherein the apparatus comprises a processor configured to construct a three-dimensional (3D) image of the volume based at least partially on the received signals.

166. The apparatus of claim 165, wherein the processor comprises the processing circuitry.

167. The apparatus of claim 153, wherein the apparatus comprises a processor configured to construct a three-dimensional (3D) temperature profile of the volume based at least partially on the received signals.

168. The apparatus of claim 167, wherein the processor comprises the processing circuitry.

169. An apparatus comprising:
multiple arrays of ultrasound sources configured to emit respective source signals;
an array of ultrasound sensors, including a first ultrasound sensor, configured to sense the respective source signals and receive radiation of wavelength $\lambda$ emitted by one or more ultrasound sources in the multiple arrays of ultrasound sources, wherein the array of ultrasound sensors is sparsely arranged such that a spacing between the first ultrasound sensor and its nearest neighboring ultrasound sensor in the array of ultrasound sensors is greater than $\lambda/2$; and
processing circuitry coupled to the array of ultrasound sensors and configured to receive and discriminate between, for at least one ultrasound sensor of the array of ultrasound sensors, the respective source signals of at least one ultrasound source from each of at least two arrays of the multiple arrays of ultrasound sources.

170. The apparatus of claim 169, wherein the multiple arrays of ultrasound sources consist of two arrays of ultrasound sources.

171. The apparatus of claim 169, wherein the multiple arrays of ultrasound sources comprise three arrays of ultrasound sources.

172. The apparatus of claim 171, wherein the three arrays of ultrasound sources and the array of ultrasound sensors are configured, in combination, to substantially surround a subject.

173. The apparatus of claim 169, wherein the multiple arrays of ultrasound sources comprise four arrays of ultrasound sources.

174. The apparatus of claim 173, wherein the four arrays of ultrasound sources and the array of ultrasound sensors are configured, in combination, to substantially form an imaging structure configured to receive a subject.

175. An apparatus, comprising:
a plurality of N×M radiation sources forming a two-dimensional or three-dimensional radiation source arrangement and configured to produce a first plurality of N×M respective source signals, wherein N is greater than or equal to M;
a plurality of X×Y radiation sensors, including a first radiation sensor, forming a two-dimensional or three-dimensional radiation sensor arrangement, the plurality of radiation sensors configured to receive radiation of wavelength $\lambda$ emitted by one or more of the plurality of radiation sources, wherein the plurality of radiation sensors is sparsely arranged such that a spacing between the first radiation sensor and its nearest neighboring radiation sensor of the plurality of radiation sensors is greater than $\lambda/2$; and
processing circuitry coupled to the plurality of radiation sensors and configured to discriminate between greater than (X×Y×N) received signals from the N×M respective source signals.

176. The apparatus of claim 175, wherein at least one of the plurality of radiation sensors is an ultrasound sensor and wherein at least one of the (X×Y×N) received signals is an ultrasound signal.

177. The apparatus of claim 175, wherein the plurality of radiation sources is a plurality of ultrasound sources and wherein the plurality of radiation sensors is a plurality of ultrasound sensors.

178. The apparatus of claim 175, wherein the processing circuitry is configured to discriminate between up to (X×Y×N×M) received signals from the N×M respective source signals.

179. The apparatus of claim 178, wherein the processing circuitry is configured to discriminate between approximately (X×Y×N×M) received signals from the N×M respective source signals.

180. The apparatus of claim 178, wherein N=M=X=Y.

181. The apparatus of claim 175, wherein N=M=X=Y.

182. The apparatus of claim 175, wherein the plurality of N×M radiation sources are configured to produce substantially concurrently the first plurality of N×M respective source signals.

183. The apparatus of claim 175, comprising a processor configured to construct a three-dimensional (3D) image of a volume based at least partially on the received signals.

184. The apparatus of claim 183, wherein the processor comprises the processing circuitry.

185. The apparatus of claim 175, comprising a processor configured to construct a three-dimensional (3D) temperature profile of a volume based at least partially on the received signals.

186. The apparatus of claim 185, wherein the processor comprises the processing circuitry.

* * * * *